United States Patent
Kubota

(10) Patent No.: US 9,403,914 B2
(45) Date of Patent: *Aug. 2, 2016

(54) ANTI-CD27 HUMANIZED MONOCLONAL ANTIBODY

(75) Inventor: Tsuguo Kubota, Machida (JP)

(73) Assignee: KYOWA HAKKO KIRIN CO., LTD, Tokyo (JP)

(*) Notice: Subject to any disclaimer, the term of this patent is extended or adjusted under 35 U.S.C. 154(b) by 1434 days.

This patent is subject to a terminal disclaimer.

(21) Appl. No.: 12/979,694

(22) Filed: Dec. 28, 2010

(65) Prior Publication Data

US 2012/0093805 A1 Apr. 19, 2012

Related U.S. Application Data

(60) Provisional application No. 61/290,542, filed on Dec. 29, 2009.

(51) Int. Cl.
- C07K 16/00 (2006.01)
- C07K 16/44 (2006.01)
- C07K 16/28 (2006.01)
- G01N 33/574 (2006.01)

(52) U.S. Cl.
CPC ............ *C07K 16/44* (2013.01); *C07K 16/2878* (2013.01); *G01N 33/57469* (2013.01); *C07K 2317/24* (2013.01); *C07K 2317/30* (2013.01); *C07K 2317/33* (2013.01); *C07K 2317/732* (2013.01); *C07K 2317/92* (2013.01); *G01N 2333/70578* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 5,747,048 A | 5/1998 | Kjeldsen et al. | |
| 9,023,999 B2 * | 5/2015 | Mori ................ | C07K 16/2878 435/7.1 |
| 2010/0173324 A1 * | 7/2010 | Mori et al. ................ | 435/7.1 |

FOREIGN PATENT DOCUMENTS

| WO | WO2010/001908 | * | 6/2009 |
|---|---|---|---|
| WO | 2010-001908 A1 | | 1/2010 |

OTHER PUBLICATIONS

Japanese Patent Office as an International Searching Authority, International Search Report (PCT/ISA/210) issued Mar. 22, 2011, in corresponding Application No. PCT/JP2010/073638.

Wil A. M. Loenen, et al.; "The CD27 membrane receptor, a lymphocyte-specific member of the nerve growth factor receptor family, gives rise to a soluble form by protein processing that does not involve receptor endocytosis"; Eur. J. Immunol., 1992, vol. 22; pp. 447-455.
Henry Y. Dong, et al; "CD148 and CD27 are Expressed in B Cell Lymphomas Derived from both Memory and Naive B Cells"; Leukemia and Lymphoma 2002; vol. 43 No. 9; pp. 1855-1858.
Avichezer, Dody, Georg F. Springer, Bilha Schechter, and Ruth Arnon. "Immunoreactivities of Polyclonal and Monoclonal Anti-T and Anti-Tn Antibodies with Human Carcinoma Cells, Grown In Vitro and in a Xenograft Model." International Journal of Cancer. vol. 72. (1997): 119-127.
Tongzhong, Ju, Grainger S. Lanneau, and Tripti Gautam. "Human Tumor Antigens Tn and Sialyl Tn Arise from Mutations in Cosmc." Cancer Research. vol. 68, No. 6, Mar. 15, 2008, : 1636-1646.
European Patent Office, Extended European Search Report dated Aug. 14, 2013 in corresponding Application No. 10841020.0.
Takashi Sano et. al.; "Enzymatically deglycosylated human IgA1 molecules accumulate and induce inflammatory cell reaction in rat glomeruli"; Nephrol Dial Transplant 2002; vol. 17; pp. 50-56.
W.Qin, et al.; "Peripheral B lymphocyte $\beta$1,3-galactosyltransferase and chaperone expression in immunoglobulin A nephropathy"; Journal of Internal Medicine 2005; vol. 258; pp. 467-477.
K. V. S. Prasad, et al.; "CD27, a member of the tumor necrosis factor receptor family, induces apoptosis and binds to Siva, a proapoptotic protein"; Proc. Natl. Acad. Sci. USA 1997; vol. 94; pp. 6346-6351.
Yoshiyuki Hiki, et al.; "Association of Asialo-galactosyl $\beta$1-3N-acetylgalactosamine on the Hinge with a Conformational Instability of Jacalin-Reactive Immunoglobulin A1 in Immunoglobulin A Nephropathy"; Journal of the American Society of Nephrology 1996; vol. 7; pp. 955-960.
Jannie Borst, et al.; "CD27 and CD70 in T cell and B cell activation"; Current Opinion in Immunology 2005; vol. 17; pp. 275-281.
Robert D. Bigler, et al.; A Modulating Disulfide-Linked T Cell Activation Antigen; The Journal of Immunology 1988; vol. 141; pp. 21-28.
A. C. Allen, et al.; "Galactosylation of N- and O-linked carbohydrate moieties of IgA1 and IgG in IgA nephropathy"; Clin Exp Immunol 1995; vol. 100; pp. 470-474.

* cited by examiner

*Primary Examiner* — Laura B Goddard
*Assistant Examiner* — Meera Natarajan
(74) *Attorney, Agent, or Firm* — Sughrue Mion, PLLC

(57) ABSTRACT

The present invention provides a monoclonal antibody which specifically recognizes CD27 containing an O-linked sugar chain to which galactose is not bound and binds to its extracellular region, or a method for using the same. The present invention can provide a monoclonal antibody or an antibody fragment thereof, which specifically recognizes a polypeptide encoded by CD27 gene containing an O-linked sugar chain to which galactose is not bound, and binds to its extracellular region; a hybridoma which produces the antibody; a DNA which encodes the antibody; a vector which comprises the DNA; a transformant obtainable by transforming the vector; a process for producing an antibody or an antibody fragment thereof using the hybridoma or the transformant; and a diagnostic agent or a therapeutic agent comprising the antibody or the antibody fragment thereof as an active ingredient.

12 Claims, 38 Drawing Sheets

Fig. 5
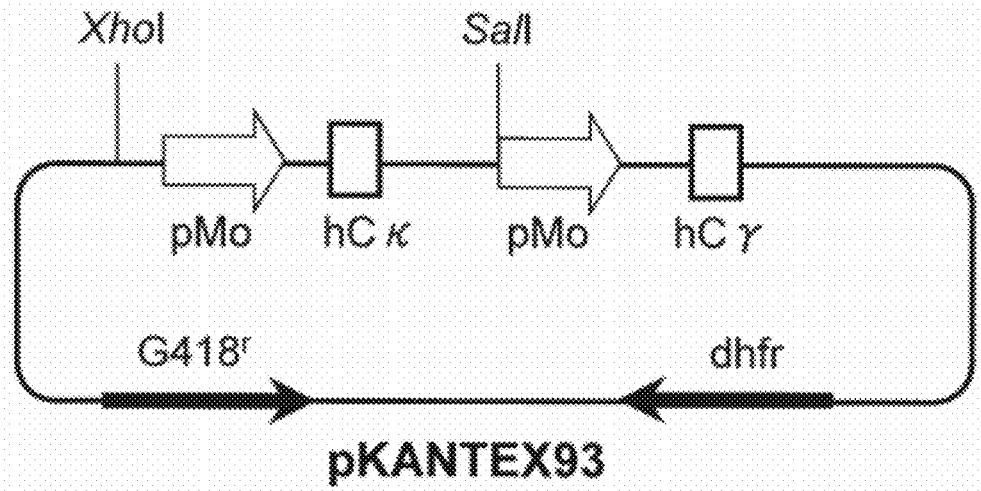
pKANTEX93
Xhol / Sall digestion
ligation reaction
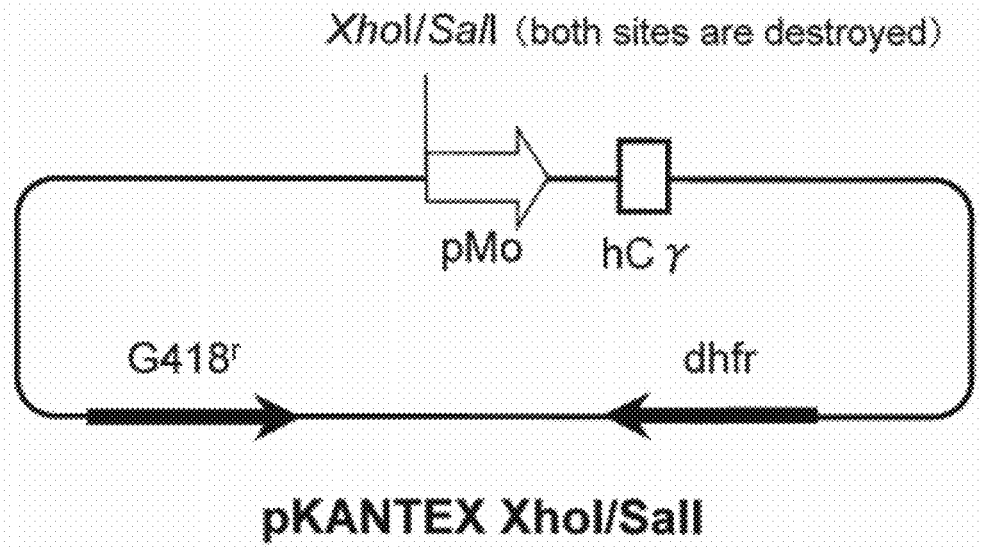
pKANTEX Xhol/Sall Fig. 7
(a)
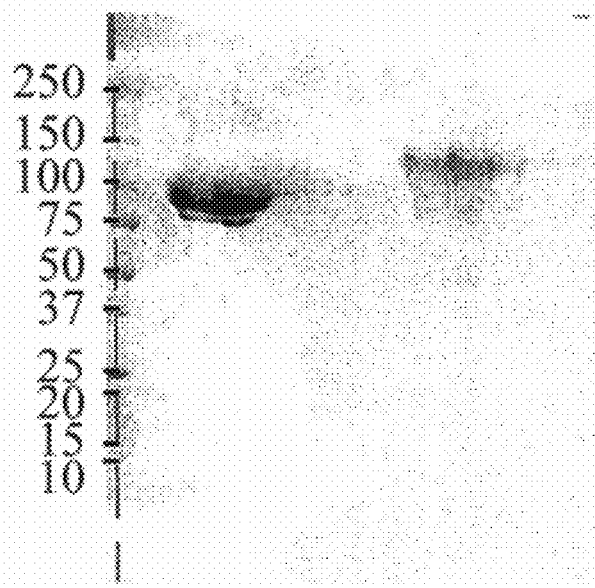
(b)
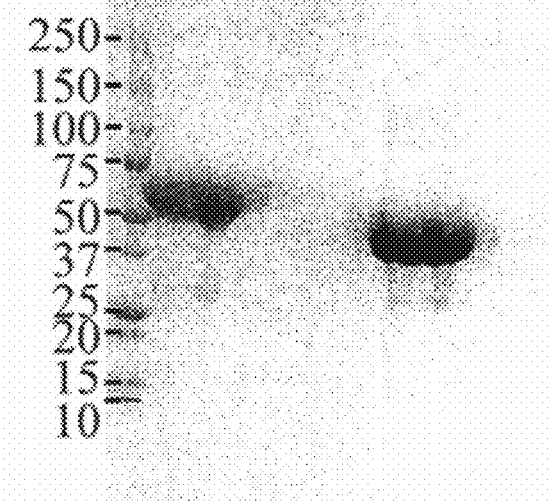

Fig. 11
(a)
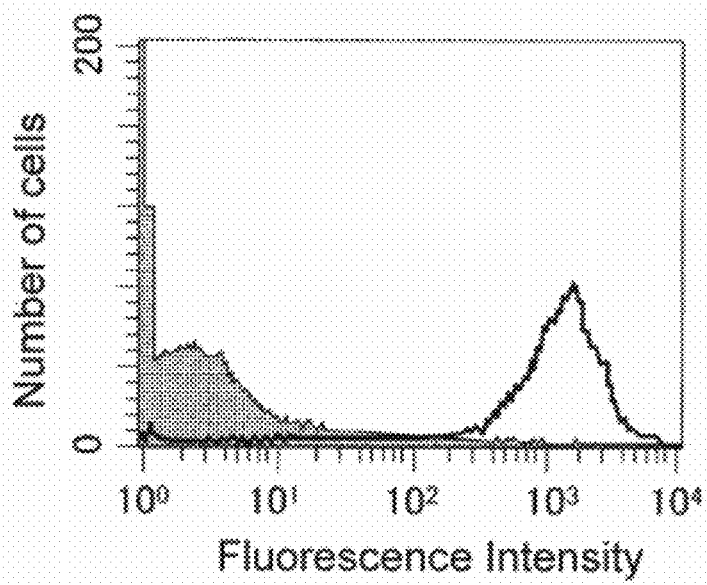
(b)
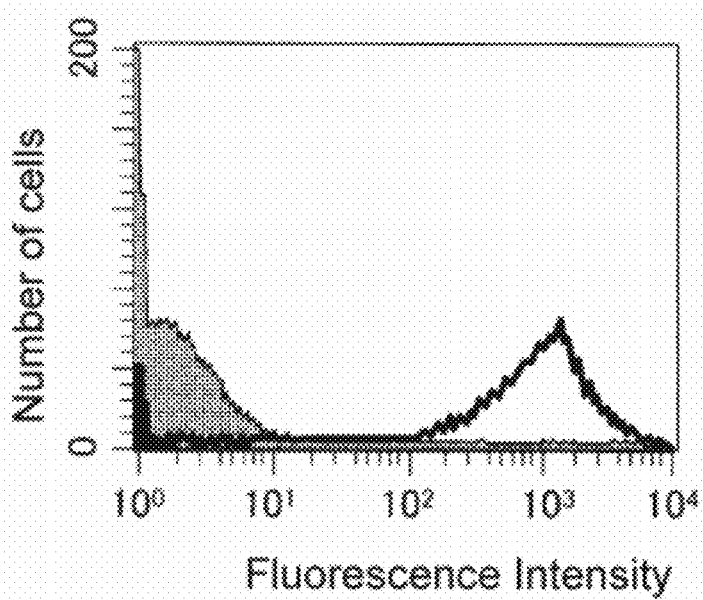

Fig. 12
(a)
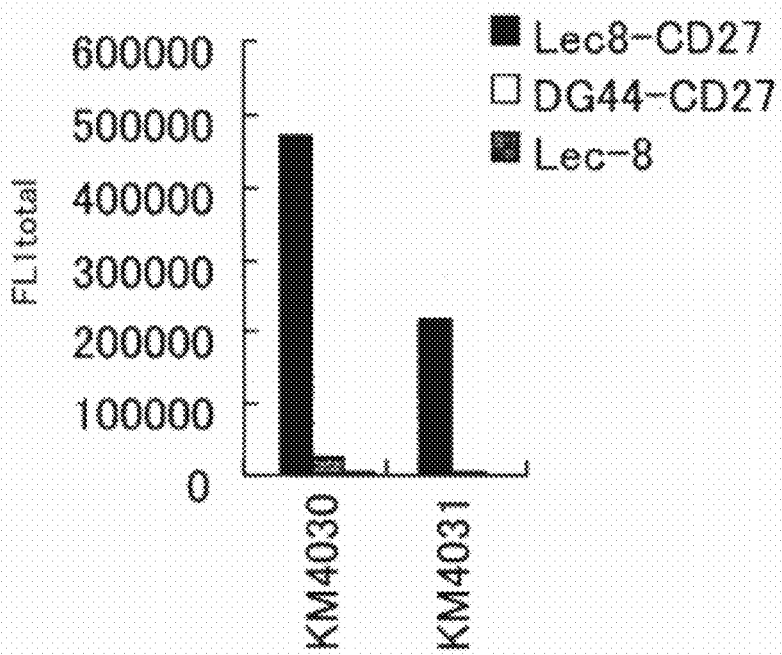
(b)
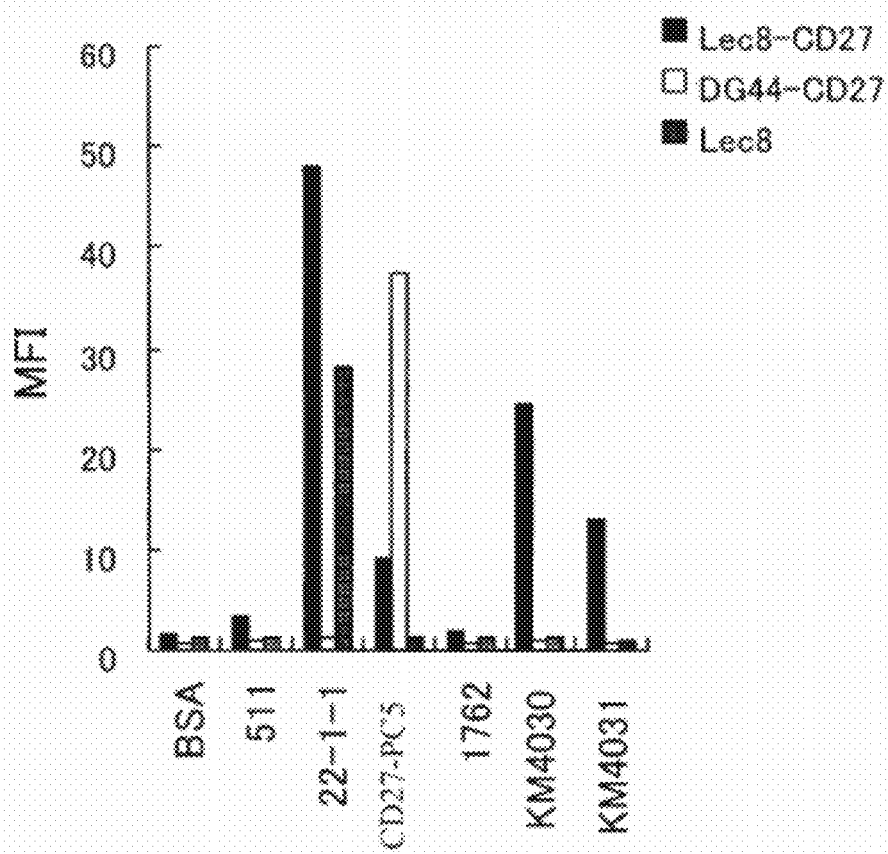

Fig. 13
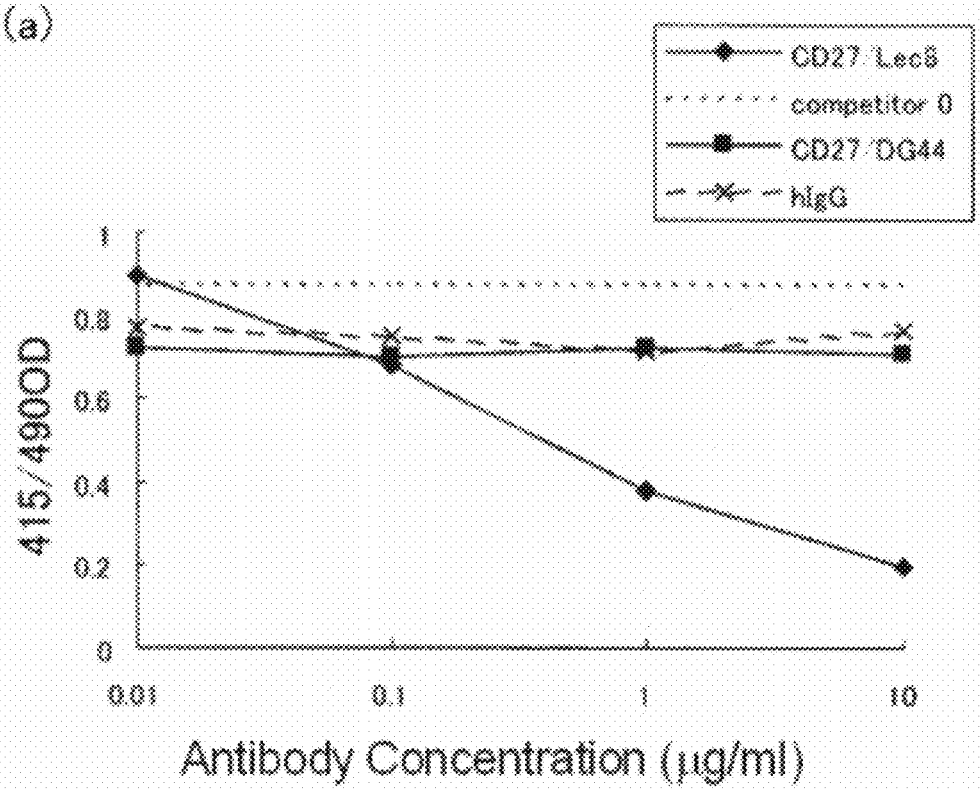
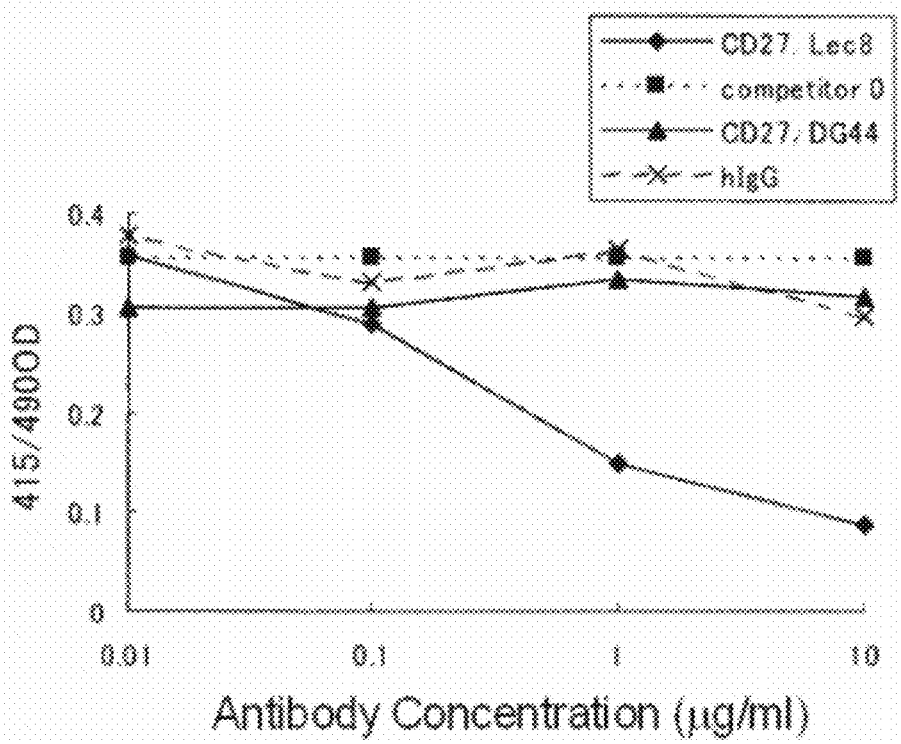

Fig. 14
(a)
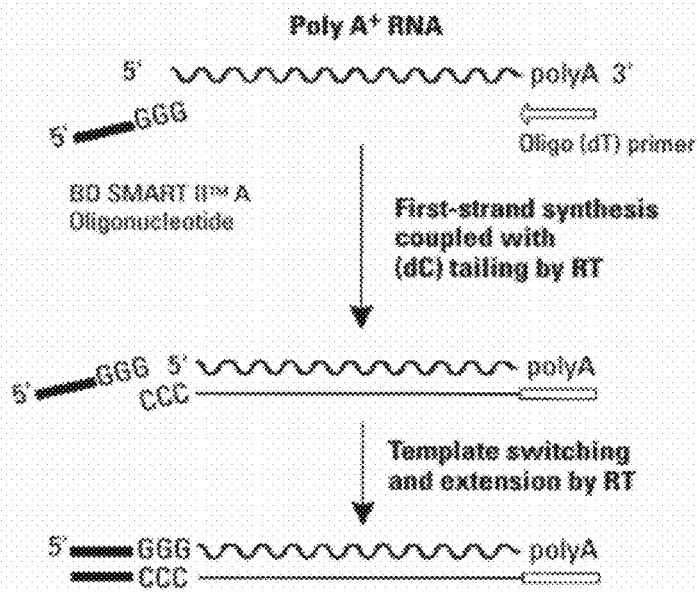
(b)
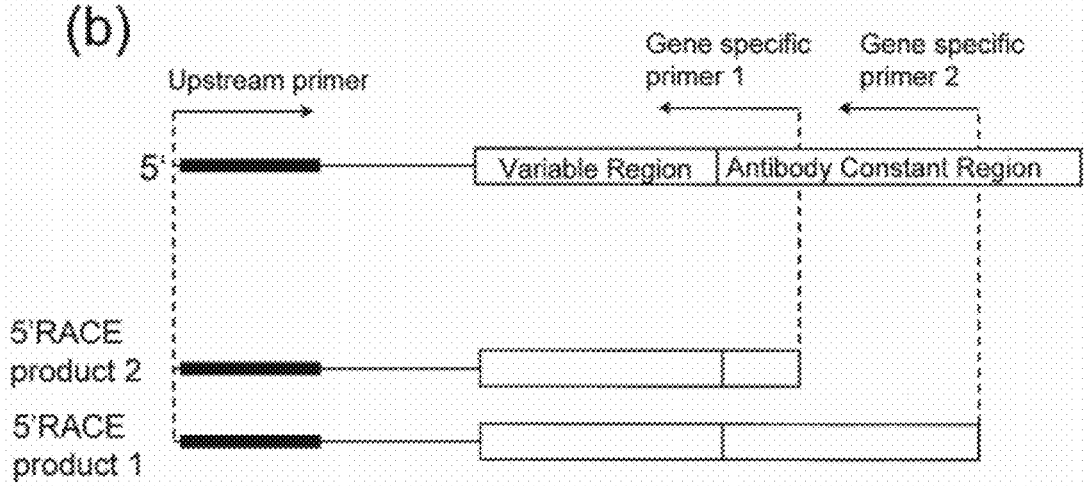
Scheme of Cloning

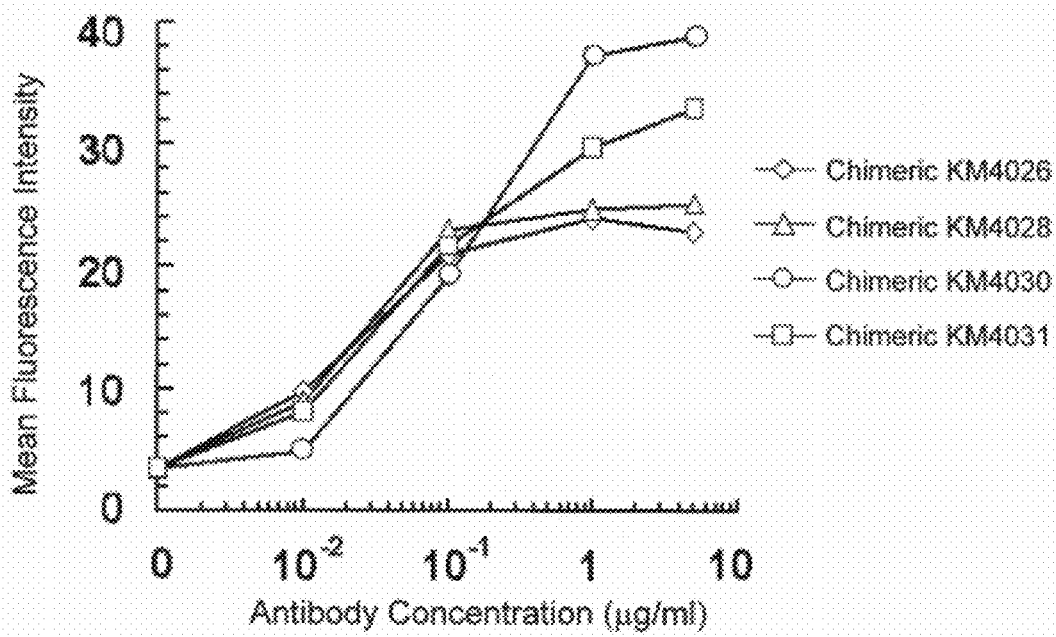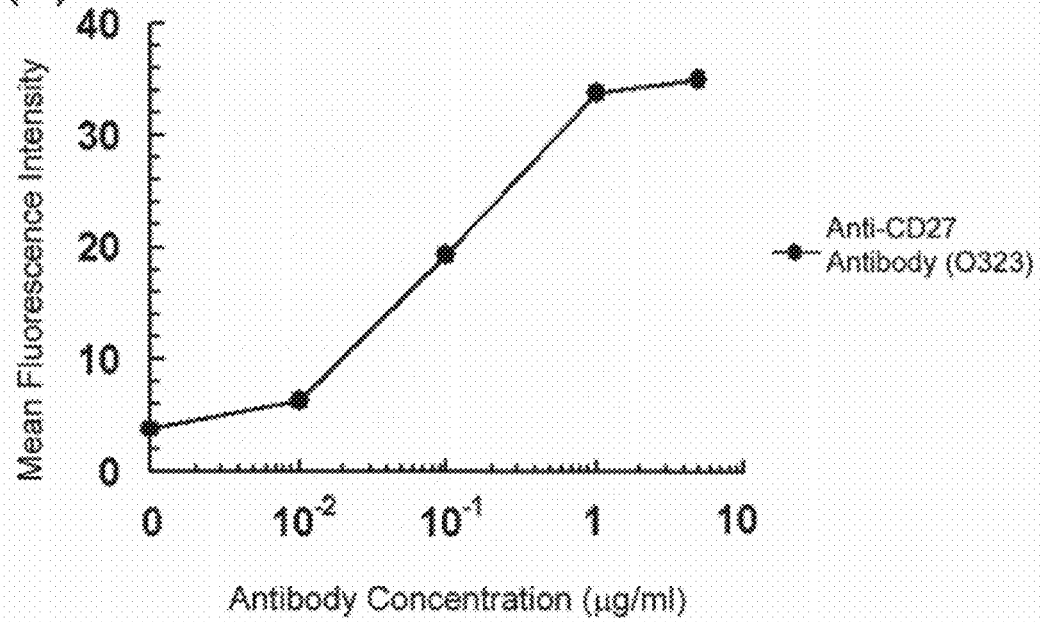
Fig. 19(A)

Fig. 19(C)
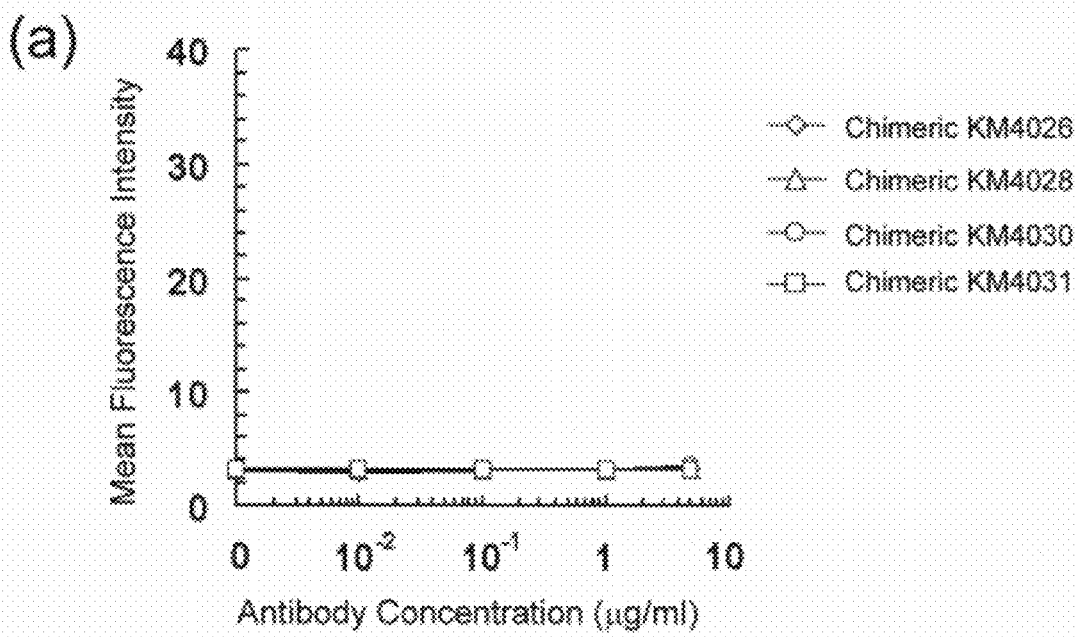
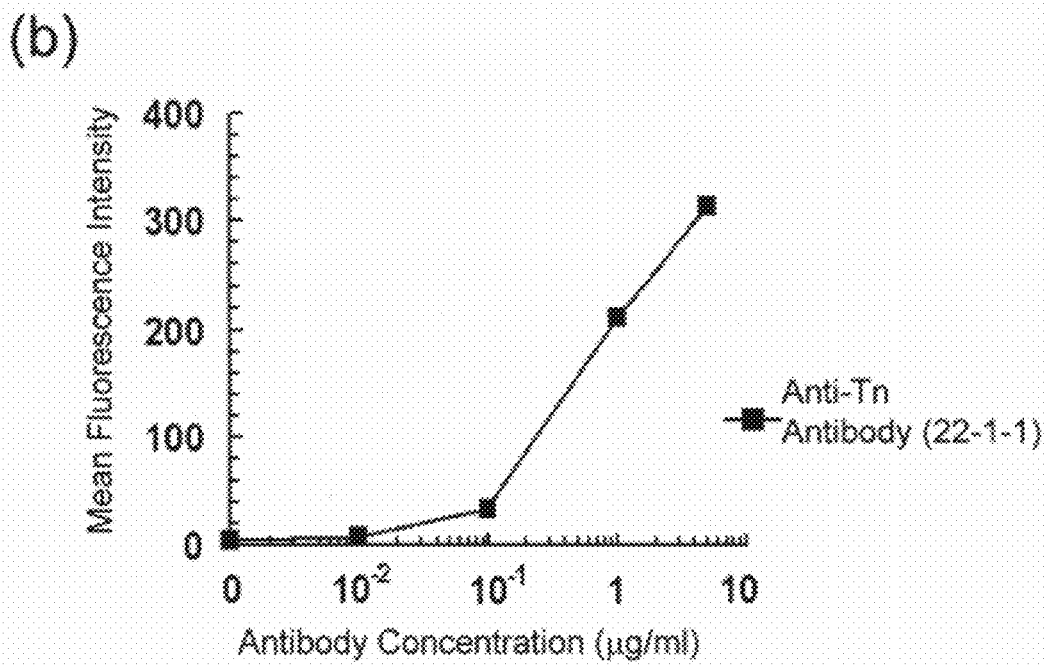

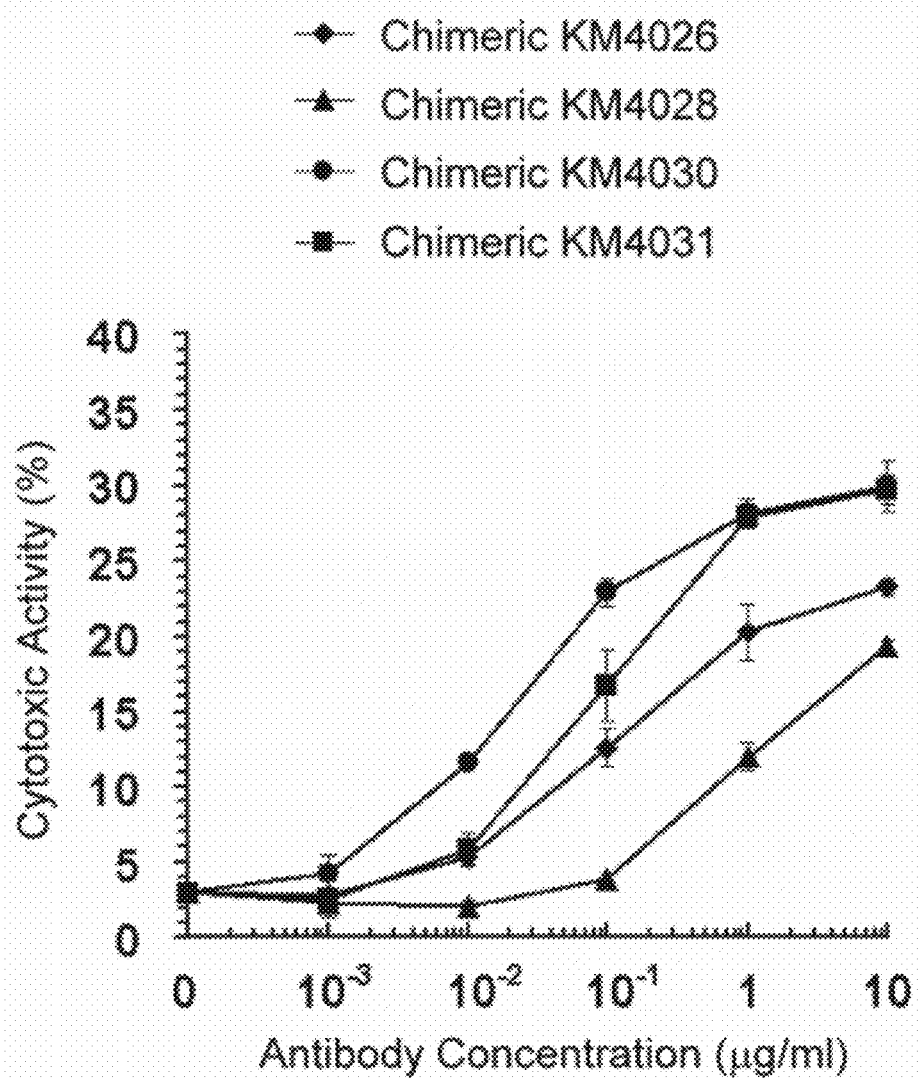

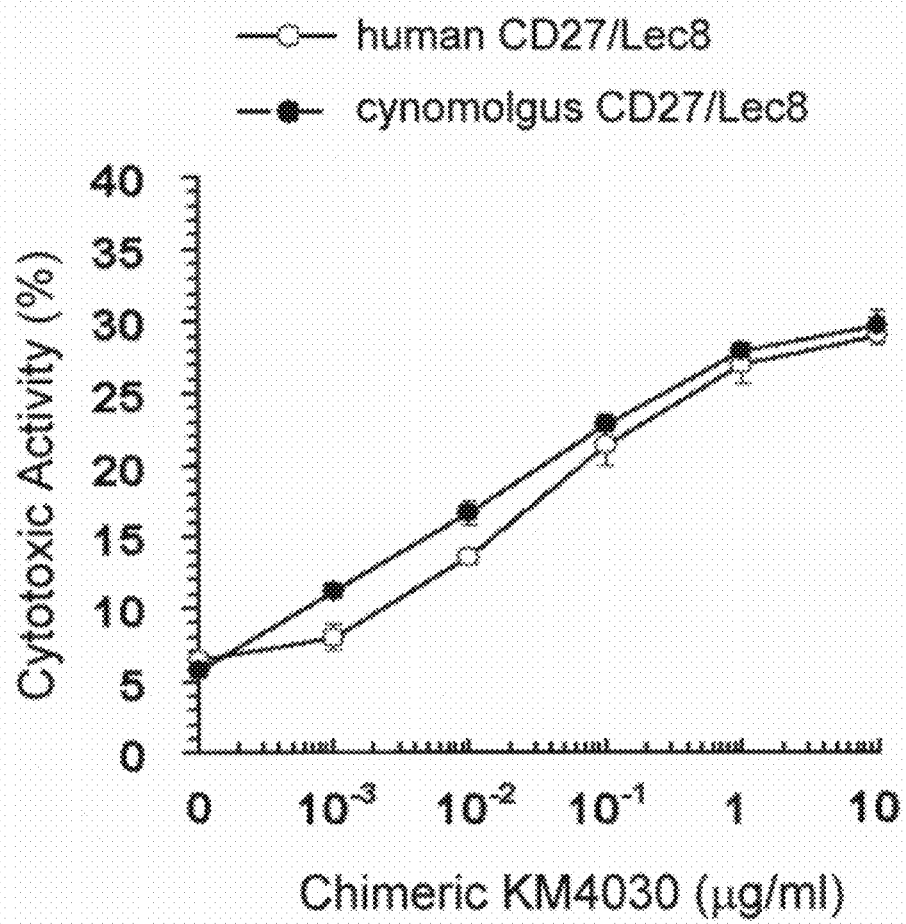

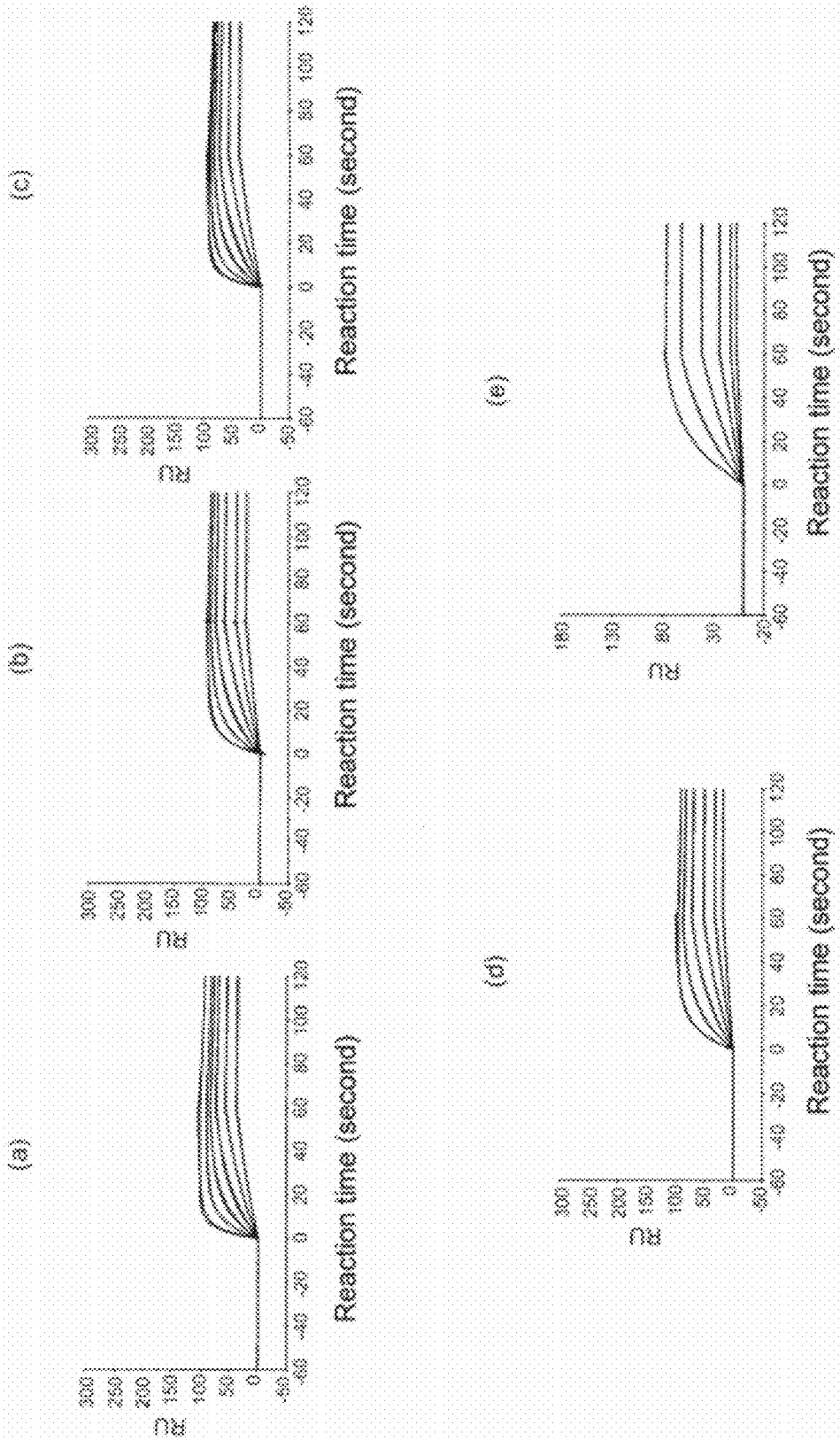

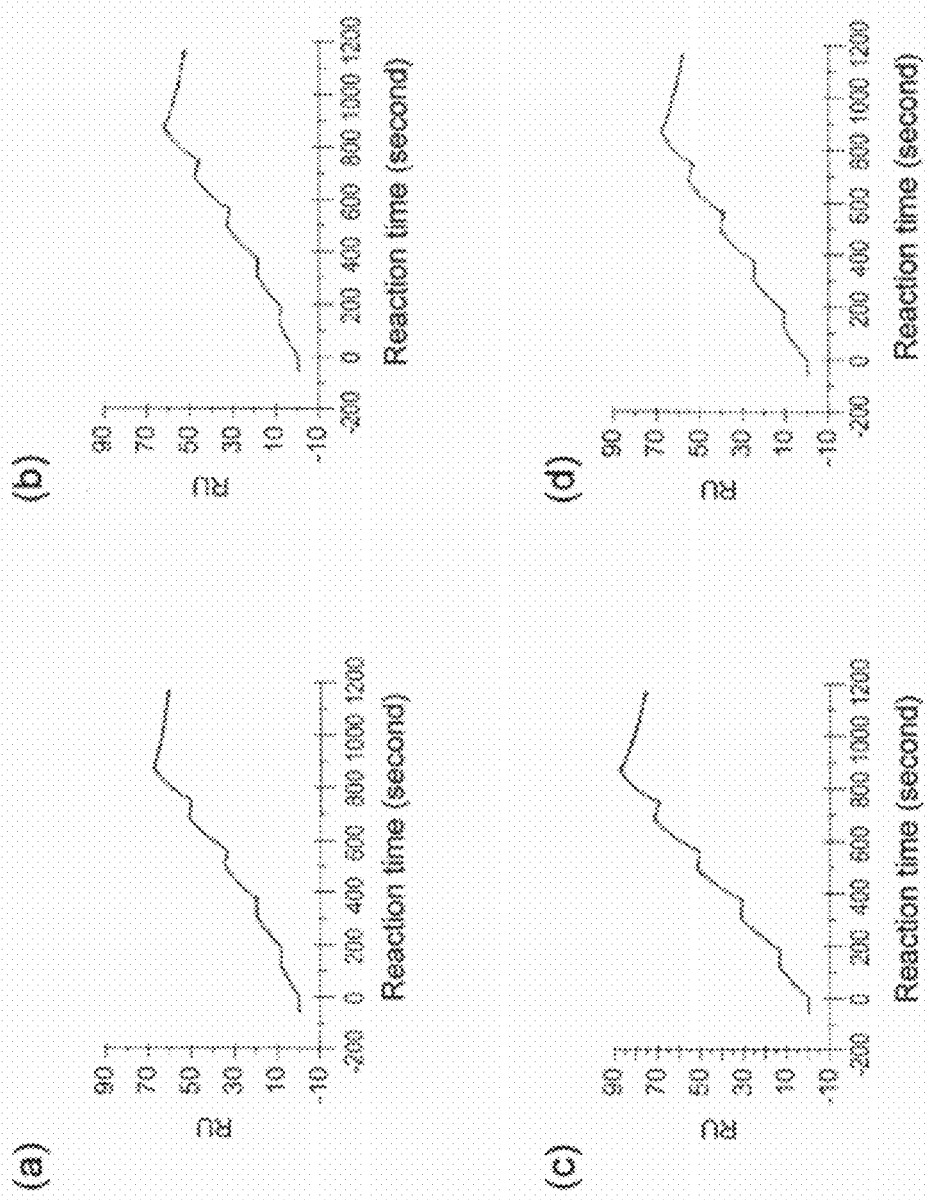

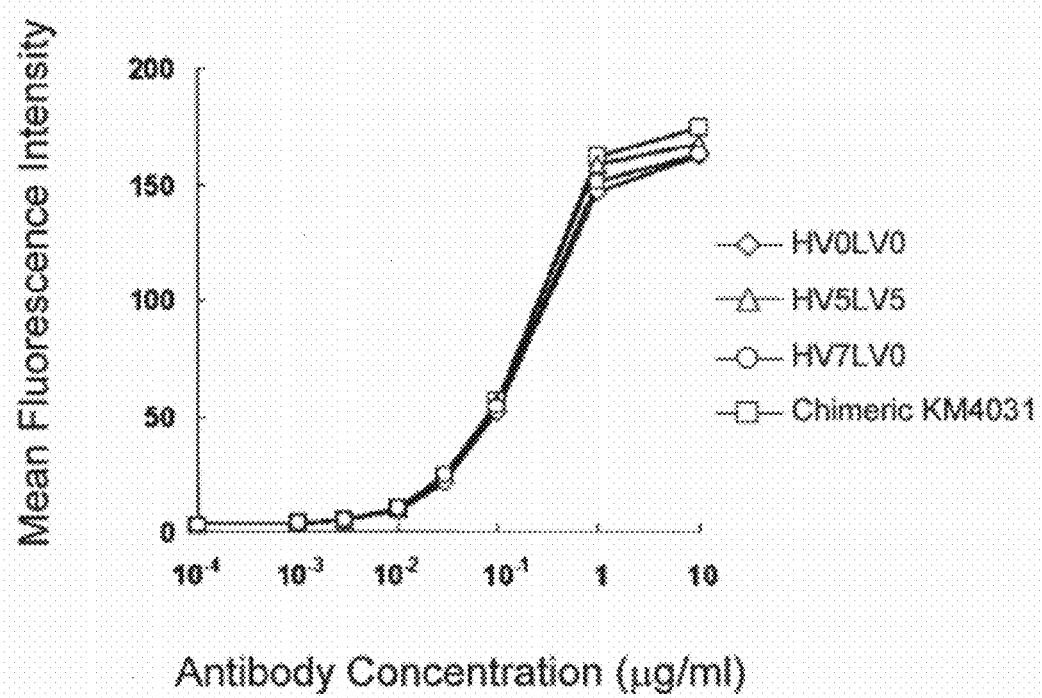

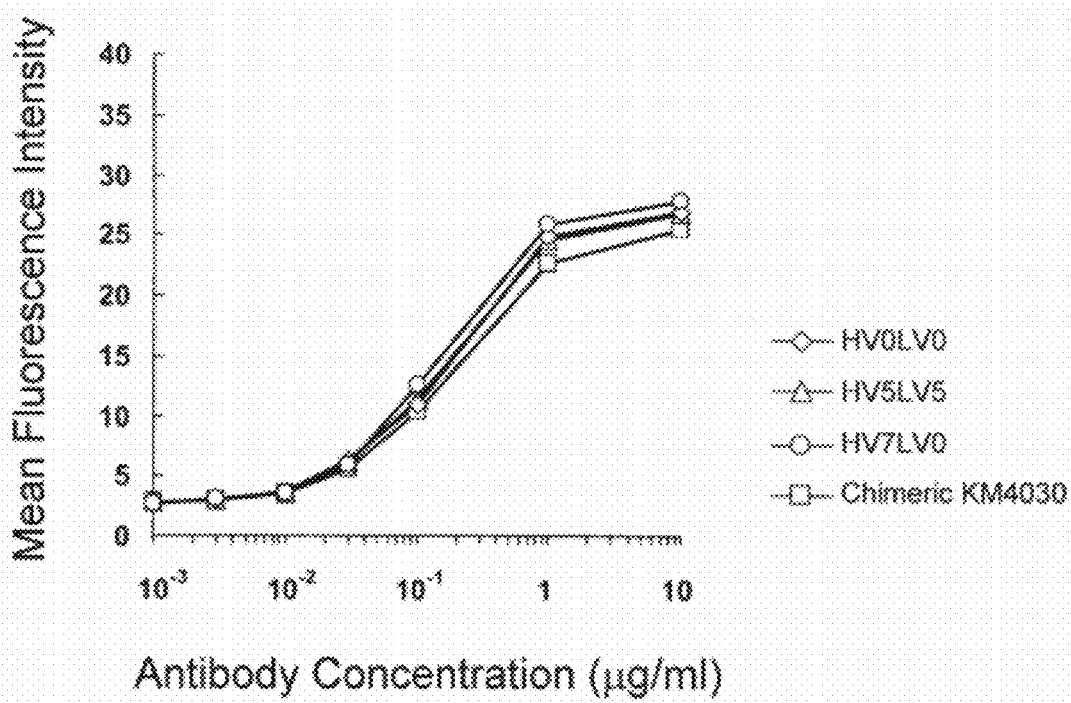

ANTI-CD27 HUMANIZED MONOCLONAL ANTIBODY

BACKGROUND OF THE INVENTION

1. Field of the Invention

The present invention relates to a humanized antibody or an antibody fragment thereof, which specifically recognizes a polypeptide encoded by CD27 gene containing an O-linked sugar chain to which galactose is not bound, and binds to its extracellular region of the peptide; a hybridoma which produces the humanized antibody; a DNA which encodes the humanized antibody; a vector which comprises the DNA; a transformant obtainable by transforming the vector; a process for producing a humanized antibody or an antibody fragment thereof using the hybridoma or the transformant; and a diagnostic agent using the antibody or the antibody fragment thereof, or a therapeutic agent comprising the humanized antibody or the antibody fragment thereof as an active ingredient.

2. Brief Description of the Background Art

In recent years, there have been reported some cases in which the onset of various diseases or the progression of pathology is accompanied by structural changes in sugar chains attached to the protein which is expressed by cells involved in the disease or pathology thereof. Representative ones among these cases are an expression of Tn antigen which is one of the O-linked (serine/threonine type) sugar chain antigens and which is found in more than 80% of human cancer types, and an expression of a sialyl-Tn antigen in which sialic acid is attached to the Tn antigen (Non-Patent Literature 2).

It is known that the expressions of these sugar chain antigens are rarely found in normal cells, and research for applying them as target molecules of cancer-specific vaccine therapies to medical care has been carried out (Non-Patent Literature 1). The expressions of the cancer-specific sugar chain antigens are under the control of the activity of enzymes constituting the complicated biosynthetic pathway of sugar chains and the complicated metabolic pathway of sugar chains in living organisms. For example, it is known that, in cancer cells, changes in the expression pattern of a gene encoding the proteins responsible for the biosynthetic pathway of sugar chains lead to brockage on the biosynthetic pathway of sugar chains.

The Tn antigen is known as an intermediate of the biosynthetic pathway of an O-linked sugar chain in normal cells, and has a structure (GalNAc α-Ser/Thr) in which N-acetylgalactosamine (GalNAc) is α-bound to a hydroxyl group on a side chain of a certain serine (Ser) or threonine (Thr) residue of an amino acid sequence of a protein.

Biosynthesis of a normal-type O-linked sugar chain (such as TF antigen) takes place by the transfer of one molecule of galactose to the non-reducing terminal of the Tn antigen by the activity of core 1β3 galactosyltransferase (core 1β3Gal-T, T-synthetase). It is considered that the biosynthetic pathway of sugar chains is blocked as a result of decrease in the activity of intracellular core 1β3 galactosyltransferase, and thereby the Tn antigen or the sialyl-Tn antigen is expressed in many types of cancer cell lines.

The mechanism of the decrease in the activity of core 1β3 galactosyltransferase in cancer cells is complicated and has not yet been fully elucidated. However, as one possible mechanism, it has been supposed that the intracellular core 1β3 galactosyltransferase activity is greatly decreased due to a mutation in a gene encoding a certain chaperone protein (Cosmc) which is necessary for the activity expression of core 1β3 galactosyltransferase (Non-Patent Literature 6).

Based on the fact that expression of the Tn antigen is commonly found among plural cancer types, it is considered that aberration in the biosynthetic pathway of sugar chains or the metabolic pathway of sugar chains in cells is a main cause of common changes in structures of sugar chains attached to many different glycoproteins expressed in the cells.

Cancer is a representative disease which is known to have a close relationship between the structural change of a sugar chain and the progression of pathology. Other than cancer, IgA nephropathy is known as another disease which is known to have a close linkage between the structural change of a sugar chain and the pathological progression. IgA nephropathy is chronic glomerular nephritis which is pathologically characterized by showing granular deposition of one of the immune globulin, immunoglobulin A (IgA), in the glomerular mesangium, and was first reported by Berger in 1968 (Non-Patent Literature 2).

IgA nephropathy is representative nephritis accounting for about half of chronic glomerular nephritis patients in Japan. It is said that about 40% of patients who have been diagnosed with IgA nephropathy will undergo a transition of the disease to late-stage renal failure within 20 years, and who will inevitably receive hemodialysis, renal transplantation or the like. As described above, even though IgA nephropathy has been generally recognized as a poor-prognosis disease, a clinically-validated therapy has not yet been established.

There is known that IgA1, out of two different IgA isotypes (IgA1 and IgA2), is mainly deposited in the kidney in the bodies of patients of IgA nephropathy. In addition, as a cause of IgA1 deposition, it has been reported that a structure of an O-linked sugar chain attached to a hinge region present on the IgA1 molecule, but absent on the IgA2 molecule, changed from a normal type to a Tn or sialyl-Tn antigen (Non-Patent Literatures 3 and 4).

It was demonstrated that once the deficiency of galactose from a O-linked type sugar chain added to the IgA1 hinge region has resulted in conversion of the sugar chain into a Tn or sialyl-Tn antigen, self-agglutination ability of the IgA1 molecule is enhanced, and deposition of the IgA1 molecule into the renal mesangial areas is accelerated (Non-Patent Literature 5).

Further, a decline of the core 1β3 galactosyltransferase activity due to a decreased expression level of Cosmc has been reported in IgA-producing cells isolated from IgA nephropathy patients (Non-Patent Literature 6).

In other words, the biosynthetic pathway of sugar chains is blocked halfway through in IgA-producing cells in the bodies of IgA nephropathy patients and as a result, sugar chain-deficient IgA1 is produced instead of IgA1 having a normal type sugar chain. As one of the pathogenic mechanisms of IgA nephropathy, it is advocated that the inflammation is induced as a result of the deposition of this sugar chain-deficient IgA1 in the renal glomerulus.

Generally, IgA is produced by B cells in blood, or plasma cells differentiated from B cells. The plasma cell is the final stage of B-cell differentiation. The plasma cells are distributed in secondary lymphoid tissues, systemic mucosal tissues, bone marrow, etc., and produce large quantities of antibodies. It is known that IgA-producing plasma cells are distributed mainly in mucosal tissues.

On the other hand, it is known that, in the germinal center of secondary lymphoid tissues, memory B cells or plasma cells are differentiated from B cell clones which have acquired an ability to produce high-affinity IgA antibodies, and the thus differentiated cells are distributed throughout target organs in whole-body and continuously produce antibodies over an extended period of time.

However, it is unclear at which stage of the B cell differentiation process, the cells which produce the sugar chain-deficient IgA involved in the pathogenesis of IgA nephropathy are developed, and to which body tissues the B cells or plasma cells which produce the sugar chain-deficient IgA are distributed.

Among proteins known as a cell membrane surface molecule expressed in B cells or plasma cells, CD27 is known as one of the molecules to which an O-linked sugar chain binds (Non-Patent Literature 7). The CD27 molecule, belonging to a member of the tumor necrosis factor receptor (TNFR) superfamily, is a type I membrane protein having a molecular weight of about 55 kDa, and is present as a disulfide-linked dimer of two monomers (Non-Patent Literature 8).

It is known that CD27 is expressed in some of T lymphocytes as well as in plasma cells and B cells. In particular, it is known that an expression level of CD27 is elevated upon differentiation of B cells into memory B cells and plasma cells in the differentiation process of B cells. It is known that CD27 to which an O-linked sugar chain binds is expressed in these cells during the differentiation process, but an amino acid residue to which the sugar chain binds is not clearly demonstrated (Non-Patent Literature 9).

As a ligand molecule of CD27, CD70 belonging to the TNF family is known. It is known that CD70 binds to CD27 expressed in some of B or T cells, induces cell proliferation signals, and stimulates B cells to produce antibodies (Non-Patent Literature 10).

In addition, it is known that the expression of CD27 is enhanced in several types of cancer cells as well as in normal cells. As types of cancer expressing CD27, there have been reported a variety of non-Hodgkin lymphomas, such as mantle cell lymphoma, chronic lymphocytic leukemia, small lymphocytic leukemia, Burkitt's lymphoma, follicular lymphoma, MALT lymphoma, diffuse large B-cell lymphoma, plasmacytoma (Non-Patent Literature 11).

Many of cancer cells are known to express a sugar chain-deficient protein containing a sugar chain including Tn antigen, sialyl-Tn antigen and the like, as described above.

As an antibody which specifically recognizes CD27, there has been reported an S152 antibody obtained by immunizing leukemia cells isolated from patients with Sezary syndrome (Non-Patent Literature 8). However, the S152 antibody is also shown to have an affinity with normal B cells and T cells. Up to date, there has not been known such an antibody which specifically recognizes CD27 molecule containing an O-linked sugar chain to which galactose is not bound.

It is generally known that, when a non-human antibody such as a mouse antibody is administered to human, it is recognized as a foreign substance so that a human antibody for mouse antibody (Human Anti Mouse Antibody; HAMA) is induced in the human body. It is known that HAMA reacts with the administered mouse antibody to thereby induce side effects (Non-patent Literatures 12 to 15), enhances disappearance of the mouse antibody from the body (Non-patent Literatures 16 to 18) and decreases therapeutic effect of the mouse antibody (Non-patent Literatures 19 and 20).

In order to solve these problems, attempts have been made to prepare a human chimeric antibody or a humanized antibody from a non-human antibody using gene recombination techniques.

A humanized antibody has various advantages in administration to human in comparison with a non-human antibody such as a mouse antibody. For example, it has been reported that the immunogenicity was decreased and the blood half-life was prolonged in a test using monkey, in comparison with a mouse antibody (Non-patent Literatures 21 and 22). That is, the humanized antibody is expected to cause fewer side effects in human than non-human antibodies and have sustained therapeutic effect for a long time.

Also, since a humanized antibody is prepared using gene recombination techniques, it can be prepared as various forms of molecules. For example, when γ1 subclass is used as a heavy chain (hereinafter referred to as "H chain") constant region (hereinafter referred to as "C region") of a human antibody (H chain C region is referred to as "CH"), a humanized antibody having high effector functions such as antibody-dependent cellular cytotoxicity (hereinafter referred to as "ADCC activity") can be prepared (Non-patent Literature 23), and prolongation of the blood half life in comparison with mouse antibodies can be expected (Non-patent Literature 24).

Particularly, in the case of treatment for removal of CD27-positive cells, cytotoxic activities such as complement-dependent cytotoxicity (hereinafter referred to as "CDC activity") and ADCC activity via the Fc region (the region after the antibody heavy chain hinge region) of an antibody are important, in order to specifically damage the target cells by accumulating effector cells near a tumor tissue via the antibody. In the treatment of humans, a human chimeric antibody, a humanized antibody or a human antibody is preferably used for exhibiting the cytotoxic activities (Non-patent Literatures 25 and 26).

In addition, with recent advance in protein engineering and genetic engineering, the humanized antibody can also be prepared as an antibody fragment having small molecular weight, such as Fab, Fab', F(ab')$_2$, a single chain antibody (hereinafter referred to as "scFv") (Non-patent Literature 27), a dimerized V region fragment (hereinafter referred to as "Diabody") (Non-patent Literature 28), a disulfide stabilized V region fragment (hereinafter referred to as "dsFv") (Non-patent Literature 29), or a peptide comprising a complementarity determining region (hereinafter referred to as "CDR") (Non-patent Literature 30). These antibody fragments are more excellent in transitivity to target tissues than complete antibody molecules (Non-patent Literature 31).

CITATION LIST

Non-Patent Literature

Non-patent Literature 1: Crit Rev Oncog., 6, 57 (1995)
Non-patent Literature 2: J Urol Nephrol., 74, 694 (1968)
Non-patent Literature 3: Clin Exp Immunol., 100, 470 (1995)
Non-patent Literature 4: J Am Soc Neph., 7, 955 (1996)
Non-patent Literature 5: Nephrol Dial Transplant., 17, 50 (2002)
Non-patent Literature 6: J Intern Med., 258, 467 (2005)
Non-patent Literature 7: Current Opinion in Immunology 17, 275 (2005)
Non-patent Literature 8: J. Immunol., 141, 21 (1988)
Non-patent Literature 9: Eur J Immunol., 22, 447 (1992))
Non-patent Literature 10: Proc. Natl. Acad. Sci., 94.6346 (1997)
Non-patent Literature 11: Leukemia and Lymphoma., 43, 1855 (2002)
Non-patent Literature 12: Hum. Pathol., 38, 564 (2007)
Non-patent Literature 13: Hum. Pathol., 36, 886 (2005)
Non-patent Literature 14: FEBS Lett., 579, 6179 (2005)
Non-patent Literature 15: Cancer Res., 65, 7378 (2005)
Non-patent Literature 16: Hum. Pathol., 36, 886 (2005)
Non-patent Literature 17: Oncogene, 13, 2328 (2006)

Non-patent Literature 18: Virchows Arch., 448, 52 (2006)
Non-patent Literature 19: J. Immunol., 135, 1530 (1985)
Non-patent Literature 20: Cancer Res., 46, 6489 (1986)
Non-patent Literature 21: Cancer Res., 56, 1118 (1996)
Non-patent Literature 22: Immunol., 85, 668 (1995)
Non-patent Literature 23: Cancer Res., 56, 1118 (1996)
Non-patent Literature 24: Immunol., 85, 668 (1995)
Non-patent Literature 25: J. Immunol., 144, 1382 (1990)
Non-patent Literature 26: Nature, 322, 323 (1988)
Non-patent Literature 27: Science, 242, 423 (1988)
Non-patent Literature 28: Nature Biotechnol., 15, 629 (1997)
Non-patent Literature 29: Molecular Immunol., 32, 249 (1995)
Non-patent Literature 30: J. Biol. Chem., 271, 2966 (1996)
Non-patent Literature 31: Cancer Res., 52, 3402 (1992)

SUMMARY OF THE INVENTION

As described above, no antibodies which specifically recognize a CD27 molecule containing an O-linked sugar chain are known. The antibody which specifically recognizes CD27 containing an O-linked sugar chain to which galactose is not bound is very useful for a diagnosis of and therapy for a disease relating to CD27 containing an O-linked sugar chain to which galactose is not bound.

Therefore, an object of the present invention is to provide a monoclonal antibody which specifically recognizes CD27 containing an O-linked sugar chain to which galactose is not bound and binds to an extracellular region of CD27, or a method of use thereof.

The humanized antibody of the present invention or the antibody fragment thereof is a monoclonal antibody which specifically recognizes and binds to an extracellular region of a polypeptide which is encoded by CD27 gene and contains an O-linked sugar chain to which galactose is not bound.

A disease relating to sugar chain-deficient CD27 is diagnosable by detecting or quantitating sugar chain-deficient CD27 or cells expressing the polypeptide, using the humanized antibody of the present invention the antibody fragment thereof.

In addition, since the humanized antibody of the present invention or the antibody fragment thereof can bind to the extracellular region of sugar chain-deficient CD27, it is preferably used for detection of cells expressing the polypeptide. Especially, since the humanized antibody of the present invention or the antibody fragment thereof can bind to the extracellular region of sugar chain-deficient CD27, it is preferably used for flow cytometric analysis to detect CD27 which is expressed on a cellular membrane and kept a three-dimensional structure of a natural form.

Moreover, the humanized antibody of the present invention or the antibody fragment thereof having an effector activity can damage a cell expressing a sugar chain-deficient CD27 polypeptide. Furthermore, the above humanized antibody or the antibody fragment can damage and reduce cells expressing sugar chain-deficient CD27 polypeptides in a living body, it is effectively used especially as a medicament.

BRIEF DESCRIPTION OF THE DRAWINGS

FIG. 5 shows the construction method of pKANTEX XhoI/SalI by inserting a DNA sequence of CD27-Fc.

FIGS. 7(*a*) and (*b*) shows the results of SDS-PAGE analysis of the CD27-Fc proteins which are expressed in CHO/DG44 cells and Lec8 cells as host cells. FIG. 7(*a*) shows non-reducing conditions without addition of β-mercaptoethanol. FIG. 7(*b*) shows reducing conditions with addition of β-mercaptoethanol. In FIGS. 7(*a*) and (*b*), from the left, a marker, a Lec8 cell fraction and a CHO/DG44 cell fraction are shown.

In FIGS. 8(*a*) and (*b*), from the left side of the lanes, a marker, a CHO/DG44 cell sample and a Lec8 cell sample are shown. The Western blot was carried out by staining using anti-RCAS1 antibody (22-1-1 antibody).

FIGS. 11(*a*) and (*b*) shows the results of flow cytometric analysis of anti-CD27 monoclonal antibodies against CD27-expressing CHO/DG44 cells and CD27-expressing Lec8 cells. FIG. 11(*a*) shows the results of histogram for CD27/Lec8-4, and FIG. 11(*b*) shows the results of histogram for CD27/DG44-8. In both of the histograms, the ordinate represents the number of cells, and the abscissa represents the fluorescence intensity.

FIGS. 12(*a*) and (*b*) shows the binding activity of anti-sugar chain-deficient CD27 monoclonal antibodies KM4030 and KM4031, to Lec8 cells, CD27/Lec8-4 cells and CD27/DG44-8 cells, as measured by fluorescent cell staining. FIG. 12(*a*) shows the measurement results using an ABI Cellular Detection System. The ordinate represents the fluorescence intensity, and the abscissa represents the reacted antibodies. FIG. 12(*b*) shows the measurement results obtained by using a flow cytometer (FCM). The ordinate represents the mean fluorescence intensity, and the abscissa represents the reacted antibodies.

FIGS. 13(*a*) and (*b*) shows the results of the competitive ELISA of anti-sugar chain-deficient CD27 monoclonal antibodies KM4030 and KM4031. FIG. 13(*a*) shows the reactivity of anti-sugar chain-deficient CD27 monoclonal antibody KM4030, and FIG. 13(*b*) shows the reactivity of anti-sugar chain-deficient CD27 monoclonal antibody KM4031. The ordinate represents the cell growth, and the abscissa represents the antibody concentration.

FIGS. 14(*a*) and (*b*) shows the gene cloning of an anti-sugar chain-deficient CD27 monoclonal antibody.

FIG. 19(A)(a) and (b) shows the result of the binding activity of various anti-sugar chain-deficient CD27 chimeric antibodies chimeric KM4026 (◇), chimeric KM4028 (Δ), chimeric KM4030 (○) and chimeric KM4031 (□) to CD27/Lec8-4 cells, measured by using a flow cytometer (FCM). In addition, FIG. 19(A)(b) shows the measurement results of the binding activity of commercially available anti-CD27 antibody O323 (●) to CD27/Lec8-4 cells using a flow cytometer (FCM). The ordinate represents the mean fluorescence intensity, and the abscissa represents a final concentration of the reacted antibodies.

FIG. 19(C)(a) shows the result of the binding activity of various anti-sugar chain-deficient CD27 chimeric antibodies chimeric KM4026 (◇), chimeric KM4028 (Δ), chimeric KM4030 (○) and chimeric KM4031 (□) to Lec8 cells, measured by using a flow cytometer (FCM). In addition, FIG. 19(C)(b) shows the measurement results of the binding activity of commercially available anti-Tn antibody 21-1-1 (■) to Lec-8 cells using a flow cytometer (FCM). The ordinate represents the mean fluorescence intensity, and the abscissa represents a final concentration of the reacted antibodies.

FIG. 26 shows the antibody-dependent cellular cytotoxicity (ADCC activity) of various anti-sugar chain-deficient CD27 chimeric antibodies chimeric KM4026 (◆), chimeric KM4028 (▲), chimeric KM4030 (●) and chimeric KM4031 (■) on cynomolgus CD27/Lec8 cells. The ordinate represents the cellular cytotoxicity (%), and the abscissa represents the final concentration of respective antibodies.

FIG. 27 shows the antibody-dependent cellular cytotoxicity (ADCC activity) of various anti-sugar chain-deficient CD27 chimeric antibodies chimeric KM4030 on cynomolgus CD27/Lec8 cells (●) or human CD27/Lec8 cells (○). The ordinate represents the cellular cytotoxicity (%), and the abscissa represents the final concentration of respective antibodies.

FIG. 28(A)(b) shows the Biacore sensorgram for binding of anti-sugar chain-deficient CD27 antibody KM4027 to sugar chain-deficient CD27-Fc (Tn antigen type CD27-Fc). FIG. 28(A)(c) shows the Biacore sensorgram for binding of anti-sugar chain-deficient CD27 antibody KM4028 to sugar chain-deficient CD27-Fc (Tn antigen type CD27-Fc). FIG. 28(A)(d) shows the Biacore sensorgram for binding of anti-sugar chain-deficient CD27 antibody KM4030 to sugar chain-deficient CD27-Fc (Tn antigen type CD27-Fc). FIG. 28(A)(e) shows the Biacore sensorgram for binding of anti-sugar chain-deficient CD27 antibody KM4031 to sugar chain-deficient CD27-Fc (Tn antigen type CD27-Fc). The ordinate represents RU (resonance unit), and the abscissa represents the reaction time (second).

FIG. 28(B)(a) shows the Biacore sensorgram for binding of anti-sugar chain-deficient CD27 antibody KM4026 to sialyl-Tn antigen type CD27-Fc. FIG. 28(B)(b) shows the Biacore sensorgram for binding of anti-sugar chain-deficient CD27 antibody KM4027 to sialyl-Tn antigen type CD27-Fc. FIG. 28(B)(c) shows the Biacore sensorgram for binding of anti-sugar chain-deficient CD27 antibody KM4028 to sialyl-Tn antigen type CD27-Fc. FIG. 28(B)(d) shows the Biacore sensorgram for binding of anti-sugar chain-deficient CD27 antibody KM4030 to sialyl-Tn antigen type CD27-Fc. FIG. 28(B)(e) shows the Biacore sensorgram for binding of anti-sugar chain-deficient CD27 antibody KM4031 to sialyl-Tn antigen type CD27-Fc. The ordinate represents RU (resonance unit), and the abscissa represents the reaction time (second).

FIG. 29(a) shows the Biacore sensorgram for binding of anti-sugar chain-deficient CD27 chimeric antibody KM4030 to sugar chain-deficient CD27-Fc (Tn antigen type CD27-Fc). FIG. 29(b) shows the Biacore sensorgram for binding of humanized antibody HV0LV0 to sugar chain-deficient CD27-Fc (Tn antigen type CD27-Fc). FIG. 29(c) shows the Biacore sensorgram for binding of humanized antibody HV5LV0 to sugar chain-deficient CD27-Fc (Tn antigen type CD27-Fc). FIG. 29(d) shows the Biacore sensorgram for binding of humanized antibody HV7LV0 to sugar chain-deficient CD27-Fc (Tn antigen type CD27-Fc). The ordinate represents RU (resonance unit), and the abscissa represents the reaction time (second).

FIG. 30(A) shows the result of the binding activity of anti-sugar chain-deficient CD27 chimeric antibody KM4030 (○), anti-sugar chain deficient CD27 humanized antibody HV0LV0 (□), HV5LV0 (Δ) and HV7LV0 (◇) to CD27/Lec8-M19 cells, measured by using a flow cytometer (FCM). The ordinate represents the mean fluorescence intensity, and the abscissa represents a final concentration of the respective antibodies.

(○), anti-sugar chain deficient CD27 humanized antibody HV0LV0 (□), HV5LV0 (Δ) and HV0LV0 (◇) to CD27/DG44-4 cells, measured by using a flow cytometer (FCM). The ordinate represents the mean fluorescence intensity, and the abscissa represents a final concentration of the reacted antibodies.

Figure 31:
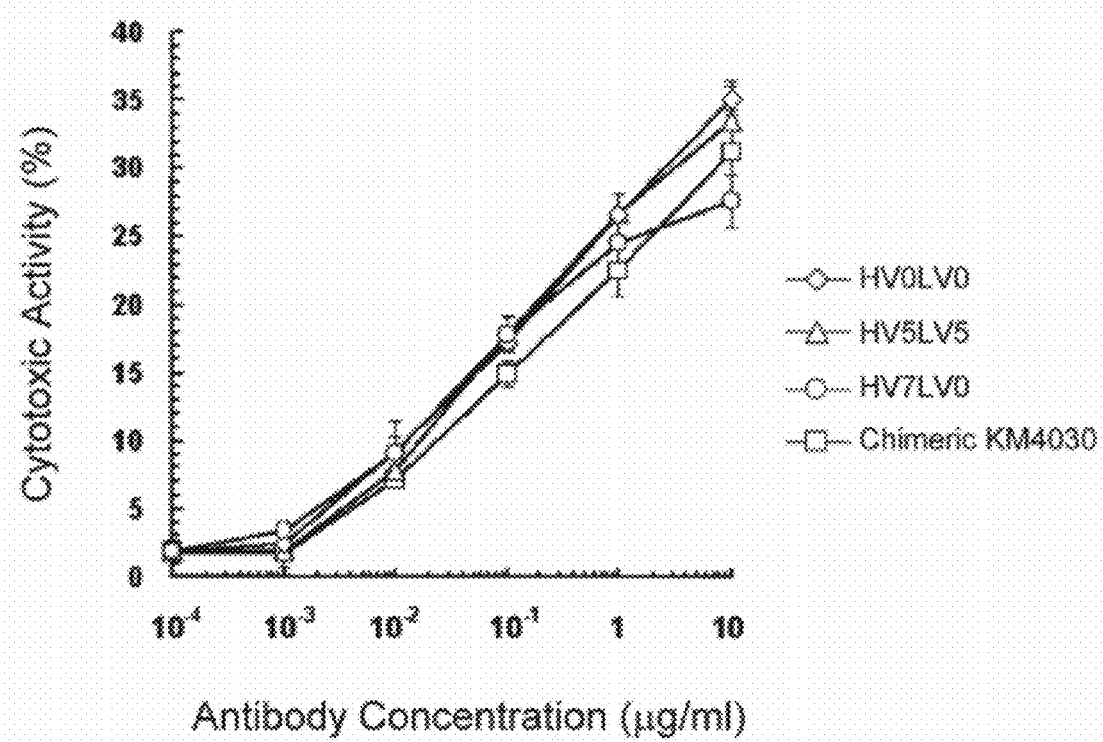

FIG. 31 shows the result of the antibody-dependent cell-mediated cytotoxicity (ADCC activity) of anti-sugar chain-deficient CD27 chimeric antibody KM4030 (○), anti-sugar chain deficient CD27 humanized antibody HV0LV0 (□), HV5LV0 (Δ) and HV7LV0 (◇) to CD27/Lec8-M19 cells. The ordinate represents the cytotoxicity (%), and the abscissa represents a final concentration of respective antibodies.

Figure 32:
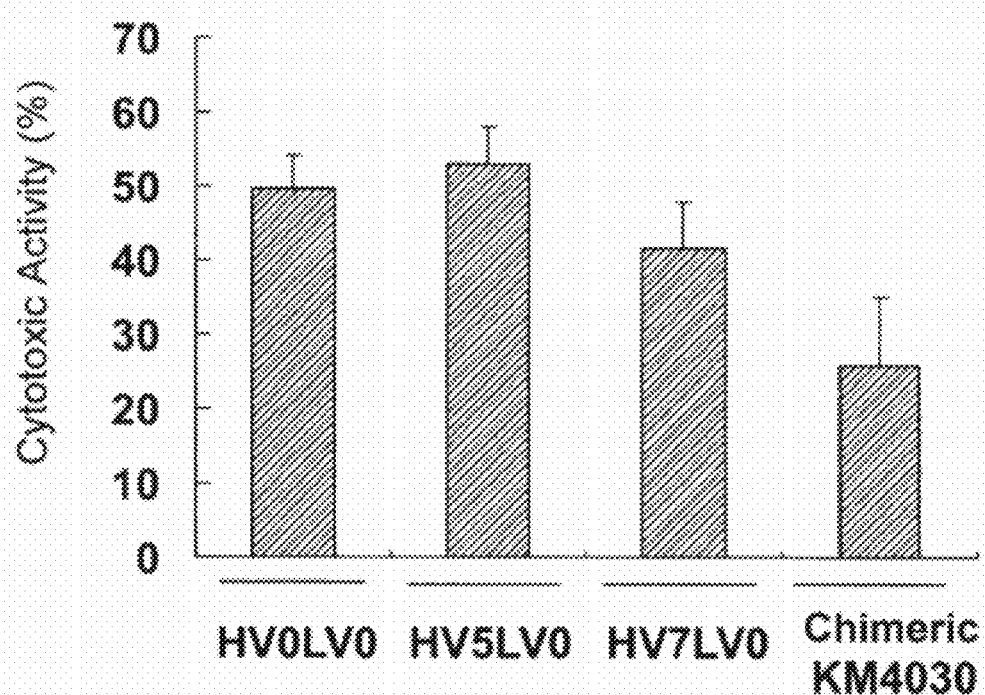

FIG. 32 shows the result of the complement dependent cytotoxicity (CDC activity) of anti-sugar chain-deficient CD27 chimeric antibody KM4030 (○), anti-sugar chain deficient CD27 humanized antibody HV0LV0 (□), HV5LV0 (Δ) and HV7LV0 (◇) to CD27/Lec8-M19 cells. The ordinate represents the cytotoxicity (%), and the abscissa represents a final concentration of the reacted antibodies.

FIG. 33(A) shows the result of the binding activity of anti-sugar chain-deficient CD27 chimeric antibody KM4030 (○), anti-sugar chain deficient CD27 humanized antibody HV0LV0 (□), HV5LV0 (Δ) and HV0LV0 (◇) to CD27/Lec8 cells, measured by using a flow cytometer (FCM). The ordinate represents the mean fluorescence intensity, and the abscissa represents a final concentration of the respective antibodies.

Figure 33B:
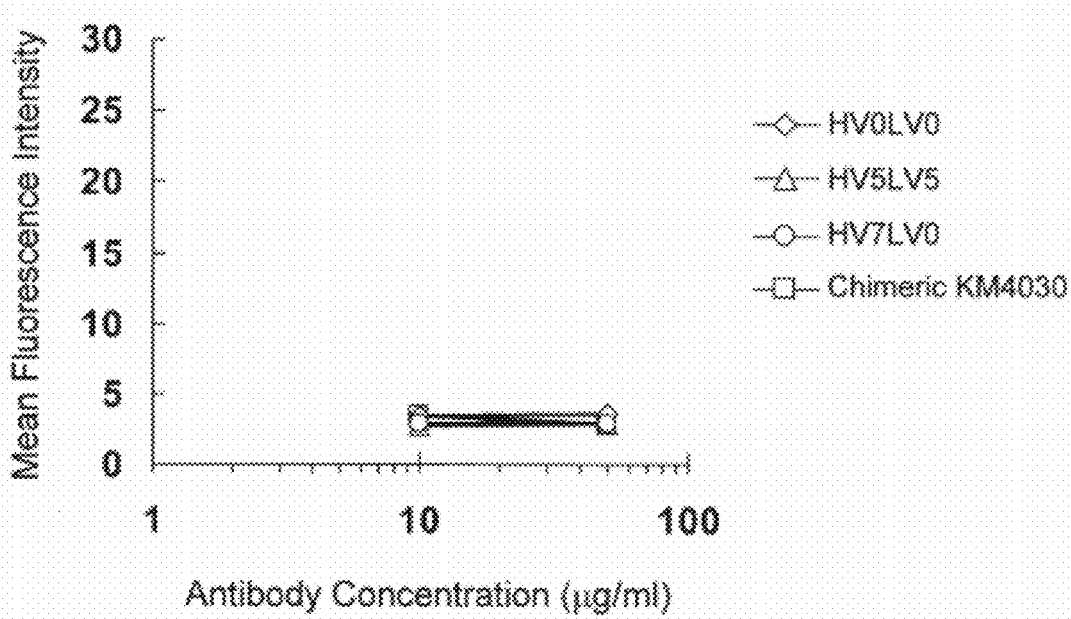

FIG. 33(B) shows the result of the binding activity of anti-sugar chain-deficient CD27 chimeric antibody KM4030 (○), anti-sugar chain deficient CD27 humanized antibody HV0LV0 (□), humanized antibody HV5LV0 (Δ) and HV0LV0 (◇) to CD27/DG44 cells, measured by using a flow cytometer (FCM). The ordinate represents the mean fluorescence intensity, and the abscissa represents a final concentration of the respective antibodies.

DETAILED DESCRIPTION OF THE INVENTION

The present invention relates to the following (1) to (23):
(1) A humanized antibody specifically recognizes and binds to an extracellular region of a polypeptide encoded by CD27 gene containing an O-linked sugar chain to which galactose is not bound; wherein the antibody comprises VH comprising the amino acid sequences of CDRs 1 to 3 represented by SEQ ID NOs:58 to 60, respectively, and the antibody comprises VL comprising the amino acid sequences of CDRs 1 to 3 represented by SEQ ID NOs:61 to 63, respectively, or an antibody fragment thereof;
(2) The humanized antibody or the antibody fragment thereof described in (1), wherein VH of the humanized antibody comprises an amino acid sequence in which at least one modification selected from substitutions of Ser at position 30 with Asn, Val at position 48 with Ile, Ser at position 49 with Ala, Asn at position 77 with Gly, Val at position 93 with Thr, Ala at position 97 with Thr, and Thr at position 117 with Val is introduced in the amino acid sequence represented by SEQ ID NO:96; and wherein VL of the humanized antibody comprises an amino acid sequence in which at least one modification selected from substitutions of Ile at position 21 with Leu, Pro at position 40 with Leu, Val at position 58 with Ile, Thr at position 85 with Ala and Tyr at position 87 with Phe is introduced in the amino acid sequence represented by SEQ ID NO:97;
(3) The humanized antibody or the antibody fragment thereof described in (1), wherein VH of the humanized antibody comprises the amino acid sequence represented by any one of SEQ ID NOs:96, 105 and 107, and VL of the humanized antibody comprises the amino acid sequence represented by SEQ ID NO:97;
(4) A DNA which encodes the humanized antibody or the antibody fragment thereof described in any one of (1) to (3);
(5) A recombinant vector which comprises the DNA described in (4);
(6) A transformant obtainable by introducing the recombinant vector described in (5) into a host cell;
(7) A process for producing the antibody or the antibody fragment thereof described in any one of (1) to (3), comprising culturing the transformant described in (6) in a medium to form and accumulate the humanized antibody or the antibody fragment thereof described in any one of (1) to (3) in the culture, and then collecting the humanized antibody or the antibody fragment thereof from the culture;
(8) A method for immunologically detecting or measuring CD27 containing an O-linked sugar chain to which galactose is not bound, comprising using the humanized antibody or the antibody fragment thereof described in any one of (1) to (3);
(9) A reagent for detecting CD27 containing an O-linked sugar chain to which galactose is not bound, comprising the humanized antibody or the antibody fragment thereof described in any one of the above (1) to (3);
(10) A diagnostic agent for a disease relating to CD27 containing an O-linked sugar chain to which galactose is not bound, comprising the humanized antibody or the antibody fragment thereof described in any one of (1) to (3);
(11) The diagnostic agent described in (10), wherein the disease relating to CD27 containing an O-linked sugar chain to which galactose is not bound is IgA nephropathy;
(12) The diagnostic agent described in (10), wherein the disease relating to CD27 containing an O-linked sugar chain to which galactose is not bound is cancer;
(13) A therapeutic agent for a disease relating to CD27 containing an O-linked sugar chain to which galactose is not bound, comprising the humanized antibody or the antibody fragment thereof described in any one of (1) to (3) as an active ingredient;
(14) The therapeutic agent described in (13), wherein the disease relating to CD27 containing an O-linked sugar chain to which galactose is not bound is IgA nephropathy;
(15) The therapeutic agent described in (13), wherein the disease relating to CD27 containing an O-linked sugar chain to which galactose is not bound is cancer;
(16) A diagnostic method for a disease relating to CD27 containing an O-linked sugar chain to which galactose is not bound, comprising detecting or measuring a cell expressing CD27 containing an O-linked sugar chain to which galactose is not bound, by using the humanized antibody or the antibody fragment thereof described in any one of (1) to (3);
(17) A diagnostic method for a disease relating to CD27 containing an O-linked sugar chain to which galactose is not bound, comprising detecting or measuring CD27 containing an O-linked sugar chain to which galactose is not bound, by using the humanized antibody or the antibody fragment thereof described in any one of (1) to (3);
(18) The diagnostic method described in (16) or (17), wherein the disease relating to CD27 containing an O-linked sugar chain to which galactose is not bound is IgA nephropathy;
(19) The diagnostic method described in (16) or (17), wherein the disease relating to CD27 containing an O-linked sugar chain to which galactose is not bound is cancer;
(20) Use of the humanized antibody or the antibody fragment thereof described in any one of (1) to (3) for manufacture of a diagnostic agent for a disease relating to CD27 containing an O-linked sugar chain to which galactose is not bound;

(21) Use of the humanized antibody or the antibody fragment thereof described in any one of (1) to (3) for manufacture of a therapeutic agent for a disease relating to CD27 containing an O-linked sugar chain to which galactose is not bound;
(22) The use of the humanized antibody or the antibody fragment thereof described in (20) or (21), wherein the disease relating to CD27 containing an O-linked sugar chain to which galactose is not bound is IgA nephropathy; and
(23) The use of the humanized antibody or the antibody fragment thereof described in (20) or (21), wherein the disease relating to CD27 containing an O-linked sugar chain to which galactose is not bound is cancer.

The present invention relates to a monoclonal antibody (hereinafter also referred to as the humanized antibody of the present invention or the antibody of the present invention) which specifically recognizes an extracellular region of a polypeptide encoded by CD27 gene containing an O-linked sugar chain to which galactose is not bound (hereinafter referred to as "CD27") and binds to the extracellular region.

The CD27 gene may be any one, so long as it encodes CD27. For example, the CD27 gene may be a gene containing a nucleotide sequence represented by SEQ ID NO:1. In addition, the CD27 gene of the present invention includes a gene which hybridizes with a DNA consisting of the nucleotide sequence represented by SEQ ID NO:1 under stringent conditions and also encodes a polypeptide having the function of CD27, and the like.

The DNA which hybridizes under stringent conditions refers to a DNA which is obtained by colony hybridization, plaque hybridization, Southern blot hybridization, DNA microarray or the like, using a DNA comprising the nucleotide sequence represented by SEQ ID NO:1 as a probe.

A specific example of such DNA is a DNA which can be identified by performing hybridization at 65° C. in the presence of 0.7 to 1.0 mol/l sodium chloride using a filter or a slide glass with colony- or plaque-derived DNA or PCR product or oligo DNA comprising the nucleotide sequence immobilized thereon, and then washing the filter or the slide glass at 65° C. with a 0.1 to 2-fold concentration of SSC solution (1-fold concentration of SSC solution: 150 mmol/l sodium chloride and 15 mmol/l sodium citrate).

Hybridization can be carried out according to the methods described in [*Molecular Cloning, A Laboratory Manual*, Second Edition, (Cold Spring) Harbor Lab. Press, 1989], *Current Protocols in Molecular Biology*, (John Wiley & Sons (1987-1997); *DNA Cloning 1: Core Techniques, A Practical Approach*, Second Edition, Oxford) University, 1995); and the like.

The DNA capable of hybridization under stringent conditions includes DNA having at least preferably 60% or more homology, more preferably 80% or more homology, and furthermore preferably 95% or more homology to the nucleotide sequence represented by SEQ ID NO:1.

In the nucleotide sequence of the gene encoding a protein of a eukaryote, genetic polymorphism is often recognized. The CD27 gene used in the present invention also includes a gene in which small modification is generated in the nucleotide sequence by such polymorphism.

CD27 includes a polypeptide comprising the amino acid sequence represented by SEQ ID NO:2; a polypeptide comprising an amino acid sequence in which at least one amino acid is deleted, substituted or added in the amino acid sequence represented by SEQ ID NO:2; a polypeptide comprising an amino acid sequence having at least preferably 60% homology, more preferably at least 80% homology, furthermore preferably at least 90% homology, and most preferably at least 95% homology, to the amino acid sequence represented by SEQ ID NO:2, and having the function of CD27; and the like.

The polypeptide comprising an amino acid sequence in which one or more amino acid residue(s) is/are deleted, substituted and/or added in the amino acid sequence represented by SEQ ID NO:2 can be obtained, for example, by introducing a site-directed mutation into DNA encoding the polypeptide comprising the amino acid sequence represented by SEQ ID NO:2 by using method for site-directed mutagenesis described in *Molecular Cloning, A Laboratory Manual*, Second Edition (Cold Spring) Harbor Laboratory Press, 1989], *Current Protocols in Molecular Biology* (John Wiley & Sons, 1987-1997), *Nucleic Acids Research*, 10, 6487 (1982), *Proc. Natl. Acad. Sci. USA*, 79, 6409 (1982), *Gene*, 34, 315 (1985), *Nucleic Acids Research*, 13, 4431 (1985), *Proc. Natl. Acad. Sci. USA*, 82, 488 (1985), or the like.

The number of amino acid residues which are deleted, substituted or added is not particularly limited, and the number is preferably, 1 to dozens, such as 1 to 20, and more preferably 1 to several, such as 1 to 5.

The number of the homology described in the present invention may be a number calculated by using a homology search program known by the skilled person, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997); *Genome Res.*, 7, 649 (1997); http://www.ncbi.nlm-.nih.gov/Education/BLASTinfo/information3.html] or the like.

As the default parameter, G (Cost to open gap) is 5 for the nucleotide sequence and 11 for the amino acid sequence; —E (Cost to extend gap) is 2 for the nucleotide sequence and 1 for the amino acid sequence; —q (Penalty for) nucleotide mismatch) is −3; —r (reward for nucleotide match) is; —e (expect value) is 10; —W (wordsize) is 11 residues for the nucleotide sequence and 3 residues for the amino acid sequence; —y (Dropoff (X) for blast extensions) in bits) is 20 for blastn and 7 for a program other than blastn; —X (X dropoff value for gapped alignment in bits) is 15; and —Z (final X dropoff value for gapped alignment in bits) is 50 for blastn and 25 for a program other than blastn (http://www-w.ncbi.nlm.nih.gov/blast/html/blastcgihelp.html).

The polypeptide comprising a partial sequence of the amino acid sequence represented by SEQ ID NO:2 can be prepared according to a method known by the skilled person. For example, it can be prepared by deleting a part of DNA encoding the amino acid sequence represented by SEQ ID NO:2 and culturing a transformant into which an expression vector containing the DNA is introduced.

Also, based on the thus prepared polypeptide or DNA, a polypeptide comprising an amino acid sequence in which one or more amino acid(s) is/are deleted, substituted or added in a partial sequence of the amino acid sequence represented by SEQ ID NO:2 can be prepared in the same manner as described above.

Examples of the extracellular region of CD27 includes a region corresponding to positions 1 to 171 of the extracellular region predicted by a reference [*The Journal of Immunology*, 147, 3165 (1991)] and the like.

In the present invention, the extracellular region of the polypeptide encoded by CD27 gene, containing an O-linked sugar chain to which galactose is not bound may be any CD27 containing an O-linked sugar chain to which galactose is not bound. Specifically, examples of the extracellular region include an extracellular region of CD27 containing an O-linked sugar chain to which galactose is not bound and is encoded by the nucleotide sequence represented by SEQ ID NO:1.

The term "O-linked sugar chain" refers to a structure in which a sugar chain is bound via an —OH group contained in each amino acid side chain of an amino acid residue of serine (Ser) or threonine (Thr) of a protein.

Among O-linked sugar chains, an O-linked sugar chain having N-acetylgalactosamine (GalNAc) bound to the —OH group of the amino acid side chain of Ser or Thr on the polypeptide is called "mucin-type sugar chain". Specific examples of the O-linked sugar chain include T antigen, sialyl T antigen, Tn antigen, sialyl-Tn antigen, and the like (Table 1).

TABLE 1

| Name of Sugar Chain Antigen | Sugar Chain Structure |
|---|---|
| Tn antigen | GalNAc1α→Ser/Thr |
| Sialyl-Tn antigen | NeuNAcα2→6GalNAc1α→Ser/Thr |
| T antigen | Galβ1→3GalNAc1α→Ser/Thr |
| Sialyl T antigen | NeuNAcα2→3Galβ1→3GalNAc1α→Ser/Thr |

(NeuNAc:N-acetylneuraminic acid)

In the present invention, the term "O-linked sugar chain to which galactose is not bound" refers to an O-linked sugar chain in which galactose (Gal) is not bound to N-acetylgalactosamine (GalNAc) bound via an —OH group of the amino acid residue of Ser or Thr in a protein. Specifically, examples include the above-mentioned Tn antigen and sialyl-Tn antigen.

The O-linked sugar chain to which galactose is not bound is an intermediate in the synthetic pathway of a normal O-linked sugar chain, and, in general, is rarely found in glycoproteins produced in normal cells, and the expression thereof is confirmed in specific diseases, such as cancer and nephropathy.

Hereinafter, in the present invention, the O-linked sugar chain to which galactose is not bound may be sometimes referred to as an abnormal sugar chain, a protein to which the abnormal sugar chain is bound may be sometimes referred to as a sugar chain-deficient protein, and CD27 to which the abnormal sugar chain is bound may be sometimes referred to as a sugar chain-deficient CD27.

Examples of the amino acid residue of a polypeptide to which an O-linked sugar chain is bound include an amino acid residue of serine (Ser) and threonine (Thr) in an amino acid sequence of the extracellular region of the CD27 protein.

In addition, the amino acid residue of a polypeptide to which the O-linked sugar chain is bound may be confirmed by a consensus sequence of O-linked sugar chain using a sequencer software, such as NetOGlyc 3.1 server (http://www.cbs.dtu.dk/services/NetOGlyc/). Alternatively, a specific sugar chain binding site may be specified by mass spectrometry (MS) analysis of a glycoprotein containing an O-linked sugar chain.

In the present invention, as the amino acid residue of the polypeptide to which the O-linked sugar chain on the CD27 protein is bound, any of Ser and Thr residues in the amino acid sequence of the CD27 protein can be bound by an O-linked sugar chain. Examples of these preferably include a sugar chain binding site comprising at least one amino acid residue selected from the group consisting of Thr at position 118, Ser at position 127, Thr at position 129, Ser at position 132, Ser at position 133, Ser at position 137, Thr at position 143, Ser at position 149, Thr at position 156, Thr at position 162, Thr at position 173, Ser at position 175 and Thr at position 176, in the CD27 protein represented by SEQ ID NO:2.

The number of an O-linked sugar chain which binds to the extracellular region per one molecule of the CD27 protein may be any number so long as an O-linked sugar chain binds to at least one Ser or Thr residue. The number of an O-linked sugar chain is not limited.

As a method for obtaining a cell which expresses the CD27 containing an O-linked sugar chain to which galactose is not bound (hereinafter referred to as "sugar chain-deficient CD27") of the present invention, a method comprising constructing a sugar chain-deficient CD27-expressing cell by introducing CD27-encoding DNA into a cell line in which the activity of an enzyme capable of adding Gal to N-acetylgalactosamine (GalNAc) bound to Ser/Thr on the polypeptide, of a protein involved in the activity of the enzyme, or of a protein involved in the transportation of uridine 5'-diphospate-galactose (UDP-galactose), is decreased or deleted in the O-linked sugar chain synthesis process, and thereby obtaining the sugar chain-deficient CD27 expressing cell.

Alternatively, for example, the cell which expresses CD27 having an O-linked sugar chain to which galactose is not bound may also be constructed by treating the cell which expresses CD27 having a normal O-linked sugar chain with a sugar chain cleavage enzyme, such as sialidase and galactosidase.

Specific examples of the enzyme capable of adding Gal to GalNAc bound to Ser or Thr on the polypeptide may include β1,3-galactosyltransferase [*The Journal of Biological Chemistry*, 277, 178-186 (2002)], and the like.

Examples of the protein involved in the activity of the enzyme adding Gal to GalNAc bound to Ser or Thr on the polypeptide include Cosmc [*Proceedings of the National Academy of Sciences of the United States of America*, 99, 16613-16618 (2002)], which is a chaperone involved in protein folding of the enzyme, and the like.

A CD27-expressing cell derived from an IgA nephropathy patient can be used as a CD27-expressing cell, based on the fact that an enzymatic activity is decreased or deleted due to the occurrence of addition, deletion, substitution, or the like in a DNA which encodes an enzyme capable of adding Gal to GalNAc bound to Ser/Thr on the polypeptide, a protein involved in the activity of the enzyme, a protein involved in the transportation of UDP-galactose, or the like.

Examples of the protein involved in the transportation of UDP-galactose include UDP-galactose transporter, and the like. Examples of the cell line in which the activity of the UDP-galactose transporter is decreased or deleted include Lec8 cells [Glycobiology, 1, 307-14 (1991)], and the like.

In the present invention, examples of the cell expressing the sugar chain-deficient CD27 include a cell which is naturally present in the human body, a cell line established from the cell which is naturally present in the human body, a cell obtained by gene recombination techniques, and the like.

Preferred are a cell line in which, in the O-linked sugar chain synthesis process, an activity of an enzyme capable of adding Gal to GalNAc bound to Ser/Thr on the polypeptide, a protein involved in the activity of the enzyme or a protein involved in the transportation of UDP-galactose, is decreased or deleted as described above, a cell having a similar property and naturally existing in the human body, and the like.

Examples of the cell naturally existing in the human body is preferably a cell line in which in the O-linked sugar chain synthesis process an activity of an enzyme capable of adding Gal to GalNAc bound to Ser/Thr on the polypeptide, a protein involved in the activity of the enzyme or a protein involved in the transportation of UDP-galactose, is decreased or deleted.

Specific examples of such a cell include a cell which expresses the CD27 protein in the bodies of patients suffering from IgA nephropathy or cancer. Examples of the cell include a cell expressing the CD27 protein among immune-related cells or tumor cells obtained by biopsy or the like.

Examples of the cell obtained by gene recombination techniques include a sugar chain-deficient CD27-expressing cell obtained by constructing a host cell in which, in the O-linked sugar chain synthesis process, an activity of an enzyme adding Gal to GalNAc bound to Ser/Thr on the polypeptide, a protein involved in the activity of the enzyme or a protein involved in the transportation of UDP-galactose, is decreased or deleted and then introducing an expression vector containing cDNA encoding a desired polypeptide into the host cell.

Specific examples of the host cell include a Lec8 cell in which the activity of the UDP-galactose transporter is decreased, or an IgA antibody-expressing cell derived from IgA nephropathy patient in which the enzymatic activity is decreased or deleted due to abnormality of β1,3-galactosyltransferase or a Cosmc chaperone protein involved in the activity of the enzyme.

In addition, the sugar chain-deficient CD27 protein may be constructed by using the above CD27-expressing cell to express and purify the sugar chain-deficient CD27 protein.

The sugar chain-deficient CD27 protein can be obtained by expressing the CD27 protein as a fusion protein with another material, followed by purification.

Examples of the material to be fused with the CD27 protein include polypeptides such as antibody constant region, antibody Fc region, GST tag, histidine tag (also referred to as "His tag"), and Myc tag. The fusion protein may be separated and purified by using an affinity column, such as Protein A, nickel column, and specific antibody column.

The monoclonal antibody or the antibody fragment of the present invention has a binding activity to the thus obtained sugar chain-deficient CD27 cell or sugar chain-deficient CD27.

Binding of the antibody or antibody fragment of the present invention to the extracellular region of a sugar chain-deficient CD27 polypeptide can be confirmed by a method in which the binding ability of a cell expressing a specified antigen and an antibody for the specific antigen is confirmed, for example, by a conventionally known immunological detection method, preferably a fluorescent cell staining method or the like.

In addition, it can also be confirmed by a combination of conventionally known immunological detection methods [*Monoclonal Antibodies-Principles and Practice*, Third edition, Academic Press (1996), *Antibodies-A Laboratory Manual*, Cold Spring Harbor Laboratory (1988), *Monoclonal Antibody Experiment Manual*, Kodansha Scientific (1987)] and the like.

The monoclonal antibody of the present invention includes an antibody produced by a hybridoma and a recombinant antibody produced by a transformant transformed with an expression vector containing a gene encoding an antibody.

The hybridoma can be prepared, for example, by preparing the above cell expressing the sugar chain-defeficient CD27 as an antigen, inducing an antibody-producing cell having antigen specificity from an animal immunized with the antigen, and fusing the antigen-producing cell with a myeloma cell. The anti-sugar chain-defeficient CD27 antibody can be obtained by culturing the hybridoma or administering the hybridoma cell into an animal to cause ascites tumor in the animal and separating and purifying the culture or the ascites.

The animal immunized with an antigen may be any animal, so long as a hybridoma can be prepared, and mouse, rat, hamster, rabbit and the like are suitably used. Also, the cell having antibody-producing activity can be obtained from such an animal, and the antibody of the present invention includes an antibody produced by a hybridoma obtained by fusion of the cell after in vitro immunization with a myeloma cell.

The monoclonal antibody is an antibody secreted by a single clone of antibody-producing cells, and recognizes only one epitope (also called antigen determinant) and has the uniformity in amino acid sequence (primary structure).

Examples of the epitope include a single amino acid sequence, a three-dimensional structure consisting of an amino acid sequence, an amino acid sequence having a sugar chain bound thereto, a three-dimensional structure consisting of an amino acid sequence having a sugar chain bound thereto, and the like, which a monoclonal antibody recognizes and binds to. Examples of the epitope of the monoclonal antibody of the present invention include a three-dimensional structure of the sugar chain-deficient CD27 protein.

Examples of the monoclonal antibody of the present invention include any monoclonal antibody, so long as it recognizes and also binds to the extracellular region of the sugar chain-deficient CD27. Specific examples of the monoclonal antibody include monoclonal antibodies KM4026, KM4027, KM4028, KM4030, KM4031, and the like.

More specifically, examples of the monoclonal antibody of the present invention include a monoclonal antibody KM4026 produced by hybridoma KM4026, a monoclonal antibody which competes with the monoclonal antibody KM4026 in the binding to the extracellular region of the sugar chain-deficient CD27, and a monoclonal antibody that binds to an epitope present in the extracellular region of the sugar chain-deficient CD27 to which the monoclonal antibody KM4026 binds.

Examples of the monoclonal antibody of the present invention include a monoclonal antibody KM4027 produced by hybridoma KM4027, a monoclonal antibody which competes with the monoclonal antibody KM4027 in the binding to the extracellular region of the sugar chain-deficient CD27, and a monoclonal antibody that binds to an epitope present in the extracellular region of the sugar chain-deficient CD27 to which the monoclonal antibody KM4027 binds.

Examples of the monoclonal antibody of the present invention include monoclonal antibody KM4028 produced by hybridoma KM4028, a monoclonal antibody which competes with the monoclonal antibody KM4028 in the binding to the extracellular region of the sugar chain-deficient CD27, and a monoclonal antibody that binds to an epitope present in the extracellular region of the sugar chain-deficient CD27 to which the monoclonal antibody KM4028 binds.

Examples of the monoclonal antibody of the present invention may include monoclonal antibody KM4030 produced by hybridoma KM4030, a monoclonal antibody which competes with the monoclonal antibody KM4030 in the binding to the extracellular region of the sugar chain-deficient CD27, and a monoclonal antibody that binds to an epitope present in the extracellular region of the sugar chain-deficient CD27 to which the monoclonal antibody KM4030 binds.

Examples of the monoclonal antibody of the present invention include monoclonal antibody KM4031 produced by hybridoma KM4031, a monoclonal antibody which competes with the monoclonal antibody KM4031 in the binding to the extracellular region of sugar chain-deficient CD27, and a monoclonal antibody that binds to an epitope present in the extracellular region of the sugar chain-deficient CD27 to which the monoclonal antibody KM4031 binds.

Examples of the monoclonal antibody which competes with the monoclonal antibody of the present invention include, specifically, a monoclonal antibody which has a competitive reaction for a variety of monoclonal antibodies and the epitope present in the extracellular region of the sugar chain-deficient CD27, as described above.

Further, examples of the monoclonal antibody that binds to an epitope to which the monoclonal antibody of the present invention binds include, specifically, a monoclonal antibody that binds to the epitope present in the extracellular region of the sugar chain-deficient CD27 which is recognized by a variety of monoclonal antibodies described above.

The hybridoma KM4030 has been deposited to International Patent Organism Depositary, National Institute of Advanced Industrial Science and Technology (Central 6, 1-1-1, Higashi, Tsukuba-shi, Ibaraki-ken 305-8566, Japan) under the Budapest Treaty as FERM BP-10976 on Jun. 5, 2008.

The recombinant antibody includes an antibody produced by gene recombination, such as a human chimeric antibody, a humanized antibody, a human antibody and an antibody fragment thereof. Among the recombinant antibodies, one having antigen binding activity, low immunogenecity and prolonged half-life in blood is preferable as a therapeutic agent.

The human chimeric antibody is an antibody comprising a heavy chain variable region (hereinafter referred to as "VH") and a light chain variable region (hereinafter referred to as "VL") of an antibody of a non-human animal and a heavy chain constant region (hereinafter referred to as "CH") and a light chain constant region (hereinafter referred to as "CL") of a human antibody.

The human chimeric antibody of the present invention can be produced as follows. Specifically, the human chimeric antibody can be produced by obtaining cDNAs encoding VH and VL from a monoclonal antibody which specifically recognizes sugar chain-deficient CD27 and binds to the extracellular region or a hybridoma which produces a monoclonal antibody which specifically recognizes the sugar chain-deficient CD27 and binds to the extracellular region, inserting each of them into an expression vector for animal cell comprising DNAs encoding CH and CL of human antibody to thereby construct a vector for expression of human chimeric antibody, and then introducing the vector into an animal cell to express the antibody.

As the CH of the human chimeric antibody, any CH can be used, so long as it belongs to human immunoglobulin (hereinafter referred to as "hIg"), and those belonging to the hIgG class are preferred. In addition, any one of the subclasses belonging to the hIgG class, such as hIgG1, hIgG2, hIgG3 and hIgG4, can be used.

As the CL of the human chimeric antibody, any CL can be used, so long as it belongs to the hIg class, and those belonging to κ class or λ class can be used.

Examples of the human chimeric antibody of the present invention include the following human chimeric antibodies (1) to (5):

(1) a human chimeric antibody in which VH of the antibody is the amino acid sequence represented by SEQ ID NO:25, and VL of the antibody is the amino acid sequence represented by SEQ ID NO:35;
(2) a human chimeric antibody in which VH of the antibody is the amino acid sequence represented by SEQ ID NO:26 and VL of the antibody is the amino acid sequence represented by SEQ ID NO:36;
(3) a human chimeric antibody in which VH of the antibody is the amino acid sequence represented by SEQ ID NO:27 and VL of the antibody is the amino acid sequence represented by SEQ ID NO:37;
(4) a human chimeric antibody in which VH of the antibody is the amino acid sequence represented by SEQ ID NO:28 and VL of the antibody is the amino acid sequence represented by SEQ ID NO:38; and
(5) a human chimeric antibody in which VH of the antibody is the amino acid sequence represented by SEQ ID NO:29 and VL of the antibody is the amino acid sequence represented by SEQ ID NO:39.

Further, examples of the human chimeric antibody of the present invention include the following human chimeric antibodies (1) to (5):
(1) a human chimeric antibody in which VH of the antibody comprises the amino acid sequences of CDRs 1 to 3 represented by SEQ ID NOs:40 to 42, respectively, and VL of the antibody comprises the amino acid sequences of CDRs 1 to 3 represented by SEQ ID NOs:43 to 45, respectively;
(2) a human chimeric antibody in which VH of the antibody comprises the amino acid sequences of CDRs 1 to 3 represented by SEQ ID NOs:46 to 48, respectively, and VL of the antibody comprises the amino acid sequences of CDRs 1 to 3 represented by SEQ ID NOs:49 to 51, respectively;
(3) a human chimeric antibody in which VH of the antibody comprises the amino acid sequences of CDRs 1 to 3 represented by SEQ ID NOs:52 to 54, respectively, and VL of the antibody comprises the amino acid sequences of CDRs 1 to 3 represented by SEQ ID NOs:55 to 57, respectively;
(4) a human chimeric antibody in which VH of the antibody comprises the amino acid sequences of CDRs 1 to 3 represented by SEQ ID NOs:58 to 60, respectively, and VL of the antibody comprises the amino acid sequences of CDRs 1 to 3 represented by SEQ ID NOs:61 to 63, respectively; and
(5) a human chimeric antibody in which VH of the antibody comprises the amino acid sequences of CDRs 1 to 3 represented by SEQ ID NOs:64 to 66, respectively, and VL of the antibody comprises the amino acid sequences of CDRs 1 to 3 represented by SEQ ID NOs:67 to 69, respectively.

A humanized antibody is an antibody in which amino acid sequences of CDRs of VH and VL of an antibody derived from a non-human animal are grafted into appropriate positions of VH and VL of a human antibody, and is also called a human CDR-grafted antibody or a reshaped-antibody.

The humanized antibody of the present invention can be produced by constructing cDNAs encoding an antibody variable region (hereinafter referred to as "V region") in which the amino acid sequences of CDRs of VH and VL of a non-human animal antibody produced by a hybridoma which produces a monoclonal antibody which specifically recognizes the sugar chain-deficient CD27 protein and binds to the extracellular region in the present invention are grafted into frameworks (hereinafter referred to as "FR") of VH and VL of any human antibody, inserting each of them into a vector for expression of animal cell comprising genes encoding CH and CL of a human antibody to thereby construct an expression vector for humanized antibody, and introducing it into an animal cell to thereby express.

As the amino acid sequences of FRs of VH and VL of the human antibody of the present invention, any amino acid sequences can be used, so long as they are amino acid sequences of VH and VL, respectively, derived from a human antibody. Examples include amino acid sequences of FRs of VH and VL of human antibodies registered in database such as Protein Data Bank, common amino acid sequences of each sub group of FRs of VH and VL of human antibodies described in, for example, *Sequences of Proteins of Immunological Interest*, US Dept. Health and Human Services (1991), and the like.

As the CH of the humanized antibody of the present invention, any CH can be used, so long as it belongs to the hIg class, and those of the hIgG class are preferred. In addition, any one of the subclasses belonging to the hIgG class, such as hIgG1, hIgG2, hIgG3 and hIgG4 can be used.

In addition, as the CL of the humanized antibody of the present invention, any CL can be used, so long as it belongs to the hIg class, and those belonging to the class or λ class can be used.

Examples of the humanized antibody of the present invention include the following humanaized antibodies (1) to (5):
(1) a humanized antibody in which CDRs 1 to 3 of VH of the antibody comprise the amino acid sequences represented by SEQ ID NO:40 to 42, respectively, and CDRs 1 to 3 of VL of the antibody comprise the amino acid sequences represented by SEQ ID NO:43 to 45, respectively;
(2) a humanized antibody in which CDRs 1 to 3 of VH of the antibody comprise the amino acid sequences represented by SEQ ID NO:46 to 48, respectively, and CDRs 1 to 3 of VL of the antibody comprise the amino acid sequences represented by SEQ ID NO:49 to 51, respectively;
(3) a humanized antibody in which CDRs 1 to 3 of VH of the antibody comprise the amino acid sequences represented by SEQ ID NO:52 to 54, respectively, and CDRs 1 to 3 of VL of the antibody comprise the amino acid sequences represented by SEQ ID NO:55 to 57, respectively;
(4) a humanized antibody in which CDRs 1 to 3 of VH of the antibody comprise the amino acid sequences represented by SEQ ID NO:58 to 60, respectively, and CDRs 1 to 3 of VL of the antibody comprise the amino acid sequences represented by SEQ ID NO:61 to 63, respectively;
(5) a humanized antibody in which CDRs 1 to 3 of VH of the antibody comprise the amino acid sequences represented by SEQ ID NO:64 to 66, respectively; and CDRs 1 to 3 of VL of the antibody comprise the amino acid sequences represented by SEQ ID NO:67 to 69, respectively.

Further, as specific examples of the humanized antibody of the present invention, a humanized antibody comprising at least one of the following (a) VH and (b) VL. In addition, in the following (a) and (b), the number of modifications which are introduced is not limited.

(a) VH comprising the amino acid sequence represented by SEQ ID NO:96, or an amino acid sequence in which Ser at position 30, Val at position 48, Ser at position 49, Asn at position 77, Val at position 93, Ala at position 97 and Thr at position 117 in the amino acid sequence represented by SEQ ID NO:96 are substituted with other amino acid residues (b) VL comprising the amino acid sequence represented by SEQ ID NO:97, or an amino acid sequence in which Ile at position 21, Pro at position 40, Val at position 58, Thr at position 85, and Tyr at position 87 in the amino acid sequence represented by SEQ ID NO:97 are substituted with other amino acid residues.

Example of VH comprised in the humanized antibody of the present invention include VH comprising an amino acid sequence in which Ser at position 30, Val at position 48, Ser at position 49, Asn at position 77, and Ala at position 97 in the amino acid sequence represented by SEQ ID NO:96 are substituted with other amino acid residues.

Among them, as VH comprised in the humanized antibody of the present invention the following (1) and (2) are preferable:
(1) VH comprising an amino acid sequence in which Val at position 48, Ser at position 49, and Ala at position 97 in the amino acid sequence represented by SEQ ID NO:96 are substituted with other amino acid residues,
(2) VH comprising an amino acid sequence in which Ser at position 30, and Ala at position 97 in the amino acid sequence represented by SEQ ID NO:96 are substituted with other amino acid residues.

Examples of the amino acid sequence of the above VH include an amino acid sequence in which at least one modification selected from amino acid modifications for substituting Ser at position 30 with Asn, Val at position 48 with Ile, Ser at position 49 with Ala, Asn at position 77 with Gly, Val at position 93 with Thr, Ala at position 97 with Thr, and Thr at position 117 with Val is introduced in the amino acid sequence represented by SEQ ID NO:96.

Specifically, as the amino acid sequence of the above VL, for example, amino acid sequences in which the following one to seven modifications are introduced can be listed.

Specific examples of the amino acid sequence of VH in which seven modifications are introduced include an amino acid sequence in which substitutions of Ser at position 30 with Asn, Val at position 48 with Ile, Ser at position 49 with Ala, Asn at position 77 with Gly, Val at position 93 with Thr, Ala at position 97 with Thr, and Thr at position 117 with Val are introduced in the amino acid sequence represented by SEQ ID NO:96.

Specific examples of the amino acid sequence of VH in which six modifications are introduced include the following amino acid sequences (1) to (7):
(1) an amino acid sequence in which substitutions of Ser at position 30 with Asn, Val at position 48 with Ile, Ser at position 49 with Ala, Asn at position 77 with Gly, Val at position 93 with Thr, and Ala at position 97 with Thr are introduced in the amino acid sequence represented by SEQ ID NO:96,
(2) an amino acid sequence in which substitutions of Ser at position 30 with Asn, Val at position 48 with Ile, Ser at position 49 with Ala, Asn at position 77 with Gly, Val at position 93 with Thr, and Thr at position 117 with Val are introduced in the amino acid sequence represented by SEQ ID NO:96,
(3) an amino acid sequence in which substitutions of Ser at position 30 with Asn, Val at position 48 with Ile, Ser at position 49 with Ala, Asn at position 77 with Gly, Ala at position 97 with Thr, and Thr at position 117 with Val are introduced in the amino acid sequence represented by SEQ ID NO:96,
(4) an amino acid sequence in which substitutions of Ser at position 30 with Asn, Val at position 48 with Ile, Ser at position 49 with Ala, Val at position 93 with Thr, Ala at position 97 with Thr, and Thr at position 117 with Val are introduced in the amino acid sequence represented by SEQ ID NO:96,
(5) an amino acid sequence in which substitutions of Ser at position 30 with Asn, Val at position 48 with Ile, Asn at position 77 with Gly, Val at position 93 with Thr, Ala at position 97 with Thr, and Thr at position 117 with Val are introduced in the amino acid sequence represented by SEQ ID NO:96,
(6) an amino acid sequence in which substitutions of Ser at position 30 with Asn, Ser at position 49 with Ala, Asn at position 77 with Gly, Val at position 93 with Thr, Ala at position 97 with Thr, and Thr at position 117 with Val are introduced in the amino acid sequence represented by SEQ ID NO:96, and
(7) an amino acid sequence in which substitutions of Val at position 48 with Ile, Ser at position 49 with Ala, Asn at position 77 with Gly, Val at position 93 with Thr, Ala at position 97 with Thr, and Thr at position 117 with Val are introduced in the amino acid sequence represented by SEQ ID NO:96.

Specific examples of the amino acid sequence of VH in which five modifications are introduced in the amino acid sequence represented by SEQ ID NO:96 include the following amino acid sequences (1) to (21):

(1) an amino acid sequence in which substitutions of Ser at position 49 with Ala, Asn at position 77 with Gly, Val at position 93 with Thr, Ala at position 97 with Thr, and Thr at position 117 with Val are introduced in the amino acid sequence represented by SEQ ID NO:96, (2) an amino acid sequence in which substitutions of Val at position 48 with Ile, Asn at position 77 with Gly, Val at position 93 with Thr, Ala at position 97 with Thr, and Thr at position 117 with Val are introduced in the amino acid sequence represented by SEQ ID NO:96, (3) an amino acid sequence in which substitutions of Val at position 48 with Ile, Ser at position 49 with Ala, Val at position 93 with Thr, Ala at position 97 with Thr, and Thr at position 117 with Val are introduced in the amino acid sequence represented by SEQ ID NO:96, (4) an amino acid sequence in which substitutions of Val at position 48 with Ile, Ser at position 49 with Ala, Asn at position 77 with Gly, Ala at position 97 with Thr, and Thr at position 117 with Val are introduced in the amino acid sequence represented by SEQ ID NO:96, (5) an amino acid sequence in which substitutions of Val at position 48 with Ile, Ser at position 49 with Ala, Asn at position 77 with Gly, Val at position 93 with Thr, and Thr at position 117 with Val are introduced in the amino acid sequence represented by SEQ ID NO:96, (6) an amino acid sequence in which substitutions of Val at position 48 with Ile, Ser at position 49 with Ala, Asn at position 77 with Gly, Val at position 93 with Thr, and Ala at position 97 with Thr are introduced in the amino acid sequence represented by SEQ ID NO:96, (7) an amino acid sequence in which substitutions of Ser at position 30 with Asn, Asn at position 77 with Gly, Val at position 93 with Thr, Ala at position 97 with Thr, and Thr at position 117 with Val are introduced in the amino acid sequence represented by SEQ ID NO:96, (8) an amino acid sequence in which substitutions of Ser at position 30 with Asn, Ser at position 49 with Ala, Val at position 93 with Thr, Ala at position 97 with Thr, and Thr at position 117 with Val are introduced in the amino acid sequence represented by SEQ ID NO:96, (9) an amino acid sequence in which substitutions of Ser at position 30 with Asn, Ser at position 49 with Ala, Asn at position 77 with Gly, Ala at position 97 with Thr, and Thr at position 117 with Val are introduced in the amino acid sequence represented by SEQ ID NO:96,

(10) an amino acid sequence in which substitutions of Ser at position 30 with Asn, Ser at position 49 with Ala, Asn at position 77 with Gly, Val at position 93 with Thr, and Thr at position 117 with Val are introduced in the amino acid sequence represented by SEQ ID NO:96,

(11) an amino acid sequence in which substitutions of Ser at position 30 with Asn, Ser at position 49 with Ala, Asn at position 77 with Gly, Val at position 93 with Thr, and Ala at position 97 with Thr are introduced in the amino acid sequence represented by SEQ ID NO:96,

(12) an amino acid sequence in which substitutions of Ser at position 30 with Asn, Val at position 48 with Ile, Val at position 93 with Thr, Ala at position 97 with Thr, and Thr at position 117 with Val are introduced in the amino acid sequence represented by SEQ ID NO:96,

(13) an amino acid sequence in which substitutions of Ser at position 30 with Asn, Val at position 48 with Ile, Asn at position 77 with Gly, Ala at position 97 with Thr, and Thr at position 117 with Val are introduced in the amino acid sequence represented by SEQ ID NO:96,

(14) an amino acid sequence in which substitutions of Ser at position 30 with Asn, Val at position 48 with Ile, Asn at position 77 with Gly, Val at position 93 with Thr, and Thr at position 117 with Val are introduced in the amino acid sequence represented by SEQ ID NO:96,

(15) an amino acid sequence in which substitutions of Ser at position 30 with Asn, Val at position 48 with Ile, Asn at position 77 with Gly, Val at position 93 with Thr, and Ala at position 97 with Thr are introduced in the amino acid sequence represented by SEQ ID NO:96,

(16) an amino acid sequence in which substitutions of Ser at position 30 with Asn, Val at position 48 with Ile, Ser at position 49 with Ala, Ala at position 97 with Thr, and Thr at position 117 with Val are introduced in the amino acid sequence represented by SEQ ID NO:96,

(17) an amino acid sequence in which substitutions of Ser at position 30 with Asn, Val at position 48 with Ile, Ser at position 49 with Ala, Val at position 93 with Thr, and Thr at position 117 with Val are introduced in the amino acid sequence represented by SEQ ID NO:96,

(18) an amino acid sequence in which substitutions of Ser at position 30 with Asn, Val at position 48 with Ile, Ser at position 49 with Ala, Val at position 93 with Thr, and Ala at position 97 with Thr are introduced in the amino acid sequence represented by SEQ ID NO:96,

(19) an amino acid sequence in which substitutions of Ser at position 30 with Asn, Val at position 48 with Ile, Ser at position 49 with Ala, Asn at position 77 with Gly, and Thr at position 117 with Val are introduced in the amino acid sequence represented by SEQ ID NO:96,

(20) an amino acid sequence in which substitutions of Ser at position 30 with Asn, Val at position 48 with Ile, Ser at position 49 with Ala, Asn at position 77 with Gly, and Ala at position 97 with Thr are introduced in the amino acid sequence represented by SEQ ID NO:96, and

(21) an amino acid sequence in which substitutions of Ser at position 30 with Asn, Val at position 48 with Ile, Ser at position 49 with Ala, Asn at position 77 with Gly, and Val at position 93 with Thr are introduced in the amino acid sequence represented by SEQ ID NO:96.

Specific examples of the amino acid sequence of VH in which four modifications are introduced in the amino acid sequence represented by SEQ ID NO:96 include the following amino acid sequences (1) to (35):

(1) an amino acid sequence in which substitutions of Asn at position 77 with Gly, Val at position 93 with Thr, Ala at position 97 with Thr, and Thr at position 117 with Val are introduced in the amino acid sequence represented by SEQ ID NO:96, (2) an amino acid sequence in which substitutions of Ser at position 49 with Ala, Val at position 93 with Thr, Ala at position 97 with Thr, and Thr at position 117 with Val are introduced in the amino acid sequence represented by SEQ ID NO:96, (3) an amino acid sequence in which substitutions of Ser at position 49 with Ala, Asn at position 77 with Gly, Ala at position 97 with Thr, and Thr at position 117 with Val are introduced in the amino acid sequence represented by SEQ ID NO:96, (4) an amino acid sequence in which substitutions of Ser at position 49 with Ala, Asn at position 77 with Gly, Val at position 93 with Thr, and Thr at position 117 with Val are introduced in the amino acid sequence represented by SEQ ID NO:96, (5) an amino acid sequence in which substitutions of Ser at position 49 with Ala, Asn at position 77 with Gly, Val at position 93 with Thr, and Ala at position 97 with Thr are introduced in the amino acid sequence represented by SEQ ID NO:96, (6) an amino acid sequence in which substitutions of Val at position 48 with Ile, Val at position 93 with Thr, Ala at position 97 with Thr, and Thr at position 117 with Val are introduced in the amino acid sequence represented by SEQ ID NO:96, (7) an amino acid sequence in which substitutions of Val at position 48 with Ile, Asn at position 77 with Gly, Ala at position 97 with Thr, and Thr at position 117 with Val are introduced in the amino acid sequence represented by SEQ ID NO:96, (8) an amino acid sequence in which substitutions of Val at position 48 with Ile, Asn at position 77 with Gly, Val at position 93 with Thr, and Thr at position 117 with Val are introduced in the amino acid sequence represented by SEQ ID NO:96, (9) an amino acid sequence in which substitutions of Val at position 48 with Ile, Asn at position 77 with Gly, Val at position 93 with Thr, and Ala at position 97 with Thr are introduced in the amino acid sequence represented by SEQ ID NO:96,

(10) an amino acid sequence in which substitutions of Val at position 48 with Ile, Ser at position 49 with Ala, Ala at position 97 with Thr, and Thr at position 117 with Val are introduced in the amino acid sequence represented by SEQ ID NO:96,

(11) an amino acid sequence in which substitutions of Val at position 48 with Ile, Ser at position 49 with Ala, Val at position 93 with Thr, and Thr at position 117 with Val are introduced in the amino acid sequence represented by SEQ ID NO:96,

(12) an amino acid sequence in which substitutions of Val at position 48 with Ile, Ser at position 49 with Ala, Val at position 93 with Thr, and Ala at position 97 with Thr are introduced in the amino acid sequence represented by SEQ ID NO:96,

(13) an amino acid sequence in which substitutions of Val at position 48 with Ile, Ser at position 49 with Ala, Asn at position 77 with Gly, and Thr at position 117 with Val are introduced in the amino acid sequence represented by SEQ ID NO:96,

(14) an amino acid sequence in which substitutions of Val at position 48 with Ile, Ser at position 49 with Ala, Asn at position 77 with Gly, and Ala at position 97 with Thr are introduced in the amino acid sequence represented by SEQ ID NO:96,

(15) an amino acid sequence in which substitutions of Val at position 48 with Ile, Ser at position 49 with Ala, Asn at position 77 with Gly, and Val at position 93 with Thr are introduced in the amino acid sequence represented by SEQ ID NO:96,

(16) an amino acid sequence in which substitutions of Ser at position 30 with Asn, Val at position 93 with Thr, Ala at position 97 with Thr, and Thr at position 117 with Val are introduced in the amino acid sequence represented by SEQ ID NO:96,

(17) an amino acid sequence in which substitutions of Ser at position 30 with Asn, Asn at position 77 with Gly, Ala at position 97 with Thr, and Thr at position 117 with Val are introduced in the amino acid sequence represented by SEQ ID NO:96,

(18) an amino acid sequence in which substitutions of Ser at position 30 with Asn, Asn at position 77 with Gly, Val at position 93 with Thr, and Thr at position 117 with Val are introduced in the amino acid sequence represented by SEQ ID NO:96,

(19) an amino acid sequence in which substitutions of Ser at position 30 with Asn, Asn at position 77 with Gly, Val at position 93 with Thr, and Ala at position 97 with Thr are introduced in the amino acid sequence represented by SEQ ID NO:96,

(20) an amino acid sequence in which substitutions of Ser at position 30 with Asn, Ser at position 49 with Ala, Ala at position 97 with Thr, and Thr at position 117 with Val are introduced in the amino acid sequence represented by SEQ ID NO:96,

(21) an amino acid sequence in which substitutions of Ser at position 30 with Asn, Ser at position 49 with Ala, Val at position 93 with Thr, and Thr at position 117 with Val are introduced in the amino acid sequence represented by SEQ ID NO:96,

(22) an amino acid sequence in which substitutions of Ser at position 30 with Asn, Set at position 49 with Ala, Val at position 93 with Thr, and Ala at position 97 with Thr are introduced in the amino acid sequence represented by SEQ ID NO:96,

(23) an amino acid sequence in which substitutions of Ser at position 30 with Asn, Ser at position 49 with Ala, Asn at position 77 with Gly, and Thr at position 117 with Val are introduced in the amino acid sequence represented by SEQ ID NO:96,

(24) an amino acid sequence in which substitutions of Ser at position 30 with Asn, Ser at position 49 with Ala, Asn at position 77 with Gly, and Ala at position 97 with Thr are introduced in the amino acid sequence represented by SEQ ID NO:96,

(25) an amino acid sequence in which substitutions of Ser at position 30 with Asn, Ser at position 49 with Ala, Asn at position 77 with Gly, and Val at position 93 with Thr are introduced in the amino acid sequence represented by SEQ ID NO:96,

(26) an amino acid sequence in which substitutions of Ser at position 30 with Asn, Val at position 48 with Ile, Ala at position 97 with Thr, and Thr at position 117 with Val are introduced in the amino acid sequence represented by SEQ ID NO:96,

(27) an amino acid sequence in which substitutions of Ser at position 30 with Asn, Val at position 48 with Ile, Val at position 93 with Thr, and Thr at position 117 with Val are introduced in the amino acid sequence represented by SEQ ID NO:96,

(28) an amino acid sequence in which substitutions of Ser at position 30 with Asn, Val at position 48 with Ile, Val at position 93 with Thr, and Ala at position 97 with Thr are introduced in the amino acid sequence represented by SEQ ID NO:96,

(29) an amino acid sequence in which substitutions of Ser at position 30 with Asn, Val at position 48 with Ile, Asn at position 77 with Gly, and Thr at position 117 with Val are introduced in the amino acid sequence represented by SEQ ID NO:96,

(30) an amino acid sequence in which substitutions of Ser at position 30 with Asn, Val at position 48 with Ile, Asn at position 77 with Gly, and Ala at position 97 with Thr are introduced in the amino acid sequence represented by SEQ ID NO:96,
(31) an amino acid sequence in which substitutions of Ser at position 30 with Asn, Val at position 48 with Ile, Asn at position 77 with Gly, and Val at position 93 with Thr are introduced in the amino acid sequence represented by SEQ ID NO:96,
(32) an amino acid sequence in which substitutions of Ser at position 30 with Asn, Val at position 48 with Ile, Ser at position 49 with Ala, and Thr at position 117 with Val are introduced in the amino acid sequence represented by SEQ ID NO:96,
(33) an amino acid sequence in which substitutions of Ser at position 30 with Asn, Val at position 48 with Ile, Ser at position 49 with Ala, and Ala at position 97 with Thr are introduced in the amino acid sequence represented by SEQ ID NO:96,
(34) an amino acid sequence in which substitutions of Ser at position 30 with Asn, Val at position 48 with Ile, Ser at position 49 with Ala, and Val at position 93 with Thr are introduced in the amino acid sequence represented by SEQ ID NO:96, and
(35) an amino acid sequence in which substitutions of Ser at position 30 with Asn, Val at position 48 with Ile, Set at position 49 with Ala, and Asn at position 77 with Gly are introduced in the amino acid sequence represented by SEQ ID NO:96.

Specific examples of the amino acid sequence of VH in which three modifications are introduced in the amino acid sequence represented by SEQ ID NO:96 include the following amino acid sequences (1) to (35):
(1) an amino acid sequence in which substitutions of Set at position 30 with Asn, Val at position 48 with Ile, and Ser at position 49 with Ala are introduced in the amino acid sequence represented by SEQ ID NO:96,
(2) an amino acid sequence in which substitutions of Ser at position 30 with Asn, Val at position 48 with Ile, and Asn at position 77 with Gly are introduced in the amino acid sequence represented by SEQ ID NO:96,
(3) an amino acid sequence in which substitutions of Ser at position 30 with Asn, Val at position 48 with Ile, and Val at position 93 with Thr are introduced in the amino acid sequence represented by SEQ ID NO:96,
(4) an amino acid sequence in which substitutions of Ser at position 30 with Asn, Val at position 48 with Ile, and Ala at position 97 with Thr are introduced in the amino acid sequence represented by SEQ ID NO:96,
(5) an amino acid sequence in which substitutions of Ser at position 30 with Asn, Val at position 48 with Ile, and Thr at position 117 with Val are introduced in the amino acid sequence represented by SEQ ID NO:96,
(6) an amino acid sequence in which substitutions of Ser at position 30 with Asn, Ser at position 49 with Ala, and Asn at position 77 with Gly are introduced in the amino acid sequence represented by SEQ ID NO:96,
(7) an amino acid sequence in which substitutions of Ser at position 30 with Asn, Ser at position 49 with Ala, and Val at position 93 with Thr are introduced in the amino acid sequence represented by SEQ ID NO:96,
(8) an amino acid sequence in which substitutions of Ser at position 30 with Asn, Ser at position 49 with Ala, and Ala at position 97 with Thr are introduced in the amino acid sequence represented by SEQ ID NO:96,
(9) an amino acid sequence in which substitutions of Ser at position 30 with Asn, Ser at position 49 with Ala, and Thr at position 117 with Val are introduced in the amino acid sequence represented by SEQ ID NO:96,
(10) an amino acid sequence in which substitutions of Ser at position 30 with Asn, Asn at position 77 with Gly, and Val at position 93 with Thr are introduced in the amino acid sequence represented by SEQ ID NO:96,
(11) an amino acid sequence in which substitutions of Ser at position 30 with Asn, Asn at position 77 with Gly, and Ala at position 97 with Thr are introduced in the amino acid sequence represented by SEQ ID NO:96,
(12) an amino acid sequence in which substitutions of Ser at position 30 with Asn, Asn at position 77 with Gly, and Thr at position 117 with Val are introduced in the amino acid sequence represented by SEQ ID NO:96,
(13) an amino acid sequence in which substitutions of Ser at position 30 with Asn, Val at position 93 with Thr, and Ala at position 97 with Thr are introduced in the amino acid sequence represented by SEQ ID NO:96,
(14) an amino acid sequence in which substitutions of Ser at position 30 with Asn, Val at position 93 with Thr, and Thr at position 117 with Val are introduced in the amino acid sequence represented by SEQ ID NO:96,
(15) an amino acid sequence in which substitutions of Ser at position 30 with Asn, Ala at position 97 with Thr, and Thr at position 117 with Val are introduced in the amino acid sequence represented by SEQ ID NO:96,
(16) an amino acid sequence in which substitutions of Val at position 48 with Ile, Ser at position 49 with Ala, and Asn at position 77 with Gly are introduced in the amino acid sequence represented by SEQ ID NO:96,
(17) an amino acid sequence in which substitutions of Val at position 48 with Ile, Ser at position 49 with Ala, and Val at position 93 with Thr are introduced in the amino acid sequence represented by SEQ ID NO:96,
(18) an amino acid sequence in which substitutions of Val at position 48 with Ile, Ser at position 49 with Ala, and Ala at position 97 with Thr are introduced in the amino acid sequence represented by SEQ ID NO:96,
(19) an amino acid sequence in which substitutions of Val at position 48 with Ile, Ser at position 49 with Ala, and Thr at position 117 with Val are introduced in the amino acid sequence represented by SEQ ID NO:96,
(20) an amino acid sequence in which substitutions of Val at position 48 with Ile, Asn at position 77 with Gly, and Val at position 93 with Thr are introduced in the amino acid sequence represented by SEQ ID NO:96,
(21) an amino acid sequence in which substitutions of Val at position 48 with Ile, Asn at position 77 with Gly, and Ala at position 97 with Thr are introduced in the amino acid sequence represented by SEQ ID NO:96,
(22) an amino acid sequence in which substitutions of Val at position 48 with Ile, Asn at position 77 with Gly, and Thr at position 117 with Val are introduced in the amino acid sequence represented by SEQ ID NO:96,
(23) an amino acid sequence in which substitutions of Val at position 48 with Ile, Val at position 93 with Thr, and Ala at position 97 with Thr are introduced in the amino acid sequence represented by SEQ ID NO:96,
(24) an amino acid sequence in which substitutions of Val at position 48 with Ile, Val at position 93 with Thr, and Thr at position 117 with Val are introduced in the amino acid sequence represented by SEQ ID NO:96,
(25) an amino acid sequence in which substitutions of Val at position 48 with Ile, Ala at position 97 with Thr, and Thr at position 117 with Val are introduced in the amino acid sequence represented by SEQ ID NO:96,

(26) an amino acid sequence in which substitutions of Ser at position 49 with Ala, Asn at position 77 with Gly, and Val at position 93 with Thr are introduced in the amino acid sequence represented by SEQ ID NO:96,
(27) an amino acid sequence in which substitutions of Ser at position 49 with Ala, Asn at position 77 with Gly, and Ala at position 97 with Thr are introduced in the amino acid sequence represented by SEQ ID NO:96,
(28) an amino acid sequence in which substitutions of Ser at position 49 with Ala, Asn at position 77 with Gly, and Thr at position 117 with Val are introduced in the amino acid sequence represented by SEQ ID NO:96,
(29) an amino acid sequence in which substitutions of Ser at position 49 with Ala, Val at position 93 with Thr, and Ala at position 97 with Thr are introduced in the amino acid sequence represented by SEQ ID NO:96,
(30) an amino acid sequence in which substitutions of Ser at position 49 with Ala, Val at position 93 with Thr, and Thr at position 117 with Val are introduced in the amino acid sequence represented by SEQ ID NO:96,
(31) an amino acid sequence in which substitutions of Ser at position 49 with Ala, Ala at position 97 with Thr, and Thr at position 117 with Val are introduced in the amino acid sequence represented by SEQ ID NO:96,
(32) an amino acid sequence in which substitutions of Asn at position 77 with Gly, Val at position 93 with Thr, and Ala at position 97 with Thr are introduced in the amino acid sequence represented by SEQ ID NO:96,
(33) an amino acid sequence in which substitutions of Asn at position 77 with Gly, Val at position 93 with Thr, and Thr at position 117 with Val are introduced in the amino acid sequence represented by SEQ ID NO:96,
(34) an amino acid sequence in which substitutions of Asn at position 77 with Gly, Ala at position 97 with Thr, and Thr at position 117 with Val are introduced in the amino acid sequence represented by SEQ ID NO:96, and
(35) an amino acid sequence in which substitutions of Val at position 93 with Thr, Ala at position 97 with Thr, and Thr at position 117 with Val are introduced in the amino acid sequence represented by SEQ ID NO:96.

Specific examples of the amino acid sequence of VH in which two modifications are introduced in the amino acid sequence represented by SEQ ID NO:96 include the following amino acid sequences (1) to (21):
(1) an amino acid sequence in which substitutions of Ser at position 30 with Asn, and Val at position 48 with Ile are introduced in the amino acid sequence represented by SEQ ID NO:96,
(2) an amino acid sequence in which substitutions of Ser at position 30 with Asn, and Ser at position 49 with Ala are introduced in the amino acid sequence represented by SEQ ID NO:96,
(3) an amino acid sequence in which substitutions of Ser at position 30 with Asn, and Asn at position 77 with Gly are introduced in the amino acid sequence represented by SEQ ID NO:96,
(4) an amino acid sequence in which substitutions of Ser at position 30 with Asn, and Val at position 93 with Thr are introduced in the amino acid sequence represented by SEQ ID NO:96,
(5) an amino acid sequence in which substitutions of Ser at position 30 with Asn, and Ala at position 97 with Thr are introduced in the amino acid sequence represented by SEQ ID NO:96,
(6) an amino acid sequence in which substitutions of Ser at position 30 with Asn, and Thr at position 117 with Val are introduced in the amino acid sequence represented by SEQ ID NO:96,
(7) an amino acid sequence in which substitutions of Val at position 48 with Ile, and Ser at position 49 with Ala are introduced in the amino acid sequence represented by SEQ ID NO:96,
(8) an amino acid sequence in which substitutions of Val at position 48 with Ile, and Asn at position 77 with Gly are introduced in the amino acid sequence represented by SEQ ID NO:96,
(9) an amino acid sequence in which substitutions of Val at position 48 with Ile, and Val at position 93 with Thr are introduced in the amino acid sequence represented by SEQ ID NO:96,
(10) an amino acid sequence in which substitutions of Val at position 48 with Ile, and Ala at position 97 with Thr are introduced in the amino acid sequence represented by SEQ ID NO:96,
(11) an amino acid sequence in which substitutions of Val at position 48 with Ile, and Thr at position 117 with Val are introduced in the amino acid sequence represented by SEQ ID NO:96,
(12) an amino acid sequence in which substitutions of Ser at position 49 with Ala, and Asn at position 77 with Gly are introduced in the amino acid sequence represented by SEQ ID NO:96,
(13) an amino acid sequence in which substitutions of Ser at position 49 with Ala, and Val at position 93 with Thr are introduced in the amino acid sequence represented by SEQ ID NO:96,
(14) an amino acid sequence in which substitutions of Ser at position 49 with Ala, and Ala at position 97 with Thr are introduced in the amino acid sequence represented by SEQ ID NO:96,
(15) an amino acid sequence in which substitutions of Ser at position 49 with Ala, and Thr at position 117 with Val are introduced in the amino acid sequence represented by SEQ ID NO:96,
(16) an amino acid sequence in which substitutions of Asn at position 77 with Gly, and Val at position 93 with Thr are introduced in the amino acid sequence represented by SEQ ID NO:96,
(17) an amino acid sequence in which substitutions of Asn at position 77 with Gly, and Ala at position 97 with Thr are introduced in the amino acid sequence represented by SEQ ID NO:96,
(18) an amino acid sequence in which substitutions of Asn at position 77 with Gly, and Thr at position 117 with Val are introduced in the amino acid sequence represented by SEQ ID NO:96,
(19) an amino acid sequence in which substitutions of Val at position 93 with Thr, and Ala at position 97 with Thr are introduced in the amino acid sequence represented by SEQ ID NO:96,
(20) an amino acid sequence in which substitutions of Val at position 93 with Thr, and Thr at position 117 with Val are introduced in the amino acid sequence represented by SEQ ID NO:96, and
(21) an amino acid sequence in which substitutions of Ala at position 97 with Thr, and Thr at position 117 with Val are introduced in the amino acid sequence represented by SEQ ID NO:96.

Specific examples of the amino acid sequence of VH in which one modification is introduced in the amino acid sequence represented by SEQ ID NO:96 include the following amino acid sequences (1) to (7):

(1) an amino acid sequence in which a substitution of Ser at position 30 with Asn is introduced in the amino acid sequence represented by SEQ ID NO:96, (2) an amino acid sequence in which a substitution of Val at position 48 with Ile is introduced in the amino acid sequence represented by SEQ ID NO:96, (3) an amino acid sequence in which a substitution of Ser at position 49 with Ala is introduced in the amino acid sequence represented by SEQ ID NO:96, (4) an amino acid sequence in which a substitution of Asn at position 77 with Gly is introduced in the amino acid sequence represented by SEQ ID NO:96, (5) an amino acid sequence in which a substitution of Val at position 93 with Thr is introduced in the amino acid sequence represented by SEQ ID NO:96, (6) an amino acid sequence in which a substitution of Ala at position 97 with Thr is introduced in the amino acid sequence represented by SEQ ID NO:96, and (7) an amino acid sequence in which a substitution of Thr at position 117 with Val is introduced in the amino acid sequence represented by SEQ ID NO:96.

More specific examples of the amino acid sequence of VH of the humanized antibody of the present invention include the amino acid sequences represented by SEQ ID NOs: 96, 105 and 107, resepectively.

As VL comprised in the humanized antibody of the present invention, an amino acid sequence in which Ile at position 21, Pro at position 40, Val at position 58, Thr at position 85, and Tyr at position 87 in the amino acid sequence represented by SEQ ID NO:97 are substituted with other amino acid residues is preferable.

Among them, as a amino acid sequence of VL of the humanized antibody of the present invention, an amino acid sequence in which Pro at position 40, Val at position 58, and Tyr at position 87 in the amino acid sequence represented by SEQ ID NO:97 are substituted with other amino acid residues is preferable.

Examples of the amino acid sequence of the above VL include an amino acid sequence in which at least one modification selected from amino acid modifications for substituting Ile at position 21 with Leu, Pro at position 40 with Leu, Val at position 58 with Ile, Thr at position 85 with Ala, and Tyr at position 87 with Phe is introduced in the amino acid sequence represented by SEQ ID NO:97.

Specifically, as the amino acid sequence of the above VH, for example, amino acid sequences in which the following one to five modifications are introduced can be listed.

Specific examples of the amino acid sequence of VL in which five modifications are introduced include an amino acid sequence in which substitutions of Ile at position 21 with Leu, Pro at position 40 with Leu, Val at position 58 with Ile, Thr at position 85 with Ala, and Tyr at position 87 with Phe are introduced in the amino acid sequence represented by SEQ ID NO:97, and the like.

Specific examples of the amino acid sequence of VL in which four modifications are introduced include the following amino acid sequences (1) to (5):

(1) an amino acid sequence in which substitutions of Pro at position 40 with Leu, Val at position 58 with Ile, Thr at position 85 with Ala, and Tyr at position 87 with Phe are introduced in the amino acid sequence represented by SEQ ID NO:97, (2) an amino acid sequence in which substitutions of Ile at position 21 with Leu, Val at position 58 with Ile, Thr at position 85 with Ala, and Tyr at position 87 with Phe are introduced in the amino acid sequence represented by SEQ ID NO:97, (3) an amino acid sequence in which substitutions of Ile at position 21 with Leu, Pro at position 40 with Leu, Thr at position 85 with Ala, and Tyr at position 87 with Phe are introduced in the amino acid sequence represented by SEQ ID NO:97, (4) an amino acid sequence in which substitutions of Ile at position 21 with Leu, Pro at position 40 with Leu, Val at position 58 with Ile, and Tyr at position 87 with Phe are introduced in the amino acid sequence represented by SEQ ID NO:97, and (5) an amino acid sequence in which substitutions of Ile at position 21 with Leu, Pro at position 40 with Leu, Val at position 58 with Ile, and Thr at position 85 with Ala are introduced in the amino acid sequence represented by SEQ ID NO:97.

Specific examples of the amino acid sequence of VL in which three modifications are introduced include the following amino acid sequences (1) to (9):

(1) an amino acid sequence in which substitutions of Ile at position 21 with Leu, Pro at position 40 with Leu, and Val at position 58 with Ile are introduced in the amino acid sequence represented by SEQ ID NO:97, (2) an amino acid sequence in which substitutions of Ile at position 21 with Leu, Pro at position 40 with Leu, and Thr at position 85 with Ala are introduced in the amino acid sequence represented by SEQ ID NO:97, (3) an amino acid sequence in which substitutions of Ile at position 21 with Leu, Pro at position 40 with Leu, and Tyr at position 87 with Phe are introduced in the amino acid sequence represented by SEQ ID NO:97, (4) an amino acid sequence in which substitutions of Ile at position 21 with Leu, Val at position 58 with Ile, and Thr at position 85 with Ala are introduced in the amino acid sequence represented by SEQ ID NO:97, (5) an amino acid sequence in which substitutions of Ile at position 21 with Leu, Val at position 58 with Ile, and Tyr at position 87 with Phe are introduced in the amino acid sequence represented by SEQ ID NO:97, (6) an amino acid sequence in which substitutions of Ile at position 21 with Leu, Thr at position 85 with Ala, and Tyr at position 87 with Phe are introduced in the amino acid sequence represented by SEQ ID NO:97, (7) an amino acid sequence in which substitutions of Pro at position 40 with Leu, Val at position 58 with Ile, and Thr at position 85 with Ala are introduced in the amino acid sequence represented by SEQ ID NO:97, (8) an amino acid sequence in which substitutions of Pro at position 40 with Leu, Val at position 58 with Ile, and Tyr at position 87 with Phe are introduced in the amino acid sequence represented by SEQ ID NO:97, and (9) an amino acid sequence in which substitutions of Val at position 58 with Ile, Thr at position 85 with Ala, and Tyr at position 87 with Phe are introduced in the amino acid sequence represented by SEQ ID NO:97.

Specific examples of the amino acid sequence of VL in which two modifications are introduced include the following amino acid sequences (1) to (10):

(1) an amino acid sequence in which substitutions of Ile at position 21 with Leu, and Pro at position 40 with Leu are introduced in the amino acid sequence represented by SEQ ID NO:97, (2) an amino acid sequence in which substitutions of Ile at position 21 with Leu, and Val at position 58 with Ile are introduced in the amino acid sequence represented by SEQ ID NO:97,
(3) an amino acid sequence in which substitutions of Ile at position 21 with Leu, and Thr at position 85 with Ala are introduced in the amino acid sequence represented by SEQ ID NO:97,
(4) an amino acid sequence in which substitutions of Ile at position 21 with Leu, and Tyr at position 87 with Phe are introduced in the amino acid sequence represented by SEQ ID NO:97,
(5) an amino acid sequence in which substitutions of Pro at position 40 with Leu, and Val at position 58 with Ile are introduced in the amino acid sequence represented by SEQ ID NO:97,
(6) an amino acid sequence in which substitutions of Pro at position 40 with Leu, and Thr at position 85 with Ala are introduced in the amino acid sequence represented by SEQ ID NO:97,
(7) an amino acid sequence in which substitutions of Pro at position 40 with Leu, and Tyr at position 87 with Phe are introduced in the amino acid sequence represented by SEQ ID NO:97,
(8) an amino acid sequence in which substitutions of Val at position 58 with Ile, and Thr at position 85 with Ala are introduced in the amino acid sequence represented by SEQ ID NO:97,
(9) an amino acid sequence in which substitutions of Val at position 58 with Ile, and Tyr at position 87 with Phe are introduced in the amino acid sequence represented by SEQ ID NO:97, and
(10) an amino acid sequence in which substitutions of Thr at position 85 with Ala, and Tyr at position 87 with Phe are introduced in the amino acid sequence represented by SEQ ID NO:97.

Specific examples of the amino acid sequence of VL in which one modification is introduced include an amino acid sequence in which a substitution of Ile at position 21 with Leu is introduced in the amino acid sequence represented by SEQ ID NO:97, an amino acid sequence in which a substitution of Pro at position 40 with Leu is introduced in the amino acid sequence represented by SEQ ID NO:97, an amino acid sequence in which a substitution of Val at position 58 with Ile is introduced in the amino acid sequence represented by SEQ ID NO:97, an amino acid sequence in which a substitution of Thr at position 85 with Ala is introduced in the amino acid sequence represented by SEQ ID NO:97, and an amino acid sequence in which a substitution of Tyr at position 87 with Phe is introduced in the amino acid sequence represented by SEQ ID NO:97.

More specific examples of the amino acid sequence of VL of the humanized antibody of the present invention include the amino acid sequence represented by SEQ ID NO: 97.

In addition, specific examples of the humanized antibody of the present invention include the following humanized antibodies (1) to (5):
(1) a humanized antibody which comprises at least one of H chain variable region comprising the amino acid sequence represented by SEQ ID NO:96 and L chain variable region comprising the amino acid sequence represented by SEQ ID NO:97,
(2) a humanized antibody which comprises at least one of H chain variable region comprising the amino acid sequence represented by SEQ ID NO:101 and L chain variable region comprising the amino acid sequence represented by SEQ ID NO:97,
(3) a humanized antibody which comprises at least one of H chain variable region comprising the amino acid sequence represented by SEQ ID NO:103 and L chain variable region comprising the amino acid sequence represented by SEQ ID NO:97,
(4) a humanized antibody which comprises at least one of H chain variable region comprising the amino acid sequence represented by SEQ ID NO:105 and L chain variable region comprising the amino acid sequence represented by SEQ ID NO:97, and
(5) a humanized antibody which comprises at least one of H chain variable region comprising the amino acid sequence represented by SEQ ID NO:107 and L chain variable region comprising the amino acid sequence represented by SEQ ID NO:97.

A human antibody is originally an antibody naturally existing in the human body, and it also includes antibodies obtained from a human antibody phage library or a human antibody-producing transgenic animal, which is prepared based on the recent advance in genetic engineering, cell engineering and developmental engineering techniques.

The antibody naturally existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment on the cell surface having the desired antigen binding activity can be recovered from the library, using its activity to bind to an antigen-immobilized substrate as the index. The antibody fragment can be converted further into a human antibody molecule consisting of two full H chains and two full L chains by genetic engineering techniques.

A human antibody-producing transgenic animal means an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it into a complete animal.

As a method for preparing a human antibody from the human antibody-producing transgenic animal, a human antibody can be prepared by obtaining a human antibody-producing hybridoma by a hybridoma preparation method usually carried out in non-human animals, culturing the obtained hybridoma and producing and accumulating the human antibody in the supernatant of the culture.

An antibody or antibody fragment thereof in which one or more amino acids are deleted, substituted, inserted or added in the amino acid sequence constituting the above antibody or antibody fragment, having activity similar to the above antibody or antibody fragment is also included in the antibody or antibody fragment of the present invention.

The number of amino acid residues which are deleted, substituted, inserted and/or added is one or more, and is not specifically limited, but it is within the range where deletion, substitution or addition is possible by known methods such as the site-directed mutagenesis described in *Molecular Cloning*, Second Edition, Cold Spring Harbor Laboratory Press (1989); *Current Protocols in Molecular Biology*, John Willy & Sons (1987-1997); *Nucleic Acids Research*, 10, 6487

(1982), *Proc. Natl. Acad. Sci. USA,* 79, 6409 (1982); *Gene,* 34, 315 (1985), *Nucleic Acids Research,* 13, 4431 (1985); *Proc. Natl. Acad. Sci. USA,* 82, 488 (1985) or the like. For example, the number is 1 to dozens, preferably 1 to 20, more preferably 1 to 10, and most preferably 1 to 5.

Deleting, substituting, inserting or adding one or more amino acids in the amino acid sequence of the above antibody means the followings. That is, it means there is deletion, substitution, insertion or addition of one or plural amino acid residues at any positions in one or plural amino acid sequences of a single sequence. Also, the deletion, substitution, insertion or addition may exist at the same case and the amino acid which is substituted, inserted or added may be either a natural type or a non-natural type.

The natural type amino acid includes L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine Effector activity of the antibody includes ADCC activity, CDC activity, antibody-dependent cellular phagocytosis (ADCP) activity, opsonization effects, and the like. It may be controlled by a variety of methods.

Examples of the method for controlling the effector activity include a method for controlling a sugar chain bound to the Fc region of the antibody, a method for carrying out amino acid modification of amino acid residue(s) in the Fc region of the antibody, and the like.

Examples of the method for controlling a sugar chain bound to the Fc region of the antibody include a method for lowering ADCC or CDC activity by eliminating a sugar chain at position 297 of the IgG antibody [*Molecular Immunology,* 32, 1311, (1995), WO2008/030564], a method for lowering CDC activity by decreasing the binding of galactose to the Fc region of the antibody, and the like.

Further, examples of the method for controlling a sugar chain bound to the Fc region of the antibody include a method for producing an antibody containing a sugar chain having no fucose bound to N-acetylglucosamine (GlcNAc) of a base to which a sugar chain is bound, in the N-linked sugar chain bound to asparagine at position 297 of the Fc region of the IgG antibody (U.S. Pat. No. 7,214,775, and U.S. Pat. No. 6,946, 292), a method for producing an antibody containing a sugar chain containing bisecting GlcNAc bound thereto [*Nature Biotechnology,* 17, 176, (1999)], a method for producing an antibody containing a sugar chain bound to galactose (Gal) in the non-reducing terminal [*Hum. Antibod. Hybridomas,* 5, 143-151. (1994)], and the like.

Examples of the method for carrying out amino acid modification of amino acid residue(s) in the Fc region of the antibody include a method for controlling the effector activity by amino acid modification of the Fc region of the antibody (*J. B. C.,* 277, 26733-26740, 2002, U.S. Pat. No. 6,737,056, U.S. Pat. No. 7,297,775, US2007/0020260, and WO2005/070963), a method for controlling the effector activity by domain exchange between respective subclasses of the antibody Fc region (WO2007/011041), and the like.

The antibody fragment of the present invention includes Fab, F(ab')$_2$, Fab', scFv, diabody, dsFv and the like.

The antibody fragment of the present invention includes Fab, Fab', F(ab')$_2$, scFv, diabody, dsFv, a peptide comprising CDR and the like.

An Fab is an antibody fragment having a molecular weight of about 50,000 and antigen binding activity, in which about a half of the N-terminal side of H chain and the entire L chain, among fragments obtained by treating an IgG antibody molecule with a protease, papain (cleaved at an amino acid residue at position 224 of the H chain), are bound together through a disulfide bond.

The Fab of the present invention can be obtained by treating a monoclonal antibody which specifically recognizes the sugar chain-deficient CD27 protein of the present invention and binds to the extracellular region with a protease, papain. Also, the Fab can be produced by inserting DNA encoding Fab of the antibody into an expression vector for prokaryote or an expression vector for eukaryote, and introducing the vector into a prokaryote or an eukaryote to express the Fab.

An F(ab')$_2$ is an antibody fragment having a molecular weight of about 100,000 and antigen binding activity and comprising two Fab regions which are bound in the hinge portion obtained by digesting the lower part of two disulfide bonds in the hinge region of IgG, with an enzyme, pepsin.

The F(ab')$_2$ of the present invention can be obtained by treating a monoclonal antibody which specifically recognizes the sugar chain-deficient CD27 protein of the present invention and binds to the extracellular region with a protease, pepsin. Also, the F(ab')$_2$ can be produced by binding Fab' described below via a thioether bond or a disulfide bond.

An Fab' is an antibody fragment having a molecular weight of about 50,000 and antigen binding activity, which is obtained by cleaving a disulfide bond at the hinge region of the above F(ab')$_2$.

The Fab' of the present invention can be obtained by treating F(ab')$_2$ which specifically recognizes the sugar chain-deficient CD27 protein of the present invention and binds to the extracellular region, with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

A scFv is a VH-P-VL or VL-P-VH polypeptide in which a VH chain and a VL chain are linked using an appropriate peptide linker (hereinafter referred to as "P") and is an antibody fragment having antigen binding activity.

The scFv of the present invention can be produced by obtaining cDNAs encoding VH and VL of a monoclonal antibody which specifically recognizes the sugar chain-deficient CD27 protein and binds to the extracellular region, constructing DNA encoding the scFv, inserting the DNA into an expression vector for prokaryote or an expression vector for eukaryote, and then introducing the expression vector into a prokaryote or eukaryote to express the scFv.

A diabody is an antibody fragment in which scFv is dimerized, and has divalent antigen binding activity. In the divalent antigen binding activity, two antigens may be the same or different.

The diabody of the present invention can be produced by obtaining cDNAs encoding VH and VL of a monoclonal antibody which specifically recognizes the sugar chain-deficient CD27 protein and binds to the extracellular region, constructing DNA encoding the scFv so that the length of the amino acid sequence of P is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. [*Protein Engineering*, 7, 697 (1994)].

The dsFv of the present invention can be produced by obtaining cDNAs encoding VH and VL of a monoclonal antibody which specifically recognizes the sugar chain-deficient CD27 protein and binds to the extracellular region, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one region or more of CDRs of VH or VL. The peptide comprising plural CDRs can be produced by connecting CDRs directly or via an appropriate peptide linker.

The peptide comprising CDR of the present invention can be produced by constructing DNA encoding CDRs of VH and VL of a monoclonal antibody which specifically recognizes the sugar chain-deficient CD27 protein and binds to the extracellular region, inserting the DNA into an expression vector for prokaryote or an expression vector for eukaryote, and then introducing the expression vector into a prokaryote or eukaryote to express the peptide.

The peptide comprising CDR can also be produced by a chemical synthesis method such as Fmoc method (fluorenylmethoxycarbonyl method) or tBoc method (t-butyloxycarbonyl method).

The antibody of the present invention includes an antibody conjugate in which a monoclonal antibody or an antibody fragment thereof which specifically recognizes the sugar chain-deficient CD27 protein and binds to the extracellular region is chemically or genetically bound to an agent, a protein, a radioisotope or the like.

The conjugate of the present invention can be produced by chemically conjugating an agent, a protein, a radioisotope or the like to the N-terminal side or C-terminal side of an H chain or an L chain of the monoclonal antibody or the antibody fragment thereof which specifically recognizes the sugar chain-deficient CD27 protein and binds to the extracellular region in the present invention, an appropriate substituent or side chain of the antibody or the antibody fragment, a sugar chain in the antibody or the antibody fragment or the like [*Antibody Engineering Handbook*, edited by Osamu Kanemitsu, published by Chijin Shokan (1994)].

Also, the conjugate can be genetically produced by linking a DNA encoding the monoclonal antibody or the antibody fragment thereof which specifically recognizes the sugar chain-deficient CD27 protein and binds to the extracellular region in the present invention to other DNA encoding a protein to be conjugated, inserting the DNA into a vector for expression, and introducing the expression vector into a host cell of a prokaryote or eukaryote.

The agent includes a chemotherapeutic agent, a therapeutic antibody, an immunostimulator, an agent having high molecular weight, and the like.

The protein includes cytokine, a growth factor, a toxic protein, and the like.

Furthermore, the agent to be conjugated to the antibody or the antibody fragment thereof may be in a form of a prodrug. The prodrug in the present invention is an agent which is subjected to chemical modification by an enzyme existing in the tumor environment and is converted to a substance having an activity of damaging the tumor cells.

The chemotherapeutic agent includes any chemotherapeutic agents such as an alkylating agent, a nitrosourea agent, a metabolism antagonist, an anticancer antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor.

Examples of the chemotherapeutic agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), doxorubicin lipo (Doxyl), epirubicin, gemcitabine (Gemsal), daunorubicin, daunorubicin lipo (Daunozome), procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, CPT-11, 10-hydroxy-7-ethylcamptothecin (SN38), floxuridine, fludarabine, hydroxyurea, iphosphamide, idarubicin, mesna, irinotecan, nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, a Flt3 inhibitor, a vascular endothelial growth facotr receptor (VEGFR) inhibitor, a fibroblast growth factor receptor (FGFR) inhibitor, an epidermal growth factor receptor (EGFR) inhibitor (such as Iressa and Tarceva), radicicol, 17-allylamino-17-demethoxygeldanamycin, rapamycin, amsacrine, all-trans-retinoic acid, thalidomide, anastrozole, fadrozole, letrozole, exemestane, gold thiomalate, D-penicillamine, bucillamine, azathioprine, mizoribine, cyclosporine, rapamycin, hydrocortisone, bexarotene (such as Targretin), tamoxifen, dexamethasone, progestin substances, estrogen substances, anastrozole (such as Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, gemtuzumab, ibritumomab tiuxetan, 131 tositumomab, Targretin, ozogamine, clarithromycin, leucovorin, ifosfamide, ketoconazole, aminoglutethimide, suramin, methotrexate, maytansinoid and derivatives thereof.

The method for conjugating the chemotherapeutic agent with the antibody includes a method in which the chemotherapeutic agent and an amino group of the antibody are conjugated via glutaraldehyde, a method in which an amino group of the chemotherapeutic agent and a carboxyl group of the antibody are bound via water-soluble carbodiimide, and the like.

The therapeutic antibody includes an antibody against an antigen in which apoptosis is induced by binding of the antibody, an antibody against an antigen participating in formation of morbid state of tumor, an antibody which regulates immunological function and an antibody relating to angiogenesis in the morbid part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, EGFR and the like.

The antigen which regulates immunological function includes CD4, CD40, CD40 ligand, B7 family molecule (such as CD80, CD86, CD274, B7-DC, B7-H2, B7-H3, and B7-H4), ligand of B7 family molecule (such as CD28, CTLA-4, ICOS, PD-1, and BTLA), OX-40, OX-40 ligand, CD137, tumor necrosis factor (TNF) receptor family molecule (such as DR4, DR5, TNFR1, and TNFR2), TNF-related apoptosis-inducing ligand receptor (TRAIL) family molecule, receptor family of TRAIL family molecule (such as TRAIL-R1, TRAIL-R2, TRAIL-R3, and TRAIL-R4), receptor activator of nuclear factor kappa B ligand (RANK), RANK ligand, CD25, folic acid receptor 4, cytokine [interleukin-1α (hereinafter interleukin is referred to as "IL"), IL-1β, IL-4, IL-5, IL-6, IL-10, IL-13, transforming growth factor (TGF)β, and TNFα], receptors of these cytokines, chemokine (such as SLC, ELC, 1-309, TARC, MDC, and CTACK) and receptors of these chemokines.

The antigen for the antibody which inhibits angiogenesis in the morbid part includes vascular endothelial growth factor (VEGF), angiopoietin, fibroblast growth factor (FGF), EGF, platelet-derived growth factor (PDGF), insulin-like growth factor (IGF), erythropoietin (EPO), TGFβ, IL-8, ephilin, SDF-1 and the like.

The immunostimulator may be any natural products known as immunoadjuvants. Examples of an agent enhancing immunogen include β-1,3-glucan (lentinan, schizophyllan), α-galactosylceramide (KRN7000), fungus powder (picibanil, BCG) and fungus extract (krestin).

The agent having high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropylmethacrylamide, and the like.

By binding these compounds having high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [*Bioconjugate Drug*, Hirokawa Shoten (1993)].

For example, the method for binding PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The cytokine or the growth factor may be any cytokine or growth factor, so long as it enhances cells such as NK cells, macrophages and neutrophils. Examples include interferon (hereinafter referred to as "IFN")-α, INF-β, INF-γ, IL-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like.

The toxic protein includes ricin, diphtheria toxin, ONTAK and the like, and also includes a toxic protein in which mutation is introduced into a protein in order to control the toxicity.

The radioisotope includes $^{131}I$, $^{125}I$, $^{90}Y$, $^{64}Cu$, $^{199}Tc$, $^{77}Lu$, $^{211}At$ and the like. The radioisotope can directly be conjugated with the antibody by Chloramine-T method. Also, a substance chelating the radioisotope can be conjugated with the antibody. The chelating agent includes methylbenzyldiethylene-triaminepentaacetic acid (MX-DTPA) and the like.

In the present invention, the antibody used in the present invention can be administered in combination with one or more of other agents, and radiation irradiation can be also used in combination. The other agent includes the above-described chemotherapeutic agent, therapeutic antibody, immunostimulator such as cytokine, and the like.

The radiation irradiation includes photon (electromagnetic) irradiation such as X-ray or γ-ray, particle irradiation such as electron beam, proton beam or heavy particle beam, and the like In the method for combined administration, the agent may be simultaneously administered with the antibody used in the present invention, or the agent may be administered before or after the administration of the antibody used in the present invention.

The detection method, determination method, detection reagent determination reagent or diagnostic agent in the present invention includes a method in which a specified label is used by labeling the antibody of the present invention. The label includes a label which is used in the general immunological detection or measuring method, and examples include enzymes such as alkaline phosphatase, peroxidase and luciferase, luminescent materials such as acridinium ester and lophine, fluorescent materials such as fluorescein isothiocyanate (FITC) and trimethylrhodamine (RITC), and the like.

Hereinafter, the production process of the antibody of the present invention will be described in more detail.
1. Production Process of Monoclonal Antibody
(1) Preparation of Antigen In accordance with the following procedure, sugar chain-deficient CD27 as an antigen or a cell expressing the sugar chain-deficient CD27 can be obtained by introducing an expression vector comprising a cDNA encoding full-length or partial-length CD27 into yeast, an insect cell, an animal cell or the like, in which an activity of an enzyme capable of adding Gal to GalNAc bound to Ser/Thr on the polypeptide, a protein involved in the activity of the enzyme or a protein involved in the transportation of UDP-galactose is decreased or deleted, in the O-linked sugar chain synthesis process.

Also, the sugar chain-deficient CD27 can be purified from a variety of human-derived cultured cells, human tissues and the like which express a large amount of the sugar chain-deficient CD27 onto a cell membrane or into a culture medium, to thereby prepare antigens. Alternatively, a synthetic peptide having a partial sequence of the sugar chain-deficient CD27 can be prepared and used as an antigen. Further, the sugar chain-deficient CD27 can also be obtained by an in vitro addition of a sugar chain to the CD27 that was expressed and purified using a prokaryote, such as *Escherichia coli*, which is devoid of a sugar chain-adding ability.

In addition, similarly, a cell which expresses CD27 containing a normal O-linked sugar chain can be obtained by introducing an expression vector comprising a cDNA encoding full-length or partial-length CD27 into a host cell (such as yeast, insect cell, or animal cell) which has a normal O-linked sugar chain synthesis process, and purifying the CD27 protein containing a normal O-linked sugar chain from the thus obtained cell.

The sugar chain-deficient CD27, the CD27 protein containing a normal O-linked sugar chain or the expression cell obtained as above can be used for screening the desired antibody, and confirming the reactivity of the obtained antibody for an antigen.

The polypeptide used in the present invention can be produced by expressing a DNA encoding the polypeptide in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like.

For example, the polypeptide used in the present invention can be produced using the following method. Firstly, a recombinant vector is prepared by introducing a full length cDNA into downstream of a promoter of an appropriate expression vector. At this time, if necessary, a DNA fragment having an appropriate length containing a region encoding the polypeptide based on the full length cDNA, and the DNA fragment may be used instead of the above full length cDNA. Next, a transformant producing the polypeptide can be obtained by introducing the recombinant vector into a host cell suitable for the expression vector.

The host cell may be any one, so long as it has the ability to add an O-linked sugar chain and can express the gene of interest, and includes *Escherichia coli*, an yeast, an insect cell, an animal cell and the like.

The expression vector includes vectors which can replicate autonomously in the host cell to be used or vectors which can be integrated into a chromosome comprising an appropriate promoter at such a position that the DNA encoding the polypeptide can be transcribed.

When a prokaryote such as *Escherichia coli* is used as the host cell, it is preferred that the recombinant vector is autonomously replicable in the prokaryote and contains a promoter, a ribosome binding sequence, the DNA used in the present invention and a transcription termination sequence. The recombinant vector may further comprise a gene regulating the promoter.

The expression vector includes, for example, pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides).

In the nucleotide sequence of DNA encoding the polypeptide used in the present invention, nucleotides can be arranged so as to obtain a suitable codon for expression in the host so that the producing ratio of the polypeptide of interest can be improved. Furthermore, the transcription termination sequence is not essential to express a gene in the above recombinant vector, it is preferred to arrange a transcription terminating sequence immediately downstream of the structural gene.

The host cell includes microorganisms belonging to the genera *Escherichia*, and examples include *Escherichia coli* XL 1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α, and the like.

Any introduction method for the recombinant vector can be used, so long as it is a method for introducing DNA into the above-described host cell, and examples include a method using a calcium ion described in *Proc. Natl. Acad. Sci. USA*, 69, 2110 (1972), methods described in *Gene*, 17, 107 (1982) and *Molecular & General Genetics*, 168, 111 (1979) and the like.

When an animal cell is used as the host cell, an expression vector includes, for example, pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840, (1987)], pcDNAI/Amp (manufactured by Invitrogen), pREP4 (manufactured by Invitrogen), pAGE103 [*J. Biochemistry*, 101, 1307 (1987)], pAGE210, pME18SFL3, pKANTEX93 (WO 97/10354) and the like.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter and the like. Also, the enhancer of the IE gene of human CMV can be used together with the promoter.

The host cell may be any one, so long as it is a cell line in which an activity of an enzyme capable of adding Gal to N-acetylgalactosamine (GalNAc) bound to Ser/Thr on the polypeptide, a protein involved in the activity of the enzyme or a protein involved in the transportation of uridine 5'-diphospate-galactose (UDP-galactose) is decreased or deleted, in the sugar chain synthesis process. Specifically, the host cell may be a Lec8 mutant [ACS Symp. Ser. 128, 214 (1980)], which is a Chinese hamster ovary (CHO) cell devoid of a UDP-galactose transporter.

Further, even though the cell is not deficient in an activity of an enzyme involved in the sugar chain synthesis process, or an activity of the transporter protein, a cell line in which the function of an enzyme such as UDP-galactose transporter (also referred to as UDP-galactose translocator, UGALT), or core 1 synthase, glycoprotein-n-acetylgalactosamine 3-beta-galactosyltransferase (C1GALT1, also referred to as core 1 beta-3-gal-t, t synthase) or C1GALT1-specific chaperone 1

(c1galt1c1, also referred to as core 1 beta-3-galactosyltransferase-specific molecular chaperone (COSMC), C1GALT2), or the function of a transporter protein is decreased or deleted may be used.

Examples of the cell in which an activity of an enzyme involved in the sugar chain synthesis process, or an activity of the transporter protein is not deleted include Namalwa cells, simian COS cells, Chinese hamster ovary (CHO) cells, HBT5637 (Japanese Published Unexamined Patent Application No. 299/88), and the like.

Examples of the method for suppressing the gene function include antisense method, ribozyme method [Proc. Natl. Acad. Sci. U.S.A., 96, 1886 (1999)], homologous recombination method [*Manipulating the Mouse Embryo A Laboratory Manual*, Second Edition, Cold Spring Harbor Laboratory Press (1994), *Gene Targeting, A Practical Approach*, IRL Press at Oxford University Press (1993)], RNA-DNA oligonucleotide (RDO) method, RNA interference (RNAi) method [*Nature*, 391, 806, (1998), *Proc. Natl. Acad. Sci. USA* 95, 15502, (1998), *Nature*, 395, 854, (1998), *Proc. Natl. Acad. Sci. USA*), 96, 5049, (1999), *Cell*, 95, 1017, (1998), *Proc. Natl. Acad. Sci. USA*, 96, 1451, (1999), *Proc. Natl. Acad. Sci. USA*, 95, 13959, (1998), *Nature Cell Biol.*, 2, 70, (2000)], method using retrovirus, method using transposon [*Nature Genetics*, 25, 35, (2000)], and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

As the expression method of the gene, in addition to direct expression, secretory production, fusion protein expression and the like in accordance with the method described in *Molecular Cloning, A Laboratory Manual*, Second Edition, Cold Spring Harbor Laboratory Press (1989) can be carried out. When expression is carried out in a cell derived from eukaryote, a polypeptide to which a sugar or a sugar chain is added can be obtained.

The polypeptide used in the present invention can be produced by culturing the thus obtained transformant in a medium to form and accumulate the polypeptide in the culture, and recovering it from the culture. The method for culturing the transformant in the medium is carried out according to the usual method used in culturing of hosts.

When a microorganism transformed with a recombinant vector containing an inducible promoter as a promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for the Biological Medicine*, 73, 1 (1950)], the media to which fetal calf serum, etc. is added, and the like.

The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Thus, the polypeptide used in the present invention can be produced by culturing a transformant derived from a microorganism, an animal cell or the like which comprises a recombinant vector into which a DNA encoding the polypeptide used in the present invention is inserted, in accordance with a general culturing method, to thereby form and accumulate the polypeptide, and then recovering the polypeptide from the culture.

Regarding the expression method of gene, in addition to direct expression, secretory production, fusion protein expression and the like can be carried out according to the method described in *Molecular Cloning, A Laboratory Manual*, Second Edition, Cold Spring Harbor Laboratory Press (1989).

The process for producing the polypeptide includes a method of intracellular expression in a host cell, a method of extracellular secretion from a host cell, a method for producing on a host cell membrane outer envelope, and the like. The appropriate method can be selected by changing the host cell used and the structure of the polypeptide produced.

When the polypeptide is produced in a host cell or on a host cell membrane outer envelope, the gene product can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and WO 94/23021, and the like.

Also, the production amount can be increased in accordance with the method described in Japanese Published Unexamined Patent Application No. 227075/90 utilizing a gene amplification system using a dihydrofolate reductase gene.

The polypeptide can be isolated and purified from the above culture, for example, as follows.

When the polypeptide is intracellularly expressed in a dissolved state, the cells after culturing are collected by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When the polypeptide is expressed intracellularly by forming an inclusion body, the cells are collected, disrupted and centrifuged in the same manner, and the inclusion body of the polypeptide are collected as a precipitation fraction. The collected inclusion body of the protein is solubilized with a protein denaturing agent. The protein is made into a normal three-dimensional structure by diluting or dialyzing the solubilized solution, and then a purified product of the polypeptide is obtained by the same isolation purification method as above.

Also, the polypeptide used in the present invention can be produced by a chemical synthesis method, such as Fmoc (fluorenylmethyloxycarbonyl) method or tBoc (t-butyloxycarbonyl) method. Also, it can be chemically synthesized using a peptide synthesizer manufactured by Advanced ChemTech, Perkin-Elmer, Pharmacia, Protein Technology Instrument, Synthcell-Vega, PerSeptive, Shimadzu Corporation, or the like.

(2) Immunization of Animal and Preparation of Antibody-Producing Cell

A mouse, rat or hamster 3 to 20 weeks old is immunized with the antigen prepared above, and antibody-producing cells are collected from the spleen, lymph node or peripheral blood of the animal. Also, when the increase of a sufficient titer in the above animal is recognized due to low immunogenecity, a CD27 knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies-A Laboratory Manual* (Cold Spring Harbor Laboratory (1988)] or the like. A mouse, rat or hamster showing a sufficient antibody titer in their sera against the antigen used for the immunization is used as the supply source of antibody-producing cells.

In fusion of the antibody-producing cells and myeloma cells, on the 3rd to 7th days after final administration of the antigen, tissue containing the antibody-producing cells such as the spleen from the immunized mouse, rat or hamster is excised to collect the antibody-producing cell. When the spleen cells are used, the spleen is cut out in an MEM medium (Nissui Pharmaceutical) and loosened by tweezers and centrifuged (at 1200 rpm, for 5 minutes). Then, the supernatant is discarded and a Tris-ammonium chloride buffer pH. 7.65) is applied for 1 to 2 minutes to remove erythrocytes. After washing 3 times with the MEM medium, antibody-producing cells for fusion are provided.

(3) Preparation of Myeloma Cell

An established cell line obtained from mouse is used as myeloma cells. Examples include 8-azaguanine-resistant mouse (derived from BALB/c mouse) myeloma cell line P3-X63Ag8-U1 (P3-U1) [*Current Topics in Microbiology and Immunology,* 18, 1-7 (1978)], P3-NS1/1-Ag41 (NS-1) [*European J. Immunology,* 6, 511-519 (1976)], SP2/0-Ag14 (SP-2) [*Nature,* 276, 269-270 (1978)], P3-X63-Ag8653 (653) [*J. Immunology,* 123, 1548-1550 (1979)], P3-X63-Ag8 (X63) [*Nature,* 256, 495-497 (1975)] and the like.

The above cell lines are subcultured in an 8-azaguanine medium [a medium in which glutamine (1.5 mM), 2-mercaptoethanol ($5 \times 10^{-5}$ M), gentamicin (10 µg/ml) and fetal calf serum (FCS) are added to RPMI-1640 medium (hereinafter referred to as "normal medium") and 8-azaguanine (15 µg/ml) is further added] and they are subcultured in the normal medium 3 or 4 days before cell fusion to ensure the cell number of $2 \times 10^7$ or more on the day for fusion.

(4) Cell Fusion

The above-described antibody-producing cells and myeloma cells were sufficiently washed with an MEM medium or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells:the myeloma cells=5 to 10:1, followed by centrifugation (1200 rpm, 5 minutes). Then, the supernatant is discarded, and precipitated cell group is sufficiently loosen. To $10^8$ of the antibody-producing cells, 0.2 to 1 mL of a mixture solution of 2 g of polyethylene glycol-1000 (PEG-1000), 2 mL of MEM and 0.7 mL of dimethylsulfoxide is added under stirring at 37° C., and 1 to 2 mL of MEM medium is added several times every one or two minutes, and MEM medium is added to give a total amount of 50 mL.

After centrifugation (900 rpm, 5 minutes), the supernatant is discarded, the cells are gently loosen, and the cells are gently suspended in 100 mL of HAT medium [a medium in which hypoxanthine ($10^{-4}$ mol/l), thymidine ($1.5 \times 10^{-5}$ mol/l) and aminopterin ($4 \times 10^{-7}$ mol/l) is added to the normal medium] by suction and sucking out using a measuring pipette. The suspension is dispensed at 100 µl/well onto a 96-well culturing plate and cultured in a 5% $CO_2$ incubator at 37° C. for 7 to 14 days.

After the culturing, a portion of the culture supernatant is sampled and a hybridoma which is reactive to an antigen containing the polypeptide used in the present invention and is not reactive to an antigen which does not contain the polypeptide is selected by binding assay as described below.

Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Monoclonal Antibody

The hybridoma cells producing an anti-CD27 monoclonal antibody obtained in (4) are administered by intraperitoneal injection into 8- to 10-week-old mice or nude mice treated with pristane (0.5 ml of 2,6,10,14-tetramethylpentadecane (pristane) is intraperitoneally administered, followed by feeding for 2 weeks) at a dose of $2 \times 10^6$ to $5 \times 10^7$ cells/animal. The hybridoma develops ascites tumor in 10 to 21 days.

The ascitic fluid is collected from the above mice, centrifuged (at 3,000 rpm, for 5 minutes) to remove solids, subjected to salting out with 40 to 50% saturated ammonium sulfate and then precipitated by caprylic acid, passed through a DEAE-Sepharose column, a protein A column or a gel filtration column to collect an IgG or IgM fraction as a purified monoclonal antibody.

The subclass of the antibody can be determined using a subclass typing kit by enzyme immunoassay. The amount of the protein can be determined by the Lowry method or from the absorbance at 280 nm.

(6) Binding Assay

As the antigen, a gene-introduced cell or a recombinant protein obtained by introducing an expression vector containing a cDNA encoding CD27 polypeptide used in the present invention into *Escherichia coli*, yeast, an insect cell, an animal cell or the like, or a purified polypeptide or partial peptide obtained from a human tissue is used.

When the antigen is a partial peptide, a conjugate is prepared with BSA (bovine serum albumin), KLH (keyhole limpet hemocyanin) or the like and is used.

After making these antigens into a solid layer by dispensing in a 96-well plate, a serum of an animal to be immunized, a culture supernatant of a monoclonal antibody-producing hybridoma or a purified antibody is dispensed therein as the primary antibody and allowed to react. After thoroughly washing with PBS or PBS-0.05% Tween, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction is carried out in response to the label of the secondary antibody.

The antibody which competes with the thus obtained monoclonal antibody for its binding to the extracellular region of CD27 can be prepared by adding an antibody to be tested to the above-mentioned binding assay system and carrying out reaction. That is, a monoclonal antibody which competes with the thus obtained monoclonal antibody for its binding to the extracellular region of the sugar chain-deficient CD27 can be prepared by carrying out a screening of an antibody by which the binding of the monoclonal antibody is inhibited when the antibody to be tested is added.

In addition, an antibody which binds to an epitope which is recognized by a monoclonal antibody that recognizes the sugar chain-deficient CD27 and binds to the extracellular region thereof, may be obtained by identifying an epitope of the antibody obtained using the above-mentioned binding assay system, and constructing a partial sugar chain binding peptide of the identified epitope, or a sugar chain binding peptide mimicking a three-dimensional structure of the epitope, followed by immunization.

2. Preparation of Recombinant Antibody

As production examples of recombinant antibodies, processes for producing a human chimeric antibody and a humanized antibody are shown below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to κ class, and the like. As the DNAs encoding CH and CL of a human antibody, a chromosomal DNA comprising an exon and an intron or cDNA can be used. As the expression vector for animal cell, any expression vector can be used, so long as a gene encoding the C region of a human antibody can be inserted thereinto and expressed therein. Examples include pAGE107 [*Cytotechnol.*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981)], pSG1bd2-4 [*Cytotechnol.*, 4, 173 (1990)], pSEIUK1Sed1-3 [*Cytotechnol.*, 13, 79 (1993)] and the like.

Examples of a promoter used for an expression vector for animal cell include an SV40 early promoter [*J. Biochem.*, 101, 1307 (1987)], a Moloney mouse leukemia virus LTR [*Biochem. Biophys. Res. Commun.*, 149, 960 (1987)], an immunoglobulin H chain promoter [*Cell*, 41, 479 (1985)] and the like. In addition, examples of enhancer used for an expression vector for animal cell include enhancer [*Cell*, 33, 717 (1983)].

The vector for expression of recombinant antibody may be either of a type in which a gene encoding an antibody H chain and a gene encoding an antibody L chain exist on separate vectors or of a type in which both genes exist on the same vector (tandem type). In respect of easiness of construction of a vector for expression of recombinant antibody, easiness of introduction into animal cells, and balance between the expression amounts of antibody H and L chains in animal cells, a tandem type of the vector for expression of recombinant antibody is more preferred [*J. Immunol. Methods*, 167, 271 (1994)]. Examples of the tandem type of the vector for expression of recombinant antibody include pKANTEX93 (WO 97/10354), pEE18 [*Hybridoma*, 17, 559 (1998)], and the like.

(2) Obtaining of cDNA Encoding V Region of Antibody Derived from Non-Human Animal and Analysis of Amino Acid Sequence cDNAs encoding VH and VL of an antibody derived from a non-human animal are obtained as follows.

mRNA is extracted from hybridoma cells producing an antibody derived from a non-human animal to synthesize cDNA. The synthesized cDNA is cloned into a vector such as a phage or a plasmid, to prepare a cDNA library. Each of a recombinant phage or recombinant plasmid containing cDNA encoding VH or VL is isolated from the library using DNA encoding a part of the C region or V region of an antibody derived from a non-human animal as the probe. The full length of the nucleotide sequences of VH and VL of the antibody derived from a non-human animal of interest on the recombinant phage or recombinant plasmid are determined, and the full length of the amino acid sequences of VH and VL are deduced from the nucleotide sequences.

The non-human animal may be any animal such as mouse, rat, hamster or rabbit, so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)] and the like. Examples of the method for preparing mRNA from total RNA include an oligo (dT) immobilized cellulose column method [*Molecular Cloning, A Laboratory Manual*, Second Edition, Cold Spring Harbor Laboratory Press (1989)] and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods [*Molecular Cloning, A Laboratory Manual*, Cold Spring Harbor Lab. Press (1989); *Current Protocols in Molecular Biology*, Supplement 1-34]; a method using a commercially available kit such as Super Script™ Plasmid System for cDNA Synthesis and Plasmid Cloning (manufactured by GIBCO BRL), ZAP-cDNA Kit (manufactured by Stratagene), etc.; and the like.

The vector into which the synthesized cDNA using mRNA extracted from a hybridoma cell as the template is inserted for preparing a cDNA library may be any vector, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning: A Practical Approach*, I, 49 (1985)], Lambda BlueMid (manufactured by Clontech), λExCell and pT7T3 18U (manufactured by Pharmacia), pcD2 [*Mol. Cell. Biol.*, 3, 280 (1983)], pUC18 [*Gene*, 33, 103 (1985)], and the like.

Any *Escherichia coli* for introducing the cDNA library constructed by a phage or plasmid vector may be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222: 778 (1983)], NM522 [*J. Mol. Biol.*, 166, 1 (1983)], K802 [*J. Mol. Biol.*, 16, 118 (1966)], JM105 [*Gene*, 38, 275 (1985)], and the like.

A colony hybridization or plaque hybridization method using an isotope- or fluorescence-labeled probe may be used for selecting cDNA clones encoding VH and VL of an antibody derived from a non-human animal from the cDNA library [*Molecular Cloning, A Laboratory Manual*, Second Edition, Cold Spring Harbor Laboratory Press (1989)]. Also, the cDNAs encoding VH and VL can be prepared through polymerase chain reaction (hereinafter referred to as "PCR"; *Molecular Cloning, A Laboratory Manual*, Second Edition, Cold Spring Harbor Laboratory Press (1989); *Current Protocols in Molecular Biology*, Supplement 1-34) by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(-) (manufactured by Stratagem), carrying out the reaction by a usually used nucleotide analyzing method such as the dideoxy method of Sanger, F. et al. [*Proc. Natl. Acad. Sci. USA*, 74, 5463 (1977)], and then analyzing the sequence using an automatic nucleotide sequence analyzer such as A.L.F. DNA sequencer (manufactured by Pharmacia).

Whether the obtained cDNAs encode the full amino acid sequences of VL and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies [*Sequences of Proteins of Immunological Interest*, US Dept. Health and Human Services (1991)], and the subgroup to which they belong can also be known. Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

Moreover, the novelty of the sequence can be examined by carrying out a homology search with sequences in any database, for example, SWISS-PROT, PIR-Protein or the like using the full length of the amino acid sequences of VH and VL, for example, according to the BLAST method [*J. Mol. Biol.*, 215, 403 (1990)] or the like.

(3) Construction of Vector for Expression of Human Chimeric Antibody cDNAs encoding VH and VL of antibody of non-human animal are cloned in the upstream of genes encoding CH or CL of human antibody of vector for expression of recombinant antibody mentioned in the above 2(1) to thereby construct a vector for expression of human chimeric antibody. For example, each cDNA encoding VH and VL of antibody of non-human animal is ligated to synthetic DNA comprising a nucleotide sequence of 3'-terminal of VH or VL of antibody of non-human animal and a nucleotide sequence of 5'-terminal of CH or CL of human antibody and having recognition sequence of an appropriate restriction enzyme at both ends, and cloned so that each of them is expressed in an appropriate form in the upstream of gene encoding CH or CL of human antibody of the vector for expression of humanized antibody mentioned in the above 2(1) to construct a vector for expression of human chimeric antibody. In addition, cDNA encoding VH or VL or non-human animal is amplified by PCR using a synthetic DNA having a recognition sequence of an appropriate restriction enzyme at both terminals and each of them is cloned to the vector for expression of recombinant antibody mentioned in the above 2(1).

(4) Construction of cDNA Encoding V Region of Humanized Antibody cDNAs encoding VH or VL of a humanized antibody can be obtained as follows. First, amino acid sequences of framework region (hereinafter referred to as "FR") in VH or VL of a human antibody to which amino acid sequences of CDRs in VH or VL of an antibody derived from a non-human animal antibody are transplanted are selected. Any amino acid sequences of FR in VH or VL of a human antibody can be used, so long as they are from human. Examples include amino acid sequences of FRs in VH or VL of human antibodies registered in database such as Protein Data Bank or the like, and amino acid sequences common to subgroups of FRs in VH or VL of human antibodies [*Sequences of Proteins of Immunological Interest*, US Dept. Health and Human Services (1991)], and the like. In order to inhibit the binding activity of the antibody, amino acid sequences having high homology (at least 60% or more) with the amino acid sequence of FR in VH or VL of the original antibody is selected. Then, amino acid sequences of CDRs of VH or VL of the original antibody are grafted to the selected amino acid sequence of FR in VH or VL of the human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed. Based on the designed nucleotide sequences, several synthetic DNAs having a length of about 100 nucleotides are synthesized, and PCR is carried out using them. In this case, it is preferred in each of the H chain and the L chain that 6 synthetic DNAs are designed in view of the reaction efficiency of PCR and the lengths of DNAs which can be synthesized.

Furthermore, the cDNA encoding VH or VL of a humanized antibody can be easily cloned into the vector for expression of humanized antibody constructed in the (1) of this item 2 by introducing the recognition sequence of an appropriate restriction enzyme to the 5' terminal of the synthetic DNAs existing on the both ends. After the PCR, an amplified product is cloned into a plasmid such as pBluescript SK (-) (manufactured by Stratagene) or the like, and the nucleotide sequence is determined according to the method described in (2) of this item 2 to obtain a plasmid having a DNA sequence encoding the amino acid sequence of VH or VL of a desired humanized antibody.

(5) Modification of Amino Acid Sequence of V Region of Humanized Antibody

It is known that when a humanized antibody is produced by simply grafting only CDRs in VH and VL of an antibody derived from a non-human animal into FRs of VH and VL of a human antibody, its antigen binding activity is lower than that of the original antibody derived from a non-human animal [*BIO/TECHNOLOGY*, 9, 266 (1991)]. As the reason, it is considered that several amino acid residues in not only CDRs but also FRs directly or indirectly relate to antigen binding activity in VH and VL of the original antibody derived from a non-human animal, and as a result of grafting of CDRs, such amino acid residues are changed to different amino acid residues of FRs in VH and VL of a human antibody. In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original antibody derived from a non-human animal to thereby increase the antigen binding activity which has been decreased [*BIO/TECHNOLOGY*, 9, 266 (1991)]. In the production of a humanized antibody, how to efficiently identify the amino acid residues relating to the antigen binding activity in FR is most important, so that the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. Although the information of the three-dimensional structure of antibodies has been useful in the production of a humanized antibody, no method for producing a humanized antibody which can be applied to any antibodies has been established yet. Therefore, various attempts must be currently be necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in (4) of this item 2. With regard to the amplified product obtained by the PCR, the nucleotide sequence is determined according to the method as described in (2) of this item 2 so that whether the objective modification has been carried out is confirmed.

(6) Construction of Vector for Expression of Humanized Antibody

A vector for expression of humanized antibody can be constructed by cloning each cDNA encoding VH or VL of a constructed recombinant antibody into upstream of each gene encoding CH or CL of the human antibody in the vector for expression of humanized antibody as described in (1) of this item 2.

For example, when recognizing sequences of an appropriate restriction enzymes are introduced to the 5'-terminal of synthetic DNAs positioned at both ends among synthetic DNAs used in the construction of VH or VL of the humanized antibody in (4) and (5) of this item 2, cloning can be carried out so that they are expressed in an appropriate form in the upstream of each gene encoding CH or CL of the human antibody in the vector for expression of humanized antibody as described in (1) of this item 2.

(7) Transient Expression of Recombinant Antibody

In order to efficiently evaluate the antigen binding activity of various humanized antibodies produced, the recombinant antibodies can be expressed transiently using the vector for expression of humanized antibody as described in (3) and (6) of this item 2 or the modified expression vector thereof. Any cell can be used as a host cell, so long as the host cell can express a recombinant antibody.

Among them, generally, COS-7 cell (ATCC CRL1651) is preferably used in view of its high expression amount [*Methods in Nucleic Acids Res.*, CRC Press, 283 (1991)].

Examples of the method for introducing the expression vector into COS-7 cell include a DEAE-dextran method [*Methods in Nucleic Acids Res.*, CRC Press, 283 (1991)], a lipofection method [*Proc. Natl. Acad. Sci. USA*, 84, 7413 (1987)], and the like.

After introduction of the expression vector, the expression amount and antigen binding activity of the recombinant antibody in the culture supernatant can be determined by the enzyme immunoassay [hereinafter referred to as "ELISA"; *Monoclonal Antibodies-Principles and practice*, Third edition, Academic Press (1996), *Antibodies-A Laboratory Manual*, Cold Spring Harbor Laboratory (1988), *Monoclonal Antibody Experiment Manual*, Kodansha Scientific (1987)] and the like.

(8) Stable Expression of Recombinant Antibody

A transformant which stably expresses a recombinant antibody can be obtained by introducing the vector for expression of recombinant antibody described in (3) and (6) of this item 2 into an appropriate host cell.

Examples of the method for introducing the expression vector into a host cell include electroporation [Japanese Published Unexamined Patent Application No. 257891/90, Cytotechnology, 3, 133 (1990)] and the like.

As the animal cell into which a vector for expression of recombinant is introduced, any cell can be used, so long as it is an animal cell which can produce the recombinant antibody.

Examples include mouse SP2/0-Ag14 cell (ATCC CRL1581), mouse P3X63-Ag8.653 cell (ATCC CRL1580), CHO/dhFr-cell (ATCC CRL9096) and CHO/DG44 cell [Somatic Cell and Molecular Genetics, 12,555 (1986)], both of which are two kinds of chinese hamster ovary cells, lection resistance-acquired Lec13 [*Somatic Cell and Molecular genetics*, 12, 55 (1986)], CHO cell in which α1,6-fucosyl-transaferse gene is defected (WO 05/35586), rat YB2/3HL.P2.G11.16Ag.20 cell (ATCC CRL1662), and the like.

In addition to the above host cells, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetyl-glucosamine in the reducing end through α-bond in a complex type N-glycoside-linked sugar chain, or a protein relating to transport of an intracellular sugar nucleotide, GDP-fucose, to the Golgi body are introduced is decreased or deleted, preferably CHO cell in which α1,6-fucosyltransferase gene is defected as described in WO 05/35586, WO 02/31140 or the like, can also be used.

After introduction of the expression vector, transformants which express a recombinant antibody stably are selected in accordance with the method disclosed in Japanese Published Unexamined Patent Application No. 257891/90, by culturing in a medium for animal cell culture containing an agent such as G418 sulfate (hereinafter referred to as "G418", manufactured by Sigma) or the like. Examples of the medium for animal cell culture include RPMI1640 medium (manufactured by Invitrogen), GIT medium (manufactured by Nissui Pharmaceutical), EX-CELL301 medium (manufactured by JRH), IMDM medium (manufactured by Invitrogen), Hybridoma-SFM medium (manufactured by Invitrogen), media obtained by adding various additives such as fetal calf serum (hereinafter referred to as "FCS") to these media, and the like. The recombinant antibody can be produced and accumulated in a culture supernatant by culturing the selected transformants in a medium. The expression amount and antigen binding activity of the recombinant antibody in the culture supernatant can be measured by ELISA or the like. Also, in the transformant, the expression amount of the recombinant antibody can be increased by using dhfr amplification system or the like according to the method disclosed in Japanese Published Unexamined Patent Application No. 257891/90.

The recombinant antibody can be purified from the culture supernatant of the transformant by using a protein A column [*Monoclonal Antibodies-Principles and practice*, Third edition, Academic Press (1996), *Antibodies-A Laboratory Manual*, Cold Spring Harbor Laboratory (1988)].

Any other conventional methods for protein purification can be used. For example, the recombinant antibody can be purified by a combination of gel filtration, ion-exchange chromatography, ultrafiltration and the like.

The molecular weight of the H chain or the L chain of the purified recombinant antibody or the antibody molecule as a whole is determined by polyacrylamide gel electrophoresis (hereinafter referred to as "SDS-PAGE") [*Nature*, 227, 680 (1970)], Western blotting [*Monoclonal Antibodies-Principles and practice*, Third edition, Academic Press (1996), *Antibodies-A Laboratory Manual*, Cold Spring Harbor Laboratory (1988)], and the like.

3. Activity Evaluation of the Antibody or Antibody Fragment of the Present Invention Reaction specificity of the purified antibody or antibody fragment of the present invention can be evaluated in the following procedure.

Using a cell expressing a normal sugar chain, and a cell line in which an activity of an enzyme capable of adding Gal to GalNAc bound to Ser/Thr on the polypeptide, a protein involved in the activity of the enzyme or a protein involved in the transportation of uridine 5'-diphospate-galactose (UDP-galactose) is decreased or deleted, in the O-linked sugar chain synthesis process, as a host, CD27-expressing cells can be respectively constructed which express CD27-encoding nucleotide sequence (SEQ ID NO:1). In this manner, a cell expressing CD27 having a normal O-linked sugar chain, and a cell expressing sugar chain-deficient CD27 can be constructed, and the reactivity of the cell lines expressing each of CD27 with the purified antibody can be estimated by ELISA, fluorescent antibody technique [Cancer Immunol. Immunother., 36, 373 (1993)], or the like.

Alternatively, the extracellular region of CD27 is expressed as a soluble form such as fusion protein in each of the above-mentioned host cells, and purified under appropriate conditions to prepare respective CD27 soluble proteins retaining a three-dimensional structure.

Examples of the fusion protein may include a fusion of the CD27 protein with another polypeptide such as antibody constant region (also referred to as Fc), GST tag, histidine tag (also referred to as His tag) or Myc tag. The fusion protein may be separated and purified by using an affinity column such as Protein A, nickel column, specific antibody column, or the like.

The reactivity of the purified CD27 soluble protein with the purified antibody can be measured by surface plasmon resonance (SPR)-aided BIAcore™, ELISA, immunoprecipitation or the like method [Monoclonal Antibodies-Principles and Practice, Third edition, Academic Press (1996), Antibodies-A Laboratory Manual, Cold Spring Harbor Laboratory (1988)].

The cytotoxic activity on the cultured cell line expressing the sugar chain-deficient CD27 can be evaluated by measuring CDC activity, ADCC activity or the like, in accordance with a known method [Cancer Immunol. Immunother., 36, 373 (1993)].

4. Method for Diagnosing a Disease Using a Monoclonal Antibody or an Antibody Fragment of the Present Invention which Specifically Recognizes the Sugar Chain-Deficient CD27 and Also Binds to the Extracellular Region Thereof A disease relating to the sugar chain-deficient CD27 can be diagnosed by detecting or quantifying sugar chain-deficient CD27 or a cell expressing the polypeptide, using the antibody or antibody fragment of the present invention.

The disease relating to the sugar chain-deficient CD27 may be any one, so long as it is a disease in which a sugar chain-deficient CD27 polypeptide-expressing cell is found in vivo. Specifically, it may be IgA nephropathy or cancer. Examples of the cancer may include cancer derived from B or T cell differentiation processes.

Specifically, examples include a variety of non-Hodgkin lymphomas which encompass mantle cell lymphoma, chronic lymphocytic leukemia, small lymphocytic leukemia, Burkitt's lymphoma, follicular lymphoma, MALT lymphoma, diffuse large B-cell lymphoma, plasmacytoma, and the like.

The living body sample to be used for the detection or measurement of a sugar chain-deficient CD27 polypeptide in the present invention is not particularly limited, so long as it has a possibility of containing the polypeptide, such as tissue cells, blood, blood plasma, serum, pancreatic juice, urine, fecal matter, tissue fluid or culture medium.

Among diseases relating to sugar chain-deficient CD27, for example, diagnosis of IgA nephropathy can be carried out in the following manner.

On the living body samples collected from two or more of the living bodies of healthy parsons, the expressed amount of the polypeptide in the living body samples of healthy parsons is confirmed by carrying out detection or measurement of a sugar chain-deficient CD27 polypeptide by the following immunological means using the antibody or antibody fragment of the present invention or derivatives thereof.

By examining the expressed amount of the polypeptide also in the living body samples of the parson to be tested in the same manner, the expressed amount is compared with the expressed amount in healthy parsons. When the expressed amount of the polypeptide in the person to be tested is increased in comparison with the healthy persons, it can be diagnosed that cancer is positive.

Among diseases relating to a sugar chain-deficient CD27, for example, diagnosis of a cancer can be carried out in the following manner.

On the living body samples collected from two or more of the living bodies of healthy parsons, the expressed amount of the polypeptide in the living body samples of healthy parsons is confirmed by carrying out detection or measurement of the sugar chain-deficient CD27 by the following immunological means using the antibody or antibody fragment of the present invention or derivatives thereof.

By examining the expressed amount of the polypeptide also in the living body samples of the parson to be tested in the same manner, the expressed amount is compared with the expressed amount in healthy parsons. When the expressed amount of the polypeptide in the person to be tested is increased in comparison with the healthy persons, it can be diagnosed that cancer is positive.

The diagnostic agent containing the antibody or antibody fragment of the present invention or derivatives thereof may further contain a reagent for carrying out an antigen-antibody reaction or a reagent for detection of the reaction depending on the desired diagnostic method. The reagent for carrying out the antigen-antibody reaction includes a buffer, a salt, and the like.

The reagent for detection includes a reagent used for common immunological detection or immunoassay such as antibody or antibody fragment thereof, derivatives thereof, labeled secondary antibody for recognizing the antibody, antibody fragment or derivatives thereof and substrate corresponding to the labeling.

As a method for detection or determination of the amount of the sugar chain-deficient CD27 in the present invention, any known method may be included. For example, an immunological detection method or immunoassay may be exemplified.

An immunological detection or immunoassay is a method in which an antibody amount or an antigen amount is detected or determined using a labeled antigen or antibody. Examples of the immunological detection or immunoassay are radioactive substance-labeled immunoantibody method (RIA), enzyme immunoassay (EIA or ELISA), fluorescent immunoassay (FIA), luminescent immunoassay, Western blotting method, physico-chemical means (such as TIA, LAPIA and PCIA) and the like.

Examples of the radioactive substance-labeled immunoantibody method (RIA) include a method, in which the antibody or antibody fragment of the present invention is allowed to react with an antigen or a cell expressing an antigen, then anti-immunoglobulin antibody subjected to radioactive labeling or a binding fragment thereof is allowed to react therewith, followed by determination using a scintillation counter or the like.

Examples of the enzyme immunoassay (EIA or ELISA) include a method, in which the antibody or antibody fragment of the present invention is allowed to react with an antigen or a cell expressing an antigen, then an anti-immunoglobulin antibody or an binding fragment thereof subjected to antibody labeling is allowed to react therewith and the colored pigment is measured by a spectrophotometer, and, for example, sandwich ELISA may be used.

As a label used in the enzyme immunoassay, any known enzyme label (*Enzyme Immunoassay* edited by Eiji Ishikawa, et al., published by Igaku Shoin) can be used as described already. Examples include alkaline phosphatase labeling, peroxidase labeling, luciferase labeling, biotin labeling and the like.

Sandwich ELISA is a method in which an antibody is bound to a solid phase, antigen to be detected or measured is trapped and another antibody is allowed to react with the trapped antigen. In the ELISA, 2 kinds of antibody which recognizes the antigen to be detected or measured or the antibody fragment thereof in which antigen recognizing site is different are prepared and one antibody or antibody fragments is previously adsorbed on a plate (such as a 96-well plate) and another antibody or antibody fragment is labeled with a fluorescent substance such as FITC, an enzyme such as peroxidase, or biotin.

The plate to which the above antibody is adsorbed is allowed to react with the cell separated from living body or disrupted cell suspension thereof, tissue or disintegrated solution thereof, cultured cells, serum, pleural effusion, ascites, eye solution or the like, then allowed to react with labeled monoclonal antibody or antibody fragment and a detection reaction corresponding to the labeled substance is carried out.

When an antigen concentration in the sample to be tested is measured by the above method, antigen concentration in the sample to be tested can be calculated from a calibration curve prepared by a stepwise dilution of antigen of known concentration.

As antibody used for sandwich ELISA, any of polyclonal antibody and monoclonal antibody may be used or antibody fragments such as Fab, Fab' and F(ab)$_2$ may be used. As a combination of 2 kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay (FIA) includes a method described in the literatures [*Monoclonal Antibodies-Principles and practice*, Third Edition, Academic Press (1996); *Manual for Monoclonal Antibody Experiments*, Kodansha Scientific (1987)] and the like. As a label for the fluorescent immunoassay, any of known fluorescent labels (*Fluorescent Immunoassay*, by Akira Kawao, Soft Science) may be used as described already. Examples include FITC labeling, RITC labeling and the like.

The luminescent immunoassay can be carried out using the methods described in such as *Monoclonal Antibodies-Principles and practice*, Third Edition, Academic Press (1996); *Manual for Monoclonal Antibody Experiments*, Kodansha Scientific (1987) and the like.

As a label used for luminescent immunoassay, any of known luminescent labels [*Bioluminescence and Chemical Luminescence*, Hirokawa Shoten; Rinsho Kensa, 42 (1998)] can be included as described above. Examples include acridinium ester labeling, lophine labeling or the like may be used.

Western blotting is a method in which an antigen or a cell expressing an antigen is fractionated by SDS-polyacrylamide gel electrophoresis [*Antibodies-A Laboratory Manual* (Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example of Western blotting is described below.

Cells or tissues in which a polypeptide having the amino acid sequence represented by SEQ ID NO:2 is expressed are dissolved in a solution and, under reducing conditions, 0.1 to 30 μg as a protein amount per lane is electrophoresed by an SDS-PAGE method. The electrophoresed protein is transferred to a PVDF membrane and allowed to react with PBS containing 1% of BSA (hereinafter referred to as "BSA-PBS") at room temperature for 30 minutes for blocking.

Here, the monoclonal antibody of the present invention is allowed to react therewith, washed with PBS containing 0.05% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL™ Western Blotting Detection Reagents (manufactured by Amersham) or the like to thereby detect a polypeptide having the amino acid sequence represented by SEQ ID NO:2.

As an antibody used for the detection in Western blotting, an antibody which can be bound to a polypeptide having no three-dimensional structure of a natural type is used.

The physicochemical method is specifically carried out using the antibody or antibody fragment of the present invention by reacting CD27 as the antigen with the antibody or antibody fragment of the present invention to form an aggregate, and detecting this aggregate. Other examples of the physicochemical methods include a capillary method, a one-dimensional immunodiffusion method, an immunoturbidimetry and a latex immunoturbidimetry [*Handbook of Clinical Test Methods*, Kanehara Shuppan, 499 (1988)].

For example, in a latex immunodiffusion method, a carrier such as polystyrene latex having a particle size of about 0.1 to 1 μm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is now possible to measure antigen concentration, etc. in the sample to be tested.

Since the antibody or antibody fragment of the present invention is capable of binding to an extracellular region of the sugar chain-deficient CD27 polypeptide, it is preferably used for detecting a cell expressing the polypeptide.

For the detection of the cell expressing the polypeptide, known immunological detection methods can be used, and an immunoprecipitation method, a fluorescent cell staining method, an immune tissue staining method and the like are preferably used. Also, an immunofluorescent staining method using FMAT 8100 HTS system (Applied Biosystem) and the like can be used.

An immunoprecipitation method is a method in which a cell expressing the polypeptide is allowed to react with the monoclonal antibody or antibody fragment of the present invention and then a carrier having specific binding ability to immunoglobulin such as protein G-Sepharose is added so that an antigen-antibody complex is precipitated. Also, the following method can be carried out.

The above-described antibody or antibody fragment of the present invention is solid-phased on a 96-well plate for ELISA and then blocked with BSA-PBS. When the antibody is in a non-purified state such as a culture supernatant of hybridoma cell, anti-mouse immunoglobulin or rat immunoglobulin or protein A or G or the like is previously adsorbed on a 96-well plate for ELISA and blocked with BSA-PBS and a culture supernatant of hybridoma cell is dispensed thereto for binding.

After BSA-PBS is discarded and the residue is sufficiently washed with PBS, reaction is carried out with a dissolved solution of cells or tissues expressing polypeptide having the amino acid sequence represented by SEQ ID NO:2. An immune precipitate is extracted from the well-washed plate with a sample buffer for SDS-PAGE and detected by the above-described Western blotting.

An immune cell staining method and an immune tissue staining method are immunofluorescent staining methods (a flow cytometry) where cells or tissues in which antigen is expressed are treated, if necessary, with a surfactant or methanol to make an antibody easily permeate to the cells or tissues, then the antibody of the present invention is allowed to react therewith, then further allowed to react with an anti-immunoglobulin antibody or binding fragment thereof subjected to fluorescent labeling such as FITC, enzyme label such as peroxidase or biotin labeling and the label is visualized and observed under a microscope or cells are allowed to react with a fluorescence-labeled antibody and analyzed by a flow cytometer.

That can be carried out by the methods described, for example, in the literatures [*Monoclonal Antibodies-Principles and practice*, Third Edition, Academic Press (1996), *Manual for Experiments of Monoclonal Antibodies*, Kodansha Scientific (1987)].

Particularly, since the antibody or antibody fragment of the present invention binds to three-dimensional structure of an extracellular region of the sugar chain-deficient CD27, it can be preferably used for detection of a cell expressing the polypeptide maintaining a natural type three-dimensional structure by a flow cytometry.

In addition, by using FMAT8100HTS system (manufactured by Applied Biosystems) which utilizes the principle of fluorescent antibody staining, the antigen quantity or antibody quantity can be measured without separating the formed antibody-antigen complex and the free antibody or antigen which is not concerned in the formation of the antibody-antigen complex.

5. Method for Diagnosing Disease Using the Monoclonal Antibody or Antibody Fragment of the Present Invention which Reacts with a Sugar Chain-Deficient CD27 Polypeptide The monoclonal antibody or the antibody fragment of the present invention which specifically recognizes a sugar chain-deficient CD27 polypeptide and binds to the extracellular region thereof can be used for treating a disease relating to a sugar chain-deficient CD27 polypeptide.

The disease relating to the sugar chain-deficient CD27 polypeptide may be any one, so long as it is a disease in which a cell expressing the polypeptide is detected in vivo. For example, it may be IgA nephropathy, cancer, or the like.

Further, the disease may also encompass a disease manifesting with nephrose syndrome or renal failure resulting from the development of IgA nephropathy.

Examples of the cancer may include a hematopoietic organ-derived tumor (also referred to as blood cancer) or an epithelial cell-derived solid cancer.

Examples of the blood cancer include, specifically, leukemia, lymphoma (Hodgkin lymphoma, non-Hodgkin lymphoma), multiple myeloma, and the like.

Specific examples of the non-Hodgkin lymphoma include mantle cell lymphoma, chronic lymphocytic leukemia, small lymphocytic leukemia, Burkitt's lymphoma, follicular lymphoma, MALT lymphoma, diffuse large B-cell lymphoma, plasmacytoma, and the like.

Specific examples of the solid cancer include breast cancer, uterine cancer, colorectal cancer, stomach cancer, ovarian cancer, lung cancer, renal cancer, rectal cancer, thyroid cancer, uterine cervix cancer, small intestinal cancer, prostate cancer, pancreatic cancer, and the like.

The therapeutic agent of the present invention includes a therapeutic agent for cancer comprising the antibody or antibody fragment of the present invention, as an active ingredient. The therapeutic agent of the present invention also includes a therapeutic agent for cancer having effector activity such as ADCC activity and CDC activity, a therapeutic agent for cancer by an apoptosis-inducing activity and the like.

Since the antibody or antibody fragment of the present invention can recognizes a sugar chain-deficient CD27 polypeptide expressed on the cell membrane, it can recognize a cell expressing a sugar chain-deficient CD27 polypeptide in vivo.

Accordingly, among the antibodies or the antibody fragments of the present invention, the antibody or antibody fragment thereof having effector activity can injure the cell expressing a sugar chain-deficient CD27 polypeptide in vivo and in vitro.

Also, since the antibody or antibody fragment of the present invention can injure and thereby decrease cells expressing a sugar chain-deficient CD27 polypeptide in vivo, it is particularly effective as a therapeutic agent.

The therapeutic agent comprising the antibody or antibody fragment of the present invention or derivatives thereof may be only the antibody or antibody fragment or derivatives thereof as an active ingredient, and is preferably supplied as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred.

The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like. Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like. Injections can be prepared using a carrier such as a salt solution, a glucose solution or a mixture of both thereof. Suppositories can be prepared using a carrier such as cacao butter, hydrogenated fat or carboxylic acid. Sprays can be prepared using the antibody or antibody fragment as such or using it together with a carrier which does not stimulate the buccal or airway mucous membrane of the patient and can facilitate absorption of the compound by dispersing it as fine particles.

The carrier includes lactose, glycerol and the like. Depending on the properties of the antibody and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration method, treating period, age, body weight and the like, it is usually 10 µg/kg to 8 mg/kg per day and per adult.

The present invention can provide a monoclonal antibody or an antibody fragment thereof, which specifically recognizes a polypeptide encoded by CD27 gene containing an O-linked sugar chain to which galactose is not bound, and binds to its extracellular region; a hybridoma which produces the antibody; a DNA which encodes the antibody; a vector which comprises the DNA; a transformant obtainable by transforming the vector; a process for producing an antibody or an antibody fragment thereof using the hybridoma or the transformant; and a diagnostic agent or a therapeutic agent comprising the antibody or the antibody fragment thereof as an active ingredient.

The present invention is described below by Examples; however, the present invention is not limited to the following Examples.

EXAMPLES

Example 1

Construction of Soluble CD27 Extracellular Domain Containing an O-Linked Sugar Chain to which Galactose is not Bound (Hereinafter, Often Referred to as "Sugar Chain-Deficient CD27")

(1) Cloning of Human CD27 Gene

In accordance with the following procedure, a gene encoding CD27 was isolated from a human peripheral blood-derived cDNA library purchased from Clontech. PCR was carried out by preparing 50 µL of a reaction solution containing 1-fold concentration BD Advantage PCR buffer (manufactured by Clontech) and 1-fold concentration attached dNTPs, 25 ng human peripheral blood monocyte-derived single-stranded cDNA, 0.2 µmol/L CD27fw (SEQ ID NO:3), 0.2 µmol CD27809B (SEQ ID NO:4) and 1-fold concentration Advantage 2 PCR polymerase Mix (manufactured by Clontech).

Figure 1:
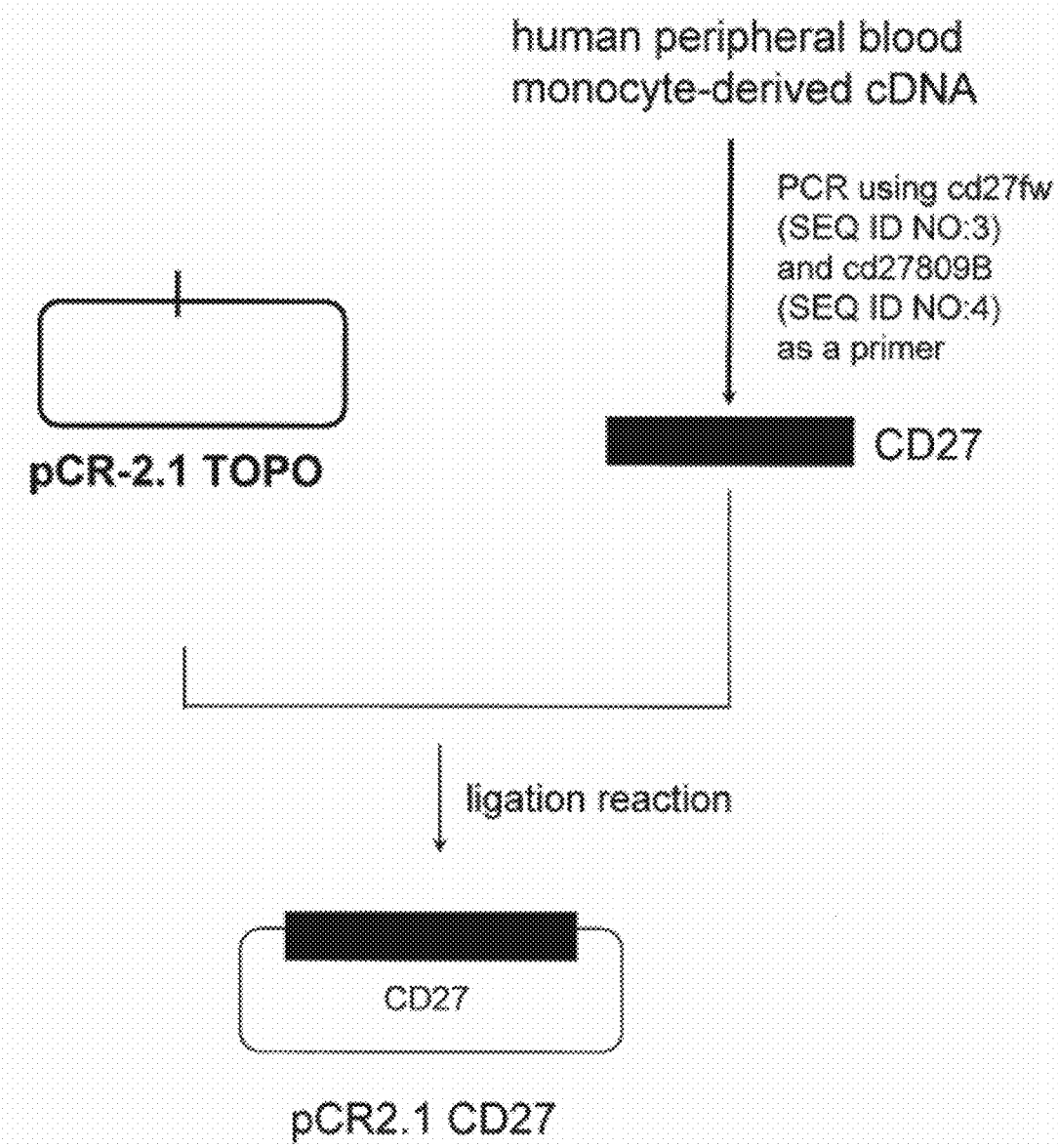
FIG. 1 shows the construction method of a plasmid vector pCR2.1 CD27 comprising a DNA sequence that encodes a human CD27 protein.

PCR was carried out under the following reaction conditions: 30 cycles each consisting of reaction at 98° C. for 15 seconds and reaction at 68° C. for 30 seconds. The reaction solution was separated by 2% agarose gel electrophoresis, and the about 1-kbp PCR product was inserted into a pCR-2.1 vector using a TOPO TA Cloning Kit (manufactured by Invitrogen) in accordance with the instructions attached thereto. *Escherichia coli* was transformed with a plasmid having the PCR-amplified fragment inserted therein, and plasmids obtained from respective clones were prepared, followed by DNA sequencing. pCR 2.1 CD27 having the DNA sequence represented by SEQ ID NO:1 was obtained (FIG. 1).

(2) Construction of Plasmid into which a Gene Having Human Cd27 Extracellular Region was Cloned A cDNA encoding CD27 with removal of a transmembrane region at the C-terminal side was isolated in accordance with the following PCR procedure. To a reaction solution containing 0.2 mmol/L dNTPs and 1 mmol/L magnesium chloride, 1 ng of pCR 2.1 CD27, 1 µmol/L CD27-A (SEQ ID NO:5), 1 µmol/L CD27-B (SEQ ID NO:6) and 2.5 units of KOD polymerase (manufactured by Toyobo) were added and the final folume was adjusted to 50 µl, followed by PCR under the following reaction conditions: 25 cycles each consisting of reaction 98° C. for 15 seconds, and reaction at 68° C. for 30 seconds.

Figure 2:
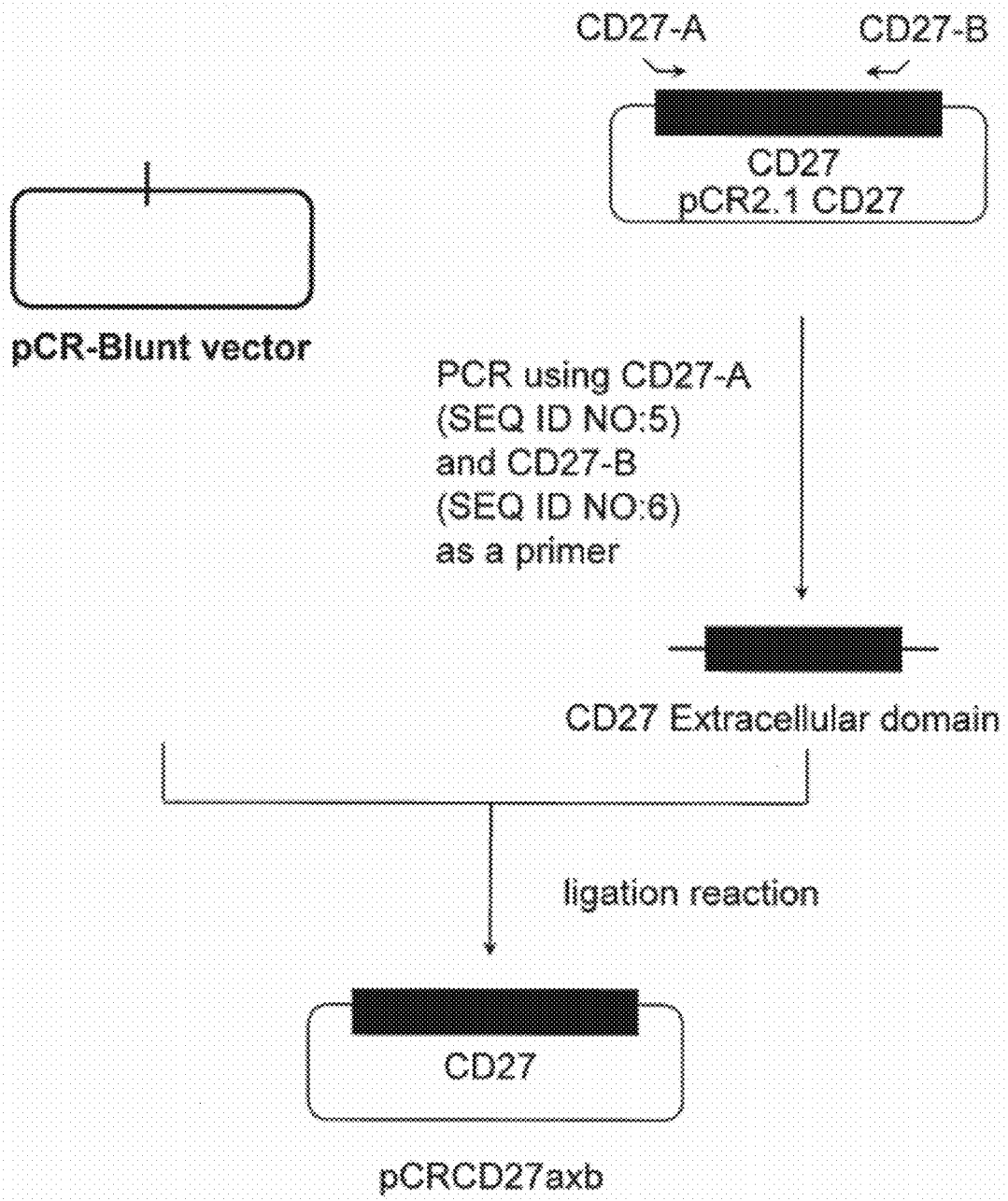
FIG. 2 shows the construction method of a plasmid vector pCR CD27axb comprising a DNA sequence that encodes an extracellular region of a human CD27 protein.

The reaction solution was separated by 2% agarose gel electrophoresis, and the about 600-bp PCR product was introduced into a pCR-Blunt vector using a Zero Blunt PCR Cloning Kit (manufactured by Invitrogen) in accordance with the instructions attached thereto. The resulting plasmid into which a gene having the human CD27 extracellular region was cloned was designated as pCRCD27axb (FIG. 2).

(3) Construction of Vector pBShCγ4SP Having Mutant Human IgG4Fc Region

Using a plasmid pBShCγ4 having a cDNA encoding a C region of a wild type IgG4 subclass as described in WO97/10354, a plasmid pBShCγ4SP was constructed which has a C region of mutant type human IgG4 subclass having a substitution of Ser at position 108 with Pro in the C region (hinge region) of the wild type human IgG4 subclass. This modification was known to result in stabilization of dimerization via the IgG hinge region (Molecular Immunology, 30, 105, 1993).

As a template, 50 µL of a reaction solution [10 mM Tris-HCl (pH 8.3), 50 mM potassium chloride, 1.5 mM magnesium chloride, 0.001% gelatin, 200 µM dNTPs, 0.5 µM Primer 1 (SEQ ID NO:7), 0.5 µM Primer 2 (SEQ ID NO:8)

and 2 units of TaKaRa Ex Taq DNA polymerase] containing 1 ng of the plasmid pBShCγ4 was prepared, followed by PCR using a GeneAmp PCR system 9700 (manufactured by Perkin-Elmer): 30 cycles each consisting of reaction at 94° C. for 2 minutes, reaction at 55° C. for 2 minutes, and reaction at 72° C. for 2 minutes.

The reaction solution was purified using a QIAquick PCR Purification Kit (manufactured by Qiagen) in accordance with the instructions attached thereto, treated with a restriction enzyme EcoT14I (manufactured by Takara Bio) and separated by 0.8% agarose gel electrophoresis, and the amplified fragment was then recovered using a QIAquick Gel Extraction Kit (manufactured by Qiagen) in accordance with the instructions attached thereto.

Figure 3:
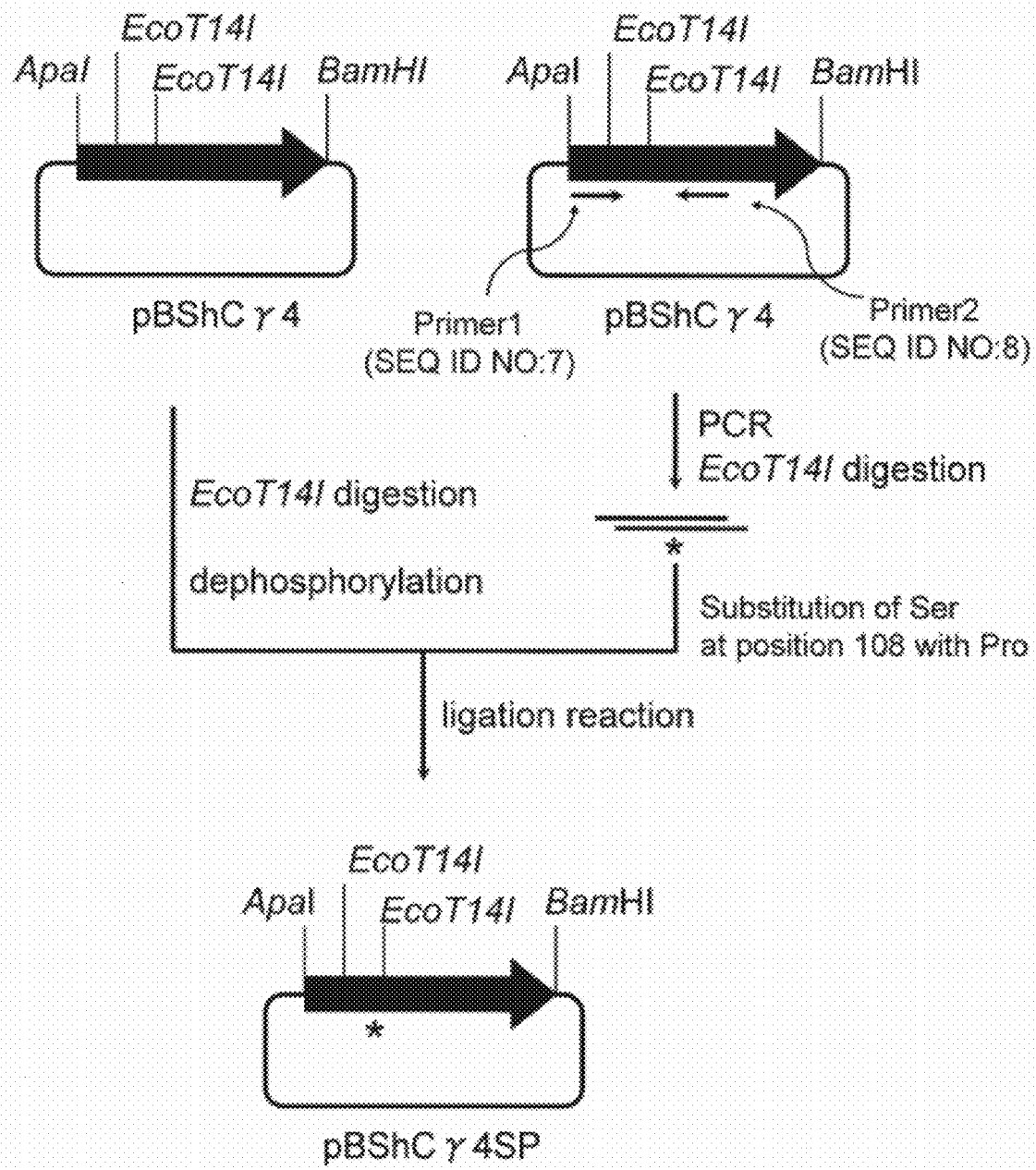
FIG. 3 shows the construction method of a plasmid vector pBShCγ4SP having mutant type human IgG4 Fc region with an amino acid substitution in a human IgG4 constant region.

The plasmid pBShCγ4 was cleaved with a restriction enzyme EcoT14I, followed by treatment with alkaline phosphatase (manufactured by Takara Bio) to remove the 5'-terminal phosphate. Similarly, the separation was carried out by 0.8% agarose gel electrophoresis, and the resulting plasmid fragment was recovered using a QIAquick Gel Extraction Kit in accordance with the instructions attached thereto. The recovered amplified fragment and the plasmid pBShCγ4-derived plasmid were ligated to construct a plasmid pBShCγ4SP comprising a desired cDNA (FIG. 3).

(4) Cloning of cDNA Comprising Partial Sequence of Human IgG4Fc

A DNA fragment encoding human IgG4Fc having a restriction enzyme BamHI site at the 5'-terminal and a restriction enzyme SalI site at the 3'-terminal was amplified in accordance with the following PCR procedure. To a reaction solution containing 0.2 mmol/L dNTPs and 1 mmol/L magnesium chloride, 25 ng of pBShCγ4SP constructed in Section (3), 1 mol/L g4A (SEQ ID NO:9), 1 µmol/L g4B (SEQ ID NO:10) and 2.5 units of KOD polymerase (manufactured by Toyobo) were added and to adjusted the final volume to 50 followed by PCR.

Figure 4:
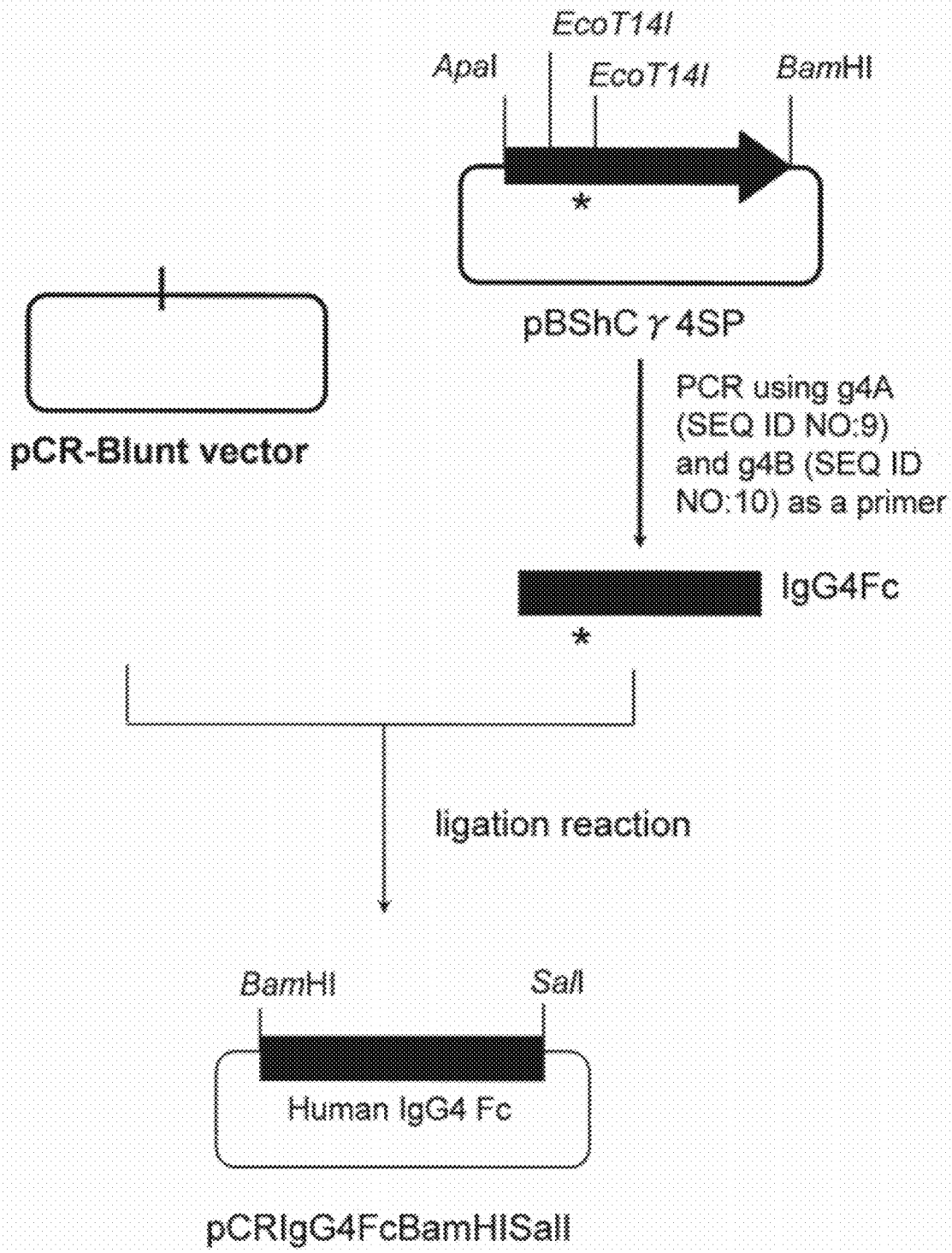
FIG. 4 shows the construction method of a plasmid vector pCR IgG4Fc BamHISalI comprising a DNA sequence in which a restriction enzyme recognition sequence is inserted into a DNA sequence of mutant type human IgG4 Fc region.

The reaction conditions are as follows: 25 cycles each consisting of reaction at 98° C. for 15 seconds and reaction at 68° C. for 30 seconds. The reaction solution was separated by 2% agarose gel electrophoresis, and the about 700-bp PCR product was introduced into a pCR-Blunt vector using a Zero Blunt PCR Cloning Kit (manufactured by Invitrogen) in accordance with the instructions attached thereto. The resulting plasmid was designated as pCRIgG4FcBamHISalI (FIG. 4).

(5) Construction of Expression Vector for Animal Cell pKANTEX XhoI/SalI

The humanized antibody expression vector pKANTEX93 as described in WO97/10354 was digested with restriction enzymes XhoI (manufactured by Takara Bio) and SalI (manufactured by Takara Bio) and separated by 0.8% agarose gel electrophoresis, and the about 9.8-kbp plasmid fragment was recovered using a Gel Extraction Kit (manufactured by Qiagen). The 5' and 3'-terminals of the recovered DNA fragment were ligated using a DNA Ligation Kit (manufactured by Takara Bio), and *Escherichia coli* DH5α (manufactured by Toyobo) was then transformed with the resulting recombinant plasmid DNA.

The recombinant plasmid DNA was isolated from a plurality of the obtained ampicillin-resistant colonies using a QIAprep Spin Miniprep Kit (manufactured by Qiagen), and then the exclusion of the expression unit of the antibody L chain was confirmed by digestion with restriction enzymes NotI (manufactured by Takara Bio) and KpnI (manufactured by Takara Bio). The resulting plasmid was designated as pKANTEX XhoI/SalI (FIG. 5).

Figure 6:
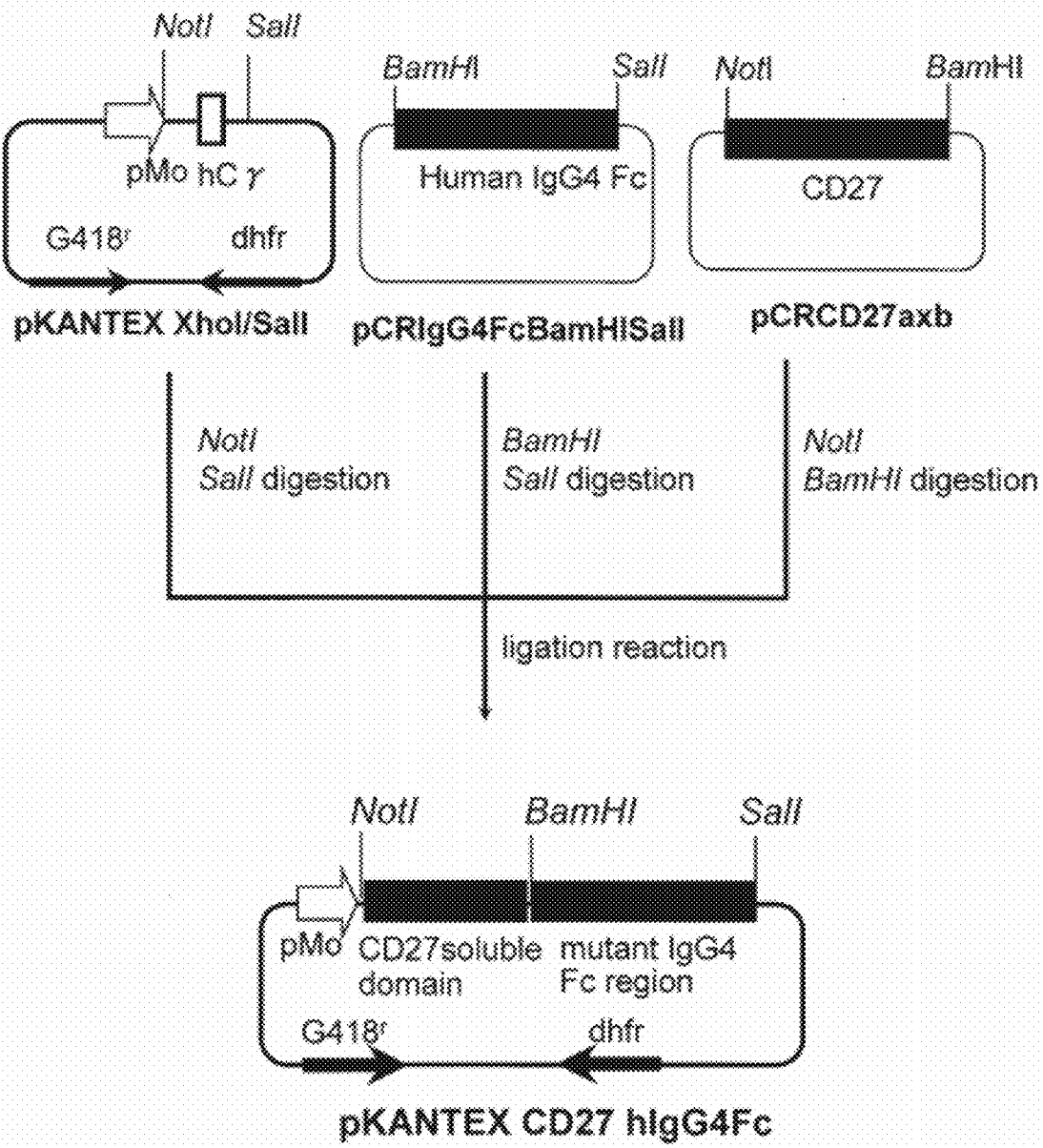
FIG. 6 shows the construction method of CD27-Fc protein expression vector pKANTEX CD27-hIgG4Fc.

(6) Construction of Plasmid pKANTEX CD27IgG4Fc Expressing Soluble CD27 Extracellular Domain The about 600-bp fragment obtained by NotI and BamHI digestion of pCR2.1 CD27axb constructed in Section (2), and the about 700-bp DNA fragment obtained by BamHI and SalI digestion of pCRIgG4FcBamHISalI constructed in Section (3) were ligated into the about 8.8-kbp DNA fragment obtained by NotI and SalI digestion of pKANTEX XhoI/SalI constructed in Section (5), thereby obtaining a plasmid pKANTEX CD27IgG4Fc for the expression of CD27-Fc (FIG. 6). A nucleotide sequence of a soluble CD27-Fc fusion protein (hereinafter, often referred to as "CD27-Fc") which is encoded by the above plasmid was described as SEQ ID NO:11, and an amino acid sequence thereof was described as SEQ ID NO:12. *Escherichia coli* transformed with that expression vector was seeded in 100 mL of an LB medium, cultured overnight and collected, and the plasmid was purified using a QIAfilter Plasmid Midi Kit (manufactured by Qiagen) in accordance with the protocols attached thereto.

After purification was complete, 30 µg of the plasmid vector was linearized by digestion with a restriction enzyme AatII. Linearization was followed by phenol/chloroform extraction, ethanol precipitation, dissolution in 0.1-fold concentration TE buffer (1 mM Tris HCl, 0.1 mM EDTA), and measurement of DNA concentration. It was provided for gene introduction.

(7) Expression of CD27-Fc

In accordance with electroporation [Cytotechnology, 3, 133 (1990)], introduction of the CD27-Fc expression plasmid pKANTEX CD27IgG4Fc into CHO/DG44 cells (Somatic Cell and Molecular Genetics, 12, 555 (1986), hereinafter referred to as "DG44") or Lec8 cells was carried out in the following manner.

Firstly, the DG44 cells, subcultured in a base medium [Iscove's Modified Dulbecco's Medium (manufactured by Invitrogen) supplemented with 10% dialyzed fetal bovine serum (manufactured by Invitrogen), 50 µg/mL of gentamycin (manufactured by Nacalai Tesque) and 1×HT supplement (manufactured by Invitrogen)], were suspended at a density of $8 \times 10^6$ cells/mL in a K-PBS buffer [a suspension of 137 mmol/L KCl, 2.7 mmol/L NaCl, 8.1 mmol/L $Na_2HPO_4$, 1.5 mmol/L $KH_2PO_4$, 4.0 mmol/L $MgCl_2$] to prepare a cell suspension.

With 10 µg of the linearized plasmid pKANTEX CD27IgG4Fc constructed in Section (6), 200 µL ($1.8 \times 10^6$ cells) of the cell suspension was mixed. The subculture of Lec8 cells was carried out in a base medium (hereinafter referred to as "HT-medium") without addition of 1×HT supplement.

The cell/DNA mixture was transferred into a Gene Pulser Cuvette (interelectrode distance: 2 mm, manufactured by Bio-Rad), and gene transfer was carried out using a GenePulser (Bio-Rad) device at a pulse voltage of 0.35 KV and an electric capacity of 250 µF.

The cell suspension was mixed with an HT-medium [10 mL of Iscove's Modified Dulbecco's Medium (manufactured by Invitrogen) supplemented with 10% fetal bovine serum (manufactured by Invitrogen) and 50 µg/mL of gentamycin (manufactured by Nacalai Tesque)], seeded in a 75-$cm^2$ tissue culture flask (manufactured by Greiner), and cultured in a 5% $CO_2$ incubator at 37° C. Three days after culturing, G418 (manufactured by Sigma) was added thereto to give a final concentration of 0.5 mg/mL, followed by culturing for another 10 days.

Ten days later, the cells were subcultured in a 182-$cm^2$ tissue culture flask (manufactured by Greiner), followed by continuous culturing to confluence. After exchange of the culture medium with a serum-free medium EXCELL 301 (manufactured by JRH Bioscience) at the point of confluence, the cells were cultured for one week, and the culture supernatant was collected and purified in accordance with the following method.

(8) Purification of CD27-Fc

The culture supernatant obtained from the culture of Section (7) was centrifuged at 3000 rpm and 4° C. for 10 minutes. The resulting supernatant was recovered and filtered through a 0.22-µm pore size PES Membrane (manufactured by Asahi Techno Glass). Into a column with a diameter of 0.8 cm, 0.5 mL of Mab select (manufactured by Amersham Pharmacia Biotech) was packed, and 3.0 mL of purified water and 3.0 mL of 0.2 M boric acid-0.15 M NaCl buffer (pH 7.5, hereinafter referred to as "borate buffer") were then sequentially passed through.

In addition, the carrier was equilibrated by sequential washing with 2.0 mL of 0.1 M citrate buffer (pH 3.5) and 1.5 mL of borate buffer. Next, the culture supernatant was passed through the column which was then washed with 3.0 mL of borate buffer. After washing, antibodies adsorbed to the carrier were eluted with 1.25 mL of 0.1M citrate buffer (pH 3.5).

Elution was carried out to obtain five divided fractions each consisting of 250 µL. Next, the obtained purified fractions were subjected to SDS-PAGE analysis, and the fractions from which elution of the desired protein was confirmed were pooled and dialyzed against PBS buffer at 4° C. overnight.

After the dialysis was complete, the CD27-Fc solution was recovered and subjected to sterile filtration using a 0.22-µm Millex GV (Millipore). Then, an absorbance (OD280 nm) was measured using a Shimadzu UV-1700 spectrophotometer and a concentration of CD27-Fc was calculated (0.68 mg/mL by taking OD280 nm=1.0; calculated from εM=134655, and MW=92840).

From about 300 mL of the serum-free culture supernatant of the CD27-Fc-expressing cells derived from respective host cells, 3.6 mg of Lec8-derived CD27-Fc, and 2.2 mg of CHO/DG44-derived CD27-Fc were obtained. For the respective proteins, the SDS-PAGE analysis results of elution fractions are given in FIG. 7.

As a result, under reducing conditions, CD27-Fc was observed at a molecular weight of about 65 kDa for DG44 as a host, and a molecular weight of about 48 kDa for Lec8 as a host. On the other hand, under non-reducing conditions, individual bands were observed at positions corresponding to a molecular weight about two-fold greater than those obtained under reducing conditions, thus confirming that CD27-Fc is present as a dimer.

(9) Confirmation of Sugar Chain Structure

To 16 µL of a 10-fold dilution of the purified CD27-Fc of Section (8) in PBS was added 4 µL of 5-fold concentration SDS sample buffer, followed by treatment at 90° C. for 5 minutes and then SDS-PAGE. Electrophoresis was carried out using 5 to 20% SDS-polyacrylamide gel e-PAGEL (manufactured by ATTO, Cat. No. E-T520L), in a RAPIDAS Mini-Slab Electrophoresis Cell (ATTO) at current of 20 mA/gel, for 90 minutes.

Transfer onto a PVDF membrane (manufactured by Millipore Immobilon, Cat. No, IPVH304F0) was carried out using an ATTO Holize blot, at 180 mA for 90 minutes. Post-transfer membrane was immersed in PBS containing 10% BSA (hereinafter referred to as "10% BSA-PBS"), and allowed to stand at 4° C. overnight for blocking.

Thereafter, 5 µg/mL of anti-RCAS1 antibody clone 22-1-1 (manufactured by MBL, Cat. No. DG60-3) prepared using 1% BSA-PBS was added thereto, followed by reaction at room temperature for 2 hours.

The membrane was washed with 0.05% Tween-20-PBS (manufactured by Wako Pure Chemical, Cat. No. 167-11515) at room temperature for 30 minutes, and allowed to react with a 2000-fold dilution of a secondary antibody peroxidase-labeled rabbit anti-mouse immunoglobulin (manufactured by DAKO, Cat. No. P0161) in 1% BSA-PBS at room temperature for 1 hour.

Figure 8:
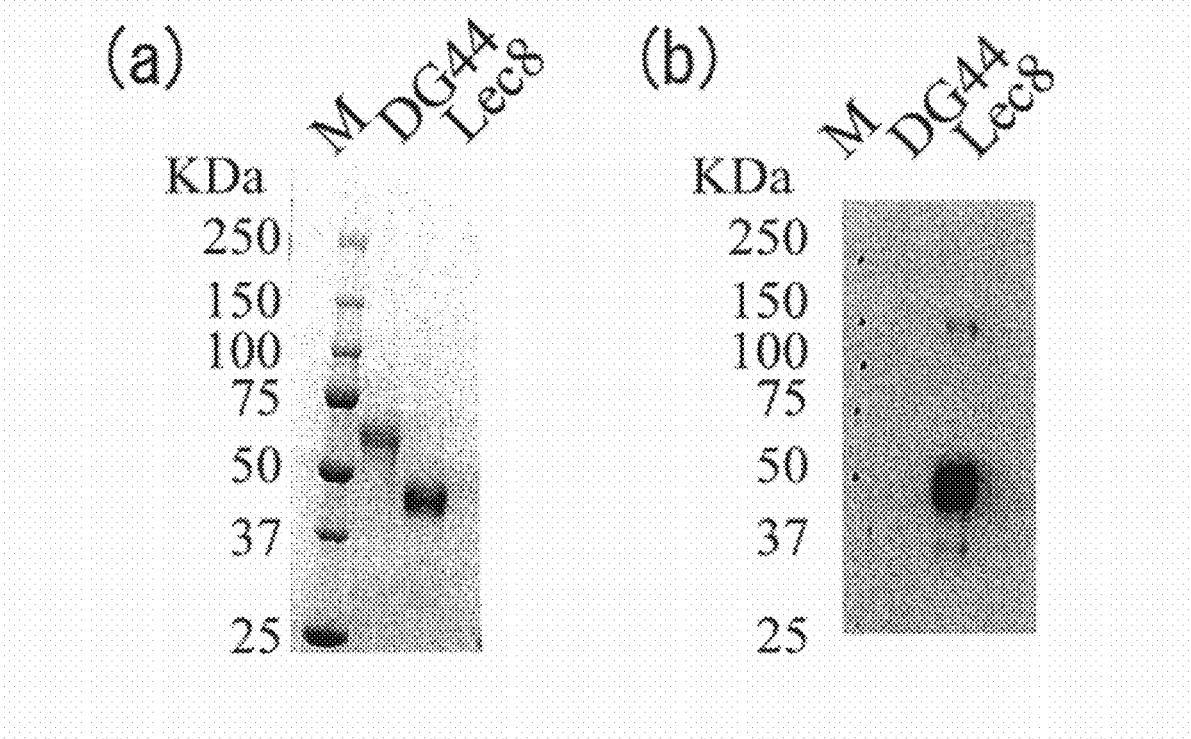
FIG. 8(*a*) shows the results of SDS-PAGE analysis of the CD27-Fc proteins which are expressed in CHO/DG44 cells and Lec8 cells as host cells. In addition, FIG. 8(*b*) shows the results of Western blot of the CD27-Fc proteins which are expressed in CHO/DG44 cells and Lec8 cells as a host cell.

The membrane was washed with 0.05% Tween-20-PBS at room temperature for 30 minutes, followed by detection using an ECL Western blotting detection reagent (manufactured by Amersham Pharmacia Biotech, Cat. No. RPN2106). The results are given in FIG. 8.

From the SDS-PAGE analysis results, it was shown that a molecular weight of DG44-derived CD27-Fc is larger than that of Lec8-derived CD27-Fc, and there is a difference in structures of the sugar chain binding to CD27-Fc, depending on host cells DG44 and Lec8.

Further, anti-RCAS1 antibody 22-1-1 apparently recognizes a Tn antigen which is an O-linked sugar chain and is known as an anti-Tn antibody [J.B.C., 278. 22998-23007, (2003)].

The anti-RCAS-1 antibody clone 22-1-1, which is an anti-Tn antibody, did not bind to the DG44-derived CD27-Fc, but specifically bound to the Lec8-derived CD27-Fc. It was confirmed that a Tn antigen, which is an O-linked sugar chain to which galactose is not bound, was bound to CD27-Fc produced by Lec8.

Example 2

Preparation of CHO Cell Expressing CD27 on Cell Membrane (1) Construction of CD27 Expression Plasmid pKANTEX CD27

From the pCR2.1 CD27 constructed in Example 1, a cDNA fragment with removal of a cDNA portion unnecessary for gene expression was constructed in accordance with the following PCR procedure.

PCR was carried out by preparing 50 µL of a reaction solution containing 0.2 mmol/L dNTPs, 1 mmol/L magnesium chloride, 1 ng of pCR2.1 CD27, 1 µmol/L CD27-A (SEQ ID NO:5), 1 µmol/L CD27-C (SEQ ID NO:13) and 2.5 units of KOD polymerase (manufactured by Toyobo). PCR was carried out.

Figure 9:
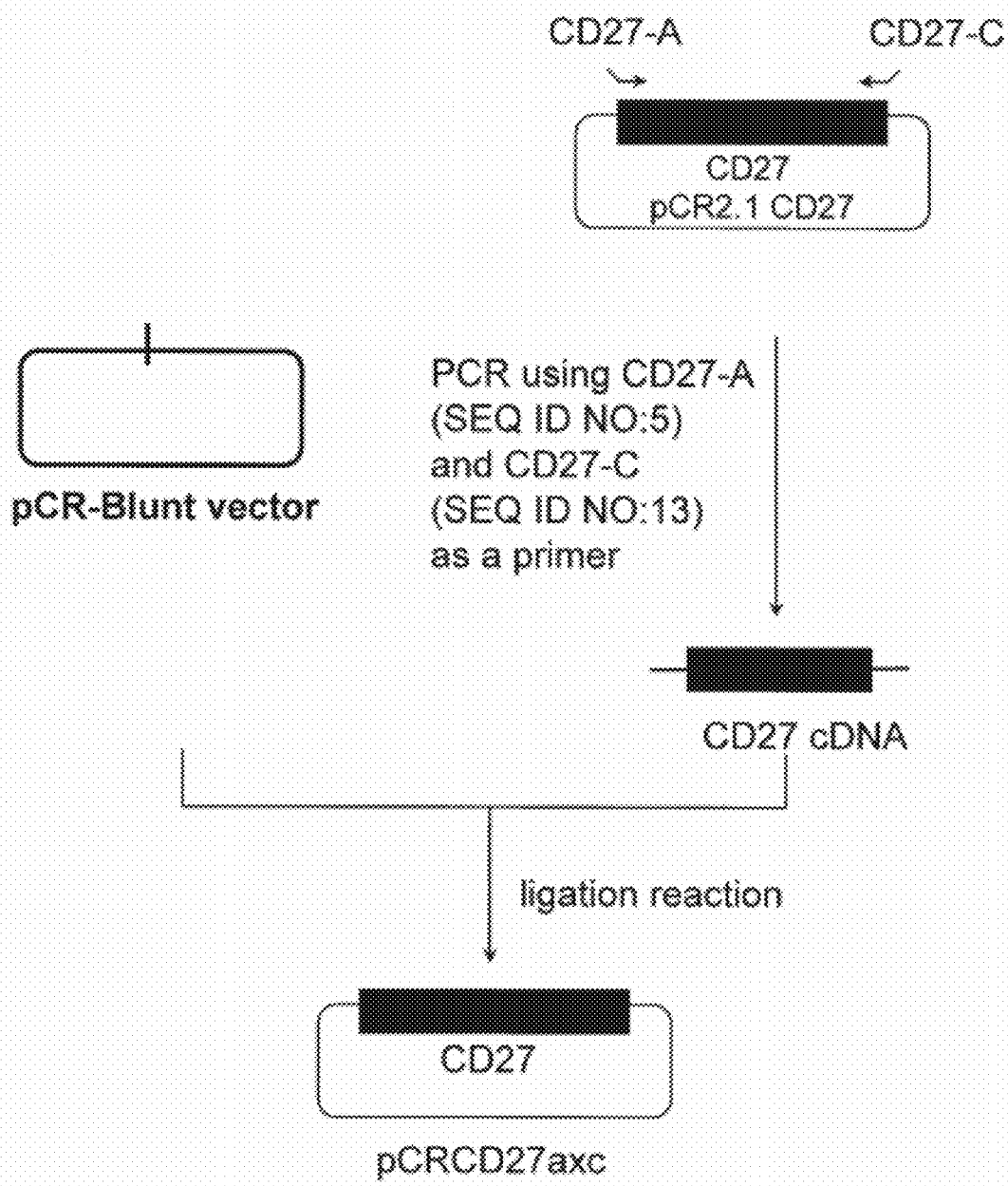
FIG. 9 shows the construction method of a plasmid vector pCRCD27 axc which comprises a DNA encoding CD27 protein and is intended for expression in animal cells.

The reaction conditions are as follows: 25 cycles each consisting of reaction at 98° C. for 15 seconds and reaction at 68° C. for 30 seconds. The reaction solution was separated by 2% agarose gel electrophoresis, and the about 800-bp PCR product was introduced into a pCR-Blunt vector using a Zero Blunt PCR Cloning Kit (manufactured by Invitrogen) in accordance with the instructions attached thereto, thereby obtaining pCR27axc having the DNA sequence as set forth in SEQ ID NO:1 (FIG. 9).

Figure 10:
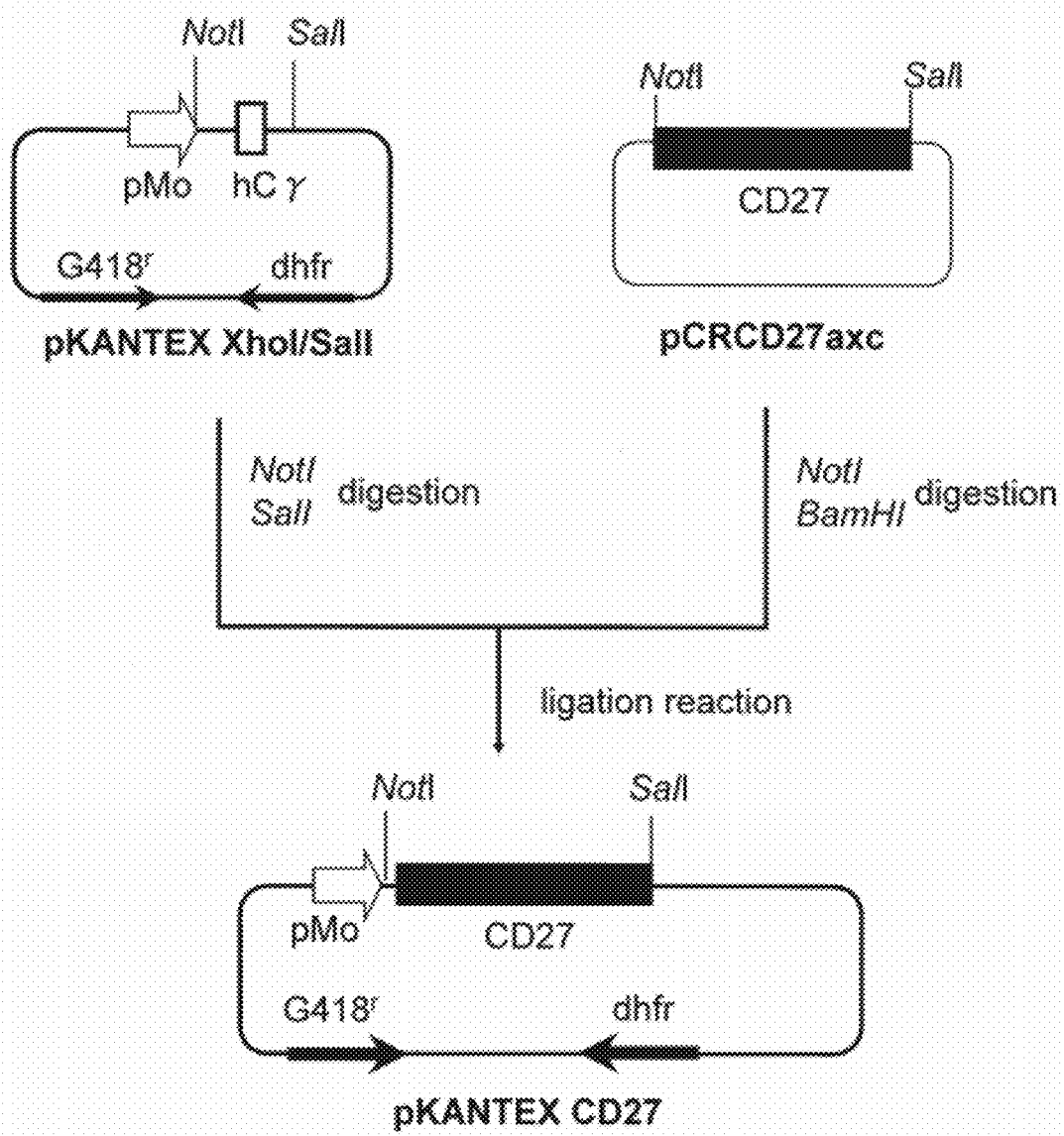
FIG. 10 shows the construction method of an animal cell expression vector pKANTEX CD27.
Figure 15:
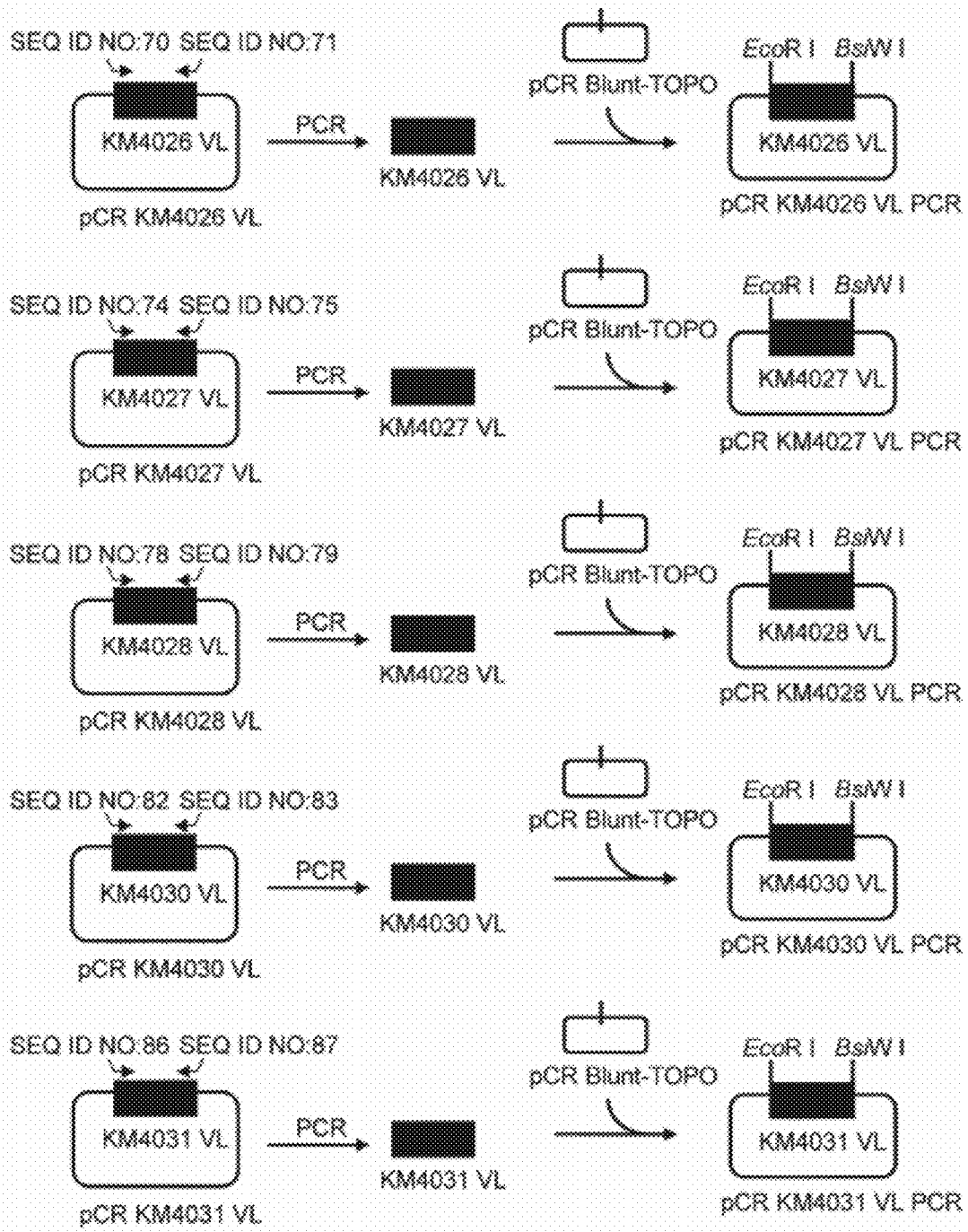
FIG. 15 shows the construction method of an anti-sugar chain-deficient CD27 chimeric antibody expression vector.
Figure 16:
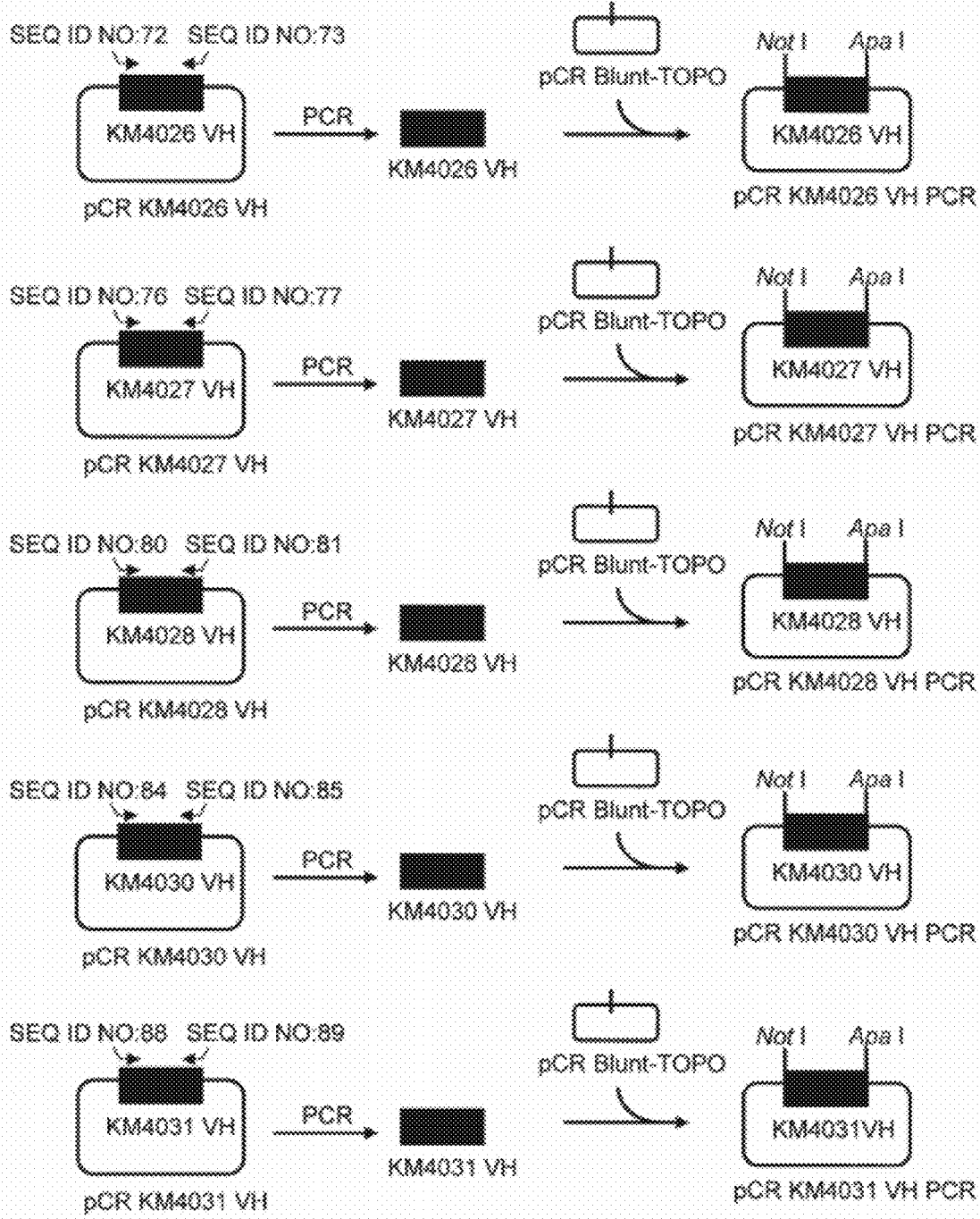
FIG. 16 shows the construction method of an anti-sugar chain-deficient CD27 chimeric antibody expression vector.
Figure 17:
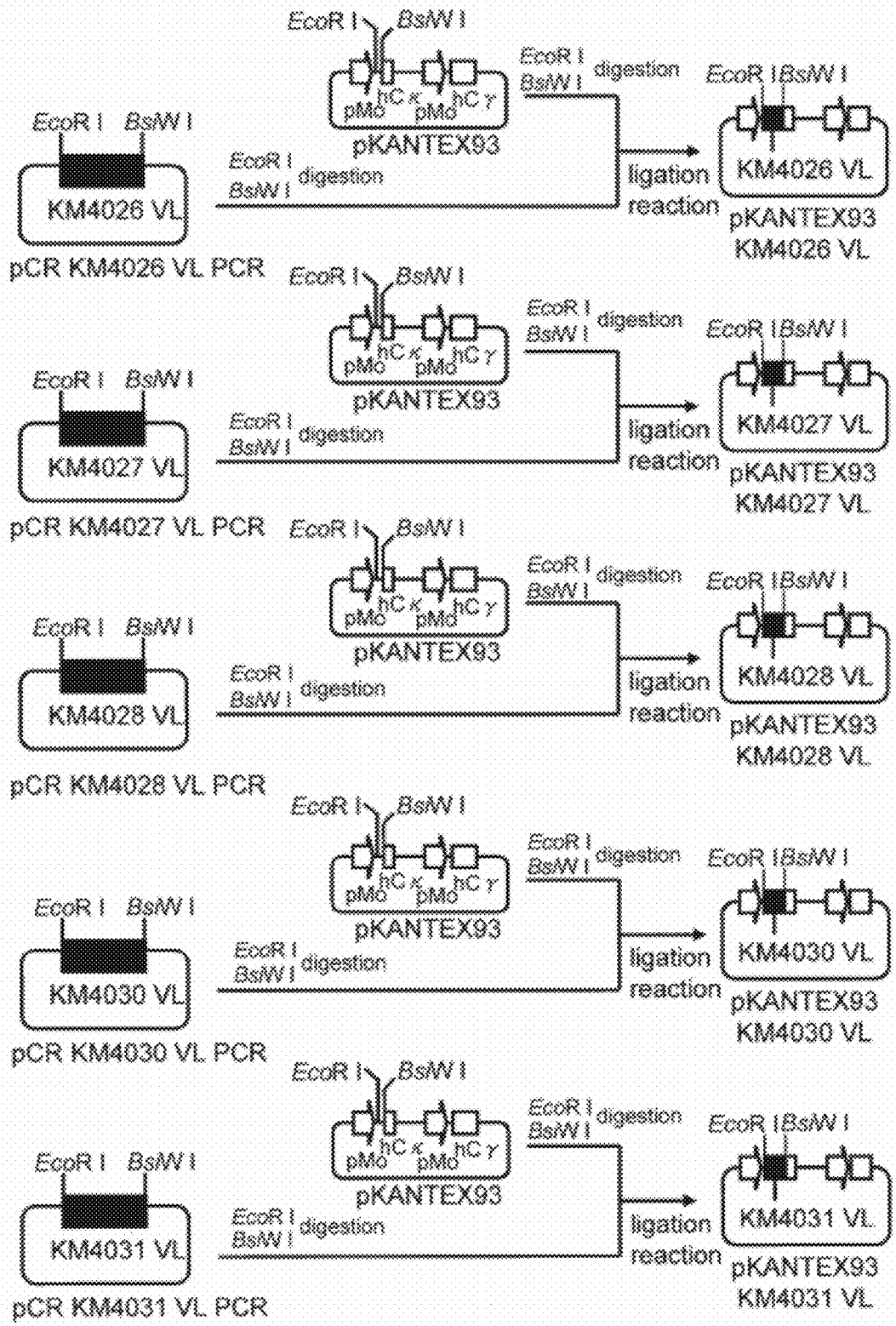
FIG. 17 shows the construction method of an anti-sugar chain-deficient CD27 chimeric antibody expression vector.
Figure 18:
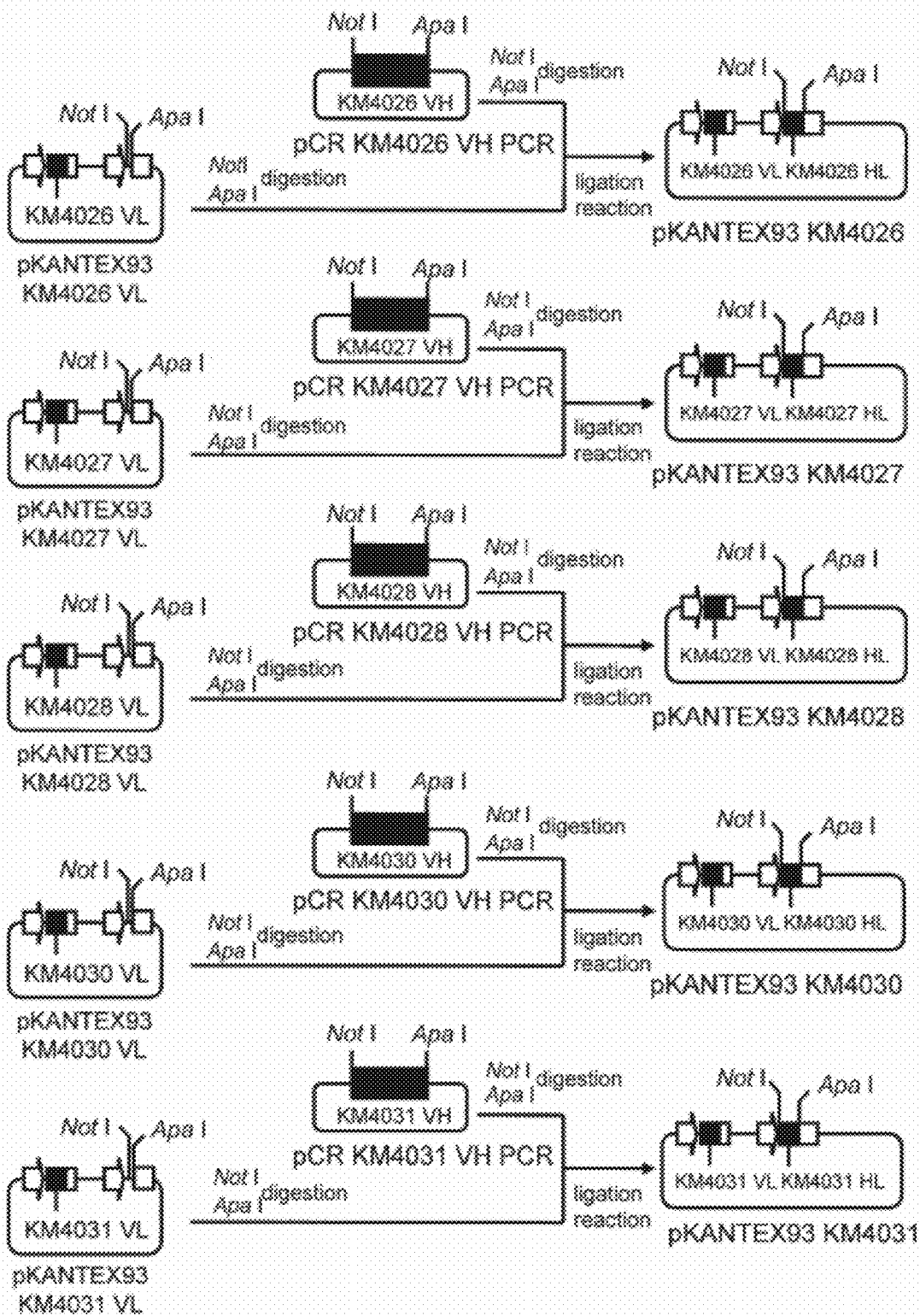
FIG. 18 shows the construction method of an anti-sugar chain-deficient CD27 chimeric antibody expression vector.

Next, the about 780-bp DNA fragment obtained by digestion of pCR27axc with restriction enzymes NotI and SalI was ligated to the about 8.9-kbp DNA fragment obtained by restriction enzymes NotI and SalI digestion of pKANTEX XhoI/SalI constructed in Example 1, thereby constructing a plasmid pKANTEX CD27 for the expression of CD27 (FIG. 10).

The CD27 nucleotide sequence encoded by this plasmid is shown in SEQ ID NO:1, and the amino acid sequence translated therefrom is shown in SEQ ID NO:2. *Escherichia coli* transformed with the thus constructed expression vector was seeded in 100 mL of an LB medium, followed by overnight culture. After culture was complete, the bacteria were recovered and the plasmid was purified using a QIAfilter Plasmid Midi Kit (manufactured by Qiagen) in accordance with the instructions attached thereto.

Thereafter, 30 μg of the plasmid vector was linearized by digestion with a restriction enzyme AatII. Linearization was followed by phenol/chloroform extraction, ethanol precipitation, dissolution in 0.1-fold concentration TE buffer (1 mM Tris HCl, 0.1 mM EDTA), measurement of DNA concentration, and gene introduction.

(2) Introduction of CD27-Expressing Plasmid pKANTEX CD27

Lec8 and DG44 cells expressing CD27 were established by gene introduction of the CD27-expressing plasmid pKANTEX CD27 constructed in Section (1) into Lec8 cells and CHO/DG44 cells. The gene introduction was carried out in the same manner as in Example 1, except that pKANTEX CD27 was used as the plasmid to be introduced.

The cells after gene introduction were suspended in 30 mL of an HT-medium, and 100 μL/well of the cell suspension was seeded on 96-well plates in triplicate. Two days after seeding, the culture medium was exchanged with a subculture medium containing 500 μg/mL G418, followed by culture for 10 days. After 10 days, the culture medium was exchanged with an HT-medium containing 50 nM MTX (manufactured by Sigma Aldrich), and the MTX-resistant cell line was obtained. The Lec8-derived CD27-expressing cell line was designated as CD27/Lec8-4, and the DG44-derived CD27-expressing cell was designated as CD27/DG44-8.

(3) Confirmation of CD27-Expressing Cell

In order to confirm CD27 expression of the CD27-expressing cells constructed in Section (2), the analysis was carried out as follows, using a flow cytometer (FCM).

Into a 15 mL tube (manufactured by Becton, Dickinson and Company), 1 to $5 \times 10^6$ of CD27-expressing cells were dispensed and centrifuged at 1500 rpm for 5 minutes. After the supernatant was discarded, the residue was suspended in PBS buffer containing 50 μL of 1% bovine serum albumin (BSA) [hereinafter referred to as "1% BSA-PBS", manufactured by Kohjin Bio)].

To the suspension, 10 μL of PC5-labeled anti-CD27 mouse monoclonal antibodies (manufactured by Beckman Coulter, Cat. No. 6607107), or 10 μL of PC5-labeled mouse IgG1 isotype control (Beckman Coulter, Cat. No. 6607012) as a primary antibody was added, followed by reaction at ice temperature for 60 minutes. After the reaction was complete, the cells were washed twice with 1 mL of 1% BSA-PBS and suspended in 500 μL of 1% BSA-PBS, and the fluorescence intensity was measured using a flow cytometer (FCM, manufactured by Becton, Dickinson and Company).

The results are shown in FIG. 11. As shown in FIG. 11, it was confirmed that CD27/Lec8-4 and CD27/DG44-8 exhibit substantially the same expression level of CD27 on the cell membrane.

Example 3

Construction of Monoclonal Antibody for CD27 Containing an O-Linked Sugar Chain to which Galactose is not Bound (Hereinafter Referred to as "Anti-Sugar Chain-Deficient CD27 Monoclonal Antibody")

(1) Preparation of Immunogen

Together with 2 mg of an aluminum hydroxide adjuvant (Antibodies-A Laboratory Manual, Cold Spring Harbor Laboratory, p 99, 1988) and $1 \times 10^9$ cells of a pertussis vaccine (manufactured by Chiba Serum Institute), 50 μg of Lec8-produced CD27-Fc obtained in Example 1 was administered to 4-week old female SD rats (n=3).

Two weeks after the administration, 50 μg of Lec8-produced CD27-Fc was administered to the animals once a week, three times in all. Blood was partially collected from caudal veins of animals, and binding activity of the obtained antisera was measured by fluorescent cell staining using an ABI8200 Cellular Detection System (manufactured by Applied Biosystems) or a flow cytometer (Cytomics FC500 MPL, manufactured by Beckman Coulter). The spleen was extracted from a mouse which showed sufficient antibody titer three days after the final immunization.

The spleen was minced into small pieces in a Minimum Essential Medium (MEM, manufactured by Nissui Pharmaceutical), unbound using a pair of forceps, and centrifuged (1200 rpm, 5 minutes). Tris-ammonium chloride buffer (pH 7.6) was added to treat the resulting precipitation fraction for 1 to 2 minutes, whereby red blood cells were removed. The resulting precipitation fraction (cell fraction) was washed with MEM three times, and used in subsequent cell fusion.

(2) Binding ELISA

Lec8-produced CD27-Fc and DG44-produced CD27-Fc obtained in Example 1 were respectively used as antigens in binding ELISA. Then, 5 μg/mL of each CD27-Fc protein was dispensed to give a concentration of 50 μL/well in a 96-well ELISA plate (Greiner), and allowed to stand at 4° C. overnight for adsorption.

After the plate was washed, 100 μL/well of 1% BSA-PBS was added to the plate which was then allowed to stand at room temperature for 1 hour so that the remaining active groups were blocked. Then, 1% BSA-PBS was discarded, 50 μL/well of the immunized animal antiserum or hybridoma culture supernatant as a primary antibody was dispensed to the plate which was then allowed to stand for 2 hours.

The plate was washed with 0.05% polyoxyethylene (20) sorbitan monolaurate [(the equivalent of ICI trade name Tween 20, manufactured by Wako Pure Chemical)]-PBS (hereinafter referred to as "Tween-PBS"), and 50 μL/well of a peroxidase-labeled rabbit anti-rat immunoglobulin (manufactured by Zymed) as a secondary antibody was added to the plate which was then allowed to stand at room temperature for 1 hour.

The plate was washed with Tween-PBS, and color-developed by addition of a 2,2-azinobis(3-ethylbenzothiazole-6-sulfonic acid)ammonium (ABTS) substrate solution [1 mmol/L ABTS-0.1 mol/L citrate buffer (pH 4.2), 0.1% $H_2O_2$]. An absorbance (OD415 nm) was measured using a plate reader (Emax; Molecular Devices).

(3) Fluorescent Cell Staining (ABI8200 Cellular Detection System Analysis)

The CD27/Lec8-4 and CD27/DG44-8 constructed in Example 2 were used as assay cells. The CD27/Lec8-4 and CD27/DG44-8, which were subcultured in a subculture medium supplemented with 50 nM MTX and 500 ng/mL G418, were peeled off using a 0.05% trypsin solution (manufactured by Invitrogen), and seeded onto an ABI8200 black 96-well plate at a density of $1 \times 10^4$ cells/100 μL medium/well, followed by culturing overnight.

Then, 10 μL/well of the immunized rat anti-serum or the hybridoma culture supernatant as a primary antibody was dispensed to the plate, and 100 μL/well of ALEXA647-labeled anti-rat immunoglobulin G(H+L) (manufactured by Invitrogen) was added thereto as a secondary antibody, followed by allowing to stand under shading for 4 hours. Fluorescence of 650 to 685 nm excited with a 633 He/Ne laser was measured by the ABI8200 Cellular Detection System (manufactured by Applied Biosystems).

(4) Fluorescent Cell Staining (Flow Cytometer Analysis)

The CD27/Lec8-4 and CD27/DG44-8 constructed in Example 2 were used as assay cells. The CD27/Lec8-4 and CD27/DG44-8, which were subcultured in an HT-medium supplemented with 50 nM MTX and 500 µg/mL G418, were peeled off using a 0.02% EDTA solution (manufactured by Nacalai Tesque), and respective cells were washed with PBS.

After washing, 1 to $5\times10^5$ cells were suspended in 50 µL of 1% BSA-PBS, and 50 µL/well of the immunized rat antiserum or the hybridoma culture supernatant as a primary antibody was dispensed thereto, followed by reaction at ice temperature for 30 minutes.

In addition, the cells were simultaneously allowed to react with bovine serum albumin (BSA), mouse IgG1 isotype control (manufactured by Cosmo Bio) and rat IgG2a isotype control (manufactured by Cosmo Bio) as a negative control, and anti-RCAS1 antibody 22-1-1 (manufactured by MBL) and anti-CD27 mouse monoclonal antibody (manufactured by Beckman Coulter) as a positive control.

After the reaction was complete, the cells were washed by centrifuging with PBS twice, and 50 µL/well of ALEXA488-labeled anti-rat immunoglobulin G(H+L) (manufactured by Invitrogen) as a secondary antibody was added thereto, followed by reaction at ice temperature under shading for 30 minutes. After the cells were washed again by centrifuging with PBS twice, the cells were suspended in 500 µL of 1% BSA-PBS, and fluorescence of 510 to 530 nm excited with a 488 nm argon laser was measured by a flow cytometer (manufactured by Beckman Coulter, Cytomics FC500 MPL).

(5) Preparation of Mouse Myeloma Cell

8-Azaguanine-resistant mouse myeloma cell line P3X63Ag8U.1 (P3-U1; purchased from ATCC) was cultured using a normal medium (10% FCS RPMI medium), and $2\times10^7$ or more of cells were saved at the time of cell fusion and subjected to the cell fusion as the parent cell line.

(6) Preparation of Hybridoma

The mouse spleen cells obtained in Example (1) and the myeloma cells obtained in the above (5) were mixed at a ratio of 10:1 and centrifuged (250×g, 5 minutes). After thoroughly loosening a group of cells of the thus obtained precipitation fraction, a mixed solution of 1 g of polyethylene glycol-1000 (PEG-1000), 1 ml of MEM medium and 0.35 ml of dimethyl sulfoxide was added thereto, in an amount of 0.5 ml per $10^8$ mouse spleen cells, at 37° C. under stirring, 1 ml of the MEM medium was added to the suspension several times at intervals of 1 to 2 minutes, and then the total volume was adjusted to 50 ml by adding the MEM medium.

The suspension was centrifuged (900 rpm, 5 minutes), cells of the thus obtained precipitation fraction were mildly loosened, and then the cells were gently suspended in 100 ml of a HAT medium [a medium prepared by adding HAT Media Supplement (manufactured by Invitrogen) to 10% fetal bovine serum-supplemented RPMI medium] by repeated drawing up into and discharging from a measuring pipette.

The suspension was dispensed at 200 µl/well into a 96-well culture plate and cultured in a 5% $CO_2$ incubator at 37° C. for 8 to 10 days.

After the culturing, the culture supernatant was sampled and a well which was reactive to CD27/Lec8-4 and was not reactive to CD27/DG44-8 and Lec8 cells was selected using fluorescent cell staining described in the above (3) and (4). Then, from the cells contained in the thus selected well, cloning was carried out twice by a limiting dilution method, and a single cell clone was obtained.

As a result, hybridomas KM4030 and KM4031 which produce monoclonal antibodies KM4030 and KM4031, respectively, specifically binding to the sugar chain-deficient CD27 were established (FIG. 12). In the same manner, hybridomas KM4026, KM4027 and KM4028 which produce monoclonal antibodies KM4026, KM4027 and KM4028, respectively, specifically reacting with the sugar chain-deficient CD27 were established.

These hybridomas which produce the monoclonal antibody specifically binding to the sugar chain-deficient CD27 were obtained by constructing recombinant cells expressing each of normal sugar chain-containing CD27 and sugar chain-deficient CD27 using a DG44 cell line with no deficiency of an activity of an enzyme involved in the sugar chain synthesis process, a transporter protein and a Lec8 cell line in which an activity of the UDF-galactose transporter is decreased or deleted; designing a system that allows for screening of a monoclonal antibody which does not bind to a normal sugar chain-containing CD27-expressing cell or Lec8 cell line, but only specifically binds to the sugar chain-deficient CD27-expressing cell; and then performing screening assay of about 6000-well scale.

(7) Purification of Monoclonal Antibody

The hybridoma cells obtained in the above (6) were administered by intraperitoneal injection into 7-week-old female nude mice (ICR) treated with pristane, at a dose of 5 to $20\times10^6$ cells/animal. The ascitic fluid (1 to 8 mL/animal) was collected from the mice when the hybridoma developed ascites tumor in 10 to 21 days, and then filtered through a syringe filter (pore size: 5 µm) to remove solids.

A purified IgG monoclonal antibody was obtained by purification with the caprylic acid precipitation method [*Antibodies-A Laboratory Manual*, Cold Spring Harbor Laboratory (1988)]. Determination of subclass of the monoclonal antibody was carried out by a binding ELISA using a subclass typing kit (rat monoclonal antibody isotyping kit, manufactured by DS Pharma Biomedical).

As a result, it was shown that the subclass of each antibody was determined as follows: anti-sugar chain-deficient CD27 monoclonal antibody KM4026 is rat IgG2a class, anti-sugar chain-deficient CD27 monoclonal antibody KM4027 is rat IgG2b class, anti-sugar chain-deficient CD27 monoclonal antibody KM4028 is rat IgG1 class, anti-sugar chain-deficient CD27 monoclonal antibody KM4030 is rat IgG2a class, and anti-sugar chain-deficient CD27 monoclonal antibody KM4031 is rat IgG1 class, respectively.

Example 4

Examination of Reactivity of Anti-Sugar Chain-Deficient CD27-Specific Monoclonal Antibody Using the following competitive ELISA system, reaction specificity of anti-sugar chain-deficient CD27 monoclonal antibodies KM4030 and KM4031 were examined. At first, 5 µg/mL/50 µL/well of Lec8-produced CD27-Fc obtained in Example 1 was dispensed into a 96-well ELISA plate (manufactured by Greiner), followed and allowed to stand at 4° C. overnight for adsorption.

After the plate was washed, 200 µL/well of 1% BSA-PBS was added to the plate which was then allowed to stand at room temperature for 1 hour such that the remaining active groups were blocked. Then, 1% BSA-PBS was discarded, 50 µL/well of diluted anti-sugar chain-deficient CD27 monoclonal antibody KM4030 purified antibody or KM4031 purified antibody was dispensed to the plate as a primary antibody.

Simultaneously, Lec8-produced CD27-Fc protein, DG44-produced CD27-Fc protein or human immunoglobulin as a binding competing material was added at concentrations of 20, 2, 0.2, and 0.02 µg/mL, so that the antibody and the binding competitive material were coexisted.

The plate was allowed to stand at room temperature for 2 hours. The plate was washed with 0.05% polyoxyethylene (20) sorbitan monolaurate [(the equivalent of ICI trade name Tween 20, manufactured by Wako Pure Chemical]-PBS (hereinafter referred to as "Tween-PBS"), and 50 µL/well of a peroxidase-labeled rabbit anti-rat immunoglobulin (manufactured by Zymed) as a secondary antibody was added to the plate which was then allowed to stand at room temperature for 1 hour.

The plate was washed with Tween-PBS, and color-developed by addition of a 2,2-azinobis(3-ethylbenzothiazole-6-sulfonic acid)ammonium (ABTS) substrate solution [1 mmol/L ABTS-0.1 mol/L citrate buffer (pH 4.2), 0.1% $H_2O_2$]. An absorbance (OD415 nm) was measured using a plate reader (Emax; Molecular Devices).

FIG. 13 shows the results of the competitive ELISA of anti-sugar chain-deficient CD27 monoclonal antibodies KM4030 and KM4031. As a result, it was demonstrated that DG44-produced CD27-Fc and human immunoglobulin did not inhibit the binding between the anti-sugar chain-deficient CD27 monoclonal antibodies KM4030 and KM4031 and the Tn antigen-bound CD27-Fc, but they inhibited the Tn antigen-bound CD27-Fc.

In addition, the same results were obtained for the anti-sugar chain-deficient CD27 monoclonal antibodies KM4026, KM4027 and KM4028. From the above, it was demonstrated that the anti-sugar chain-deficient CD27 monoclonal antibodies KM4026, KM4027, KM4028, KM4030 and KM4031 of the present invention specifically recognize the sugar chain-deficient CD27.

Figure 28A:
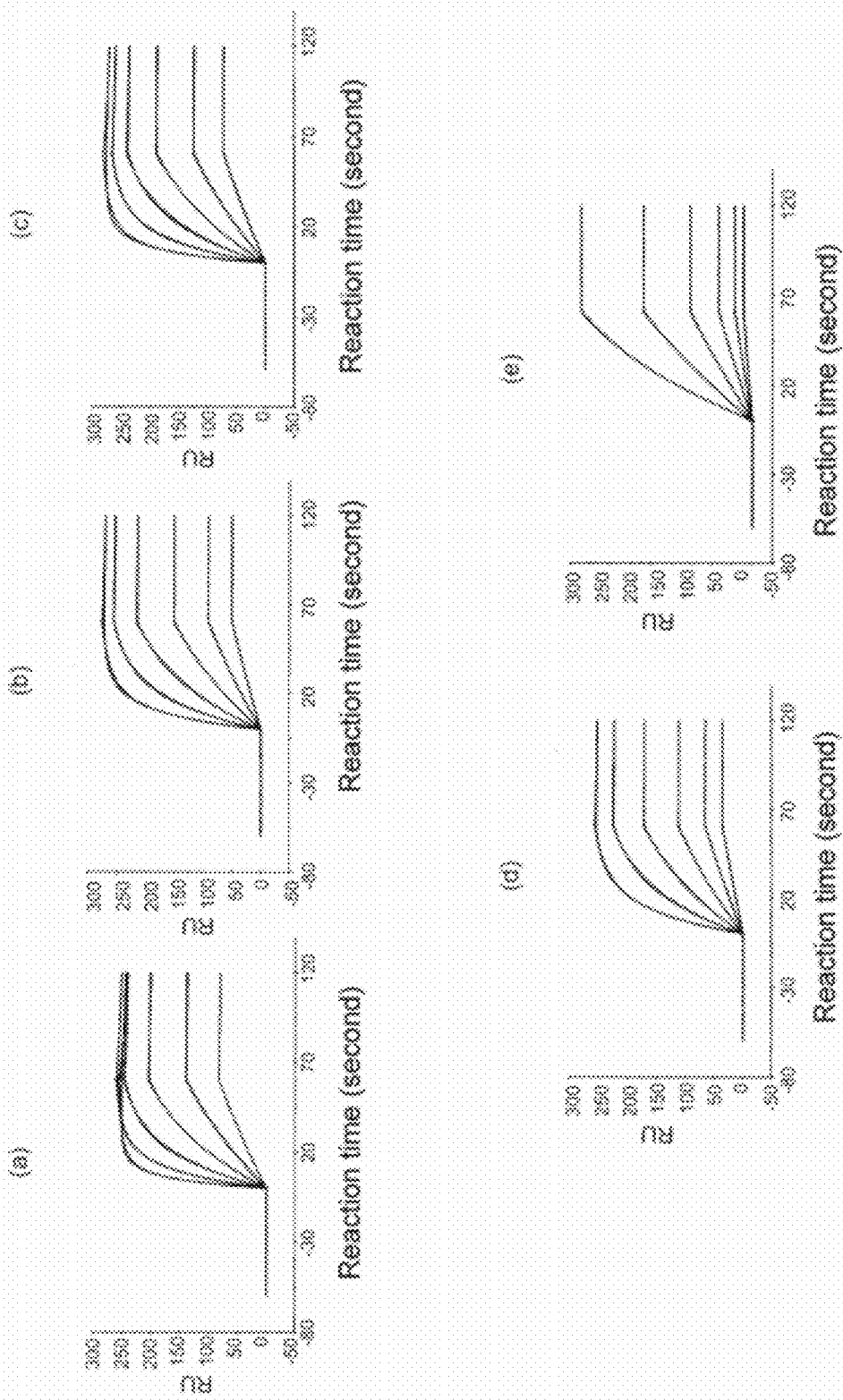
FIG. 28(A)(a) shows the Biacore sensorgram for binding of anti-sugar chain-deficient CD27 antibody KM4026 to sugar chain-deficient CD27-Fc (Tn antigen type CD27-Fc).

FIGS. 28(A) and 28(B) show the Biacore-based evaluation results of binding activity of the anti-sugar chain-deficient CD27 monoclonal chimeric antibodies KM4026, KM4027, KM4028, KM4030 and KM4031 to the sugar chain-deficient CD27-Fc. The binding activity was assayed by surface plasmon resonance method (SPR method) using a Biacore T100 (manufactured by GE Healthcare Bio-Sciences).

The anti-human IgG4 antibody (manufactured by Pharmingen) was immobilized on a CM5 sensor chip (manufactured by GE Healthcare Bio-Sciences) by amine coupling using an Amine Coupling Kit (manufactured by Biacore) in accordance with the instructions attached thereto.

For DG44-produced CD27-Fc obtained in Example 1 (7), Tn antigen type CD27-Fc or sialyl-Tn antigen type CD27-Fc, treated with a sugar chain-digestive enzyme using sialidase A or β(1-4) galactosidase of a Prozyme Glyco Enzymatic Deglycosylation Kit (manufactured by Prozyme) and a ProO-Link Extender Deglycosylation Plus (manufactured by Prozyme) in accordance with the protocols attached thereto, was added to be captured on the anti-human IgG4 antibody-immobilized chip to achieve 200 to 250 RU (resonance unit).

Thereafter, assay samples (anti-sugar chain-deficient CD27 monoclonal antibodies KM4026, KM4027, KM4028, KM4030 and KM4031) diluted from 20000 ng/mL in five steps were allowed to run at a flow rate of 30 µL/min onto the chip, and the sensorgram corresponding to each concentration was obtained and analyzed using an analysis software, Biacore T100 Evaluation software (manufactured by Biacore) installed on the apparatus.

As a result, it was demonstrated that the anti-sugar chain-deficient CD27 monoclonal antibody exhibit the binding activity to the Tn antigen type CD27-Fc and the sialyl-Tn antigen type CD27-Fc. From the above, it was demonstrated that all of the anti-sugar chain-deficient CD27 monoclonal antibodies of the present invention bind to Tn and sialyl-Tn antigens.

Example 5

Isolation and Analysis of cDNA Encoding the Variable Regions of Anti-Sugar Chain-Deficient CD27 Monoclonal Antibody (1) Preparation of mRNA from Anti-Sugar Chain-Deficient CD27 Monoclonal Antibody-Producing Hybridoma Cell From $5 \times 10^7$ to $1 \times 10^8$ cells of the respective hybridomas KM4026, KM4027, KM4028, KM4030 and KM4031 obtained in Example 3, mRNA of the respective anti-sugar chain-deficient CD27 monoclonal antibodies was prepared using RNAeasy Mini kit (manufactured by Qiagen) and Oligotex™-dT30<Super>mRNA Purification Kit (manufactured by Takara) in accordance with the instructions attached thereto.

(2) Gene Cloning of H Chain and L Chain Variable Regions of Anti-Sugar Chain-Deficient CD27 Monoclonal Antibody Using a BD SMART RACE cDNA Amplification Kit (manufactured by BD Biosciences) in accordance with the instructions attached thereto, cDNA was obtained from mRNA of the monoclonal antibody obtained in Example 5(1).

cDNA fragments of heavy chain variable regions (hereinafter referred to as "VH") of respective antibodies were amplified by carrying out PCR using the thus obtained cDNA as a template and using a rat IgG1-specific primer (SEQ ID NO:14), rat IgG2a-specific primer (SEQ ID NO:15), rat IgG2b-specific primer (SEQ ID NO:16), or rat CH1-specific primer (SEQ ID NO:17).

Also, cDNA fragments of light chain variable regions (hereinafter referred to as "VL") of respective antibodies were amplified by carrying out PCR using rat Ig (κ)-specific primers (SEQ ID NO:18) and (SEQ ID NO:19) instead of the respective subclass-specific primers of the antibody. PCR for amplifying VL and VH of KM4026, KM4030 and KM4031 was carried out using an Advantage 2 PCR kit (manufactured by Clontech) in accordance with the instructions attached thereto, whereas PCR for amplifying VL and VH of KM4027 and KM4028 was carried out using a KOD Plus Polymerase (manufactured by Toyobo) in accordance with the instructions attached thereto.

Next, in order to determine the nucleotide sequence by cloning, the obtained PCR products were separated by agarose gel electrophoresis, and each of the PCR products derived from KM4026, KM4030 and KM4031 was inserted into a pCR vector using a TOPO TA Cloning Kit (manufactured by Invitrogen) in accordance with the instructions attached thereto, whereas each of the PCR products derived from KM4027 and KM4028 was inserted into a pCR vector using a Zero Blunt TOPO PCR Cloning Kit for Sequencing (manufactured by Invitrogen) in accordance with the instructions attached thereto.

*Escherichia coli* was transformed with a plasmid having the PCR-amplified fragment inserted therein, and plasmids obtained from respective clones were prepared, followed by DNA sequencing. As a result, a plasmid comprising full-length VH cDNA and a plasmid comprising full-length VL cDNA, in which an ATG sequence considered to be the initiation codon is present in the 5'-terminal of the cDNA, were obtained. A scheme of cloning is shown in FIG. 14.

(3) Analysis of Gene Sequence of Anti-CD27 Monoclonal Antibody Variable Region

Complete nucleotide sequences of VH of the anti-sugar chain-deficient CD27 monoclonal antibodies KM4026, KM4027, KM4028, KM4030 and KM4031 contained in the plasmid obtained in Example 5(2) are represented by SEQ ID NOs:20 to 24, complete amino acid sequences of VH including a signal sequence deduced from these nucleotide sequences are represented by SEQ ID NOs:25 to 29, complete nucleotide sequences of VL contained in the plasmid are represented by SEQ ID NOs:30 to 34, and complete amino acid sequence of VL including a signal sequence deduced from these nucleotide sequences are represented by SEQ ID NOs:35 to 39, respectively.

Further, based on the comparison with amino acid sequences of conventional antibodies, CDRs of VH and VL of the respective monoclonal antibodies were identified. Amino acid sequences of CDR1, CDR2 and CDR3 of VH of the anti-sugar chain-deficient CD27 monoclonal antibody KM4026 are represented by SEQ ID NO:40, SEQ ID NO:41 and SEQ ID NO:42, respectively, whereas amino acid sequences of CDR1, CDR2 and CDR3 of VL are represented by SEQ ID NO:43, SEQ ID NO:44 and SEQ ID NO:45, respectively.

Amino acid sequences of CDR1, CDR2 and CDR3 of VH of the anti-sugar chain-deficient CD27 monoclonal antibody KM4027 are represented by SEQ ID NO:46, SEQ ID NO:47 and SEQ ID NO:48, respectively, whereas amino acid sequences of CDR1, CDR2 and CDR3 of VL are represented by SEQ ID NO:49, SEQ ID NO:50 and SEQ ID NO:51, respectively.

Amino acid sequences of CDR1, CDR2 and CDR3 of VH of the anti-sugar chain-deficient CD27 monoclonal antibody KM4028 are represented by SEQ ID NO:52, SEQ ID NO:53 and SEQ ID NO:54, respectively, whereas amino acid sequences of CDR1, CDR2 and CDR3 of VL are represented by SEQ ID NO:55, SEQ ID NO:56 and SEQ ID NO:57, respectively.

Amino acid sequences of CDR1, CDR2 and CDR3 of VH of the anti-sugar chain-deficient CD27 monoclonal antibody KM4030 are represented by SEQ ID NO:58, SEQ ID NO:59 and SEQ ID NO:60, respectively, and amino acid sequences of CDR1, CDR2 and CDR3 of VL are represented by SEQ ID NO:61, SEQ ID NO:62 and SEQ ID NO:63, respectively.

Amino acid sequences of CDR1, CDR2 and CDR3 of VH of the anti-sugar chain-deficient CD27 monoclonal antibody KM4031 are represented by SEQ ID NO:64, SEQ ID NO:65 and SEQ ID NO:66, respectively, whereas amino acid sequences of CDR1, CDR2 and CDR3 of VL are represented by SEQ ID NO:67, SEQ ID NO:68 and SEQ ID NO:69, respectively.

Example 6

Preparation of Anti-Sugar Chain-Deficient CD27 Chimeric Antibody (1) Construction of Anti-Sugar Chain-Deficient CD27 Chimeric Antibody Expression Vector The chimeric antibody prepared in accordance with the present invention is a chimeric antibody in which an H chain constant region of human IgG1 and an L chain constant region of human κ, disclosed in US97/10354, were ligated to variable regions of H and L chains, respectively, of the anti-CD27 rat monoclonal antibody obtained in Example 5(3).

For this purpose, using a pCR vector comprising VL or VH of each monoclonal antibody obtained in Example 5(3), and an antibody expression vector pKANTEX93 comprising the H chain constant region of human IgG1 and the L chain constant region of human κ disclosed in US97/10354, an anti-sugar chain-deficient CD27 chimeric antibody expression vector was constructed in accordance with the following procedure (FIGS. 15, 16, 17 and 18).

Using 10 ng of a pCR vector comprising VL or VH of KM4026, KM4027, KM4028, KM4030 or KM4031 as a template, total 20 μL of a solution containing 2 μL of 10×KOD Plus buffer, 2 μL of 2 mmol/L dNTPs, 1 μL of 25 mmol/L magnesium sulfate, 1 μL of KOD Plus polymerase (manufactured by Toyobo), each 1 μL of 10 μmol/L primers specific to VL and VH of each anti-CD27 monoclonal antibody was prepared. Using the thus prepared solution, PCR was carried out as follows: heating at 94° C. for 5 minutes, followed by 30 cycles each consisting of reaction at 94° C. for 1 minute, and reaction at 68° C. for 2 minutes.

Primers of VL of KM4026 are represented by SEQ ID NOs:70 and 71, and primers of VH of KM4026 are represented by SEQ ID NOs:72 and 73; primers of VL of KM4027 are represented by SEQ ID NOs:74 and 75, and primers of VH of KM4027 are represented by SEQ ID NOs:76 and 77; primers of VL of KM4028 are represented by SEQ ID NOs:78 and 79, and primers of VH of KM4028 are represented by SEQ ID NOs:80 and 81; primers of VL of KM4030 are represented by SEQ ID NOs:82 and 83, and primers of VH of KM4030 are represented by SEQ ID NOs:84 and 85; and primers of VL of KM4031 are represented by SEQ ID NOs:86 and 87, and primers of VH of KM4031 are represented by SEQ ID NOs:88 and 89, respectively.

Each PCR product was separated by 1% agarose gel electrophoresis. A specific PCR-amplified band was collected and inserted into a pCR Blunt-TOPO vector, using a Zero Blunt TOPO PCR Cloning Kit for Sequencing (manufactured by Invitrogen) in accordance with the instructions attached thereto.

VL of each antibody obtained was digested with restriction enzymes EcoRI (manufactured by New England Biolabs) and BsiWI (manufactured by New England Biolabs), thereby obtaining EcoRI-BsiWI fragment of VL. Further, VH of each antibody was digested with restriction enzymes NotI (manufactured by New England Biolabs) and ApaI (manufactured by New England Biolabs), thereby obtaining a NotI-ApaI fragment.

Each EcoRI-BsiWI fragment of VL of the anti-CD27 monoclonal antibodies KM4026, KM4027, KM4028, KM4030, and KM4031 was ligated into a DNA fragment obtained by digestion of pKANTEX93 with restriction enzymes EcoRI and BsiWI, using a Ligation High (manufactured by Toyobo) in accordance with the instructions attached thereto.

*Escherichia coli* DH5α (manufactured by Toyobo) was transformed with the ligated DNA fragment, and plasmids obtained from respective clones were prepared and allowed to react using a BigDye Terminator Cycle Sequencing FS Ready Reaction Kit (manufactured by PE Biosystems) in accordance with the instructions attached thereto, and then their nucleotide sequences were analyzed by a sequencer of the same company, ABI PRISM3700.

As a result, pKANTEX93 into which a cDNA encoding VL of the anti-CD27 monoclonal antibodies KM4026, KM4027, KM4028, KM4030, or KM4031 was inserted was obtained.

Subsequently, the NotI-ApaI fragment of VH of the anti-CD27 monoclonal antibody KM4026, KM4027, KM4028, KM4030 or KM4031 was ligated into a DNA fragment obtained by digestion of pKANTEX93 having an insertion of each VL of the anti-CD27 monoclonal antibody with restriction enzymes NotI and ApaI, using a Ligation High (manufactured by Toyobo) in accordance with the instructions attached thereto.

Escherichia coli DH5α (manufactured by Toyobo) was transformed with the ligated DNA fragment, and plasmids obtained from respective clones were prepared and allowed to react using a BigDye Terminator Cycle Sequencing FS Ready Reaction Kit (manufactured by PE Biosystems) in accordance with the instructions attached thereto, and then their nucleotide sequences were analyzed by a sequencer of the same company, ABI PRISM3700.

As a result, an anti-CD27 chimeric antibody expression vector was obtained having an insertion of each cDNA encoding VL and VH of the anti-CD27 monoclonal antibodies KM4026, KM4027, KM4028, KM4030, or KM4031.

(2) Expression of Anti-Sugar Chain-Deficient CD27 Chimeric Antibody in Animal Cell Using the anti-sugar chain-deficient CD27 chimeric antibody expression vector obtained in Section (1), expression of the anti-sugar chain-deficient CD27 chimeric antibody in an animal cell was carried out by a conventional method [Antibody Engineering, A Practical Guide, W.H. Freeman and Company (1992)] to obtain transformants which produce anti-sugar chain-deficient CD27 chimeric antibodies (chimeric KM4026, chimeric KM4028, chimeric KM4030 and chimeric KM4031).

As an animal cell for the expression of the desired antibody, a CHO/DG44 cell line in which a gene of α1,6-fucosyltransferase (FUT8) was double-knockout (hereinafter referred to as "FUT8 knockout CHO cell") was used. It is known that fucose is not added to a core of a complex N-linked sugar chain of the antibody expressed in this host cell [WO2002/31140].

(3) Preparation of Purified Chimeric Antibody

After culturing each of the transformants chimeric KM4026, chimeric KM4028, chimeric KM4030 and chimeric KM4031 obtained in Section (2) by a general culturing method, cell suspensions were recovered and centrifuged at 3000 rpm and 4° C. for 20 minutes to recover the culture supernatants, and then the culture supernatants were filtration-sterilized using a 0.22-μm pore size Millex GV filter.

The anti-sugar chain-deficient CD27 chimeric antibodies chimeric KM4026, chimeric KM4028, chimeric KM4030 and chimeric KM4031 were purified from the thus obtained culture supernatants, in the same manner as in Example 1(7), using Mab Select.

(4) Determination of Fucose Content of Anti-Sugar Chain-Deficient CD27 Chimeric Antibody In accordance with the method described in WO2002/31140, a proportion of sugar chains in which 1-position 1 of fucose is bound to 6-position of N-acetylglucosamine in the reducing end thorough α-bond in the complex N-linked sugar chain of the Fc region of each anti-sugar chain-deficient CD27 chimeric antibody. The results are given in Table 2 below.

TABLE 2

Contents of fucose in anti-sugar chain-deficient CD27 chimeric antibodies

| | |
|---|---|
| Chimeric KM4026 | 0% |
| Chimeric KM4028 | 0% |
| Chimeric KM4030 | 0% |
| Chimeric KM4031 | 0% |

As shown in Table 2, it was demonstrated that fucose was not added to the chimeric antibody constructed in Example 6(3).

Example 7

Evaluation of Activity of Anti-Sugar Chain-Deficient CD27 Chimeric Antibody

In the following Sections (1) to (3), the activity of the anti-sugar chain-deficient CD27 chimeric antibodies obtained in Example 6 was evaluated for chimeric KM4026, chimeric KM4028, chimeric KM4030 and chimeric KM4031.

(1) Biacore-Based Evaluation of Binding Activity of Anti-Sugar Chain-Deficient CD27 Chimeric Antibody to Human Sugar Chain-Deficient CD27-Fc In order to kinetically analyze the binding activity of the anti-sugar chain-deficient CD27 chimeric antibodies chimeric KM4026, chimeric KM4028, and chimeric KM4030 to the human sugar chain-deficient CD27-Fc, the binding activity was measured by surface plasmon resonance method (SPR method). All of the following manipulations were carried out using Biacore T100 (manufactured by GE Healthcare Bio-Sciences).

The Lec8-derived CD27-Fc obtained in Example 1(7) was immobilized on a CM5 sensor chip (manufactured by GE Healthcare Bio-Sciences) by amine coupling. Assay samples (chimeric KM4026, chimeric KM4028, chimeric KM4030 and chimeric KM4031), which were serially 3-fold diluted from 9 μg/mL to give 5 different concentrations, were sequentially and continuously added to the CD27-Fc-immobilized chip in order of increasing concentrations, in accordance with an automated program (Single Kinetix), followed by measurement.

Using the analysis software, Biacore T100 Evaluation software (manufactured by Biacore) installed on the apparatus, the analysis was carried out using Bivalent Analyte Model to calculate thereby an association rate constant ka and a dissociation rate constant kd of each antibody for the human sugar chain-deficient CD27-Fc.

The association rate constant ka1, dissociation rate constant kd1 and dissociation constant KD (kd1/ka1) of each antibody thus obtained are given in Table 3 below.

As shown in Table 3, all of chimeric KM4026, chimeric KM4028, chimeric KM4030 and chimeric KM4031 exhibited a high affinity in the range of $1 \times 10^{-8}$ to $1 \times 10^{-9}$ mol/L for the human sugar chain-deficient CD27-Fc.

TABLE 3

Binding activity of anti-sugar chain-deficient CD27 chimeric antibodies to human sugar chain-deficient CD27-Fc

| Antibodies | ka (1/Ms) | kd (1/s) | KD (mol/L) |
|---|---|---|---|
| Chimeric KM4026 | $1.8 \times 10^5$ | $83.1 \times 10^{-4}$ | $46.65 \times 10^{-9}$ |
| Chimeric KM4028 | $11.7 \times 10^5$ | $9.2 \times 10^{-4}$ | $0.79 \times 10^{-9}$ |
| Chimeric KM4030 | $2.9 \times 10^5$ | $3.4 \times 10^{-4}$ | $1.07 \times 10^{-9}$ |
| Chimeric KM4031 | $4.0 \times 10^5$ | $2.0 \times 10^{-4}$ | $0.51 \times 10^{-9}$ |

(2) Evaluation of Reaction Specificity of Anti-Sugar Chain-Deficient CD27 Chimeric Antibody by Fluorescent Cell Staining (Flow Cytometer Analysis)

The CD27/DG44-4, CD27/Lec8-4 and Lec8 cells constructed in the same manner as in Example 2 were used as assay cells. The CD27/DG44-4 subcultured in an HT-medium supplemented with 500 μg/mL of G418, and the CD27/

Lec8-4 subcultured in an HT-medium supplemented with 50 nmol/L of MTX and 500 µg/mL of G418 were peeled off using a 0.02% EDTA solution, and then washed with PBS.

After washing, 5×10$^5$ cells were suspended in 50 µL of 1% BSA-PBS, each antibody solution of the anti-sugar chain-deficient CD27 chimeric antibodies (chimeric KM4026, chimeric KM4028, chimeric KM4030 and chimeric KM4031 was prepared to give concentrations of 0.02, 0.2, 2 and 10 µg/mL and then 50 µL/well of each antibody solution was dispensed to the plate as a primary antibody, followed by reaction at ice temperature for 1 hour.

As a positive control, an anti-RCAS1 mouse antibody 22-1-1 (manufactured by MBL) and an anti-CD27 mouse antibody O323 (manufactured by Santa Cruz Biotechnology) which are anti-Tn antibodies were used.

After the reaction was complete, centrifugation was carried out twice with PBS, and ALEXA Fluoro 488-labeled anti-human immunoglobulin G(H+L), ALEXA Fluoro 488-labeled anti-mouse immunoglobulin G(H+L) or ALEXA Fluoro 488-labeled anti-human immunoglobulin M(µ) as a secondary antibody was added at a concentration of 50 µL/well, followed by reaction at ice temperature under shading for 30 minutes.

Figure 19B:
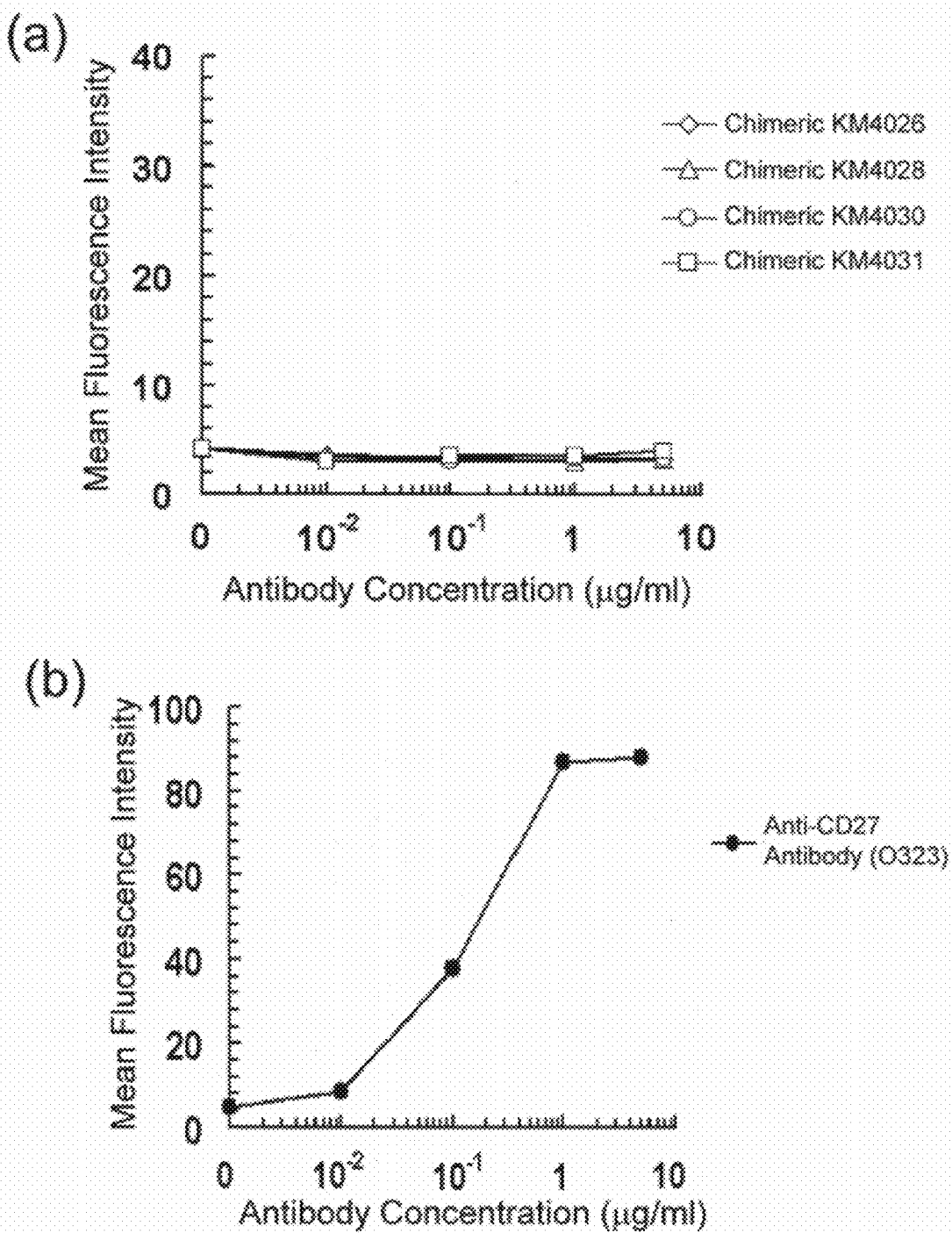
FIG. 19(B)(a) shows the result of the binding activity of various anti-sugar chain-deficient CD27 chimeric antibodies chimeric KM4026 (◇), chimeric KM4028 (Δ), chimeric KM4030 (○) and chimeric KM4031 (□) to CD27/DG44-4 cells, measured by using a flow cytometer (FCM). In addition, FIG. 19(B)(b) shows the measurement results of the binding activity of commercially available anti-CD27 antibody O323 (●) to CD27/DG44-4 cells using a flow cytometer (FCM). The ordinate represents the mean fluorescence intensity, and the abscissa represents a final concentration of the reacted antibodies.

Again, centrifugation was repeated twice using PBS, and the cells were washed and suspended in 500 µL of 1% BSA-PBS. The fluorescence of 510 to 530 nm excited with a 488 nm argon laser was measured by a flow cytometer (manufactured by Beckman Coulter, Cytomics FC500 MPL). The results are shown in FIGS. 19(A) to (C).

As a result, all of the anti-sugar chain-deficient CD27 chimeric antibodies did not bind to Lec8 cells and CD27/DG44-4 cells, but exhibited binding only to the CD27/Lec8-4 cells expressing the sugar chain-deficient CD27.

From these results, it was demonstrated that the anti-sugar chain-deficient CD27 chimeric antibodies chimeric KM4026, chimeric KM4028, chimeric KM4030 and chimeric KM4031 of the present invention specifically recognize the sugar chain-deficient CD27 that is expressed on the cell surface.

(3) Evaluation of Antibody-Dependent Cellular Cytotoxicity (ADCC Activity) of Anti-Sugar Chain-Deficient CD27 Chimeric Antibody ADCC activity of the anti-sugar chain-deficient CD27 chimeric antibodies chimeric KM4026, chimeric KM4028, chimeric KM4030 and chimeric KM4031 on the CD27/Lec8-4 cells constructed in Example 2 was measured in the following manner.

(3)-1 Preparation of Target Cell Suspension

CD27/Lec8-4 cells subcultured in an HT-medium supplemented with 50 nmol/L of MTX and 500 µg/mL of G418 were peeled off using a 0.02% EDTA solution, washed with PBS, washed with a phenol red-free RPMI1640 medium (manufactured by Invitrogen, hereinafter referred to as "ADCC medium") containing 5% dialyzed fetal bovine serum (dFBS, manufactured by Invitrogen), and then suspended in the same medium to give an optimum concentration and used as the target cell suspension.

(3)-2 Preparation of Effector Cell Suspension

From healthy human peripheral blood, peripheral blood mononuclear cells (PBMCs) were isolated in the following manner. From healthy volunteers, 50 mL of healthy human peripheral blood was collected using a syringe to which 0.5 mL of heparin sodium (manufactured by Shimizu Pharmaceutical) was added.

On a Mono-poly resolving medium (manufactured by DS Pharma Biomedical), 3.5 mL of the collected peripheral blood was gently layered 3 mL of which was dispensed into each of 15-mL tubes. Then, the mononuclear layer was separated by centrifugation at 400×g, break off, and room temperature for 20 minutes. The thus obtained mononuclear fraction was washed twice with an ADCC medium, and then suspended in the same medium to give an optimum cell counts and used as an effector cell suspension.

(3)-3 Measurement of ADCC Activity

ADCC activity was measured in the following manner, using a LDH-Cytotoxic Test Wako (manufactured by Wako) in accordance with the instructions attached thereto.

Figure 20:
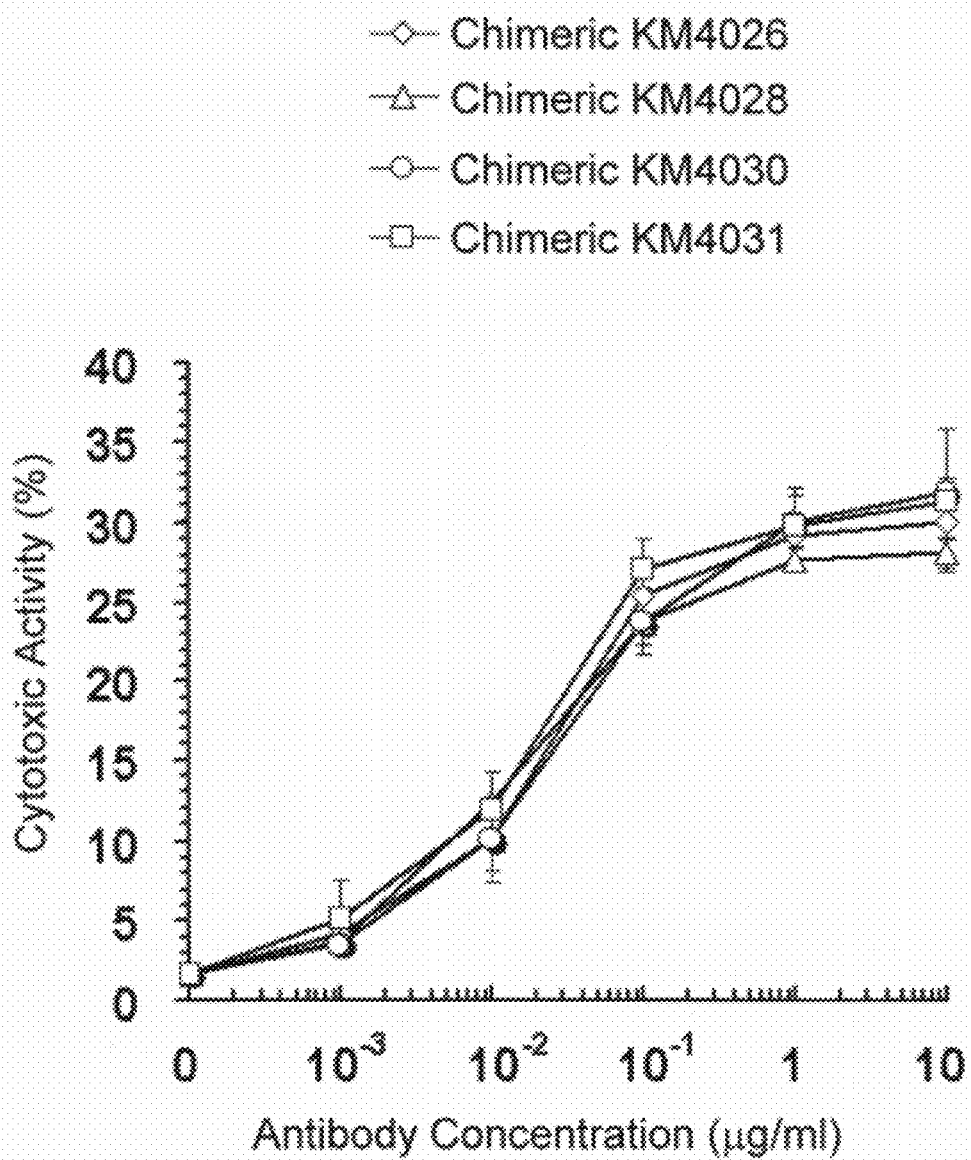
FIG. 20 shows the antibody-dependent cellular cytotoxicity (ADCC activity) of various anti-sugar chain-deficient CD27 chimeric antibodies chimeric KM4026 (◇), chimeric KM4028 (Δ), chimeric KM4030 and chimeric KM4031 (□) on CD27/Lec8-4 cells. The ordinate represents the cellular cytotoxicity (%), and the abscissa represents the final concentration of respective antibodies.

At first, 50 µL/well of an antibodisolution, in which each antibody was 10-fold diluted from 30 µg/mL to give a concentration of 0.003 µg/mL, was dispensed into a 96-well U bottom plate (manufactured by Falcon). Next, 1×10$^4$ cells/50 µL/well of the target cell suspension prepared in Section (3)-1 were dispensed thereto. Finally, 2.5×10$^5$ cells/50 µL/well of the effector cell suspension prepared in Section (3)-2 were dispensed thereto to give a total volume of 150 µL, followed by reaction at 37° C. for 4 hours. Therefore, the experiment was carried out at a 25:1 ratio of effector cell (E):target cell (T). The ADCC activity was calculated by the following formula. The results are shown in FIG. 20.

ADCC activity(%)={([absorbance of sample]−[absorbance of target cell spontaneous release]−[absorbance of effector cell spontaneous release])/([absorbance of target cell total release]−[absorbance of target cell spontaneous release])}×100 (Formula)

As a result, all of the anti-sugar chain-deficient CD27 chimeric antibodies chimeric KM4026, chimeric KM4028, chimeric KM4030 and chimeric KM4031, in which no core fucose binds to the complex N-linked sugar chain of the Fc region of the antibody, exhibited a high ADCC activity on CD27/Lec8-4 cells.

From these results, it was demonstrated that all of the anti-sugar chain-deficient CD27 chimeric antibodies chimeric KM4026, chimeric KM4028, chimeric KM4030 and chimeric KM4031 of the present invention have a high ADCC activity on the cells expressing the sugar chain-deficient CD27.

(4) Evaluation of Complement-Dependent Cytotoxicity (CDC Activity) of Anti-Sugar Chain-Deficient CD27 Chimeric Antibody The CDC activity of the anti-sugar chain-deficient CD27 chimeric antibodies chimeric KM4026, chimeric KM4028, chimeric KM4030 and chimeric KM4031 on the CD27/Lec8-4 cell constructed in Example 2 was measured in the following manner.

CD27/Lec8-4 cells were washed with PBS, washed with an RPMI1640 medium supplemented with 10% dFBS, and then suspended in the same medium to give an optimum concentration and used as the target cell suspension. The target cell suspension were dispensed into a 96-well flat bottom plate (manufactured by Greiner) to give a density of 5×10$^4$ cells/50 µL/well.

Further, the anti-sugar chain-deficient CD27 chimeric antibody solution prepared to have an appropriate concentration and the human complement (manufactured by Sigma) were added thereto to give a total volume of 150 µL/well. In addition, an antibody-free reaction well (0% cytotoxicity well) as a negative control, and a cell-free reaction well (100% cytotoxicity well) as a positive control were respectively prepared. The reaction was carried out in a 5% CO2 incubator at 37° C. for 2 hours.

Figure 21:
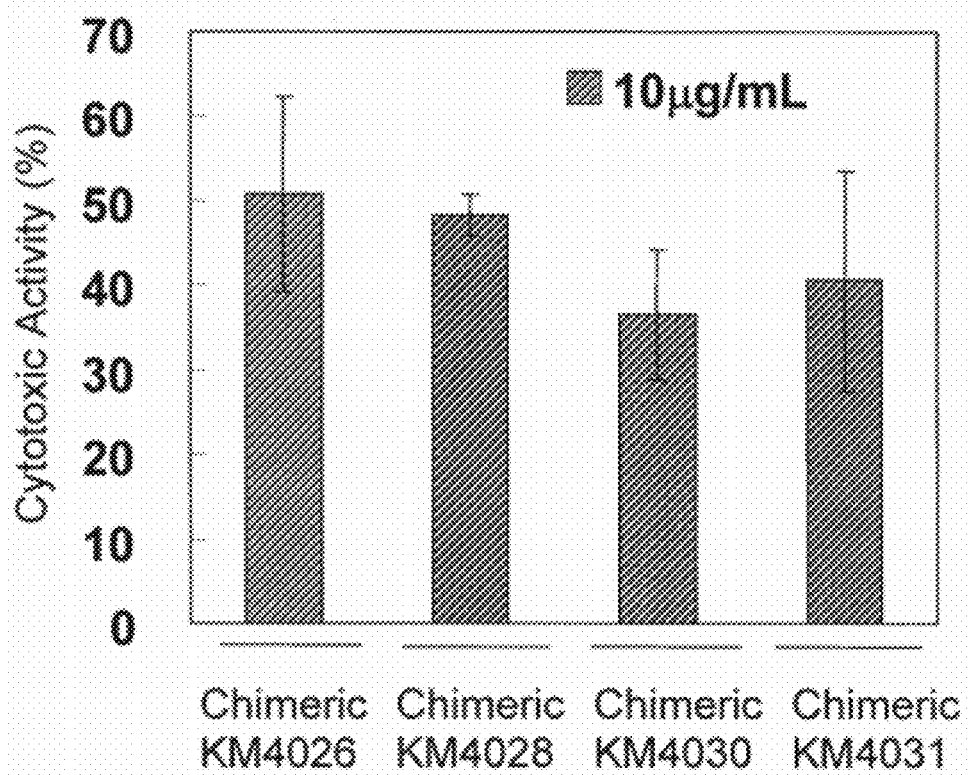
FIG. 21 shows the complement-dependent cytotoxicity (CDC activity) of various anti-sugar chain-deficient CD27 chimeric antibodies chimeric KM4026, chimeric KM4028, chimeric KM4030 and chimeric KM4031 on CD27/Lec8-4 cells. The ordinate represents the cellular cytotoxicity (%), and the abscissa represents the reacted antibodies.

After the reaction was complete, 15 µL of a WST-1 reagent (manufactured by Roche) was added to respective reaction wells, followed by reaction at 37° C. for about 4 hours. The absorbance (OD450 nm-OD690 nm) for each well was measured using a plate reader (Emax). From the absorbance of each well, the CDC activity (cytotoxicity [%]) was calculated by the following formula. The results are given in FIG. 21.

CDC activity (cytotoxicity [%])={1−(absorbance of reaction well-absorbance of 100% Lysis well)/(absorbance of 0% Lysis well-absorbance of 100% Lysis well)}×100       (Formula)

As a result, all of the anti-sugar chain-deficient CD27 chimeric antibodies chimeric KM4026, chimeric KM4028, chimeric KM4030 and chimeric KM4031 obtained in accordance with the present invention exhibited a CDC activity.

Example 8

Construction of CHO Cell Expressing Cynomolgus CD27 on Cell Membrane (1) Cloning of Cynomolgus CD27 Gene From the cynomolgus peripheral blood-derived RNA, CD27-encoding gene was isolated in accordance with the following procedure. Total 5 μL of a solution was prepared which contains 3.3 μg of RNA isolated from the cynomolgus peripheral blood using Trizol (manufactured by Invitrogen) as a template, and 1 μL of oligo dT and 1 μL of dNTP Mix attached to a SuperScript III First-Strand kit (manufactured by Invitrogen).

The thus prepared solution was allowed to react at 65° C. for 5 minutes and quenched on ice for 1 minute. Then, 2 μL of 10×RT buffer, 2 μL of DTT, 1 μL of RNase OUT, and 1 μL of RT attached to the SuperScript III First-Strand kit were added thereto, followed by reverse reaction at 50° C. for 50 minutes. After the reaction was complete, the reaction solution was heated at 85° C. for 5 minutes to deactivate the reverse transcriptase, and 1 μL of RNase H attached to the SuperScript III First-Strand kit was added, followed by reaction at 37° C. for 20 minutes to completely degrade RNA. This cynomolgus peripheral blood-derived single-stranded cDNA was stored at −20° C. until use.

Total 25 μL of a solution was prepared which contains 1.25 μL of the above-prepared cynomolgus peripheral blood-derived single-stranded cDNA as a template, 2.5 μL of 10×KOD Plus buffer, 2.5 μL of 2 mmol/L dNTPs, 1 μL of 25 mmol/L magnesium sulfate, 0.5 μL of KOD Plus polymerase (manufactured by Toyobo), 20 μmol of mfCD27_5UTR (SEQ ID NO:90) designed from the 5' non-translated region sequence of rhesus monkey CD27, and 20 pmol of mfCD27_3UTR (SEQ ID NO:91) designed from the 3' non-translated region sequence of rhesus monkey CD27.

The thus prepared solution was heated at 94° C. for 5 minutes, and PCR was carried out under the following reaction conditions: 30 cycles each consisting of reaction at 94° C. for 30 seconds, and reaction at 68° C. for 2 minutes. The reaction solution was separated by 1% agarose gel electrophoresis, and the about 800-bp PCR product was inserted into a pCR Blunt-TOPO vector using a Zero Blunt TOPO PCR Cloning Kit for Sequencing (manufactured by Invitrogen) in accordance with the instructions attached thereto.

Figure 22:
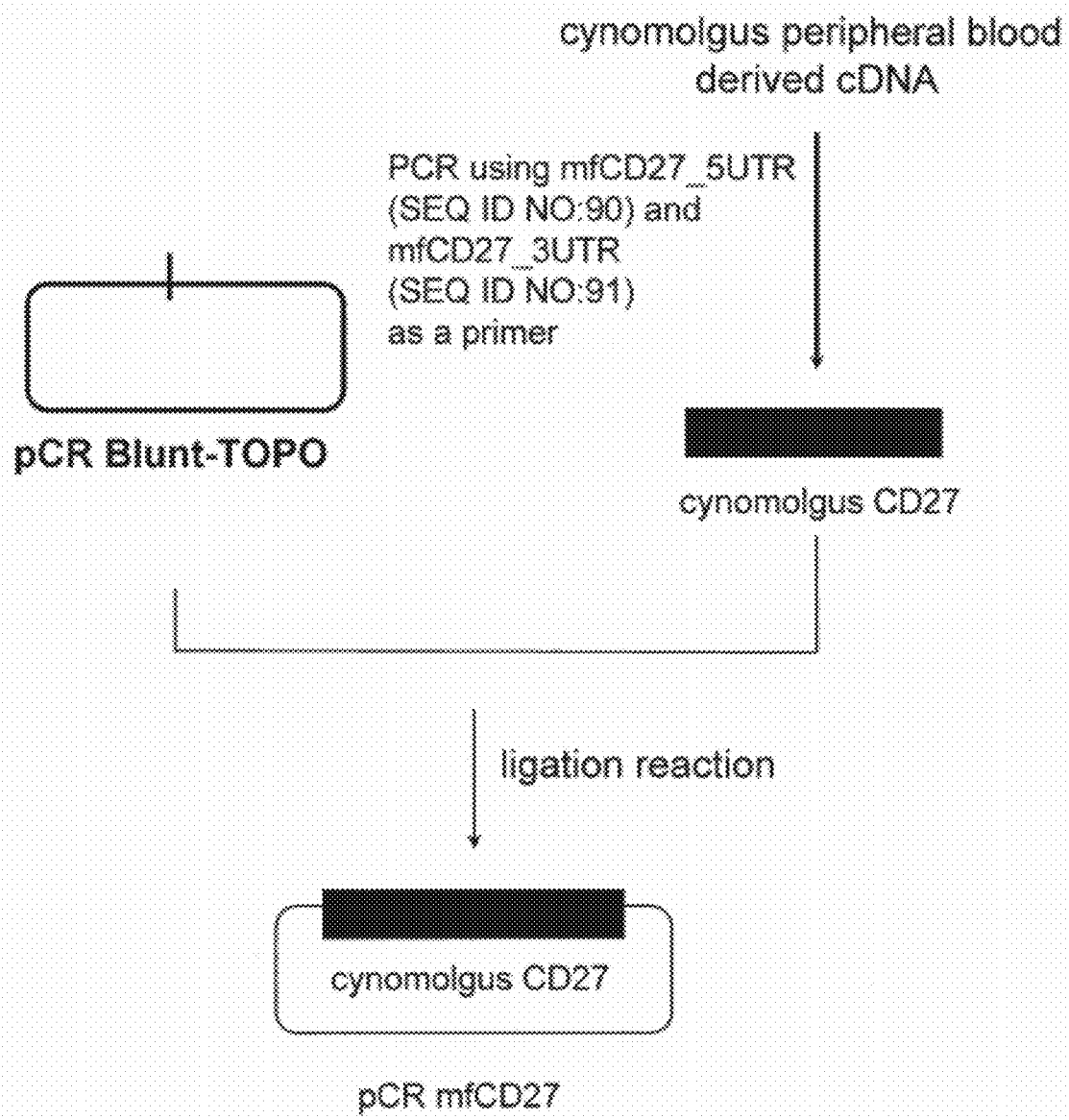
FIG. 22 shows the construction method of a plasmid vector pCR mfCD27 comprising a DNA that encodes a cynomolgus CD27 protein.

*Escherichia coli* DH5α (manufactured by Toyobo) was transformed with the vector into which the PCR-amplified fragment was inserted, and plasmids obtained from respective clones were prepared and allowed to react using a BigDye Terminator Cycle Sequencing FS Ready Reaction Kit (manufactured by PE Biosystems) in accordance with the instructions attached thereto, and then their nucleotide sequences were analyzed by a sequencer of the same company, ABI PRISM3700. As a result, a plasmid pCR mfCD27 was obtained into which the cynomolgus CD27-encoding cDNA (SEQ ID NO:92) was cloned (FIG. 22).

(2) Construction of Simian CD27-Expressing Plasmid pKANTEX mfCD27His

The cynomolgus CD27-expressing vector pKANTEX mfCD27His having a His tag attached to the C-terminal was constructed in accordance with the following procedure.

Total 50 μL of a solution was prepared which contains 10 ng of pCR mfCD27 as a template, 5 μL of 10×KOD Plus buffer, 5 μL of 2 mmol/L dNTP, 2 μL of 25 mmol/L magnesium sulfate, 1 μL of KOD Plus polymerase (manufactured by Toyobo), 0.2 μL of 100 μmol/L mfCD27toKAN_5 (SEQ ID NO:93) and 0.2 μL of 100 μmol/L mfCD27HisKAN_3 (SEQ ID NO:94).

The thus prepared solution was heated at 94° C. for 5 minutes, and PCR was carried out under the following reaction conditions: heating at 94° C. for 5 minutes, followed by 30 cycles each consisting of reaction at 94° C. for 30 seconds, and reaction at 68° C. for 2 minutes. The reaction solution was separated by 1% agarose gel electrophoresis, and the about 800-bp PCR product was inserted into a pCR Blunt-TOPO vector using a Zero Blunt TOPO PCR Cloning Kit for Sequencing (manufactured by Invitrogen) in accordance with the instructions attached thereto.

*Escherichia coli* DH5α (manufactured by Toyobo) was transformed with the vector into which the PCR-amplified fragment was inserted, and plasmids obtained from respective clones were prepared and allowed to react using a BigDye Terminator Cycle Sequencing FS Ready Reaction Kit (manufactured by PE Biosystems) in accordance with the instructions attached thereto, and then their nucleotide sequences were analyzed by a sequencer of the same company, ABI PRISM3700.

Figure 23:
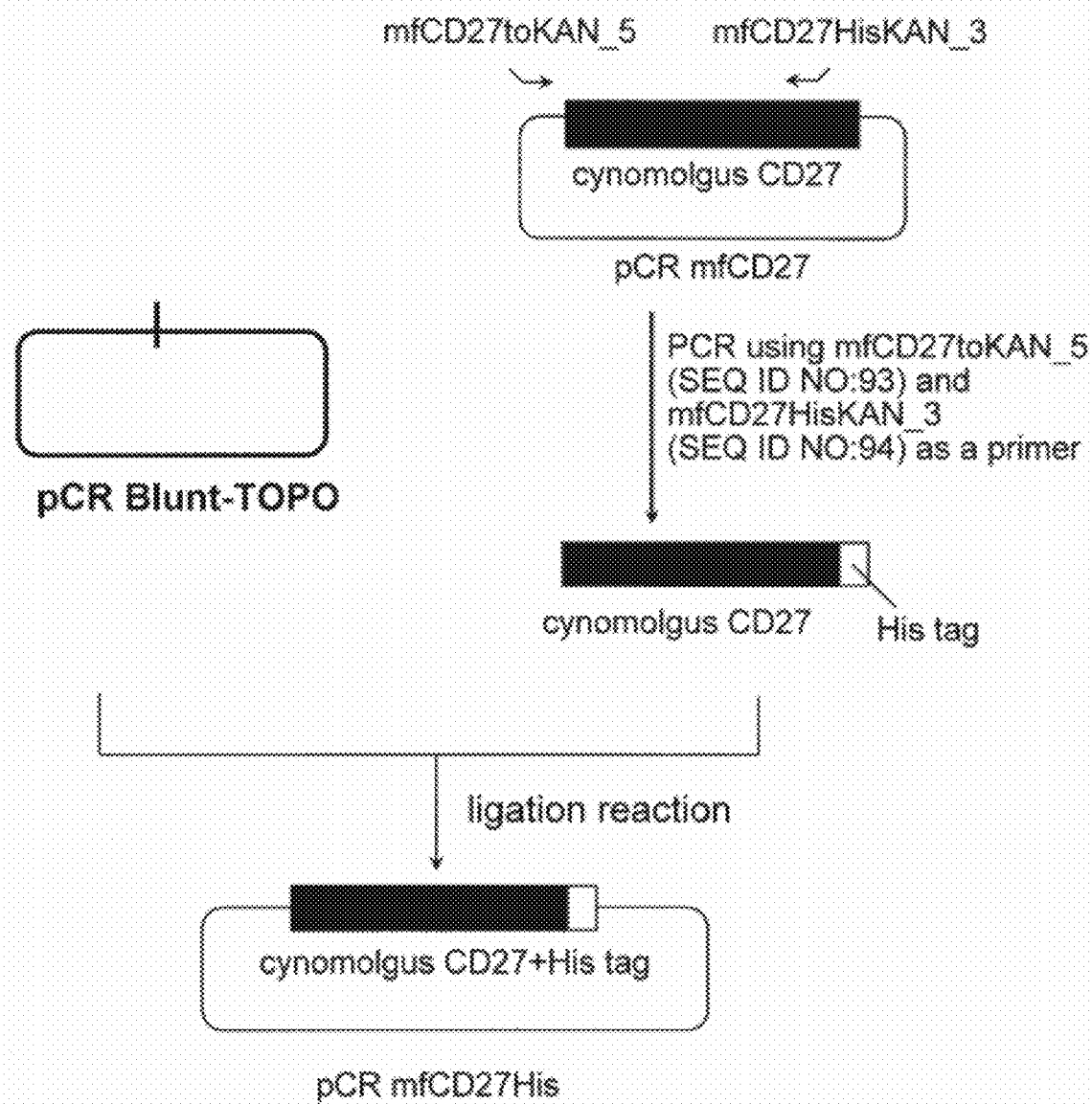
FIG. 23 shows the construction method of a plasmid vector mfCD27His comprising a DNA that encodes a cynomolgus CD27 protein.

As a result, a plasmid pCR mfCD27His was obtained into which a cDNA (SEQ ID NO:95) encoding the cynomolgus CD27 having a His tag attached to the C-terminal thereof was cloned (FIG. 23).

The about 800-bp DNA fragment obtained by digestion of pCR mfCD27His with restriction enzymes NotI and SalI (manufactured by Takara Bio) was ligated into the about 10-kbp DNA fragment obtained by digestion of pKANTEX CD27 constructed in Example 2 with restriction enzymes NotI and SalI (manufactured by Takara Bio) using a Ligation High (manufactured by Toyobo) in accordance with the instructions attached thereto.

*Escherichia coli* DH5α (manufactured by Toyobo) was transformed with the ligated DNA fragment, and plasmids obtained from respective clones were prepared and allowed to react using a BigDye Terminator Cycle Sequencing FS Ready Reaction Kit (manufactured by PE Biosystems) in accordance with the instructions attached thereto, and then their nucleotide sequences were analyzed by a sequencer of the same company, ABI PRISM3700.

Figure 24:
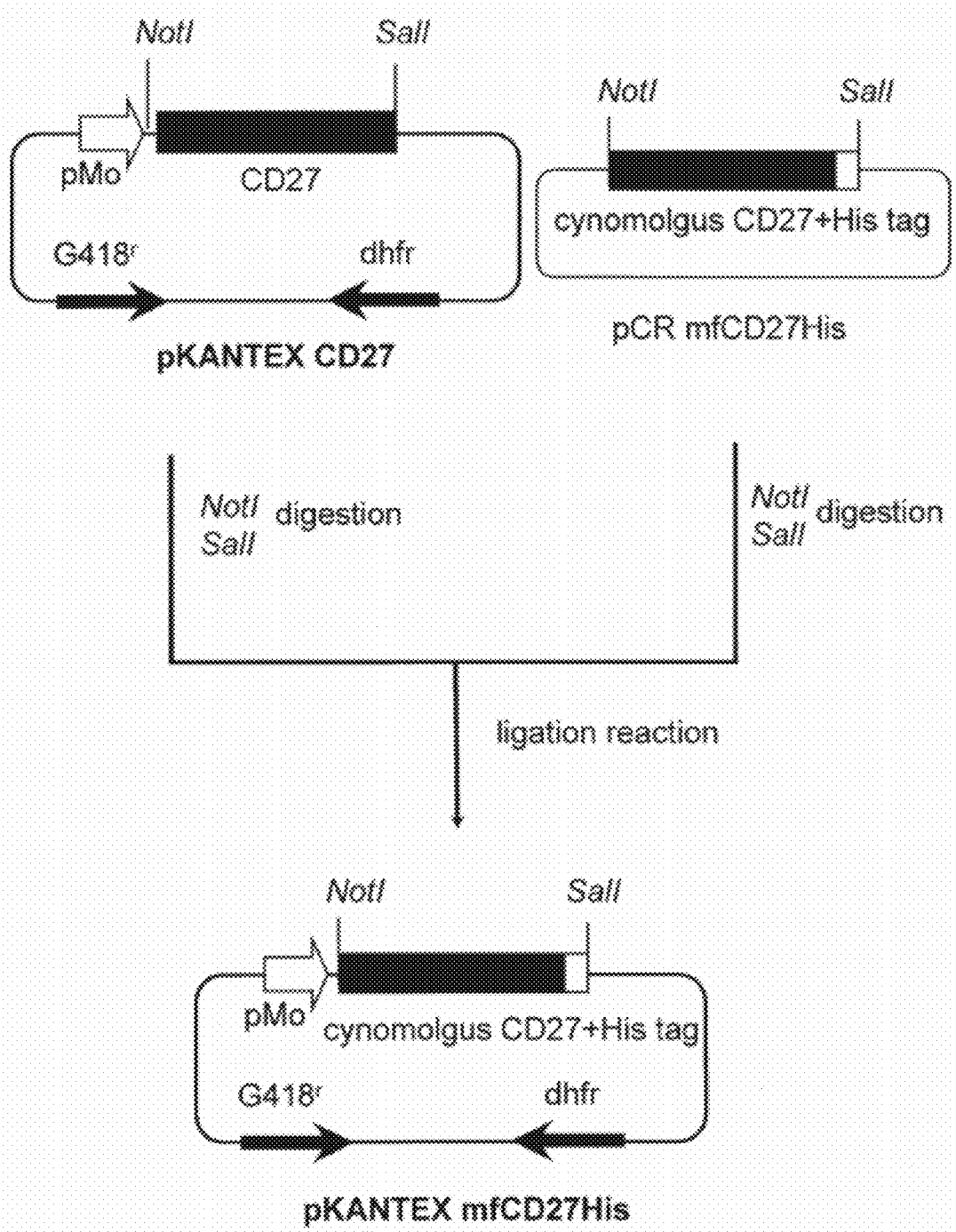
FIG. 24 shows the construction method of a cynomolgus CD27 expression vector pKATEX mfCD27His.

As a result, a plasmid pKANTEX mfCD27His was obtained for the expression of the cynomolgus CD27 having a His tag attached to the C-terminal thereof (FIG. 24).

*Escherichia coli* DH5α transformed with pKANTEX mfCD27His was seeded in 200 mL of an LB medium, followed by overnight culture. After the culture was complete, the bacteria were recovered and the plasmid was purified using a QIAfilter Plasmid Midi Kit (manufactured by Qiagen) in accordance with the instructions attached thereto. Then, 50 μg of the purified plasmid was linearized by digestion with a restriction enzyme AatII (manufactured by New England Biolabs).

(3) Introduction of Simian CD27-Expressing Plasmid pKANTEX mfCD27His

Lec8 and DG44 cells expressing cynomolgus CD27 were established by gene introduction of the cynomolgus CD27-expressing plasmid pKANTEX mfCD27His constructed in Section (2) into Lec8 cells and CHO/DG44 cells.

The gene introduction was carried out in the same manner as in Example 1(6), except that pKANTEX mfCD27His was used as the plasmid to be introduced. The cells after gene introduction were suspended in 30 mL of an HT-medium, and 100 µL/well of the cell suspension was seeded on 96-well plates in triplicate.

One day after seeding, the culture medium was exchanged with a subculture medium containing 500 µg/mL G418, followed by culturing for 10 days. Thereafter, the G418-resistant clone was obtained. The Lec8-derived cynomolgus CD27-expressing cell line was designated as a cynomolgus CD27/Lec8 cell, whereas the DG44-derived cynomolgus CD27-expressing cell line was designated as a cynomolgus CD27/DG44 cell.

Example 9

Evaluation of Cross Reactivity of Anti-Sugar Chain-Deficient CD27 Chimeric Antibody with Simian CD27 Protein The cynomolgus CD27/DG44 and cynomolgus CD27/Lec8 cells constructed in Example 8 were used as assay cells.

(1) Evaluation of Reactivity of Anti-Sugar Chain-Deficient CD27 Chimeric Antibody with Simian CD27-Expressing Cell by Fluorescent Cell Staining (Flow Cytometer Analysis)

Each of the binding activity of anti-sugar chain-deficient CD27 chimeric antibodies chimeric KM4026, chimeric KM4028, chimeric KM4030 and chimeric KM4031 to the cynomolgus CD27-expressing cells was measured in accordance with the following procedure.

The cynomolgus CD27/DG44 and cynomolgus CD27/Lec8 cells, which were subcultured in an HT-medium supplemented with 500 µg/mL of G418, were peeled off using a 0.02% EDTA solution, and respective cells were washed with PBS.

After washing, $5 \times 10^5$ cells were suspended in 50 µL of 1% BSA-PBS, and 50 µL/well of each antibody solution prepared to contain 10 µg/mL of anti-sugar chain-deficient CD27 chimeric antibodies (chimeric KM4026, chimeric KM4028, chimeric KM4030 and chimeric KM4031) as a primary antibody was dispensed thereto, followed by reaction at ice temperature for 1 hour.

As a positive control, the anti-CD27 mouse antibody O323 was used. After the reaction was complete, the cells were washed by centrifuging with PBS twice, and 50 µL/well of ALEXA Fluoro 488-labeled anti-human immunoglobulin G(H+L) or ALEXA Fluoro 488-labeled anti-mouse immunoglobulin G(H+L) (all manufactured by BioLegend) was added thereto as a secondary antibody, followed by reaction at ice temperature under shading for 30 minutes.

Figure 25:
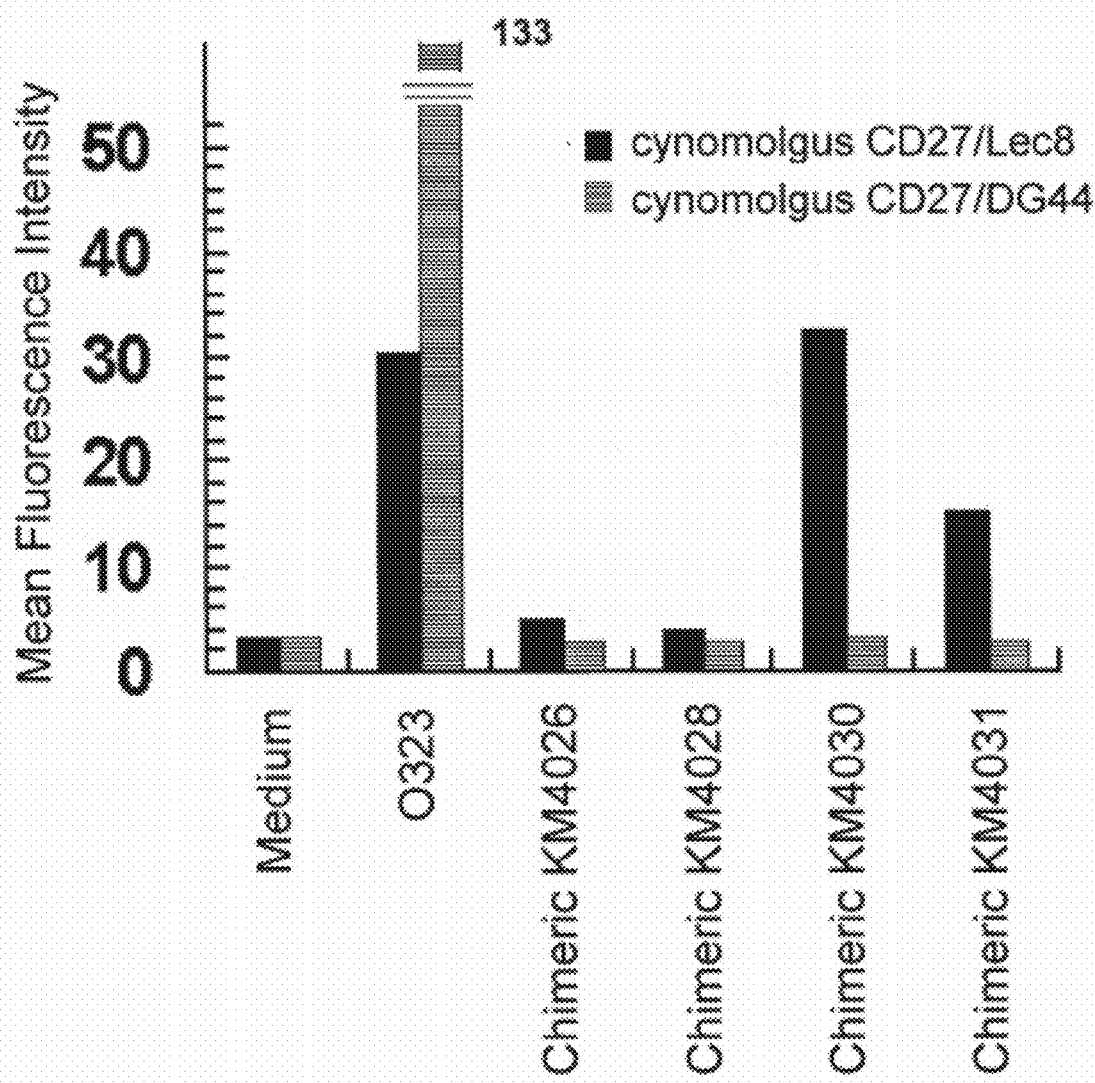
FIG. 25 shows the result of the binding activity of various anti-sugar chain-deficient CD27 chimeric antibodies chimeric KM4026, chimeric KM4020, chimeric KM4030, chimeric KM4031 and commercially available anti-CD27 antibody O323 to cynomolgus CD27/Lec8 cells or cynomolgus CD27/DG44 cells, measured by using a flow cytometer (FCM). The ordinate represents the mean fluorescence intensity, and the abscissa represents the reacted antibodies.

After the cells were washed again by centrifuging with PBS twice, the cells were suspended in 500 µL of 1% BSA-PBS, and fluorescence of 510 to 530 nm excited with a 488 nm argon laser was measured by a flow cytometer (manufactured by Beckman Coulter, Cytomics FC500 MPL). The results obtained are given in FIG. 25.

As a result, it was demonstrated that the anti-sugar chain-deficient CD27 chimeric antibodies chimeric KM4030 and chimeric KM4031 react with the cynomolgus CD27/Lec8 cells expressing the sugar chain-deficient CD27.

On the other hand, the reactivity of the anti-sugar chain-deficient CD27 chimeric antibodies chimeric KM4026 and chimeric KM4028 to the cynomolgus CD27/Lec8 cells was insignificant. Further, it was confirmed that all of the anti-sugar chain-deficient CD27 chimeric antibodies did not bind to the cynomolgus CD27/DG44 cells.

(2) Evaluation of ADCC Activity of Anti-Sugar Chain-Deficient CD27 Chimeric Antibody on Simian CD27-Expressing Cells Cynomolgus CD27/Lec8 cells, which were subcultured in an HT-medium supplemented with 500 µg/mL of G418, were peeled off using a 0.02% EDTA solution, washed with PBS, washed with an ADCC medium, and then suspended in the same medium to give an optimum concentration and used as the target cell suspension. Further, preparation of an effector cell suspension and measurement of ADCC activity were carried out in the same manner as in Example 7. The results are shown in FIG. 26.

As a result, all of the anti-sugar chain-deficient CD27 chimeric antibodies chimeric KM4026, chimeric KM4028, chimeric KM4030 and chimeric KM4031 exhibited ADCC activity on the cynomolgus CD27/Lec8 cell containing an O-linked sugar chain to which galactose is not bound (sugar chain-deficient cynomolgus CD27 cell).

From the above, it was demonstrated that all of the anti-sugar chain-deficient CD27 chimeric antibodies chimeric KM4026, chimeric KM4028, chimeric KM4030 and chimeric KM4031 in accordance with the present invention exhibit the cross reactivity for the sugar chain-deficient cynomolgus CD27 cells. It was suggested that each of anti-sugar chain-deficient CD27 chimeric antibodies shows strength and weakness in their reactivity to the sugar chain-deficient cynomolgus CD27 and differences in the type of epitopes which will be recognized.

Further, the ADCC activity of the anti-sugar chain-deficient CD27 chimeric antibody chimeric KM4030 was measured using the cells in which CD27 expression amount on the cell surface was confirmed to be almost equal by flow cytometric analysis, among the human CD27/Lec8 cells constructed in Example 2 and the cynomolgus CD27/Lec8 cells constructed in Example 8. The effector cell suspension was prepared from the same healthy human peripheral blood. The results are shown in FIG. 27.

As a result, it was suggested that the sugar chain-deficient CD27 chimeric antibody chimeric KM4030 exhibit an equal ADCC activity on the cynomolgus CD27/Lec8 cells and the human CD27/Lec8 cells.

Example 10

Preparation of Humanized Antibody (1) Design of Amino Acid Sequences of VH and VL of Anti-Sugar Chain-Deficient CD27 Humanized Antibody An amino acid sequence of VH of an anti-sugar chain-deficient CD27 humanized antibody was designed in the following manner.

Firstly, the amino acid sequence of FR of VH of a human antibody for grafting amino acid sequences of CDR1 to CDR3 of an anti-sugar chain-deficient CD27 rat monoclonal antibody KM4030VH represented by SEQ ID NOs:58, 59 and 60, respectively, was selected.

Using a GCG Package (manufactured by Genetics Computer Group) as a sequence analysis system, based on the amino acid sequence data base of conventional proteins by the BLASTP method [Nucleic Acids Res., 25, 3389 (1997)], a human antibody having a high homology with the anti-sugar chain-deficient CD27 rat monoclonal antibody KM4030 was searched.

When the homology score was compared with the homology of an actual amino acid sequence, SWISSPROT data base accession no. BAH04525, the repertoire of neutralizing monoclonal antibodies against H3N2 influenza viruses in human (hereinafter referred to as "BAH04525") exhibited a homology of 83.9%, and it was a human antibody which had the highest homology, therefore the amino acid sequence of FR of this antibody was selected.

An amino acid sequence of CDR of VH of the anti-sugar chain-deficient CD27 rat monoclonal antibody KM4030 represented by SEQ ID NO:58 to 60 was grafted into an appropriate position of the thus determined amino acid sequence of FR of the human antibody. In this manner, an amino acid sequence HV0 of VH of the anti-sugar chain-deficient CD27 humanized antibody represented by SEQ ID NO:96 was designed.

Next, an amino acid sequence of VL of an anti-sugar chain-deficient CD27 humanized antibody was designed in the following manner.

An amino acid sequence of FR of VL of a human antibody for grafting amino acid sequences of CDR1 to CDR3 of an anti-sugar chain-deficient CD27 rat monoclonal antibody KM4030VL represented by SEQ ID NO:61 to 63, respectively, was selected.

Kabat et al., have classified VL of conventionally known various human antibodies into four subgroups (HSG I to IV) based on the homology of their amino acid sequences and reported on the consensus sequences for each of the subgroups [Sequences of Proteins of Immunological Interest, US Dept. Health and Human Services (1991)]. Accordingly, the homology was examined between the amino acid sequences of FR of consensus sequences of subgroups I to IV of VL of the human antibody and the amino acid sequence of FR of VL of the anti-sugar chain-deficient CD27 rat antibody KM4030.

As a result of the homology analysis, the homology of HSGI, HSGII, HSGIII, and HSGIV was 86.3%, 60.0%, 73.8%, and 73.8%, respectively. Therefore, the amino acid sequence of FR of KM4030VL had the highest homology with subgroup I.

Based on these results, the amino acid sequence of CDR of VL of the anti-sugar chain-deficient CD27 rat monoclonal antibody KM4030 was grafted into an appropriate position of an amino acid sequence of FR of consensus sequences of subgroup I of VL of the human antibody.

However, since Leu at position 124 in the amino acid sequence of VL of the anti-sugar chain-deficient CD27 rat monoclonal antibody KM4030 represented by SEQ ID NO:38 is not the amino acid residue having the highest use frequency in the region which corresponds to the amino acid sequence of the human antibody FR cited by Kabat, but is an amino acid residue which is used at a relatively high frequency, the above-mentioned amino acid residues which are recognized in the amino acid sequence of the anti-sugar chain-deficient CD27 rat monoclonal antibody KM4030 were used.

In this manner, an amino acid sequence LV0 of VL of an anti-sugar chain-deficient CD27 humanized antibody represented by SEQ ID NO:97 was designed.

The amino acid sequence HV0 of VH and amino acid sequence LV0 of VL of the anti-sugar chain-deficient CD27 humanized antibody designed in the above are sequences in which the CDR amino acid sequence of the anti-sugar chain-deficient CD27 rat monoclonal antibody KM4030 alone was grafted into the selected human antibody FR amino acid sequence.

However, in general, when a humanized antibody is prepared, its binding activity is frequently lowered in the case of merely a simple grafting of CDR amino acid sequence of a rat antibody to a human antibody FR. For these reasons, in order to avoid lowering of the binding activity, modifications of the amino acid residues considered to have an influence on the binding activity, among the FR amino acid residues which are different between human antibodies and rat antibodies, are carried out together with the grafting of the CDR amino acid sequence.

Thus, the amino acid residues of FR considered to have an influence on the binding activity were identified in this Example in the following manner.

Firstly, a three-dimensional structure of an antibody V region (HV0LV0) comprising the amino acid sequence HV0 of VH and amino acid sequence LV0 of VL of anti-sugar chain-deficient CD27 humanized antibody designed in the above was constructed using a computer modeling technique.

In addition, preparation of the three dimensional structure coordinates and display of the three-dimensional structure were carried out using software Discovery Studio (manufactured by Accelrys) in accordance with instructions attached thereto. In addition, a computer model of the three-dimensional structure of the V region of the anti-sugar chain-deficient CD27 rat monoclonal antibody KM4030 was also constructed in the same manner.

Further, by similarly constructing a three-dimensional structure model comprising an amino acid sequence in which the amino acid residues in the FR amino acid sequences of VH and VL of HV0LV0, which are different from those of the anti-sugar chain-deficient CD27 rat antibody KM4030, were selected and modified into the amino acid residues of the anti-sugar chain-deficient CD27 rat monoclonal antibody KM4030, three-dimensional structures of the V regions of anti-sugar chain-deficient CD27 rat monoclonal antibody KM4030, HV0LV0 and modified product were compared, whereby the amino acid residues predicted to have an influence on the binding activity of the antibody were identified.

As a result, as the amino acid residues among amino acid residues of FR of HV0LV0, which are considered to change a three-dimensional structure of the antigen binding region and therefore have an influence on the binding activity of the antibody, Ser at position 30, Val at position 48, Ser at position 49, Asn at position 77, Val at position 93, Ala at position 97 and Thr at position 117 in the HV0 sequence, and Ile at position 21, Pro at position 40, Val at position 58, Thr at position 85, and Tyr at position 87 in the LV0 sequence were respectively selected.

By modifying at least one or more amino acid sequences of these selected amino acid residues into the amino acid residues which are present at the same positions of the amino acid sequence of the anti-sugar chain-deficient CD27 rat monoclonal antibody KM4030, VH and VL of a humanized antibody having various modifications were designed.

Specifically, regarding the antibody VH, at least one modification was introduced among the amino acid modifications for substituting Ser at position 30 with Asn, Val at position 48 with Ile, Ser at position 49 with Ala, Asn at position 77 with Gly, Val at position 93 with Thr, Ala at position 97 with Thr, and Thr at position 117 with Val in the amino acid sequence represented by SEQ ID NO:96.

Further, regarding the antibody VL, at least one modification was introduced among the amino acid modifications for substituting Ile at position 21 with Leu, Pro at position 40 with Leu, Val at position 58 with Ile, Thr at position 85 with Ala, and Tyr at position 87 with Phe in the amino acid sequence represented by SEQ ID NO:97.

By designing amino acid sequences of variable regions of HV2LV0, HV3LV0, HV5LV0, and HV7LV0 with modifications of at least one of amino acid residues present in FR of HV0LV0, amino acid sequences of H chain variable regions HV2, HV3, HV5, and HV7 are represented by SEQ ID NOs: 101, 103, 105, and 107, respectively.

(2) Preparation and Evaluation of Anti-Sugar Chain-Deficient CD27 Humanized Antibody DNA encoding the amino acid sequence of the variable region of the anti-sugar chain-deficient CD27 humanized antibody was constructed in mammalian cells using a codon which is used at a high frequency, when amino acid modification(s) are carried out using a codon which is used as DNA encoding the amino acid sequence of VH or VL of the anti-sugar chain-deficient CD27 rat monoclonal antibody KM4030.

The DNA sequences encoding the amino acid sequence of HV0 and LV0 of the anti-sugar chain-deficient CD27 humanized antibody are respectively represented by SEQ ID NOs: 98 and 99, whereas the DNA sequences encoding the amino acid sequences of variable regions HV2, HV3, HV5, and HV7 on which amino acid modification(s) were made are respectively represented by SEQ ID NOs:100, 102, 104, and 106.

(3) Construction of cDNA Coding for VH of Anti-Sugar Chain-Deficient CD27 Humanized Antibody A cDNA encoding the amino acid sequence HV0, HV5 or HV7 of the VH of the anti-sugar chain-deficient CD27 humanized antibody represented by SEQ ID NO:98, 104 or 106 designed in the above (1) of this Example was prepared by total synthesis.

(4) Construction of cDNA Encoding VL of Anti-Sugar Chain-Deficient CD27 Humanized Antibody A cDNA encoding the amino acid sequence LV0 of the VL of the anti-sugar chain-deficient CD27 humanized antibody represented by SEQ ID NO:99 designed in item (1) of this Example was prepared by total synthesis.

(5) Construction of Anti-Sugar Chain-Deficient CD27 Humanized Antibody Expression Vector Various anti-sugar chain-deficient CD27 humanized antibody expression vectors were constructed by inserting a cDNA encoding any one of the HV0, HV5 and HV7 and a cDNA encoding the LV0, obtained in the above (2) and (3) of this Example, into appropriate positions of the humanized antibody expression vector pKANTEX93 described in WO97/10354.

(6) Stable Expression of Anti-Sugar Chain-Deficient CD27 Humanized Antibody Using Animal Cell and Preparation of Purified Antibody Stable expression of the anti-sugar chain-deficient CD27 humanized antibody using an animal cell and purification of the antibody from culture supernatant were carried out in the same manner as the methods described in Example 6(2) and (3).

As a result, an anti-sugar chain-deficient CD27 humanized antibody HV0LV0 wherein VH of the antibody consists of HV0, and VL of LV0, HV5LV0 wherein VH of the antibody consists of HV5, and VL of LV0 and HV7LV0 wherein VH of the antibody consists of HV7, and VL of LV0, three kinds in total, were prepared.

Example 11

Activity Evaluation of Anti-Sugar Chain-Deficient CD27 Humanized Antibody

In the following (1) to (5), activity evaluation of the anti-sugar chain-deficient CD27 chimeric antibody KM4030 obtained in Example 6 and the anti-sugar chain-deficient CD27 humanized antibodies HV0LV0, HV5LV0 and HV7LV0 obtained in Example 10 was carried out.

(1) Evaluation of the Binding Activity of Anti-Sugar Chain-Deficient CD27 Chimeric Antibody and Humanized Antibody to Human Sugar Chain-Deficient CD27-Fc by BIACORE In order to analyze binding activity of anti-sugar chain-deficient CD27 humanized antibody to human sugar chain-deficient CD27 reaction kinetically, it was measured in the same manner as in Example 7(1) using BIACORE T100 (manufactured by BIACORE).

The binding rate constant Ka1, dissociation rate constant Kd1 and dissociation constant KD (Kd1/Ka1) obtained as the results are shown in FIG. 29.

As shown in Table 4, each of the humanized antibodies HV0LV0, HV5LV0 and HV7LV0 showed a high affinity of $2\times10^{-9}$ mol/l and maintained an antigen binding activity similar to that of the anti-sugar chain-deficient CD27 chimeric antibody.

TABLE 4

Binding activity of anti-sugar chain-deficient CD27 chimeric antibody and humanized antibody to human sugar chain-deficient CD27-Fc

| Antibody | Ka1(1/Ms) | Kd1(1/s) | KD (mol/L) |
|---|---|---|---|
| KM4030 | $7.4 \times 10^5$ | $8.2 \times 10^{-4}$ | $1.1 \times 10^{-9}$ |
| HV0LV0 | $5.1 \times 10^5$ | $14.1 \times 10^{-4}$ | $2.8 \times 10^{-9}$ |
| HV5LV0 | $3.4 \times 10^5$ | $7.5 \times 10^{-4}$ | $2.2 \times 10^{-9}$ |
| HV7LV0 | $4.0 \times 10^5$ | $8.8 \times 10^{-4}$ | $2.2 \times 10^{-9}$ |

(2) Evaluation of Reaction Specificity of Anti-Sugar Chain-Deficient CD27 Humanized Antibody by Fluorescent Cell Staining Method (Flow Cytometer Analysis)

Reaction specificity of the anti-sugar chain-deficient CD27 humanized antibody was measured in the same manner as in Example 7(2). Regarding the cell lines, the CD27/DG44-4 cell and CD27/Lec8-M19 cell having almost the same antigen expression quantity, prepared by the same method of Example 2, were used as assaying cells.

Figure 30B:
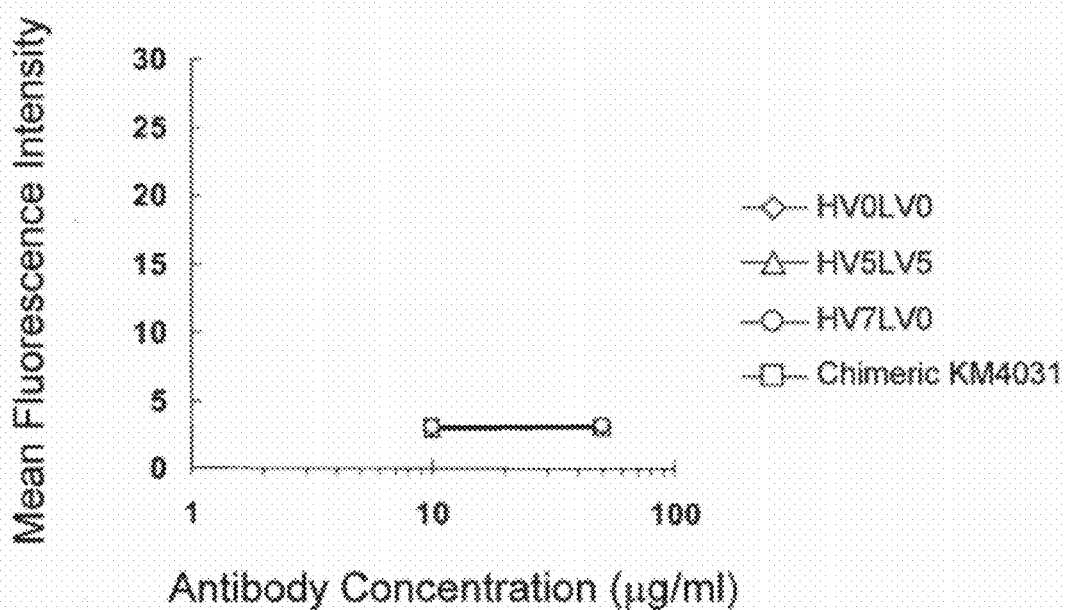
FIG. 30(B) shows the result of the binding activity of anti-sugar chain-deficient CD27 chimeric antibody KM4030

The anti-sugar chain-deficient CD27 humanized antibody HV0LV0, HV5LV0 or HV7LV0 was adjusted to a final concentration of 0.0001, 0.001, 0.003, 0.01, 0.03, 0.1, 1 or 10 μg/ml and used as the primary antibody. Results thereof are shown in FIG. 30(A) and FIG. 30(B).

As a result, all of the anti-sugar chain-deficient CD27 humanized antibodies HV0LV0, HV5LV0 and HV7LV0 did not bind to the CD27/DG44-4 cell, and their binding was observed only to the CD27/Lec8-M19 cell expressing the sugar chain-deficient CD27. In addition, reactivity of the anti-sugar chain-deficient CD27 humanized antibodies for the CD27/Lec8-M19 cell expressing the sugar chain-deficient CD27 was almost equal to the anti-sugar chain-deficient CD27 chimeric antibody KM4030.

(3) Evaluation of Antibody-Depended Cellular Toxicity (ADCC Activity) of Anti-Sugar Chain-Deficient CD27 Humanized Antibodies The ADCC activity of the anti-sugar chain-deficient CD27 humanized antibodies HV0LV0, HV5LV0 and HV7LV0 was measured in the same manner as in Example 7(3). The CD27/DG44-4 cell and CD27/Lec8-M19 cell prepared by the same method of Example 2 were used as the target cells. In addition, the test was carried out at an effector cell (E)/target cell (T) ratio of 12.5:1. The results are shown in FIG. 31.

As a result, ADCC activity of the humanized antibody HV0LV0 slightly lower than that of the anti-sugar chain-deficient CD27 chimeric antibody KM4030, but anti-sugar chain-deficient CD27 humanized antibodies HV5LV0 and HV7LV0 showed the ADCC activity almost equal to or higher than that of the anti-sugar chain-deficient CD27 chimeric antibody KM4030.

(4) Evaluation of Complement-Depended Cytotoxicity (CDC Activity) of Anti-Sugar Chain-Deficient CD27 Humanized Antibodies The CDC activity of the anti-sugar chain-deficient CD27 humanized antibodies HV0LV0, HV5LV0 and HV7LV0 was measured in the same manner as in Example 7(4). Each antibody was adjusted to a final concentration of 100 μg/ml.

As a result, the anti-sugar chain-deficient CD27 humanized antibodies HV0LV0, HV5LV0 and HV7LV0 showed higher CDC activity than that of the anti-sugar chain-deficient CD27 chimeric antibody KM4030.

(5) Evaluation of Cross Reactivity of Anti-Sugar Chain-Deficient CD27 Humanized Antibody with Monkey CD27 Protein Binding activity of the anti-sugar chain-deficient CD27 humanized antibodies HV0LV0, HV5LV0 and HV7LV0 for cynomolgus CD27 expression cells was measured by a fluorescent cell staining method (cytometer analysis) in the same manner as in Example 9(1). The cynomolgus CD27/DG44 cell and cynomolgus CD27/Lec8 cell prepared in Example 8 were used as the cynomolgus CD27 expression cells. The results are shown in FIG. 33(A) and FIG. 33(B).

As a result, the anti-sugar chain-deficient CD27 humanized antibodies HV0LV0, HV5LV0 and HV7LV0 did not bind to the cynomolgus CD27/DG44 cell. On the other hand, the anti-sugar chain-deficient CD27 humanized antibodies HV0LV0, HV5LV0 and HV7LV0 reacted with the sugar chain-deficient CD27-expressing cynomolgus CD27/Lec8 cell in the same manner as the case of the anti-sugar chain-deficient CD27 chimeric antibody KM4030. Based on the above, it was revealed that each of the anti-sugar chain-deficient CD27 humanized antibodies HV0LV0, HV5LV0 and HV7LV0 shows cross reactivity with the sugar chain-deficient cynomolgus CD27 cell.

The hybridoma KM4030 has been deposited to International Patent Organism Depositary, National Institute of Advanced Industrial Science and Technology (Central 6, 1-1-1, Higashi, Tsukuba-shi, Ibaraki-ken 305-8566, Japan) under the Budapest Treaty as FERM BP-10976 on Jun. 5, 2008.

While the invention has been described in detail and with reference to specific embodiments thereof, it will be apparent to one skill in the art that various changes and modifications can be made therein without departing from the spirit and scope thereof.

This application is based on U.S. provisional application No. 61/290,542, filed on Dec. 29, 2009, the entire contents of which are incorporated hereinto by reference. All references cited herein are incorporated in their entirety.

REFERENCE TO DEPOSITED BIOLOGICAL MATERIAL

IPOD FREM BP-10976

SEQUENCE LISTING FREE TEXT

SEQ ID NO:1—human CD27 nucleotide sequence
SEQ ID NO:2—human CD27 amino acid sequence
SEQ ID NO:3—Description of artificial sequence: CD27 forward primer
SEQ ID NO:4—Description of artificial sequence: CD27809B
SEQ ID NO:5—Description of artificial sequence: CD27-A primer
SEQ ID NO:6—Description of artificial sequence: CD27-B primer
SEQ ID NO:7—Description of artificial sequence: primer 1
SEQ ID NO:8—Description of artificial sequence: primer 2
SEQ ID NO:9—Description of artificial sequence: g4A primer
SEQ ID NO:10—Description of artificial sequence: g4B primer
SEQ ID NO:11—Description of artificial sequence: CD27-Fc protein nucleotide sequence
SEQ ID NO:12—Description of artificial sequence: CD27-Fc protein amino acid sequence
SEQ ID NO:13—Description of artificial sequence: CD27-C primer
SEQ ID NO:14—Description of artificial sequence: primer specific for rat IgG1
SEQ ID NO:15—Description of artificial sequence: primer specific for rat IgG2a
SEQ ID NO:16—Description of artificial sequence: primer specific for rat IgG2b
SEQ ID NO:17—Description of artificial sequence: primer specific for rat CH1
SEQ ID NO:18—Description of artificial sequence: primer specific for rat Ig(κ) 1
SEQ ID NO:19—Description of artificial sequence: primer specific for rat Ig(κ) 2
SEQ ID NO:20—KM4026 VH nucleotide sequence
SEQ ID NO:21—KM4027 VH nucleotide sequence
SEQ ID NO:22—KM4028 VH nucleotide sequence
SEQ ID NO:23—KM4030 VH nucleotide sequence
SEQ ID NO:24—KM4031 VH nucleotide sequence
SEQ ID NO:25—KM4026 VH amino acid sequence
SEQ ID NO:26—KM4027 VH amino acid sequence
SEQ ID NO:27—KM4028 VH amino acid sequence
SEQ ID NO:28—KM4030 VH amino acid sequence
SEQ ID NO:29—KM4031 VH amino acid sequence
SEQ ID NO:30—KM4026 VL nucleotide sequence
SEQ ID NO:31—KM4027 VL nucleotide sequence
SEQ ID NO:32—KM4028 VL nucleotide sequence
SEQ ID NO:33—KM4030 VL nucleotide sequence
SEQ ID NO:34—KM4031 VL nucleotide sequence
SEQ ID NO:35—KM4026 VL amino acid sequence
SEQ ID NO:36—KM4027 VL amino acid sequence
SEQ ID NO:37—KM4028 VL amino acid sequence
SEQ ID NO:38—KM4030 VL amino acid sequence
SEQ ID NO:39—KM4031 VL amino acid sequence
SEQ ID NO:40—KM4026 VH CDR1
SEQ ID NO:41—KM4026 VH CDR2
SEQ ID NO:42—KM4026 VH CDR3
SEQ ID NO:43—KM4026 VL CDR1
SEQ ID NO:44—KM4026 VL CDR2
SEQ ID NO:45—KM4026 VL CDR3
SEQ ID NO:46—KM4027 VH CDR1
SEQ ID NO:47—KM4027 VH CDR2
SEQ ID NO:48—KM4027 VH CDR3
SEQ ID NO:49—KM4027 VL CDR1
SEQ ID NO:50—KM4027 VL CDR2
SEQ ID NO:51—KM4027 VL CDR3
SEQ ID NO:52—KM4028 VH CDR1
SEQ ID NO:53—KM4028 VH CDR2
SEQ ID NO:54—KM4028 VH CDR3
SEQ ID NO:55—KM4028 VL CDR1
SEQ ID NO:56—KM4028 VL CDR2

SEQ ID NO:57—KM4028 VL CDR3
SEQ ID NO:58—KM4030 VH CDR1
SEQ ID NO:59—KM4030 VH CDR2
SEQ ID NO:60—KM4030 VH CDR3
SEQ ID NO:61—KM4030 VL CDR1
SEQ ID NO:62—KM4030 VL CDR2
SEQ ID NO:63—KM4030 VL CDR3
SEQ ID NO:64—KM4031 VH CDR1
SEQ ID NO:65—KM4031 VH CDR2
SEQ ID NO:66—KM4030 VH CDR3
SEQ ID NO:67—KM4031 VL CDR1
SEQ ID NO:68—KM4031 VL CDR2
SEQ ID NO:69—KM4031 VL CDR3
SEQ ID NO:70—Description of artificial sequence: KM4026 VL chimera primer 1
SEQ ID NO:71—Description of artificial sequence: KM4026 VL chimera primer 2
SEQ ID NO:72—Description of artificial sequence: KM4026 VH chimera primer 1
SEQ ID NO:73—Description of artificial sequence: KM4026 VH chimera primer 2
SEQ ID NO:74—Description of artificial sequence: KM4027 VL chimera primer 1
SEQ ID NO:75—Description of artificial sequence: KM4027 VL chimera primer 2
SEQ ID NO:76—Description of artificial sequence: KM4027 VH chimera primer 1
SEQ ID NO:77—Description of artificial sequence: KM4027 VH chimera primer 2
SEQ ID NO:78—Description of artificial sequence: KM4028 VL chimera primer 1
SEQ ID NO:79—Description of artificial sequence: KM4028 VL chimera primer 2
SEQ ID NO:80—Description of artificial sequence: KM4028 VH chimera primer 1
SEQ ID NO:81—Description of artificial sequence: KM4028 VH chimera primer 2
SEQ ID NO:82—Description of artificial sequence: KM4030 VL chimera primer 1
SEQ ID NO:83—Description of artificial sequence: KM4030 VL chimera primer 2
SEQ ID NO:84—Description of artificial sequence: KM4030 VH chimera primer 1
SEQ ID NO:85—Description of artificial sequence: KM4030 VH chimera primer 2
SEQ ID NO:86—Description of artificial sequence: KM4031 VL chimera primer 1
SEQ ID NO:87—Description of artificial sequence: KM4031 VL chimera primer 2
SEQ ID NO:88—Description of artificial sequence: KM4031 VH chimera primer 1
SEQ ID NO:89—Description of artificial sequence: KM4031 VH chimera primer 2
SEQ ID NO:90—Description of artificial sequence: primer mfCD27_5UTR
SEQ ID NO:91—Description of artificial sequence: primer mfCD27_3UTR
SEQ ID NO:92—cynomolgus CD27 cDNA sequence
SEQ ID NO:93—Description of artificial sequence: primer mfCD27toKAN_5
SEQ ID NO:94—Description of artificial sequence: primer mfCD27HisKAN_3
SEQ ID NO:95—Description of artificial sequence: His-tagged cynomolgus CD27 cDNA sequence
SEQ ID NO:96—Description of artificial sequence: KM4030 HV0 amino acid sequence
SEQ ID NO:97—Description of artificial sequence: KM4030 LV0 amino acid sequence
SEQ ID NO:98—Description of artificial sequence: KM4030 HV0 nucleotide sequence
SEQ ID NO:99—Description of artificial sequence: KM4030 LV0 nucleotide sequence
SEQ ID NO:100—Description of artificial sequence: KM4030 HV2 nucleotide sequence
SEQ ID NO:101—Description of artificial sequence: KM4030 HV2 amino acid sequence
SEQ ID NO:102—Description of artificial sequence: KM4030 HV3 nucleotide sequence
SEQ ID NO:103—Description of artificial sequence: KM4030 HV3 amino acid sequence
SEQ ID NO:104—Description of artificial sequence: KM4030 HV5 nucleotide sequence
SEQ ID NO:105—Description of artificial sequence: KM4030 HV5 amino acid sequence
SEQ ID NO:106—Description of artificial sequence: KM4030 HV7 nucleotide sequence
SEQ ID NO:107—Description of artificial sequence: KM4030 HV7 amino acid sequence

What is claimed is:

1. A humanized antibody specifically recognizes and binds to an extracellular region of a polypeptide encoded by CD27 gene containing an O-linked sugar chain to which galactose is not bound; wherein the antibody comprises VH comprising the amino acid sequences of CDR1 to 3 represented by SEQ ID NOs:58 to 60, respectively, and the antibody comprises VL comprising the amino acid sequences of CDR1 to 3 represented by SEQ ID NOs:61 to 63, respectively, or an antigen-binding fragment thereof.

2. The humanized antibody or the antigen-binding fragment thereof according to claim 1,
    (a) wherein VH of the humanized antibody comprises an amino acid sequence in which at least one modification selected from substitutions of Ser at position 30 with Asn, Val at position 48 with Ile, Ser at position 49 with Ala, Asn at position 77 with Gly, Val at position 93 with Thr, Ala at position 97 with Thr, and Thr at position 117 with Val is introduced in the amino acid sequence represented by SEQ ID NO:96; and wherein VL of the humanized antibody comprises an amino acid sequence in which at least one modification selected from substitutions of Ile at position 21 with Leu, Pro at position 40 with Leu, Val at position 58 with Ile, Thr at position 85 with Ala, and Tyr at position 87 with Phe is introduced in the amino acid sequence represented by SEQ ID NO:97, or
    (b) wherein VH of the humanized antibody comprises the amino acid sequence represented by any one of SEQ ID NOs:96, 105 and 107, and VL of the humanized antibody comprises the amino acid sequence represented by SEQ ID NO:97.

3. A DNA which encodes the humanized antibody or the antibody fragment thereof according to claim 1.

4. A recombinant vector which comprises the DNA according to claim 3.

5. A transformant comprising the recombinant vector according to claim 4.

6. A process for producing the antibody or the antibody fragment thereof according to claim 1, comprising culturing a transformant in a medium to form and accumulate the humanized antibody or the antigen-binding fragment thereof described in claim 1 in the culture, and then collecting the humanized antibody or the antigen-binding fragment thereof from the culture, wherein said transformant comprises a recombinant vector including a DNA encoding the humanized antibody or the antigen-binding fragment.

7. A method for immunologically detecting or measuring CD27 containing an O-linked sugar chain to which galactose is not bound, comprising contacting the humanized antibody or the antigen-binding fragment thereof according to claim 1 with a sample containing CD 27 containing an O-linked sugar chain.

8. A diagnostic method for a disease relating to CD27 containing an O-linked sugar chain to which galactose is not bound, comprising
    (a) detecting or measuring a cell expressing CD27 containing an O-linked sugar chain to which galactose is not bound, by contacting the humanized antibody or the antigen-binding fragment thereof according to claim 1 with the cell; or
    (b) detecting or measuring CD27 containing an O-linked sugar chain to which galactose is not bound, by contacting the humanized antibody or the antigen-binding fragment thereof according to claim 1 with the CD27 containing an O-linked sugar chain.

9. The diagnostic method according to claim 8, wherein the disease relating to CD27 containing an O-linked sugar chain to which galactose is not bound is IgA nephropathy or cancer.

10. A method for treating a disease relating to CD27 containing an O-linked sugar chain to which galactose is not bound, comprising administering the humanized antibody or the antigen-binding fragment thereof according to claim 1 to a subject in need thereof.

11. The method according to claim 10, wherein the disease relating to CD27 containing an O-linked sugar chain to which galactose is not bound is IgA nephropathy or cancer.

12. A pharmaceutical composition comprising the humanized antibody or the antigen-binding fragment thereof according to claim 1 and a pharmaceutically acceptable carrier.

* * * * *

```
                        SEQUENCE LISTING

<160> NUMBER OF SEQ ID NOS: 107

<210> SEQ ID NO 1
<211> LENGTH: 783
<212> TYPE: DNA
<213> ORGANISM: Homo sapiens
<220> FEATURE:
<221> NAME/KEY: CDS
<222> LOCATION: (1)..(783)
<223> OTHER INFORMATION: human CD27 DNA sequence

<400> SEQUENCE: 1 atg gca cgg cca cat ccc tgg tgg ctg tgc gtt ctg ggg acc ctg gtg      48
Met Ala Arg Pro His Pro Trp Trp Leu Cys Val Leu Gly Thr Leu Val
1               5                   10                  15 ggg ctc tca gct act cca gcc ccc aag agc tgc cca gag agg cac tac      96
Gly Leu Ser Ala Thr Pro Ala Pro Lys Ser Cys Pro Glu Arg His Tyr
            20                  25                  30 tgg gct cag gga aag ctg tgc tgc cag atg tgt gag cca gga aca ttc     144
```

```
Trp Ala Gln Gly Lys Leu Cys Cys Gln Met Cys Glu Pro Gly Thr Phe
         35                  40                  45 ctc gtg aag gac tgt gac cag cat aga aag gct gct cag tgt gat cct      192
Leu Val Lys Asp Cys Asp Gln His Arg Lys Ala Ala Gln Cys Asp Pro
 50                  55                  60 tgc ata ccg ggg gtc tcc ttc tct cct gac cac cac acc cgg ccc cac      240
Cys Ile Pro Gly Val Ser Phe Ser Pro Asp His His Thr Arg Pro His
 65                  70                  75                  80 tgt gag agc tgt cgg cac tgt aac tct ggt ctt ctc gtt cgc aac tgc      288
Cys Glu Ser Cys Arg His Cys Asn Ser Gly Leu Leu Val Arg Asn Cys
                 85                  90                  95 acc atc act gcc aat gct gag tgt gcc tgt cgc aat ggc tgg cag tgc      336
Thr Ile Thr Ala Asn Ala Glu Cys Ala Cys Arg Asn Gly Trp Gln Cys
            100                 105                 110 agg gac aag gag tgc acc gag tgt gat cct ctt cca aac cct tcg ctg      384
Arg Asp Lys Glu Cys Thr Glu Cys Asp Pro Leu Pro Asn Pro Ser Leu
        115                 120                 125 acc gct cgg tcg tct cag gcc ctg agc cca cac cct cag ccc acc cac      432
Thr Ala Arg Ser Ser Gln Ala Leu Ser Pro His Pro Gln Pro Thr His
    130                 135                 140 tta cct tat gtc agt gag atg ctg gag gcc agg aca gct ggg cac atg      480
Leu Pro Tyr Val Ser Glu Met Leu Glu Ala Arg Thr Ala Gly His Met
145                 150                 155                 160 cag act ctg gct gac ttc agg cag ctg cct gcc cgg act ctc tct acc      528
Gln Thr Leu Ala Asp Phe Arg Gln Leu Pro Ala Arg Thr Leu Ser Thr
                165                 170                 175 cac tgg cca ccc caa aga tcc ctg tgc agc tcc gat ttt att cgc atc      576
His Trp Pro Pro Gln Arg Ser Leu Cys Ser Ser Asp Phe Ile Arg Ile
            180                 185                 190 ctt gtg atc ttc tct gga atg ttc ctt gtt ttc acc ctg gcc ggg gcc      624
Leu Val Ile Phe Ser Gly Met Phe Leu Val Phe Thr Leu Ala Gly Ala
        195                 200                 205 ctg ttc ctc cat caa cga agg aaa tat aga tca aac aaa gga gaa agt      672
Leu Phe Leu His Gln Arg Arg Lys Tyr Arg Ser Asn Lys Gly Glu Ser
    210                 215                 220 cct gtg gag cct gca gag cct tgt cgt tac agc tgc ccc agg gag gag      720
Pro Val Glu Pro Ala Glu Pro Cys Arg Tyr Ser Cys Pro Arg Glu Glu
225                 230                 235                 240 gag ggc agc acc atc ccc atc cag gag gat tac cga aaa ccg gag cct      768
Glu Gly Ser Thr Ile Pro Ile Gln Glu Asp Tyr Arg Lys Pro Glu Pro
                245                 250                 255 gcc tgc tcc ccc tga                                                   783
Ala Cys Ser Pro
            260

<210> SEQ ID NO 2
<211> LENGTH: 260
<212> TYPE: PRT
<213> ORGANISM: Homo sapiens

<400> SEQUENCE: 2

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60
```

```
Cys Ile Pro Gly Val Ser Phe Ser Pro Asp His His Thr Arg Pro His
 65                  70                  75                  80

Cys Glu Ser Cys Arg His Cys Asn Ser Gly Leu Leu Val Arg Asn Cys
                 85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 3
<211> LENGTH: 65
<212> TYPE: DNA
<213> ORGANISM: Artificial sequence
<220> FEATURE:
<223> OTHER INFORMATION: Synthetic construct of CD27 forward primer

<400> SEQUENCE: 3
gggcggccgc tcctcaggct gtctcctcag gttgcctcct caaaatggca cggccacatc    60
cctgg                                                                65

<210> SEQ ID NO 4
<211> LENGTH: 29
<212> TYPE: DNA
<213> ORGANISM: Artificial sequence
<220> FEATURE:
<223> OTHER INFORMATION: Synthetic construct of CD27809B

<400> SEQUENCE: 4
ggggatccca gggatctttg gggtggcca                                       29

<210> SEQ ID NO 5
<211> LENGTH: 65
<212> TYPE: DNA
<213> ORGANISM: Artificial sequence
<220> FEATURE:
<223> OTHER INFORMATION: Synthetic construct of CD27-A primer

<400> SEQUENCE: 5
gggcggccgc tcctcaggct gtctcctcag gttgcctcct caaaatggca cggccacatc    60
cctgg                                                                65
```

<210> SEQ ID NO 6
<211> LENGTH: 29
<212> TYPE: DNA
<213> ORGANISM: Artificial sequence
<220> FEATURE:
<223> OTHER INFORMATION: Synthetic construct of CD27-B primer

<400> SEQUENCE: 6
ggggatccca gggatctttg ggtggcca                                29

<210> SEQ ID NO 7
<211> LENGTH: 62
<212> TYPE: DNA
<213> ORGANISM: Artificial sequence
<220> FEATURE:
<223> OTHER INFORMATION: Synthetic construct of Primer1

<400> SEQUENCE: 7
caacaccaag gtggacaaga gagttgagtc caaatatggt cccccatgcc caccatgccc    60
ag                                                                  62

<210> SEQ ID NO 8
<211> LENGTH: 60
<212> TYPE: DNA
<213> ORGANISM: Artificial sequence
<220> FEATURE:
<223> OTHER INFORMATION: Synthetic construct of Primer2

<400> SEQUENCE: 8
acgcacgtga cctcaggggt ccgggagatc atgagagtgt ccttgggttt tggggggaac    60

<210> SEQ ID NO 9
<211> LENGTH: 35
<212> TYPE: DNA
<213> ORGANISM: Artificial sequence
<220> FEATURE:
<223> OTHER INFORMATION: Synthetic construct of g4A primer

<400> SEQUENCE: 9
ggggatccga gtccaaatat ggtcccccat gccca                              35

<210> SEQ ID NO 10
<211> LENGTH: 32
<212> TYPE: DNA
<213> ORGANISM: Artificial sequence
<220> FEATURE:
<223> OTHER INFORMATION: Synthetic construct of g4B primer

<400> SEQUENCE: 10
gggtcgactc atttacccag agacagggag ag                                 32

<210> SEQ ID NO 11
<211> LENGTH: 1248
<212> TYPE: DNA
<213> ORGANISM: Artificial sequence
<220> FEATURE:
<223> OTHER INFORMATION: Synthetic construct of CD27-Fc protein
<220> FEATURE:
<221> NAME/KEY: CDS
<222> LOCATION: (1)..(1248)
<223> OTHER INFORMATION: CD27-Fc fusion protein DNA sequence

<400> SEQUENCE: 11 atg gca cgg cca cat ccc tgg tgg ctg tgc gtt ctg ggg acc ctg gtg    48
Met Ala Arg Pro His Pro Trp Trp Leu Cys Val Leu Gly Thr Leu Val
1               5                   10                  15

```
ggg ctc tca gct act cca gcc ccc aag agc tgc cca gag agg cac tac    96
Gly Leu Ser Ala Thr Pro Ala Pro Lys Ser Cys Pro Glu Arg His Tyr
             20              25              30 tgg gct cag gga aag ctg tgc tgc cag atg tgt gag cca gga aca ttc   144
Trp Ala Gln Gly Lys Leu Cys Cys Gln Met Cys Glu Pro Gly Thr Phe
         35              40              45 ctc gtg aag gac tgt gac cag cat aga aag gct gct cag tgt gat cct   192
Leu Val Lys Asp Cys Asp Gln His Arg Lys Ala Ala Gln Cys Asp Pro
     50              55              60 tgc ata ccg ggg gtc tcc ttc tct cct gac cac cac acc cgg ccc cac   240
Cys Ile Pro Gly Val Ser Phe Ser Pro Asp His His Thr Arg Pro His
65              70              75              80 tgt gag agc tgt cgg cac tgt aac tct ggt ctt ctc gtt cgc aac tgc   288
Cys Glu Ser Cys Arg His Cys Asn Ser Gly Leu Leu Val Arg Asn Cys
                 85              90              95 acc atc act gcc aat gct gag tgt gcc tgt cgc aat ggc tgg cag tgc   336
Thr Ile Thr Ala Asn Ala Glu Cys Ala Cys Arg Asn Gly Trp Gln Cys
             100             105             110 agg gac aag gag tgc acc gag tgt gat cct ctt cca aac cct tcg ctg   384
Arg Asp Lys Glu Cys Thr Glu Cys Asp Pro Leu Pro Asn Pro Ser Leu
         115             120             125 acc gct cgg tcg tct cag gcc ctg agc cca cac cct cag ccc acc cac   432
Thr Ala Arg Ser Ser Gln Ala Leu Ser Pro His Pro Gln Pro Thr His
     130             135             140 tta cct tat gtc agt gag atg ctg gag gcc agg aca gct ggg cac atg   480
Leu Pro Tyr Val Ser Glu Met Leu Glu Ala Arg Thr Ala Gly His Met
145             150             155             160 cag act ctg gct gac ttc agg cag ctg cct gcc cgg act ctc tct acc   528
Gln Thr Leu Ala Asp Phe Arg Gln Leu Pro Ala Arg Thr Leu Ser Thr
                 165             170             175 cac tgg cca ccc caa aga tcc ctg gga tcc gag tcc aaa tat ggt ccc   576
His Trp Pro Pro Gln Arg Ser Leu Gly Ser Glu Ser Lys Tyr Gly Pro
             180             185             190 cca tgc cca cca tgc cca gca cct gag ttc ctg ggg gga cca tca gtc   624
Pro Cys Pro Pro Cys Pro Ala Pro Glu Phe Leu Gly Gly Pro Ser Val
         195             200             205 ttc ctg ttc ccc cca aaa ccc aag gac act ctc atg atc tcc cgg acc   672
Phe Leu Phe Pro Pro Lys Pro Lys Asp Thr Leu Met Ile Ser Arg Thr
     210             215             220 cct gag gtc acg tgc gtg gtg gtg gac gtg agc cag gaa gac ccc gag   720
Pro Glu Val Thr Cys Val Val Val Asp Val Ser Gln Glu Asp Pro Glu
225             230             235             240 gtc cag ttc aac tgg tac gtg gat ggc gtg gag gtg cat aat gcc aag   768
Val Gln Phe Asn Trp Tyr Val Asp Gly Val Glu Val His Asn Ala Lys
                 245             250             255 aca aag ccg cgg gag gag cag ttc aac agc acg tac cgt gtg gtc agc   816
Thr Lys Pro Arg Glu Glu Gln Phe Asn Ser Thr Tyr Arg Val Val Ser
             260             265             270 gtc ctc acc gtc ctg cac cag gac tgg ctg aac ggc aag gag tac aag   864
Val Leu Thr Val Leu His Gln Asp Trp Leu Asn Gly Lys Glu Tyr Lys
         275             280             285 tgc aag gtc tcc aac aaa ggc ctc ccg tcc tcc atc gag aaa acc atc   912
Cys Lys Val Ser Asn Lys Gly Leu Pro Ser Ser Ile Glu Lys Thr Ile
     290             295             300 tcc aaa gcc aaa ggg cag ccc cga gag cca cag gtg tac acc ctg ccc   960
Ser Lys Ala Lys Gly Gln Pro Arg Glu Pro Gln Val Tyr Thr Leu Pro
305             310             315             320 cca tcc cag gag gag atg acc aag aac cag gtc agc ctg acc tgc ctg  1008
Pro Ser Gln Glu Glu Met Thr Lys Asn Gln Val Ser Leu Thr Cys Leu
```

```
                       325                 330                 335
gtc aaa ggc ttc tac ccc agc gac atc gcc gtg gag tgg gag agc aat    1056
Val Lys Gly Phe Tyr Pro Ser Asp Ile Ala Val Glu Trp Glu Ser Asn
            340                 345                 350 ggg cag ccg gag aac aac tac aag acc acg cct ccc gtg ctg gac tcc    1104
Gly Gln Pro Glu Asn Asn Tyr Lys Thr Thr Pro Pro Val Leu Asp Ser
        355                 360                 365 gac ggc tcc ttc ttc ctc tac agc agg cta acc gtg gac aag agc agg    1152
Asp Gly Ser Phe Phe Leu Tyr Ser Arg Leu Thr Val Asp Lys Ser Arg
    370                 375                 380 tgg cag gag ggg aat gtc ttc tca tgc tcc gtg atg cat gag gct ctg    1200
Trp Gln Glu Gly Asn Val Phe Ser Cys Ser Val Met His Glu Ala Leu
385                 390                 395                 400 cac aac cac tac aca cag aag agc ctc tcc ctg tct ctg ggt aaa tga    1248
His Asn His Tyr Thr Gln Lys Ser Leu Ser Leu Ser Leu Gly Lys
                405                 410                 415

<210> SEQ ID NO 12
<211> LENGTH: 415
<212> TYPE: PRT
<213> ORGANISM: Artificial sequence
<220> FEATURE:
<223> OTHER INFORMATION: Synthetic Construct

<400> SEQUENCE: 12

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Gly Ser Glu Ser Lys Tyr Gly Pro
            180                 185                 190

Pro Cys Pro Pro Cys Pro Ala Pro Glu Phe Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser Gln Glu Asp Pro Glu
225                 230                 235                 240

Val Gln Phe Asn Trp Tyr Val Asp Gly Val Glu Val His Asn Ala Lys
                245                 250                 255
```

```
            Thr Lys Pro Arg Glu Glu Gln Phe Asn Ser Thr Tyr Arg Val Val Ser
                            260                 265                 270

Val Leu Thr Val Leu His Gln Asp Trp Leu Asn Gly Lys Glu Tyr Lys
                        275                 280                 285

Cys Lys Val Ser Asn Lys Gly Leu Pro Ser Ser Ile Glu Lys Thr Ile
                    290                 295                 300

Ser Lys Ala Lys Gly Gln Pro Arg Glu Pro Gln Val Tyr Thr Leu Pro
            305                 310                 315                 320

Pro Ser Gln Glu Glu Met Thr Lys Asn Gln Val Ser Leu Thr Cys Leu
                            325                 330                 335

Val Lys Gly Phe Tyr Pro Ser Asp Ile Ala Val Glu Trp Glu Ser Asn
                        340                 345                 350

Gly Gln Pro Glu Asn Asn Tyr Lys Thr Thr Pro Pro Val Leu Asp Ser
                    355                 360                 365

Asp Gly Ser Phe Phe Leu Tyr Ser Arg Leu Thr Val Asp Lys Ser Arg
                370                 375                 380

Trp Gln Glu Gly Asn Val Phe Ser Cys Ser Val Met His Glu Ala Leu
            385                 390                 395                 400

His Asn His Tyr Thr Gln Lys Ser Leu Ser Leu Ser Leu Gly Lys
                            405                 410                 415

<210> SEQ ID NO 13
<211> LENGTH: 30
<212> TYPE: DNA
<213> ORGANISM: Artificial sequence
<220> FEATURE:
<223> OTHER INFORMATION: Synthetic construct of CD27-C primer

<400> SEQUENCE: 13
gggtcgacct caggggagc aggcaggctc                                       30

<210> SEQ ID NO 14
<211> LENGTH: 27
<212> TYPE: DNA
<213> ORGANISM: Artificial sequence
<220> FEATURE:
<223> OTHER INFORMATION: Synthetic construct of a primer for rat IgG1

<400> SEQUENCE: 14
gcaatcacct ccacagtttc tgggcac                                         27

<210> SEQ ID NO 15
<211> LENGTH: 26
<212> TYPE: DNA
<213> ORGANISM: Artificial sequence
<220> FEATURE:
<223> OTHER INFORMATION: Synthetic construct of a primer for rat IgG2a

<400> SEQUENCE: 15
ccacaaggat tgcattccct tggcac                                          26

<210> SEQ ID NO 16
<211> LENGTH: 28
<212> TYPE: DNA
<213> ORGANISM: Artificial sequence
<220> FEATURE:
<223> OTHER INFORMATION: Synthetic construct of a primer for rat IgG2b

<400> SEQUENCE: 16
gggcatgtag ggcatttgtg tccaatgc                                        28
```

```
<210> SEQ ID NO 17
<211> LENGTH: 24
<212> TYPE: DNA
<213> ORGANISM: Artificial sequence
<220> FEATURE:
<223> OTHER INFORMATION: Synthetic construct of a primer for rat CH1

<400> SEQUENCE: 17
cgctggacag ggctccagag ttcc                                            24

<210> SEQ ID NO 18
<211> LENGTH: 31
<212> TYPE: DNA
<213> ORGANISM: Artificial sequence
<220> FEATURE:
<223> OTHER INFORMATION: Synthetic construct of a primer for rat Ig
      kappa

<400> SEQUENCE: 18
gactgaggca cctccagttg ctaactgttc c                                    31

<210> SEQ ID NO 19
<211> LENGTH: 29
<212> TYPE: DNA
<213> ORGANISM: Artificial sequence
<220> FEATURE:
<223> OTHER INFORMATION: Synthetic construct of a primer for rat Ig
      kappa

<400> SEQUENCE: 19
cctgttgaag ctcttgacga cgggtgagg                                       29

<210> SEQ ID NO 20
<211> LENGTH: 405
<212> TYPE: DNA
<213> ORGANISM: Rattus norvegicus

<400> SEQUENCE: 20
atgagaacgt tgggtcttct gtacctgttg acagcccttc ctggtatcct gtctgaggtg     60
cagcttcagg agtcaggacc tggccttgtg aaaccctcac agtcactctc cctcacctgt    120
tctgtcactg gtttctccat cactagtagt tactgggct ggatccggaa gttcccagga    180
aataaaatgg agtggatggg atacataaac tacagtggta gcactagcta caacccatct    240
ctcaaaagtc gaatctccat tactagagac acatcgaaga tcagttcttc ctgcagttg    300 aactctataa ctactgagga cacagccgca tatttctgtg caagatggac tgggcagtac    360
tactttgatt actggggcca aggagtcatg gtcacagtct cctca                    405

<210> SEQ ID NO 21
<211> LENGTH: 411
<212> TYPE: DNA
<213> ORGANISM: Rattus norvegicus

<400> SEQUENCE: 21
atggacatca ggctcagctt ggctttcctt gtccttttca taaaggtgt ccagtgtgag     60 gtgcagctgg tagagtctgg gggcggttta gtgcagcctg gaaggtccat gaaaatctcc    120
tgtgtagcct caggatccac tttcagtaac tatggcatgg cctgggtccg ccaggctcca    180
acgaaggggc tggagtggct tgcaaccatt acttatgatg gtagtaccac ttactatcga    240
gactccgtga agggccgatt cactatctcc agagataatg caaaaagcac cctatacctg    300
caaatgaaca gtctgaggtc tgaggacacg gccacttatt actgtacaag agatctggga    360
```

```
ctctactact ttgattactg gggccaagga gtcatggtca cagtctcctc a         411
```

<210> SEQ ID NO 22
<211> LENGTH: 411
<212> TYPE: DNA
<213> ORGANISM: Rattus norvegicus

<400> SEQUENCE: 22

```
atggacatca ggctcagctt ggctttcctt gtccttttca taaaaggtgt ccagtgtgag   60
gtgcagctgg tagagtctgg gggcggttta gtgcagcctg aaggtccat gaaactctcc   120
tgtgcagcct caggattcac tttcagtaac tatggcatgg cctgggtccg ccaggctcca   180
acgaaggggc tggagtgggt tgcaaccatt agttatgatg gtagtagtat ttactatcga   240
gactccgtga agggccgatt tattatctcc agagataatg caaaaagcac cctatacctg   300
caaatgaaca gtctgaggtc tgaggacacg gccacttatt actgtacaag agatccgggg   360
gtctactact ttgattactg gggccaagga gtcatggtca cagtctcctc a           411
```

<210> SEQ ID NO 23
<211> LENGTH: 426
<212> TYPE: DNA
<213> ORGANISM: Rattus norvegicus

<400> SEQUENCE: 23

```
atggacatca ggctcagctt ggttttcctt gtccttttca taaaaggtgt ccagtgtgag   60
gtgcagttgg tggagtctgg gggaggccta gtgcagcctg aaggtctct gaaactatcc   120
tgtgtagcct ctggattcac attcaataac tactggatga cctggatccg ccaggctcca   180
gggaaggggc tggagtggat tgcatccatt actaatagtg gtggtagcac ttactatcca   240
gactctgtga agggccgatt cactatctcc agagataatg caaaaggcac cctatacctg   300
caaatgaaca gtctgaggtc tgaggacacg gccacttatt actgtacaag agatgttaac   360
acatactatg gtataacgc cctctttgat tactggggcc aaggagtcat ggtcacagtc   420
tcctca                                                              426
```

<210> SEQ ID NO 24
<211> LENGTH: 408
<212> TYPE: DNA
<213> ORGANISM: Rattus norvegicus

<400> SEQUENCE: 24

```
atggacatca ggctcagctt ggctttcatt gtccttttca taaaaggtgt cccgtgtgag   60
gtacagttgg tagagtctgg gggcggttta gtggagcctg aaggtccat gaaactctcc   120
tgtgcagcct caggattcac cttcagtgac tatggcatgg cctgggtccg ccaggctcca   180
acgaaggggc tggagtgggt tgcaaccatt acttatgatg gtagcattta ctatcgagac   240
tccgtgaagg gccgattcac aatctccaga gataatgcaa aaagcacccct ttacctgcaa   300
atgaacagtc tgaggtctga ggacacggcc acttattact gtacaagaga cccgggtctc   360
tactactttg atttctgggg ccaaggagtc atggtcacag tctcctca               408
```

<210> SEQ ID NO 25
<211> LENGTH: 135
<212> TYPE: PRT
<213> ORGANISM: Rattus norvegicus

<400> SEQUENCE: 25

Met Arg Thr Leu Gly Leu Leu Tyr Leu Leu Thr Ala Leu Pro Gly Ile
1               5                   10                  15

Leu Ser Glu Val Gln Leu Gln Glu Ser Gly Pro Gly Leu Val Lys Pro
                20                  25                  30

Ser Gln Ser Leu Ser Leu Thr Cys Ser Val Thr Gly Phe Ser Ile Thr
            35                  40                  45

Ser Ser Tyr Trp Gly Trp Ile Arg Lys Phe Pro Gly Asn Lys Met Glu
50                  55                  60

Trp Met Gly Tyr Ile Asn Tyr Ser Gly Ser Thr Ser Tyr Asn Pro Ser
65                  70                  75                  80

Leu Lys Ser Arg Ile Ser Ile Thr Arg Asp Thr Ser Lys Asn Gln Phe
                85                  90                  95

Phe Leu Gln Leu Asn Ser Ile Thr Thr Glu Asp Thr Ala Ala Tyr Phe
            100                 105                 110

Cys Ala Arg Trp Thr Gly Gln Tyr Tyr Phe Asp Tyr Trp Gly Gln Gly
            115                 120                 125

Val Met Val Thr Val Ser Ser
    130                 135

<210> SEQ ID NO 26
<211> LENGTH: 137
<212> TYPE: PRT
<213> ORGANISM: Rattus norvegicus

<400> SEQUENCE: 26

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Gly Arg Ser Met Lys Ile Ser Cys Val Ala Ser Gly Ser Thr Phe
            35                  40                  45

Ser Asn Tyr Gly Met Ala Trp Val Arg Gln Ala Pro Thr Lys Gly Leu
50                  55                  60

Glu Trp Leu Ala Thr Ile Thr Tyr Asp Gly Ser Thr Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Asp Leu Gly Leu Tyr Tyr Phe Asp Tyr Trp Gly
            115                 120                 125

Gln Gly Val Met Val Thr Val Ser Ser
    130                 135

<210> SEQ ID NO 27
<211> LENGTH: 137
<212> TYPE: PRT
<213> ORGANISM: Rattus norvegicus

<400> SEQUENCE: 27

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Gly Arg Ser Met Lys Leu Ser Cys Ala Ala Ser Gly Phe Thr Phe
            35                  40                  45

```
Ser Asn Tyr Gly Met Ala Trp Val Arg Gln Ala Pro Thr Lys Gly Leu
    50                  55                  60

Glu Trp Val Ala Thr Ile Ser Tyr Asp Gly Ser Ser Ile Tyr Tyr Arg
65                  70                  75                  80

Asp Ser Val Lys Gly Arg Phe Ile Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Asp Pro Gly Val Tyr Tyr Phe Asp Tyr Trp Gly
        115                 120                 125

Gln Gly Val Met Val Thr Val Ser Ser
    130                 135
```

<210> SEQ ID NO 28
<211> LENGTH: 142
<212> TYPE: PRT
<213> ORGANISM: Rattus norvegicus

<400> SEQUENCE: 28

```
Met Asp Ile Arg Leu Ser Leu Val Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Gly Arg Ser Leu Lys Leu Ser Cys Val Ala Ser Gly Phe Thr Phe
            35                  40                  45

Asn Asn Tyr Trp Met Thr Trp Ile Arg Gln Ala Pro Gly Lys Gly Leu
        50                  55                  60

Glu Trp Ile Ala Ser Ile Thr Asn Ser Gly Gly Ser Thr Tyr Tyr Pro
65                  70                  75                  80

Asp Ser Val Lys Gly Arg Phe Thr Ile Ser Arg Asp Asn Ala Lys Gly
                85                  90                  95

Thr Leu Tyr Leu Gln Met Asn Ser Leu Arg Ser Glu Asp Thr Ala Thr
            100                 105                 110

Tyr Tyr Cys Thr Arg Asp Val Asn Thr Tyr Tyr Gly Tyr Asn Ala Leu
        115                 120                 125

Phe Asp Tyr Trp Gly Gln Gly Val Met Val Thr Val Ser Ser
    130                 135                 140
```

<210> SEQ ID NO 29
<211> LENGTH: 136
<212> TYPE: PRT
<213> ORGANISM: Rattus norvegicus

<400> SEQUENCE: 29

```
Met Asp Ile Arg Leu Ser Leu Ala Phe Ile Val Leu Phe Ile Lys Gly
1               5                   10                  15

Val Pro Cys Glu Val Gln Leu Val Glu Ser Gly Gly Gly Leu Val Glu
                20                  25                  30

Pro Gly Arg Ser Met Lys Leu Ser Cys Ala Ala Ser Gly Phe Thr Phe
            35                  40                  45

Ser Asp Tyr Gly Met Ala Trp Val Arg Gln Ala Pro Thr Lys Gly Leu
        50                  55                  60

Glu Trp Val Ala Thr Ile Thr Tyr Asp Gly Ser Ile Tyr Tyr Arg Asp
65                  70                  75                  80

Ser Val Lys Gly Arg Phe Thr Ile Ser Arg Asp Asn Ala Lys Ser Thr
                85                  90                  95
```

Leu Tyr Leu Gln Met Asn Ser Leu Arg Ser Glu Asp Thr Ala Thr Tyr
            100                 105                 110

Tyr Cys Thr Arg Asp Pro Gly Leu Tyr Tyr Phe Asp Phe Trp Gly Gln
        115                 120                 125

Gly Val Met Val Thr Val Ser Ser
    130                 135

<210> SEQ ID NO 30
<211> LENGTH: 399
<212> TYPE: DNA
<213> ORGANISM: Rattus norvegicus

<400> SEQUENCE: 30
atggaatcac agacccaggt cctcatgtcc ctgctgctct ggatttctgg tacctgtggg      60
gacattgtga tgacccaatc tccatcctct ctggctgtgt cagcaggaga gacggtcact     120
ataaactgca gtccagtca gagtctttta tacagtggaa accaaaagaa ctatttggcc      180
tggtaccagc agaaaccagg gcagtctcct aaattgctga tctactgggc atctactagg     240
caatctggtg tccctgatcg cttcataggc agtggatctg gacagactt cactctgacc      300 atcagcagtg tgcaggcaga agatctggca atttattact gtcagcagta ttatgatact     360
cctccggcgt ttggagctgg gaccaagctg gaactgaaa                            399

<210> SEQ ID NO 31
<211> LENGTH: 399
<212> TYPE: DNA
<213> ORGANISM: Rattus norvegicus

<400> SEQUENCE: 31
atggaatcac agacccaggt cctcatgtcc ctgctgctct ggatttctgg tacccgtggg      60
gacattgtga tgacccaatc accatcctct ctggctgtgt cagcaggaga gacggtcact     120
ataaactgca gtccagtca gagtctttta tacagtggaa accaaaagaa ctacttggcc      180
tggtaccagc agaaaccagg gcagtctcct aaactgctga tctactgggc atcttctagg     240
caatctggtg tccctgatcg cttcataggc agtggatctg gacagacttc actctgacc     300 atcagcagtg tgcaggcaga agatccggca atttattact gtcagcagta ttatgatgct     360
cctcggacgt tcggtggagg ctccaagctg gaattgaaa                            399

<210> SEQ ID NO 32
<211> LENGTH: 399
<212> TYPE: DNA
<213> ORGANISM: Rattus norvegicus

<400> SEQUENCE: 32
atggaatcac agacccaggt cctcatgtcc ctgctgctct ggatttctgg tacctgtggg      60
gacattgtga tgacccaatc tccatcctct ctggctgtgt cagcaggaga gacggtcact     120
ataaactgta gtccagtca gagtcttttg tacagtggaa accaaaggaa ctatttggcc      180
tggtatcagc agaaacccgg gcagtctcct aaactgctga tctactgggc atctactagg     240
caatctggtg tccctgatcg cttcataggc agtggatctg gacaaacttc actctgacc      300 atcagcagtg tgcaggcaga agatctggca atttattact gtcaacagta ttatgatact     360
cctcggacgt tcggtggagg caccaagctg gaattgaaa                            399

<210> SEQ ID NO 33
<211> LENGTH: 381
<212> TYPE: DNA

<213> ORGANISM: Rattus norvegicus

<400> SEQUENCE: 33

```
atgatggctg cacttcaact cttagggctg ctgctgctct ggctcccagg catgagatgt      60
gacatccaga tgacccagtc tccttcagtc ctgtctgcat ctgtgggaga cagagtcact     120
ctcaactgca aagcaagtca gaatattaat gagtacttaa actggtatca gcaaaagctt     180
ggagaagctc ccaaactcct gatatataat acaaacaatt tgcaaacggg catcccatca     240
aggttcagtg gcagtggatc tggtacagat ttcacactca ccatcagcag cctgcagcct     300
gaggattttg ccgcatattt ctgctttcag cataatagtt ggccgtacac gtttggagct     360
gggaccaagc tggaactgaa a                                               381
```

<210> SEQ ID NO 34
<211> LENGTH: 399
<212> TYPE: DNA
<213> ORGANISM: Rattus norvegicus

<400> SEQUENCE: 34

```
atggaatcac agacccaggt cctcatgtcc ctgctgctct ggatttctgg tacctgtggg      60
gacattgtga tgacccagtc tccatcctct ctggctgtgt cagcaggaga gacggtcact     120
ctaaactgcc agtccagtca gagtctttta tacagtggaa accagaagaa ctacttggcc     180
tggtaccagc agaaaccagg tcagtctcct aaacttctga tctactgggc atctactcgg     240
caatctggtg tccctgatcg cttcataggc agtggatctg gacagacttt cactctgacc     300
atcagcagtg tgcaggcaga agatctggca atttattact gtcagcagta ttataatact     360
cctcggacgt tcggtggagg caccaagctg gaattgaaa                            399
```

<210> SEQ ID NO 35
<211> LENGTH: 133
<212> TYPE: PRT
<213> ORGANISM: Rattus norvegicus

<400> SEQUENCE: 35

```
Met Glu Ser Gln Thr Gln Val Leu Met Ser Leu Leu Trp Ile Ser
1               5                  10                  15

Gly Thr Cys Gly Asp Ile Val Met Thr Gln Ser Pro Ser Ser Leu Ala
                20                  25                  30

Val Ser Ala Gly Glu Thr Val Thr Ile Asn Cys Lys Ser Ser Gln Ser
            35                  40                  45

Leu Leu Tyr Ser Gly Asn Gln Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Gln Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Ile Tyr
            100                 105                 110

Tyr Cys Gln Gln Tyr Tyr Asp Thr Pro Pro Ala Phe Gly Ala Gly Thr
        115                 120                 125

Lys Leu Glu Leu Lys
    130
```

<210> SEQ ID NO 36
<211> LENGTH: 133
<212> TYPE: PRT

<213> ORGANISM: Rattus norvegicus

<400> SEQUENCE: 36

Met Glu Ser Gln Thr Gln Val Leu Met Ser Leu Leu Leu Trp Ile Ser
1               5                   10                  15

Gly Thr Arg Gly Asp Ile Val Met Thr Gln Ser Pro Ser Ser Leu Ala
            20                  25                  30

Val Ser Ala Gly Glu Thr Val Thr Ile Asn Cys Lys Ser Ser Gln Ser
        35                  40                  45

Leu Leu Tyr Ser Gly Asn Gln Lys Asn Tyr Leu Ala Trp Tyr Gln Gln
    50                  55                  60

Lys Pro Gly Gln Ser Pro Lys Leu Leu Ile Tyr Trp Ala Ser Ser Arg
65                  70                  75                  80

Gln Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Pro Ala Ile Tyr
            100                 105                 110

Tyr Cys Gln Gln Tyr Tyr Asp Ala Pro Arg Thr Phe Gly Gly Gly Ser
        115                 120                 125

Lys Leu Glu Leu Lys
    130

<210> SEQ ID NO 37
<211> LENGTH: 133
<212> TYPE: PRT
<213> ORGANISM: Rattus norvegicus

<400> SEQUENCE: 37

Met Glu Ser Gln Thr Gln Val Leu Met Ser Leu Leu Leu Trp Ile Ser
1               5                   10                  15

Gly Thr Cys Gly Asp Ile Val Met Thr Gln Ser Pro Ser Ser Leu Ala
            20                  25                  30

Val Ser Ala Gly Glu Thr Val Thr Ile Asn Cys Lys Ser Ser Gln Ser
        35                  40                  45

Leu Leu Tyr Ser Gly Asn Gln Arg Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Gln Ser Gly Val Pro Asp Arg Phe Ile Gly Ser Gly Ser Gly Thr Asn
                85                  90                  95

Phe Thr Leu Thr Ile Ser Ser Val Gln Ala Glu Asp Leu Ala Ile Tyr
            100                 105                 110

Tyr Cys Gln Gln Tyr Tyr Asp Thr Pro Arg Thr Phe Gly Gly Gly Thr
        115                 120                 125

Lys Leu Glu Leu Lys
    130

<210> SEQ ID NO 38
<211> LENGTH: 127
<212> TYPE: PRT
<213> ORGANISM: Rattus norvegicus

<400> SEQUENCE: 38

Met Met Ala Ala Leu Gln Leu Leu Gly Leu Leu Leu Leu Trp Leu Pro
1               5                   10                  15

Gly Met Arg Cys Asp Ile Gln Met Thr Gln Ser Pro Ser Val Leu Ser
            20                  25                  30

```
Ala Ser Val Gly Asp Arg Val Thr Leu Asn Cys Lys Ala Ser Gln Asn
            35                  40                  45

Ile Asn Glu Tyr Leu Asn Trp Tyr Gln Gln Lys Leu Gly Glu Ala Pro
 50                  55                  60

Lys Leu Leu Ile Tyr Asn Thr Asn Asn Leu Gln Thr Gly Ile Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Ala Tyr Phe Cys Gln His Asn
                100                 105                 110

Ser Trp Pro Tyr Thr Phe Gly Ala Gly Thr Lys Leu Glu Leu Lys
                115                 120                 125
```

<210> SEQ ID NO 39
<211> LENGTH: 133
<212> TYPE: PRT
<213> ORGANISM: Rattus norvegicus

<400> SEQUENCE: 39

```
Met Glu Ser Gln Thr Gln Val Leu Met Ser Leu Leu Leu Trp Ile Ser
 1               5                  10                  15

Gly Thr Cys Gly Asp Ile Val Met Thr Gln Ser Pro Ser Ser Leu Ala
                20                  25                  30

Val Ser Ala Gly Glu Thr Val Thr Leu Asn Cys Gln Ser Ser Gln Ser
            35                  40                  45

Leu Leu Tyr Ser Gly Asn Gln Lys Asn Tyr Leu Ala Trp Tyr Gln Gln
 50                  55                  60

Lys Pro Gly Gln Ser Pro Lys Leu Leu Ile Tyr Trp Ala Ser Thr Arg
 65                  70                  75                  80

Gln Ser Gly Val Pro Asp Arg Phe Ile Gly Ser Gly Ser Gly Thr Asp
                 85                  90                  95

Phe Thr Leu Thr Ile Ser Ser Val Gln Ala Glu Asp Leu Ala Ile Tyr
                100                 105                 110

Tyr Cys Gln Gln Tyr Tyr Asn Thr Pro Arg Thr Phe Gly Gly Gly Thr
                115                 120                 125

Lys Leu Glu Leu Lys
            130
```

<210> SEQ ID NO 40
<211> LENGTH: 5
<212> TYPE: PRT
<213> ORGANISM: Rattus norvegicus

<400> SEQUENCE: 40

```
Ser Ser Tyr Trp Gly
 1               5
```

<210> SEQ ID NO 41
<211> LENGTH: 16
<212> TYPE: PRT
<213> ORGANISM: Rattus norvegicus

<400> SEQUENCE: 41

```
Tyr Ile Asn Tyr Ser Gly Ser Thr Ser Tyr Asn Pro Ser Leu Lys Ser
 1               5                  10                  15
```

<210> SEQ ID NO 42
<211> LENGTH: 9

```
<212> TYPE: PRT
<213> ORGANISM: Rattus norvegicus

<400> SEQUENCE: 42

Trp Thr Gly Gln Tyr Tyr Phe Asp Tyr
1               5

<210> SEQ ID NO 43
<211> LENGTH: 17
<212> TYPE: PRT
<213> ORGANISM: Rattus norvegicus

<400> SEQUENCE: 43

Lys Ser Ser Gln Ser Leu Leu Tyr Ser Gly Asn Gln Lys Asn Tyr Leu
1               5                   10                  15
Ala

<210> SEQ ID NO 44
<211> LENGTH: 7
<212> TYPE: PRT
<213> ORGANISM: Rattus norvegicus

<400> SEQUENCE: 44

Trp Ala Ser Thr Arg Gln Ser
1               5

<210> SEQ ID NO 45
<211> LENGTH: 9
<212> TYPE: PRT
<213> ORGANISM: Rattus norvegicus

<400> SEQUENCE: 45

Gln Gln Tyr Tyr Asp Thr Pro Pro Ala
1               5

<210> SEQ ID NO 46
<211> LENGTH: 5
<212> TYPE: PRT
<213> ORGANISM: Rattus norvegicus

<400> SEQUENCE: 46

Asn Tyr Gly Met Ala
1               5

<210> SEQ ID NO 47
<211> LENGTH: 17
<212> TYPE: PRT
<213> ORGANISM: Rattus norvegicus

<400> SEQUENCE: 47

Thr Ile Thr Tyr Asp Gly Ser Thr Thr Tyr Tyr Arg Asp Ser Val Lys
1               5                   10                  15
Gly

<210> SEQ ID NO 48
<211> LENGTH: 9
<212> TYPE: PRT
<213> ORGANISM: Rattus norvegicus

<400> SEQUENCE: 48

Asp Leu Gly Leu Tyr Tyr Phe Asp Tyr
1               5
```

```
<210> SEQ ID NO 49
<211> LENGTH: 17
<212> TYPE: PRT
<213> ORGANISM: Rattus norvegicus

<400> SEQUENCE: 49

Lys Ser Ser Gln Ser Leu Leu Tyr Ser Gly Asn Gln Lys Asn Tyr Leu
1               5                   10                  15
Ala

<210> SEQ ID NO 50
<211> LENGTH: 8
<212> TYPE: PRT
<213> ORGANISM: Rattus norvegicus

<400> SEQUENCE: 50

Trp Ala Ser Ser Arg Gln Ser Gly
1               5

<210> SEQ ID NO 51
<211> LENGTH: 9
<212> TYPE: PRT
<213> ORGANISM: Rattus norvegicus

<400> SEQUENCE: 51

Gln Gln Tyr Tyr Asp Ala Pro Arg Thr
1               5

<210> SEQ ID NO 52
<211> LENGTH: 5
<212> TYPE: PRT
<213> ORGANISM: Rattus norvegicus

<400> SEQUENCE: 52

Asn Tyr Gly Met Ala
1               5

<210> SEQ ID NO 53
<211> LENGTH: 17
<212> TYPE: PRT
<213> ORGANISM: Rattus norvegicus

<400> SEQUENCE: 53

Thr Ile Ser Tyr Asp Gly Ser Ser Ile Tyr Tyr Arg Asp Ser Val Lys
1               5                   10                  15
Gly

<210> SEQ ID NO 54
<211> LENGTH: 10
<212> TYPE: PRT
<213> ORGANISM: Rattus norvegicus

<400> SEQUENCE: 54

Asp Pro Gly Val Tyr Tyr Phe Asp Tyr Trp
1               5                   10

<210> SEQ ID NO 55
<211> LENGTH: 16
<212> TYPE: PRT
<213> ORGANISM: Rattus norvegicus

<400> SEQUENCE: 55

Lys Ser Ser Gln Ser Leu Leu Tyr Ser Gly Asn Gln Arg Asn Tyr Leu
1               5                   10                  15
```

<210> SEQ ID NO 56
<211> LENGTH: 7
<212> TYPE: PRT
<213> ORGANISM: Rattus norvegicus

<400> SEQUENCE: 56

Trp Ala Ser Thr Arg Gln Ser
1               5

<210> SEQ ID NO 57
<211> LENGTH: 9
<212> TYPE: PRT
<213> ORGANISM: Rattus norvegicus

<400> SEQUENCE: 57

Gln Gln Tyr Tyr Asp Thr Pro Arg Thr
1               5

<210> SEQ ID NO 58
<211> LENGTH: 5
<212> TYPE: PRT
<213> ORGANISM: Rattus norvegicus

<400> SEQUENCE: 58

Asn Tyr Trp Met Thr
1               5

<210> SEQ ID NO 59
<211> LENGTH: 17
<212> TYPE: PRT
<213> ORGANISM: Rattus norvegicus

<400> SEQUENCE: 59

Ser Ile Thr Asn Ser Gly Gly Ser Thr Tyr Tyr Pro Asp Ser Val Lys
1               5                   10                  15

Gly

<210> SEQ ID NO 60
<211> LENGTH: 14
<212> TYPE: PRT
<213> ORGANISM: Rattus norvegicus

<400> SEQUENCE: 60

Asp Val Asn Thr Tyr Tyr Gly Tyr Asn Ala Leu Phe Asp Tyr
1               5                   10

<210> SEQ ID NO 61
<211> LENGTH: 11
<212> TYPE: PRT
<213> ORGANISM: Rattus norvegicus

<400> SEQUENCE: 61

Lys Ala Ser Gln Asn Ile Asn Glu Tyr Leu Asn
1               5                   10

<210> SEQ ID NO 62
<211> LENGTH: 7
<212> TYPE: PRT
<213> ORGANISM: Rattus norvegicus

<400> SEQUENCE: 62

Asn Thr Asn Asn Leu Gln Thr
1               5

<210> SEQ ID NO 63
<211> LENGTH: 9
<212> TYPE: PRT
<213> ORGANISM: Rattus norvegicus

<400> SEQUENCE: 63

Phe Gln His Asn Ser Trp Pro Tyr Thr
1               5

<210> SEQ ID NO 64
<211> LENGTH: 5
<212> TYPE: PRT
<213> ORGANISM: Rattus norvegicus

<400> SEQUENCE: 64

Asp Tyr Gly Met Ala
1               5

<210> SEQ ID NO 65
<211> LENGTH: 16
<212> TYPE: PRT
<213> ORGANISM: Rattus norvegicus

<400> SEQUENCE: 65

Thr Ile Thr Tyr Asp Gly Ser Ile Tyr Tyr Arg Asp Ser Val Lys Gly
1               5                   10                  15

<210> SEQ ID NO 66
<211> LENGTH: 9
<212> TYPE: PRT
<213> ORGANISM: Rattus norvegicus

<400> SEQUENCE: 66

Asp Pro Gly Leu Tyr Tyr Phe Asp Phe
1               5

<210> SEQ ID NO 67
<211> LENGTH: 17
<212> TYPE: PRT
<213> ORGANISM: Rattus norvegicus

<400> SEQUENCE: 67

Gln Ser Ser Gln Ser Leu Leu Tyr Ser Gly Asn Gln Lys Asn Tyr Leu
1               5                   10                  15

Ala

<210> SEQ ID NO 68
<211> LENGTH: 11
<212> TYPE: PRT
<213> ORGANISM: Rattus norvegicus

<400> SEQUENCE: 68

Trp Ala Ser Thr Arg Gln Ser Gly Val Pro Asp
1               5                   10

<210> SEQ ID NO 69
<211> LENGTH: 9
<212> TYPE: PRT
<213> ORGANISM: Rattus norvegicus

<400> SEQUENCE: 69

Gln Gln Tyr Tyr Asn Thr Pro Arg Thr
1               5

<210> SEQ ID NO 70
<211> LENGTH: 49
<212> TYPE: DNA
<213> ORGANISM: Artificial sequence
<220> FEATURE:
<223> OTHER INFORMATION: Synthetic construct of KM4026 VL primer 1

<400> SEQUENCE: 70
gcgaattcgc ctcctcaaaa tggaatcaca gacccaggtc ctcatgtcc                49

<210> SEQ ID NO 71
<211> LENGTH: 39
<212> TYPE: DNA
<213> ORGANISM: Artificial sequence
<220> FEATURE:
<223> OTHER INFORMATION: Synthetic construct of KM4026 VL primer 2

<400> SEQUENCE: 71
gccgtacgtt tcagttccag cttggtccca gctccaaac                           39

<210> SEQ ID NO 72
<211> LENGTH: 51
<212> TYPE: DNA
<213> ORGANISM: Artificial sequence
<220> FEATURE:
<223> OTHER INFORMATION: Synthetic construct of KM4026 VH primer 1

<400> SEQUENCE: 72
atgcggccgc gacccctcac catgagaacg ttgggtcttc tgtacctgtt g             51

<210> SEQ ID NO 73
<211> LENGTH: 49
<212> TYPE: DNA
<213> ORGANISM: Artificial sequence
<220> FEATURE:
<223> OTHER INFORMATION: Synthetic construct of KM4026 VH primer 2

<400> SEQUENCE: 73
gcgggccctt ggtggaggct gaggagactg tgaccatgac tccttggcc                49

<210> SEQ ID NO 74
<211> LENGTH: 45
<212> TYPE: DNA
<213> ORGANISM: Artificial sequence
<220> FEATURE:
<223> OTHER INFORMATION: Synthetic construct of KM4027 VL primer 1

<400> SEQUENCE: 74
ggaattcgcc tcctcaaaat ggaatcacag acccaggtcc tcatg                    45

<210> SEQ ID NO 75
<211> LENGTH: 34
<212> TYPE: DNA
<213> ORGANISM: Artificial
<220> FEATURE:
<223> OTHER INFORMATION: Synthetic construct of KM4027 VL primer 2

<400> SEQUENCE: 75
ccgtacgttt caattccagc ttggagcctc cacc                                34

<210> SEQ ID NO 76
<211> LENGTH: 47
<212> TYPE: DNA
<213> ORGANISM: Artificial sequence
<220> FEATURE:

<223> OTHER INFORMATION: Synthetic construct of KM4027 VH primer 1

<400> SEQUENCE: 76
ggcggccgcg acccctcacc atggacatca ggctcagctt ggctttc        47

<210> SEQ ID NO 77
<211> LENGTH: 45
<212> TYPE: DNA
<213> ORGANISM: Artificial sequence
<220> FEATURE:
<223> OTHER INFORMATION: Synthetic construct of KM4027 VH primer 2

<400> SEQUENCE: 77
ggggcccttg gtggaggctg aggagactgt gaccatgact ccttg        45

<210> SEQ ID NO 78
<211> LENGTH: 45
<212> TYPE: DNA
<213> ORGANISM: Artificial sequence
<220> FEATURE:
<223> OTHER INFORMATION: Synthetic construct of KM4028 VL primer 1

<400> SEQUENCE: 78
ggaattcgcc tcctcaaaat ggaatcacag acccaggtcc tcatg        45

<210> SEQ ID NO 79
<211> LENGTH: 34
<212> TYPE: DNA
<213> ORGANISM: Artificial sequence
<220> FEATURE:
<223> OTHER INFORMATION: Synthetic construct of KM4028 VL primer 2

<400> SEQUENCE: 79
ccgtacgttt caattccagc ttggtgcctc cacc        34

<210> SEQ ID NO 80
<211> LENGTH: 47
<212> TYPE: DNA
<213> ORGANISM: Artificial sequence
<220> FEATURE:
<223> OTHER INFORMATION: Synthetic construct of KM4028 VH primer 1

<400> SEQUENCE: 80
ggcggccgcg acccctcacc atggacatca ggctcagctt ggctttc        47

<210> SEQ ID NO 81
<211> LENGTH: 45
<212> TYPE: DNA
<213> ORGANISM: Artificial sequence
<220> FEATURE:
<223> OTHER INFORMATION: Synthetic construct of KM4028 VH primer 2

<400> SEQUENCE: 81
ggggcccttg gtggaggctg aggagactgt gaccatgact ccttg        45

<210> SEQ ID NO 82
<211> LENGTH: 49
<212> TYPE: DNA
<213> ORGANISM: Artificial sequence
<220> FEATURE:
<223> OTHER INFORMATION: Synthetic construct of KM4030 VL primer 1

<400> SEQUENCE: 82
gcgaattcgc ctcctcaaaa tgatggctgc acttcaactc ttagggctg        49

-continued

```
<210> SEQ ID NO 83
<211> LENGTH: 39
<212> TYPE: DNA
<213> ORGANISM: Artificial sequence
<220> FEATURE:
<223> OTHER INFORMATION: Synthetic construct of KM4030 VL primer 2

<400> SEQUENCE: 83
gccgtacgtt tcagttccag cttggtccca gctccaaac                               39

<210> SEQ ID NO 84
<211> LENGTH: 52
<212> TYPE: DNA
<213> ORGANISM: Artificial sequence
<220> FEATURE:
<223> OTHER INFORMATION: Synthetic construct of KM4030 VH primer 1

<400> SEQUENCE: 84
atgcggccgc gacccctcac catggacatc aggctcagct tggttttcct tg               52

<210> SEQ ID NO 85
<211> LENGTH: 49
<212> TYPE: DNA
<213> ORGANISM: Artificial sequence
<220> FEATURE:
<223> OTHER INFORMATION: Synthetic construct of KM4030 VH primer 2

<400> SEQUENCE: 85
gcgggccctt ggtggaggct gaggagactg tgaccatgac tccttggcc                   49

<210> SEQ ID NO 86
<211> LENGTH: 49
<212> TYPE: DNA
<213> ORGANISM: Artificial sequence
<220> FEATURE:
<223> OTHER INFORMATION: Synthetic construct of KM4031 VL primer 1

<400> SEQUENCE: 86
gcgaattcgc ctcctcaaaa tggaatcaca gacccaggtc ctcatgtcc                   49

<210> SEQ ID NO 87
<211> LENGTH: 39
<212> TYPE: DNA
<213> ORGANISM: Artificial sequence
<220> FEATURE:
<223> OTHER INFORMATION: Synthetic construct of KM4031 VL primer 2

<400> SEQUENCE: 87
gccgtacgtt tcaattccag cttggtgcct ccaccgaac                              39

<210> SEQ ID NO 88
<211> LENGTH: 52
<212> TYPE: DNA
<213> ORGANISM: Artificial sequence
<220> FEATURE:
<223> OTHER INFORMATION: Synthetic construct of KM4031 VH primer 1

<400> SEQUENCE: 88
atgcggccgc gacccctcac catggacatc aggctcagct tggctttcat tg               52

<210> SEQ ID NO 89
<211> LENGTH: 49
<212> TYPE: DNA
<213> ORGANISM: Artificial sequence
<220> FEATURE:
<223> OTHER INFORMATION: Synthetic construct of KM4031 VH primer 2
```

```
<400> SEQUENCE: 89
gcgggccctt ggtggaggct gaggagactg tgaccatgac tccttggcc          49

<210> SEQ ID NO 90
<211> LENGTH: 30
<212> TYPE: DNA
<213> ORGANISM: Artificial sequence
<220> FEATURE:
<223> OTHER INFORMATION: Synthetic construct of mfCD27_5UTR

<400> SEQUENCE: 90
gcacagaaag gcgctccctg ggcaggaacc                               30

<210> SEQ ID NO 91
<211> LENGTH: 30
<212> TYPE: DNA
<213> ORGANISM: Artificial sequence
<220> FEATURE:
<223> OTHER INFORMATION: Synthetic construct of mfCD27_3UTR

<400> SEQUENCE: 91
ggctgtagtg cagctcccgc aggtgctggc                               30

<210> SEQ ID NO 92
<211> LENGTH: 783
<212> TYPE: DNA
<213> ORGANISM: Macaca fascicularis

<400> SEQUENCE: 92
atggcacggc cacatccctg gtggctgtgc tttctgggga ccctggtggg gctctcagct    60
actccagccc ccaagagctg cccagagagg cactactggg ctcagggaaa actgtgctgc   120
cagatgtgtg agccaggaac attccttgtg aaggactgtg accagcacag aaaggctgcc   180
cagtgtcatc cttgcatacc aggggtctcc ttctctccag accaccacac ccggcctcac   240
tgtgagagct gtcggcactg taactctggt cttctcattc gcaactgcac catcactgcc   300
aacgctgtgt gtgcctgtcg caatggctgg cagtgcaggg acaaggagtg tactgagtgt   360
gatcctcctc caaacccttc gctgaccact tggccatctc aggccctggg cccacaccct   420
cagcccaccc acttacctta tgtcaatgag atgctggagg ccagaacagc agggcacatg   480
cagactctgg ctgacttcag gcacctgcct gcccggactc tctctaccca ctggccaccc   540
caaagatccc tgtgcagctc agattttatt cgtatccttg tgatcttctc cggaatgttt   600
cttgttttca ccctggccgg aaccctgttc ctccatcaac aaaggaaata tagatcaaac   660
aaaggagaaa gtcccatgga gcctgcagaa ccttgtcctt acagctgccc cagggaggag   720
gaaggcagca ccatccccat ccaagaggat taccgaaaac cggagcctgc ctcctccccg   780
tga                                                               783

<210> SEQ ID NO 93
<211> LENGTH: 71
<212> TYPE: DNA
<213> ORGANISM: Artificial sequence
<220> FEATURE:
<223> OTHER INFORMATION: Synthetic construct of mfCD27toKAN_5

<400> SEQUENCE: 93
gggcggccgc tcctcaggct gtcctcag gttgcctcct caaaatggca cggccacatc    60
cctggtggct g                                                     71
```

```
<210> SEQ ID NO 94
<211> LENGTH: 56
<212> TYPE: DNA
<213> ORGANISM: Artificial sequence
<220> FEATURE:
<223> OTHER INFORMATION: Synthetic construct of mfCD27HisKAN_3

<400> SEQUENCE: 94
gggtcgactc aatgatgatg atgatgatgc ggggaggagg caggctccgg ttttcg          56

<210> SEQ ID NO 95
<211> LENGTH: 801
<212> TYPE: DNA
<213> ORGANISM: Artificial sequence
<220> FEATURE:
<223> OTHER INFORMATION: Synthetic construct of His tag-fusioned mucaca
      fascicularis CD27 cDNA sequence

<400> SEQUENCE: 95
atggcacggc cacatccctg gtggctgtgc tttctgggga ccctggtggg gctctcagct       60
actccagccc ccaagagctg cccagagagg cactactggg ctcagggaaa actgtgctgc     120
cagatgtgtg agccaggaac attccttgtg aaggactgtg accagcacag aaaggctgcc     180
cagtgtcatc cttgcatacc aggggtctcc ttctctccag accaccacac ccggcctcac     240
tgtgagagct gtcggcactg taactctggt cttctcattc gcaactgcac catcactgcc     300
aacgctgtgt gtgcctgtcg caatggctgg cagtgcaggg acaaggagtg tactgagtgt     360
gatcctcctc aaaaccttc gctgaccact tggccatctc aggccctggg cccacaccct     420
cagcccaccc acttaccttgg gtcaatgag atgctggagg ccagaacagc agggcacatg     480
cagactctgg ctgacttcag gcacctgcct gcccggactc tctctaccca ctggccaccc     540
caaagatccc tgtgcagctc agattttatt cgtatccttg tgatcttctc cggaatgttt     600
cttgttttca ccctggccgg aaccctgttc ctccatcaac aaaggaaata tagatcaaac     660
aaaggagaaa gtcccatgga gcctgcagaa ccttgtcctt acagctgccc cagggaggag     720
gaaggcagca ccatccccat ccaagaggat taccgaaaac cggagcctgc ctcctccccg     780
catcatcatc atcatcattg a                                                801

<210> SEQ ID NO 96
<211> LENGTH: 123
<212> TYPE: PRT
<213> ORGANISM: Artificial sequence
<220> FEATURE:
<223> OTHER INFORMATION: Synthetic construct of KM4030 HV0 amino acid
      sequence

<400> SEQUENCE: 96

Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ser Ser Ile Thr Asn Ser Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Asp Val Asn Thr Tyr Tyr Gly Tyr Asn Ala Leu Phe Asp Tyr
            100                 105                 110

Trp Gly Leu Gly Thr Leu Val Thr Val Ser Ser
        115                 120

<210> SEQ ID NO 97
<211> LENGTH: 107
<212> TYPE: PRT
<213> ORGANISM: Artificial
<220> FEATURE:
<223> OTHER INFORMATION: Synthetic construct of KM4030 LV0 amino acid
      sequence

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Glu Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln His Asn Ser Trp Pro Tyr
                85                  90                  95

Thr Phe Gly Gln Gly Thr Lys Leu Glu Ile Lys
            100                 105

<210> SEQ ID NO 98
<211> LENGTH: 369
<212> TYPE: DNA
<213> ORGANISM: Artificial
<220> FEATURE:
<223> OTHER INFORMATION: Synthetic construct of KM4030 HV0 DNA sequence

<400> SEQUENCE: 98
gaggtgcagc tggtggagtc tgggggtggc ttggtaaagc ctggcggtc cctgcgactc      60 tcctgtgcag cctctggttt cacctttagc aactactgga tgacctggat ccgccaggct    120
ccagggaagg ggctggagtg gtctcatcc attactaata gtggtggtag cacttactat     180
ccagactctg tgaagggccg gttcaccatc tcccgagaca atgccaagaa cagcctgtat    240
ctgcaaatga acagcctgcg agccgaggac acagccgtat attactgtgc ccgagatgtt    300
aacacatact atgggtataa cgccctcttt gattactggg gcctgggtac cctggtcacc    360
gtctcctca                                                            369

<210> SEQ ID NO 99
<211> LENGTH: 321
<212> TYPE: DNA
<213> ORGANISM: Artificial sequence
<220> FEATURE:
<223> OTHER INFORMATION: Synthetic construct of KM4030 LV0 DNA sequence

<400> SEQUENCE: 99
gacatccaga tgacccagtc tccttcctca ctgtctgcat ctgtaggtga ccgagtcacc      60
atcacttgca aagcaagtca gaatattaat gagtacttaa actggtatca gcagaaacca    120
gggaaagccc ctaagctcct gatctataat acaaacaatt tgcaaacggg ggtcccatca    180
cggttcagcg gcagtggttc tgggacagat ttcactctca ccatcagcag tctgcagcct    240

```
gaagatttcg caacttatta ctgctttcag cataatagtt ggccgtacac gttcggccaa    300
gggaccaagc tggagatcaa a                                              321
```

<210> SEQ ID NO 100
<211> LENGTH: 369
<212> TYPE: DNA
<213> ORGANISM: Artificial sequence
<220> FEATURE:
<223> OTHER INFORMATION: Synthetic construct of KM4030 HV2 DNA Sequence

<400> SEQUENCE: 100

```
gaggtgcagc tggtggagtc tgggggtggc ttggtaaagc ctgggcggtc cctgcgactc    60
tcctgtgcag cctctggttt cacctttaat aactactgga tgacctggat ccgccaggct   120
ccagggaagg ggctggagtg gtctcatcc attactaata gtggtggtag cacttactat    180
ccagactctg tgaagggccg gttcaccatc tcccgagaca atgccaagaa cagcctgtat   240
ctgcaaatga acagcctgcg agccgaggac acagccgtat attactgtac acgagatgtt   300
aacacatact atgggtataa cgccctcttt gattactggg gcctgggtac cctggtcacc   360
gtctcctca                                                           369
```

<210> SEQ ID NO 101
<211> LENGTH: 123
<212> TYPE: PRT
<213> ORGANISM: Artificial sequence
<220> FEATURE:
<223> OTHER INFORMATION: Synthetic construct of KM4030 HV2 amino acid
      sequence

<400> SEQUENCE: 101

```
Glu Val Gln Leu Val Glu Ser Gly Gly Gly Leu Val Lys Pro Gly Arg
 1               5                  10                  15

Ser Leu Arg Leu Ser Cys Ala Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ser Ser Ile Thr Asn Ser Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Val Asn Thr Tyr Tyr Gly Tyr Asn Ala Leu Phe Asp Tyr
            100                 105                 110

Trp Gly Leu Gly Thr Leu Val Thr Val Ser Ser
        115                 120
```

<210> SEQ ID NO 102
<211> LENGTH: 369
<212> TYPE: DNA
<213> ORGANISM: Artificial sequence
<220> FEATURE:
<223> OTHER INFORMATION: Synthetic construct of KM4030 HV3 DNA Sequence

<400> SEQUENCE: 102

```
gaggtgcagc tggtggagtc tgggggtggc ttggtaaagc ctgggcggtc cctgcgactc    60
tcctgtgcag cctctggttt cacctttagc aactactgga tgacctggat ccgccaggct   120
ccagggaagg ggctggagtg gattgcatcc attactaata gtggtggtag cacttactat    180
```

```
ccagactctg tgaagggccg gttcaccatc tcccgagaca atgccaagaa cagcctgtat    240
ctgcaaatga acagcctgcg agccgaggac acagccgtat attactgtac acgagatgtt    300
aacacatact atgggtataa cgccctcttt gattactggg cctgggtac cctggtcacc    360 gtctcctca                                                            369
```

```
<210> SEQ ID NO 103
<211> LENGTH: 123
<212> TYPE: PRT
<213> ORGANISM: Artificial sequence
<220> FEATURE:
<223> OTHER INFORMATION: Synthetic construct of HV3 amino acid sequence

<400> SEQUENCE: 103
```

Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Ile
        35                  40                  45

Ala Ser Ile Thr Asn Ser Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Val Asn Thr Tyr Tyr Gly Tyr Asn Ala Leu Phe Asp Tyr
            100                 105                 110

Trp Gly Leu Gly Thr Leu Val Thr Val Ser Ser
        115                 120

```
<210> SEQ ID NO 104
<211> LENGTH: 369
<212> TYPE: DNA
<213> ORGANISM: Artificial sequence
<220> FEATURE:
<223> OTHER INFORMATION: Synthetic construct of KM4030 HV5 DNA Sequence

<400> SEQUENCE: 104
gaggtgcagc tggtggagtc tgggggtggc ttggtaaagc ctggggcggtc cctgcgactc    60 tcctgtgcag cctctggttt cacctttaat aactactgga tgacctggat ccgccaggct   120
ccagggaagg ggctggagtg gattgcatcc attactaata gtggtggtag cacttactat   180
ccagactctg tgaagggccg gttcaccatc tcccgagaca atgccaaggg cagcctgtat   240
ctgcaaatga acagcctgcg agccgaggac acagccgtat attactgtac acgagatgtt   300
aacacatact atgggtataa cgccctcttt gattactggg cctgggtac cctggtcacc   360 gtctcctca                                                            369
```

```
<210> SEQ ID NO 105
<211> LENGTH: 123
<212> TYPE: PRT
<213> ORGANISM: Artificial sequence
<220> FEATURE:
<223> OTHER INFORMATION: Synthetic construct of KM4030 HV5 amino acid
      sequence

<400> SEQUENCE: 105
```

Glu Val Gln Leu Val Glu Ser Gly Gly Gly Leu Val Lys Pro Gly Arg

```
1               5                   10                  15
Ser Leu Arg Leu Ser Cys Ala Ala Ser Gly Phe Thr Phe Asn Asn Tyr
            20                  25                  30

Trp Met Thr Trp Ile Arg Gln Ala Pro Gly Lys Gly Leu Glu Trp Ile
        35                  40                  45

Ala Ser Ile Thr Asn Ser Gly Gly Ser Thr Tyr Tyr Pro Asp Ser Val
        50                  55                  60

Lys Gly Arg Phe Thr Ile Ser Arg Asp Asn Ala Lys Gly Ser Leu Tyr
65                  70                  75                  80

Leu Gln Met Asn Ser Leu Arg Ala Glu Asp Thr Ala Val Tyr Tyr Cys
            85                  90                  95

Thr Arg Asp Val Asn Thr Tyr Tyr Gly Tyr Asn Ala Leu Phe Asp Tyr
            100                 105                 110

Trp Gly Leu Gly Thr Leu Val Thr Val Ser Ser
        115                 120
```

<210> SEQ ID NO 106
<211> LENGTH: 369
<212> TYPE: DNA
<213> ORGANISM: Artificial sequence
<220> FEATURE:
<223> OTHER INFORMATION: Synthetic construct of KM4030 HV7 DNA Sequence

<400> SEQUENCE: 106

```
gaggtgcagc tggtggagtc tgggggtggc ttggtaaagc ctgggcggtc cctgcgactc      60
tcctgtgcag cctctggttt cacctttaat aactactgga tgacctggat ccgccaggct     120
ccagggaagg ggctggagtg gattgcatcc attactaata gtggtggtag cacttactat     180
ccagactctg tgaagggccg gttcaccatc tcccgagaca atgccaaggg cagcctgtat     240
ctgcaaatga acagcctgcg agccgaggac acagccactt attactgtac acgagatgtt     300
aacacatact atgggtataa cgccctcttt gattactggg gcctgggtgt cctggtcacc     360
gtctcctca                                                             369
```

<210> SEQ ID NO 107
<211> LENGTH: 123
<212> TYPE: PRT
<213> ORGANISM: Artificial sequence
<220> FEATURE:
<223> OTHER INFORMATION: Synthetic construct of KM4030 HV7 amino acid
      sequence

<400> SEQUENCE: 107

```
Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Asn Tyr
            20                  25                  30

Trp Met Thr Trp Ile Arg Gln Ala Pro Gly Lys Gly Leu Glu Trp Ile
        35                  40                  45

Ala Ser Ile Thr Asn Ser Gly Gly Ser Thr Tyr Tyr Pro Asp Ser Val
        50                  55                  60

Lys Gly Arg Phe Thr Ile Ser Arg Asp Asn Ala Lys Gly Ser Leu Tyr
65                  70                  75                  80

Leu Gln Met Asn Ser Leu Arg Ala Glu Asp Thr Ala Thr Tyr Tyr Cys
            85                  90                  95
```

```
Thr Arg Asp Val Asn Thr Tyr Tyr Gly Tyr Asn Ala Leu Phe Asp Tyr
            100                 105                 110

Trp Gly Leu Gly Val Leu Val Thr Val Ser Ser
        115                 120
```